US011676685B2

(12) United States Patent
Jaganathan et al.

(10) Patent No.: US 11,676,685 B2
(45) Date of Patent: Jun. 13, 2023

(54) ARTIFICIAL INTELLIGENCE-BASED QUALITY SCORING

(71) Applicant: Illumina, Inc., San Diego, CA (US)

(72) Inventors: Kishore Jaganathan, San Francisco, CA (US); John Randall Gobbel, Brisbane, CA (US); Amirali Kia, San Mateo, CA (US)

(73) Assignee: Illumina, Inc., San Diego, CA (US)

( * ) Notice: Subject to any disclaimer, the term of this patent is extended or adjusted under 35 U.S.C. 154(b) by 413 days.

(21) Appl. No.: 16/826,134

(22) Filed: Mar. 20, 2020

(65) Prior Publication Data

US 2020/0327377 A1 Oct. 15, 2020

Related U.S. Application Data

(60) Provisional application No. 62/821,602, filed on Mar. 21, 2019, provisional application No. 62/821,618, (Continued)

(30) Foreign Application Priority Data

Jun. 14, 2019 (NL) ...................................... 2023310
Jun. 14, 2019 (NL) ...................................... 2023311
(Continued)

(51) Int. Cl.
*G06K 9/00* (2022.01)
*G16B 40/20* (2019.01)
(Continued)

(52) U.S. Cl.
CPC ............ *G16B 40/20* (2019.02); *G06F 16/907* (2019.01); *G06F 18/213* (2023.01);
(Continued)

(58) Field of Classification Search
CPC .. G06K 9/6218; G06K 9/6222; G06K 9/6256; G06K 9/6232; G06K 9/6262;
(Continued)

(56) References Cited

U.S. PATENT DOCUMENTS 5,641,658 A 6/1997 Adams et al.
6,090,592 A 7/2000 Adams et al.
(Continued)

FOREIGN PATENT DOCUMENTS

CA 2894317 A1 12/2016
CA 3104851 A1 11/2020
(Continued)

OTHER PUBLICATIONS

Angermueller, Christof, et. al., "Deep learning for computational biology", Jun. 6, 2016, 16 pages.
(Continued)

*Primary Examiner* — Khai M Nguyen
(74) *Attorney, Agent, or Firm* — Keller Preece

(57) ABSTRACT

The technology disclosed assigns quality scores to bases called by a neural network-based base caller by (i) quantizing classification scores of predicted base calls produced by the neural network-based base caller in response to processing training data during training, (ii) selecting a set of quantized classification scores, (iii) for each quantized classification score in the set, determining a base calling error rate by comparing its predicted base calls to corresponding ground truth base calls, (iv) determining a fit between the quantized classification scores and their base calling error rates, and (v) correlating the quality scores to the quantized classification scores based on the fit.

20 Claims, 80 Drawing Sheets
(62 of 80 Drawing Sheet(s) Filed in Color)

Related U.S. Application Data filed on Mar. 21, 2019, provisional application No. 62/821,681, filed on Mar. 21, 2019, provisional application No. 62/821,724, filed on Mar. 21, 2019, provisional application No. 62/821,766, filed on Mar. 21, 2019.

(30) Foreign Application Priority Data

| Jun. 14, 2019 | (NL) | ...................................... | 2023312 |
| Jun. 14, 2019 | (NL) | ...................................... | 2023314 |

(51) Int. Cl.

| *G06N 3/08* | (2023.01) |
| *G16B 40/00* | (2019.01) |
| *G06N 3/04* | (2023.01) |
| *G06F 16/907* | (2019.01) |
| *G06N 3/084* | (2023.01) |
| *G06V 10/82* | (2022.01) |
| *G06F 18/23* | (2023.01) |
| *G06F 18/24* | (2023.01) |
| *G06F 18/213* | (2023.01) |
| *G06F 18/214* | (2023.01) |
| *G06F 18/21* | (2023.01) |
| *G06F 18/2415* | (2023.01) |
| *G06F 18/2431* | (2023.01) |
| *G06F 18/23211* | (2023.01) |
| *G06N 7/01* | (2023.01) |
| *G06V 10/762* | (2022.01) |
| *G06V 10/764* | (2022.01) |
| *G06V 10/77* | (2022.01) |
| *G06V 10/778* | (2022.01) |
| *G06V 10/44* | (2022.01) |
| *G06V 10/98* | (2022.01) |
| *G06N 5/046* | (2023.01) |

(52) U.S. Cl.
CPC .......... *G06F 18/214* (2023.01); *G06F 18/217* (2023.01); *G06F 18/23* (2023.01); *G06F 18/23211* (2023.01); *G06F 18/24* (2023.01); *G06F 18/2415* (2023.01); *G06F 18/2431* (2023.01); *G06N 3/04* (2013.01); *G06N 3/08* (2013.01); *G06N 3/084* (2013.01); *G06N 7/01* (2023.01); *G06V 10/454* (2022.01); *G06V 10/763* (2022.01); *G06V 10/764* (2022.01); *G06V 10/7715* (2022.01); *G06V 10/7784* (2022.01); *G06V 10/82* (2022.01); *G06V 10/993* (2022.01); *G16B 40/00* (2019.02); *G06N 5/046* (2013.01)

(58) Field of Classification Search
CPC .... G06K 9/6267; G06K 9/6277; G06K 9/628; G06F 16/907; G16B 40/00; G06V 10/82; G06V 10/751; G06N 3/04; G06N 3/08; G06N 3/084; G06N 7/005; G06N 5/046
See application file for complete search history.

(56) References Cited

U.S. PATENT DOCUMENTS

| 7,057,026 | B2 | 6/2006 | Barnes et al. |
| 7,115,400 | B1 | 10/2006 | Adessi et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,427,673 | B2 | 9/2008 | Balasubramanian et al. |
| 7,541,444 | B2 | 6/2009 | Milton et al. |
| 7,566,537 | B2 | 7/2009 | Balasubramanian et al. |
| 7,592,435 | B2 | 9/2009 | Milton et al. |
| 8,182,993 | B2 | 5/2012 | Tomaney et al. |
| 8,241,573 | B2 | 8/2012 | Banerjee et al. |
| 8,392,126 | B2 | 3/2013 | Mann |
| 8,401,258 | B2 | 3/2013 | Hargrove et al. |
| 8,407,012 | B2 | 3/2013 | Erlich et al. |
| 8,594,439 | B2 | 11/2013 | Staelin et al. |
| 8,725,425 | B2 | 5/2014 | Heiner et al. |
| 8,795,971 | B2 | 8/2014 | Kersey et al. |
| 8,965,076 | B2 | 2/2015 | Garcia et al. |
| 9,279,154 | B2 | 3/2016 | Previte et al. |
| 9,453,258 | B2 | 9/2016 | Kain et al. |
| 9,708,656 | B2 | 7/2017 | Turner et al. |
| 10,023,911 | B2 | 7/2018 | Tomaney et al. |
| 10,068,054 | B2 | 9/2018 | Van Rooyen et al. |
| 10,152,776 | B2 | 12/2018 | Langlois et al. |
| 10,168,438 | B2 | 1/2019 | Dennis et al. |
| 10,241,075 | B2 | 3/2019 | Davey et al. |
| 10,354,747 | B1 | 7/2019 | DePristo et al. |
| 10,423,861 | B2 | 9/2019 | Gao et al. |
| 10,491,239 | B1 | 11/2019 | Hubara |
| 10,527,549 | B2 | 1/2020 | Rebetez et al. |
| 10,540,591 | B2 | 1/2020 | Gao et al. |
| 10,619,195 | B2 | 4/2020 | Lamb et al. |
| 10,648,027 | B2 | 5/2020 | Mannion et al. |
| 10,711,299 | B2 | 7/2020 | Rothberg et al. |
| 10,713,794 | B1 | 7/2020 | He et al. |
| 10,740,880 | B2 | 8/2020 | Paik et al. |
| 10,740,883 | B2 | 8/2020 | Zerfass et al. |
| 10,755,810 | B2 | 8/2020 | Buckler et al. |
| 10,943,255 | B1* | 3/2021 | Andreou ............ G06Q 30/0244 |
| 10,963,673 | B2 | 3/2021 | Schaumberg et al. |
| 11,056,220 | B2* | 7/2021 | Lyman ..................... G06T 7/10 |
| 11,138,496 | B2* | 10/2021 | Seth .................... G06K 9/6271 |
| 2002/0055100 | A1 | 5/2002 | Kawashima et al. |
| 2003/0062485 | A1 | 4/2003 | Fernandez et al. |
| 2004/0002090 | A1 | 1/2004 | Mayer et al. |
| 2004/0096853 | A1 | 5/2004 | Mayer |
| 2006/0014151 | A1 | 1/2006 | Ogura et al. |
| 2006/0040297 | A1 | 2/2006 | Leamon et al. |
| 2006/0064248 | A1 | 3/2006 | Saidi et al. |
| 2006/0188901 | A1 | 8/2006 | Barnes et al. |
| 2006/0240439 | A1 | 10/2006 | Smith et al. |
| 2006/0269130 | A1 | 11/2006 | Maroy et al. |
| 2007/0128624 | A1 | 6/2007 | Gormley et al. |
| 2007/0166705 | A1 | 7/2007 | Milton et al. |
| 2008/0009420 | A1 | 1/2008 | Schroth et al. |
| 2008/0234136 | A1 | 9/2008 | Drmanac et al. |
| 2008/0242560 | A1 | 10/2008 | Gunderson et al. |
| 2009/0081775 | A1 | 3/2009 | Hodneland et al. |
| 2010/0046830 | A1 | 2/2010 | Wang et al. |
| 2010/0111370 | A1 | 5/2010 | Black et al. |
| 2010/0157086 | A1 | 6/2010 | Segale et al. |
| 2011/0059865 | A1 | 3/2011 | Smith et al. |
| 2011/0065607 | A1 | 3/2011 | Kersey et al. |
| 2011/0281736 | A1 | 11/2011 | Drmanac et al. |
| 2011/0286628 | A1 | 11/2011 | Goncalves et al. |
| 2011/0295902 | A1 | 12/2011 | Mande et al. |
| 2012/0015825 | A1 | 1/2012 | Zhong et al. |
| 2012/0020537 | A1 | 1/2012 | Garcia et al. |
| 2013/0059740 | A1 | 3/2013 | Drmanac et al. |
| 2013/0079232 | A1 | 3/2013 | Kain et al. |
| 2013/0124100 | A1 | 5/2013 | Drmanac et al. |
| 2013/0188866 | A1 | 7/2013 | Obrador et al. |
| 2013/0250407 | A1 | 9/2013 | Schaffer et al. |
| 2014/0051588 | A9 | 2/2014 | Drmanac et al. |
| 2014/0152801 | A1 | 6/2014 | Fine et al. |
| 2015/0079596 | A1 | 3/2015 | Eltoukhy et al. |
| 2015/0117784 | A1 | 4/2015 | Lin et al. |
| 2015/0169824 | A1 | 6/2015 | Kermani et al. |
| 2016/0042511 | A1 | 2/2016 | Chukka et al. |
| 2016/0078272 | A1 | 3/2016 | Hammoud |
| 2016/0110498 | A1 | 4/2016 | Bruand et al. |
| 2016/0196479 | A1 | 7/2016 | Chertok et al. |
| 2016/0247034 | A1* | 8/2016 | Lee ..................... G06V 10/993 |
| 2016/0350914 | A1 | 12/2016 | Champlin et al. |
| 2016/0356715 | A1 | 12/2016 | Zhong et al. |
| 2016/0357903 | A1 | 12/2016 | Shendure et al. |

(56) References Cited

U.S. PATENT DOCUMENTS

| | | |
|---|---|---|
| 2016/0371431 A1 | 12/2016 | Haque et al. |
| 2017/0044601 A1 | 2/2017 | Crnogorac et al. |
| 2017/0098032 A1 | 4/2017 | Desai et al. |
| 2017/0116520 A1 | 4/2017 | Min et al. |
| 2017/0161545 A1 | 6/2017 | Champlin et al. |
| 2017/0169313 A1 | 6/2017 | Choi et al. |
| 2017/0249421 A1 | 8/2017 | Eberle et al. |
| 2017/0249744 A1 | 8/2017 | Wang et al. |
| 2017/0362634 A1 | 12/2017 | Ota et al. |
| 2018/0075279 A1 | 3/2018 | Gertych et al. |
| 2018/0107927 A1 | 4/2018 | Frey |
| 2018/0114337 A1 | 4/2018 | Li et al. |
| 2018/0189613 A1 | 7/2018 | Wolf et al. |
| 2018/0195953 A1 | 7/2018 | Langlois et al. |
| 2018/0201992 A1 | 7/2018 | Wu et al. |
| 2018/0211001 A1 | 7/2018 | Gopalan et al. |
| 2018/0274023 A1 | 9/2018 | Belitz et al. |
| 2018/0286040 A1 | 10/2018 | Sashida |
| 2018/0305751 A1 | 10/2018 | Vermaas et al. |
| 2018/0322327 A1 | 11/2018 | Smith et al. |
| 2018/0330824 A1 | 11/2018 | Athey |
| 2018/0334711 A1 | 11/2018 | Kelley et al. |
| 2018/0334712 A1 | 11/2018 | Singer et al. |
| 2018/0340234 A1 | 11/2018 | Scafe et al. |
| 2019/0034586 A1 | 1/2019 | Pirrotte et al. |
| 2019/0080450 A1 | 3/2019 | Arar et al. |
| 2019/0107642 A1 | 4/2019 | Farhadi Nia et al. |
| 2019/0114544 A1 | 4/2019 | Sundaram et al. |
| 2019/0156915 A1 | 5/2019 | Zhang et al. |
| 2019/0164010 A1 | 5/2019 | Ma et al. |
| 2019/0170680 A1 | 6/2019 | Sikora et al. |
| 2019/0180153 A1 | 6/2019 | Buckler et al. |
| 2019/0213473 A1 | 7/2019 | Dutta et al. |
| 2019/0237160 A1 | 8/2019 | Rothberg et al. |
| 2019/0237163 A1 | 8/2019 | Wang et al. |
| 2019/0244348 A1 | 8/2019 | Buckler et al. |
| 2019/0266491 A1 | 8/2019 | Gao et al. |
| 2019/0272638 A1 | 9/2019 | Mouton et al. |
| 2019/0332118 A1 | 10/2019 | Wang et al. |
| 2019/0392578 A1 | 12/2019 | Chukka et al. |
| 2020/0027002 A1 | 1/2020 | Hickson et al. |
| 2020/0054306 A1 | 2/2020 | Mehanian et al. |
| 2020/0057838 A1 | 2/2020 | Yekhanin et al. |
| 2020/0065675 A1 | 2/2020 | Sundaram et al. |
| 2020/0125947 A1 | 4/2020 | Park et al. |
| 2020/0176082 A1 | 6/2020 | Massingham |
| 2020/0193597 A1 | 6/2020 | Fan et al. |
| 2020/0226368 A1 | 7/2020 | Bakalo et al. |
| 2020/0256856 A1 | 8/2020 | Chou et al. |
| 2020/0302223 A1 | 9/2020 | Dutta et al. |
| 2020/0302224 A1 | 9/2020 | Jaganathan et al. |
| 2020/0302297 A1 | 9/2020 | Jaganathan et al. |
| 2020/0302603 A1 | 9/2020 | Barnes et al. |
| 2020/0320294 A1 | 10/2020 | Mangal et al. |
| 2020/0342955 A1 | 10/2020 | Guo et al. |
| 2020/0364565 A1 | 11/2020 | Kostem |
| 2020/0388029 A1 | 12/2020 | Saltz et al. |
| 2021/0027462 A1 | 1/2021 | Bredno et al. |
| 2021/0056287 A1 | 2/2021 | Schaumburg et al. |
| 2021/0072391 A1 | 3/2021 | Li et al. |
| 2021/0089827 A1 | 3/2021 | Kumagai et al. |
| 2021/0115490 A1 | 4/2021 | Embree et al. |
| 2021/0390278 A1 | 12/2021 | Van Leeuwen et al. |

FOREIGN PATENT DOCUMENTS

| | | | |
|---|---|---|---|
| CN | 110245685 A | 9/2019 | |
| EP | 3130681 A1 | 2/2017 | |
| EP | 3373238 A1 | 9/2018 | |
| JP | 2007199397 A | 8/2007 | |
| RU | 2750706 C2 * | 7/2021 | ............ G01N 33/48 |
| WO | 9106678 A1 | 5/1991 | |
| WO | 2004018497 A2 | 3/2004 | |
| WO | 2005065814 A1 | 7/2005 | |
| WO | 2006064199 A1 | 6/2006 | |
| WO | 2007010251 A2 | 1/2007 | |
| WO | 2007123744 A2 | 11/2007 | |
| WO | 2008154317 A1 | 12/2008 | |
| WO | 2012058096 A1 | 5/2012 | |
| WO | 2014142921 A1 | 9/2014 | |
| WO | 2015084985 A2 | 6/2015 | |
| WO | 2016145516 A1 | 9/2016 | |
| WO | 2016201564 A1 | 12/2016 | |
| WO | 2017184997 A1 | 10/2017 | |
| WO | 2018129314 A1 | 7/2018 | |
| WO | 2018165099 A1 | 9/2018 | |
| WO | 2018203084 A1 | 11/2018 | |
| WO | 2019027767 A1 | 2/2019 | |
| WO | 2019028047 A1 | 2/2019 | |
| WO | 2019055856 A1 | 3/2019 | |
| WO | 2019079182 A1 | 4/2019 | |
| WO | 2019079202 A1 | 4/2019 | |
| WO | 2019090251 A2 | 5/2019 | |
| WO | 2019136284 A1 | 7/2019 | |
| WO | 2019136388 A1 | 7/2019 | |
| WO | 2019140402 A1 | 7/2019 | |
| WO | 2019147904 A1 | 8/2019 | |
| WO | 2020014280 A1 | 1/2020 | |
| WO | 2020123552 A1 | 6/2020 | |

OTHER PUBLICATIONS

PCT/US2021/018258 International Search Report and Written Opinion, dated May 26, 2021, 17 pages.
Smith et. al., Barcoding and demultiplexing Oxford nanopore native RNA sequencing reads with deep residual learning, bioRxiv, dated Dec. 5, 2019, 18 pages.
PCT/US2021/018910 Partial Search Report and Invitation to pay fee, dated May 31, 2021, 14 pages.
PCT/US2021/018422 International Search Report and Written Opinion, dated Jun. 10, 2021, 12 pages.
Aggarwal, Neural Networks and Deep Learning: A Textbook, Springer, dated Aug. 26, 2018, 512 pages.
Wang et. al., Deep Neural Netwotk Approximation for Custom Hardware: Where We've Been, Where We're Going, Cornell University, dated Jan. 21, 2019, 37 pages.
Lavin et. al., Fast Algorithms for Convolutional Neural Networks, dated Nov. 10, 2015, 9 pages.
Liu et. al., A Uniform Architecture Design for Accelerating 2D and 3D CNNs on FPGAs, published Jan. 7, 2019, 19 pages.
PCT/US2021/018427 International Search Report and Written Opinion, dated Jun. 1, 2021, 15 pages.
PCT/US2021/018913 International Search Report and Written Opinion, dated Jun. 10, 2021, 11 pages.
Zeng et. al., Causalcall: Nanopore Basecalling Using a Temporal Convolutional Network, dated Jan. 20, 2020, 11 pages.
PCT/US2021/018915 International Search Report and Written Opinion, dated Jun. 15, 2021, 13 pages.
Kwon et. al., Understanding Reuse, Performance, and Hardware Cost of DNN Dataflow—A Data-Centric Approach, Proceedings of the 52nd Annual IEEE/ACM International Symposium on Microarchitecture, dated Oct. 12, 2019, 13 pages.
Sze et. al., Efficient Processing of Deep Neural Networks: A Tutorial and Survey, Cornell University Library, dated Mar. 27, 2017, 21 pages.
Sundaram, L. et. al., "Predicitng the clinical impact of human mutation with deep neural networks", Nat. Genet. 50, 1161-1170 (2018).
Jaganathan, K. et al., "Predicting splicing from primary sequence with deep learning", Cell 176, 535-548, (2019).
Kircher, Martin, et al. "A general framework for estimating the relative pathogenicity of human genetic variants." Nature genetics 46.3 (2014): 310. (Year:2014).
Henikoff, S. & Henikoff, J. G. Amino acid substitution matrices from protein blocks. Proc. Natl. Acad. Sci. USA 89, 10915-10919 (1992).
Li, W. H., Wu, C. I. & Luo, C. C. Nonrandomness of point mutation as reflected in nucleotide substitutions in pseudogenes and its evolutionary implications. J. Molec. Evol. 21, 58-71 (1984).

(56) References Cited

OTHER PUBLICATIONS

Grantham, R. Amino acid difference formula to help explain protein evolution. Science 185, 862-864 (1974).
LeCun, Y., Botlou, L., Bengio, Y., & Haffner, P. Gradient based learning applied to document recognition. Proc. IEEE 86, 2278-2324 (1998).
Vissers, L. E., Gilissen, C., & Veltman, J. A. Genetic studies in intellectual disability and related disorders. Nat. Rev. Genet. 17, 9-18 (2016).
Neale, B. M. et al. Patterns and rates of exonicde novo mutations in autism spectrum disorders. Nature 485, 242-245 (2012).
Sanders, S. J. et al. De novo mutations revealed by whole-exome sequencing are strongly associated with autism. Nature 485, 237-241 (2012).
De Rubeis, S. et al. Synaptic, transcriptional and chromatin genes disrupted in autism. Nature 515, 209-215 (2014).
Deciphering Developmental Disorders Study. Large-scale discovery of novel genetic causes of developmental disorders. Nature 519, 223-228 (2015).
Deciphering Developmental Disorders Study. Prevalence and architecture of de novo mutations in developmental disorders. Nature 542, 433-438 (2017).
Iossifov, I. et al. The contribution of de novo coding mutations to autism spectrum disorder. Nature 515, 216-221 (2014).
Zhu, X. Need, A. C., Petrovski, S. & Goldstein, D. B. One gene, many neuropsychiatric disorders: lessons from Mendelian diseases. Nat. Neurosci. 17, 773-781, (2014).
Leffler, E. M. et al. Revisiting an old riddle: what determines genetic diversity levels within species? PLoS Biol. 10, e1001388 (2012), 9pages.
Estrada, A. et al. Impending extinction crisis of the world's primates—why primates matter. Sc. Adv. 3, e1600946 (2017), 17 pages.
Kent, W. J. et al. The human genome browser at UCSC. Genome Res. 12, 996-1006 (2002).
Tyner, C. et al. The UCSC Genome Browser database—2017 update. Nucleic Acids Res. 45, D626-D634 (2017).
Kabsch, W., & Sander, C. Dictionary of protein secondary structure—pattern recognition of hydrogen-bonded and geometrical features. Biopolymers 22, 2577-2637 (1983).
Joosten, R. P. et al. A series of PDB related databases for everyday needs. Nucleic Acids Res. 39, 411-419 (2011).
He, K, Zhang, X., Ren, S., & Sun, J. Identity mappings in deep residual networks, in 14th European Conference on Computer Vision—ECCV 2016. ECCV 2016. Lecture Notes in Computer Science, vol. 9908; 630 6,15 (Springer, Cham, Switzerland; 2016).
Ionita-Laza, I., McCallum, K., Xu, B., & Buxbaum, J. D. A spectral approach integrating functional genomic annotations for coding and noncoding variants. Nat. Genet. 48, 214-220 (2016).
Li, B. et al. Automated inference of molecular mechanisms of disease from amino acid substitutions. Bioinformatics 25, 2744-2750 (2009).
Lu, Q. et al. A statistical framework to predict functional non-coding regions in the human genome through integrated analysis of annotation data. Sci. Rep. 5, 10576 (2015), 13pgs.
Shihab, H. A. et al. Predicting the functional, molecular, and phenotypic consequences of amino acid substitutions using hidden Markov models. Human. Mutat. 34, 57-65 (2013).
Davydov, E. V. et al. Identifying a high fraction of the human genome to be under selective constraint using GERP++. PLoS Comput. Biol. 6, Dec. 2, 2010, 13 pages.
Liu, X., Wu, C., Li, C., & Boerwinkle, E. dbNSFPv3.0 a one-stop database of functional predictions and annotations for human nonsynonymous and splice-site SNVs. Human. Mutat. 37, 235-241 (2016).
Jain, S., White, M., Radivojac, P. Recovering true classifier performance in positive-unlabeled learning, in Proceedings Thirty-First AAAI Conference on Artificial Intelligence. 2066-2072 (AAAI Press, San Francisco; 2017).
De Ligt, J. et al. Diagnostic exome sequencing in persons with severe intellectual disability. N. Engl. J. Med. 367, 1921-1929 (2012).
Iossifov, I. et al. De novo gene disruptions in children on the autistic spectrum. Neuron 74, 285-299 (2012).
O'Roak, B. J. et al. Sporadic autism exomes reveal a highly interconnected protein network of de novo mutations. Nature 485, 246-250 (2012).
Rauch, A. et al. Range of genetic mutations associated with severe non-syndromic sporadic intellectual disability—an exome sequencing study. Lancet 380, 1674-1682 (2012).
Epi, K. C. et al. De novo mutations in epileptic encephalopathies. Nature 501, 217-221 (2013).
EuroEPINOMICS-RES Consortium, Epilepsy Phenome/Genome Project, Epi4K Consortium. De novo mutations in synaptic transmission genes including DNM1 cause epileptic encephalopathies. Am. J. Hum. Genet. 95, 360-370 (2014).
PCT/US2020/024090 Article 34 Amendment, dated Dec. 4, 2020, 6 pages.
PCT/US2020/024090 Article 34 Amendment, dated Mar. 18, 2021, 3 pages.
Albrecht et. al., Deep learning for single-molecule science, Nanotechnology (28), dated 2017, 423001, 11 pages.
MiSEQ: Imaging and Base Calling: Illumina, Inc. Online Training Course, dated Jan. 1, 2013 [retrieved on Jul. 13, 2020], Retrieved from <URL: https://support.illumina.com/training.html >, 13 pages.
MiSEQ: Imaging and Base Calling Script, retrieved on [Jun. 14, 2021], Retrieved from the internet <URL: https://support.illumina.com/content/dam/illumina-support/courses/MiSeq_Imaging_and_Base_Calling/story_content/external_files/MiSeq%20Imaging%20and%20Base%20Calling%20Script.pdf >.
PCT/US2020/024087 PCT Direct Letter, dated Mar. 21, 2020, 5 pages.
PCT/US2020/024087 International Search Report and Written Opinion, dated Aug. 28, 2020, 24 pages.
PCT/US2020/024087 Article 34 Amendment, filed Mar. 21, 2020, 7 pages.
PCT/US2020/024087 Second Written Opinion, dated Apr. 7, 2021, 12 pages.
PCT/US2020/024087 Article 34 Letter Response to Second Written Opinion, dated May 7, 2021, 7 pages.
Zhao et. al., Object detection with Deep Learning: A Review, dated Jul. 15, 2018, 22 pages.
Lee et. al., Fast Object Localization Using a CNN Feature Map Based Multi-Scale Search, dated Apr. 12, 2016, 16 pages.
PCT/US2020/24088 PCT Direct Letter, filed Mar. 21, 2020, 4 pages.
PCT/US2020/024088 Article 34 Letter in response to Second Written Opinion, dated May 28, 2021, 9 pages.
PCT/US2020/024088 Second Written Opinion, dated Apr. 20, 2021, 17 pages.
PCT/US2020/024088 International Search Report and Written Opinion, dated Sep. 7, 2020, 29 pages.
PCT/US2020/024088 Article 34 Letter in Response to Written Opinion, dated Mar. 9, 2021, 11 pages.
PCT/US2020/024088 Partial Search Report and Invitation to Pay Fees, dated Jul. 8, 2020, 22 pages.
Misiunas et. al., QuipuNet: convolutional neural network for single-molecule nanopore sensing, dated May 30, 2018, 7 pages.
Boza et. al., Deep Recurrent Neural Networks for Base Calling in MinION Nanopore Reads, dated Mar. 30, 2016, 12 pages.
Kao et. al., BayesCall: A model-based base-calling algorithm for high-throughput short-read sequencing, Genome Research (19), pp. 1884-1895, dated 2009.
Rang et. al., From squiggle to basepair: computational approaches for improving nanopore sequencing read accuracy, Genome Biology 2018, (19), 30.
Wang et. al., An adaptive decorrelation method removes Illumina DNA base-calling errors caused by crosstalk between adjacent clusters, Scientific Reports, published Feb. 20, 2017, 11 pages.
Cacho et. al., A comparison of Base Calling Algorithms for Illumina Sequencing Technology, dated Oct. 5, 2015, Briefings in Bioinformatics 2016 (17), 786-795.

(56) References Cited

OTHER PUBLICATIONS

PCT/US2020/024091 PCT Direct Letter, dated Mar. 21, 2020, 5 pages.
PCT/US2020/024091 Partial Search Report and Invitation to Pay Fee, dated Jul. 3, 2020, 17 pages.
PCT/US2020/024091 International Search Report and Written Opinion, dated Oct. 23, 2020, 24 pages.
PCT/US2020/024091 Article 34 Letter in Reponse to International Search Report and Written Opinion, filed Mar. 8, 2021, 10 pages.
PCT/US2020/024091 Second Article 34 Amendment Letter, dated Mar. 22, 2021, 10 pages.
PCT/US2020/024091 Written Opinion of the International Preliminary Examining Authority (Second Written Opinon), dated Apr. 20, 2021, 14 pages.
PCT/US2020/024091 Second Article 34 Amendment in response to Second Written Opinion, dated May 30, 2021, 9 pages.
Luo et al., G-softmax: Improving Intra-class Compactness and Inter-class Separability of Features, dated Apr. 8, 2019, 15 pages.
Luo et al., A multi-task convolutional deep neural network for variant calling in single molecule sequencing, Nature Communications (10), No. 1, dated Mar. 1, 2019.
Kingma et. al., Adam: A method for Stochastic Optimization, ICLR 2015, dated Jul. 23, 2015.
Luo et. al., Skyhawk: An Artificial Neural Network-based discriminator for reviewing clinically significant genomic variants, dated Jan. 28, 2019, 8 pages.
Anonymous, Calculating Percent Passing Filter for Patterned and Nonpatterned Flow Cells, Illumina, 2 pages.
MiSEQ: Imaging and Base Calling: Illumina, Inc. Online Training Course, colored version, [retrieved on Oct. 10, 2020], Retrieved from <URL: https://supportillumina.com/training.html >, 9 pages.
PCT/US2020/024092 PCT Direct Letter, dated Mar. 21, 2020, 5 pages.
PCT/US2020/024092 Partial Search Report and Invitation to Pay Fees, dated Sep. 11, 2020, 22 pages.
PCT/US2020/024092 International Search Report and Written Opinion, dated Nov. 2, 2020, 24 pages.
PCT/US2020/024092 Article 34 Amendment in Response to International Search Report and Written Opinion, dated Mar. 4, 20221, 7 pages.
PCT/US2020/024092 Second Written Opinion dated Apr. 7, 2021, 13 pages.
PCT/US2020/024092 Article 34 Amendment Response to Second Written Opinion, dated May 7, 2021, 10 pages.
PCT/US2021/018910—Partial Search Report and Invitation to Pay Fees dated May 31, 2021, 14 pgs.
PCT/US2020/033280 International Search Report and Written Opinion, dated Jul. 22, 2020, 18 pages.
PCT/US2020/033280 Article 34 Amendment, dated Apr. 19, 2021, 10 pages.
PCT/US2020/033281 International Search Report and Written Opinion, dated Aug. 14, 2020, 15 pages.
Kircher et. al., Improved base-calling for the Illumina Genome Analyzer using Machine Learning Strategies, Genome Biology, published Aug. 14, 2009, 9 pages.
PCT/US2020/033281 Article 34 Amendment, dated Apr. 19, 2021, 8 pages.
PCT/US2020/033281 Second Written Opinion, dated May 10, 2021, 8 pages.
U.S. Appl. No. 16/825,991—Notice of Allowance dated Aug. 5, 2021, 10 pages.
Krishnakumar et. al., Systematic and stochastic influences on the performance of the MinION nanopore sequencer across a range of nucleotide bias, Scientific Reports, published Feb. 16, 2018, 13 pages.
Tegfalk, Application of Machine Learning techniques to perform base-calling in next-generation DNA sequencing, KTH Royal Institue of Technology, dated 2020, 53 pages.
U.S. Appl. No. 16/826,168—Office Action dated Aug. 31, 2021, 55 pages.
Kircher et al., "Improved base-calling for the Illlumina Genome Analyzer using Machine Learning Strategies", Genome Biology 2009, 10:R83, Aug. 14, 2009, 10 pages.
Albrecht etal, "Deep Learning for single-molecule science", Nanotechnology 28, IOP Publishuigm Sep. 18, 2017 11 pages.
U.S. Appl. No. 16/825,987—Office Action (Quayle) dated Oct. 19, 2021, 85 pages.
PCT/US2021047763—International Search Report and Written Opinion, dated Dec. 20, 2021, 11 pages.
PCT/US2021/018422 Second Written Opinion, dated Feb. 4, 2022, 8 pages.
Adriana Romero et. al., FitNets: Hints for Thin Deep Nets, published Mar. 27, 2015, 13 pages.
U.S. Appl. No. 16/874,599—Notice of Allowance dated Dec. 3, 2021, 12 pages.
U.S. Appl. No. 16/825,987—Response to Office Action (Quayle) dated Oct. 19, 2021, filed Jan. 13, 2022, 11 pages.
U.S. Appl. No. 16/825,987—Notice of Allowance, dated Jan. 28, 2022, 12 pages.
U.S. Appl. No. 16/825,987—Supplemental Notice of Allowance, dated Feb. 7, 2022, 8 pages.
U.S. Appl. No. 16/826,168—Response to Office Action dated Aug. 31, 2021, filed Jan. 31, 2022, 15 pages.
CN 2020800036223—Voluntary Amendments, filed May 20, 2021, 26 pages.
EP 20719053.9—Rules 161(2) and 162 Communication, dated Oct. 28, 2021, 3 pages.
IL 279522—Notice Before Acceptance (in Hebrew), dated Aug. 1, 2021, 2 pages.
IL 279522—Response to Notice Before Acceptance dated Aug. 1, 2021, filed Nov. 28, 2021, 3 pages.
KR 10-2020-7037712—Voluntary Amendments with translation, dated Nov. 9, 2021, 7 pages.
EP 20719052.1—Rules 161(1) and 162 Communication, dated Oct. 28, 2021. 3 pages.
IL 279525—Notice Before Acceptance (in Hebrew), dated Aug. 1, 2021, 2 pages.
IL 279525—Response to Notice Before Acceptance dated Aug. 1, 2021, filed Nov. 28, 2021, 4 pages.
KR 10-2020-7037713—Voluntary Amendments with translation, dated Nov. 9, 2021, 26 pages.
ZA 2020/07998—Notice of Allowance, dated Aug. 12, 2021, 2 pages.
EP 20718112.4—Rules 161(2) and 162 Communication, dated Oct. 28, 2021, 3 pages.
IL 279527—Notice Before Examination (in Hebrew), dated Aug. 1, 2021, 2 pages.
IL 279527—Response to Notice Before Examination dated Aug. 1, 2021, filed Nov. 28, 2021, 3 pages.
KR 10-2021-7003269—Voluntary Amendments with translation, dated Nov. 9, 2021, 7 pages.
ZA 2020/07999—Notice of Allowance, dated Aug. 12, 2021, 2 pages.
EP 20719294.9—Rules 161(1) and 162 Communication, dated Oct. 28, 2021, 3 pages.
IL 281668—Notice Before Examination, dated Oct. 10, 2021, 2 pages.
IL 281668—Response to Notice Before Examination dated Oct. 10, 2021, filed Feb. 8, 2022, 4 pages.
KR 10-2021-7009877—Voluntary Amendments with translation, dated Nov. 9, 2021, 21 pages.
EP 20757979.8—Rules 161(2) and 162 Communication, dated Oct. 28, 2021, 3 pages.
IL 279533—Notice Before Examination, dated Aug. 1, 2021, 2 pages.
IL 279533—Response to Notice Before Examination dated Aug. 1, 2021, filed Nov. 29, 2021, 3 pages.
KR 10-2021-7003270—Voluntary Amendments with translation, dated Nov. 9, 2021, 29 pages.
ZA 2020/08000—Notice of Acceptance, dated Aug. 12, 2021, 2 pages.
Robinson et al., Computational Exome and Genome Analysis—Chapter 3 Illumina Technology, dated 2018, 25 pages.

(56) References Cited

OTHER PUBLICATIONS

Wang et. al., An adaptive decorrelation method removes Illumina DNA base-calling errors caused by crosstalk between adjacent clusters—with Supplemental Materials, Scientific Reports, published Feb. 20, 2017, 17 pages.
PCT/US2020/033280—International Preliminary Report on Patentability, dated Jul. 23, 2021, 11 pages.
Pfeiffer et. al., Systematic evaluation of error rates and causes in short samples in next-generation sequencing, Scientific Reports, published Jul. 19, 2018, 14 pages.
PCT/US2020/033281—International Preliminary Report on Patentability, dated Aug. 31, 2021, 10 pages.
PCT/US2021/018258—Second Written Opinion, dated Jan. 25, 2022, 11 pages.
PCT/US2021/018910—International Search Report and Written Opinion, dated Aug. 25, 2021, 24 pages.
Puckelwartz et al., Supercomputing for the parallelization of whole genome analysis, Bioinformatics, dated Feb. 12, 2014, pp. 1508-1513, 6 pages.
Kelly et al., Churchill: an ultra-fast, deterministic, highly scalable and balanced parallelization strategy for the discovery of human genetic variation in clinical and population-scale genomics, Genome Biology, Bio-Med Central Ltd, vol. 16, No. 1, dated Jan. 20, 2015, 14 pages.
PCT/US2021/018910—Article 34 Amendment, filed Dec. 19, 2021, 9 pages.
PCT/US2021/018910—Second Written Opinion, dated Feb. 21, 2022, 17 pages.
Ramesh, Nisha, et. al., "Cell Segmentation Using a Similarity Interface With a Multi-Task Convolutional Neural Network"; IEEE Journal of Biomedical and Health Informatics, vol. 23, No. 4, Jul. 2019, 12 pages.
U.S. Appl. No. 16/825,991—Notice of Allowance dated Apr. 19, 2021, 12 pages.
Arpali et. al., High-throughput screening of large volumes of whole blood using structured illumination and fluorescenl on-chip imaging, Lab on a Chip, United Kingdom, Royal Society of Chemistry, Sep. 12, 2012, vol. 12, pp. 4968-4971.
Liu et al., 3D Stacked Many Core Architecture for Biological Sequence Analysis Problems, 2017, Int J Parallel Prog, 45:1420-1460.
Wu et. al., FPGA-Based DNA Basecalling Hardware Acceleration, in Proc. IEEE 61st Int. Midwest Symp. Circuits Syst., Aug. 2018, pp. 1098-1101.
Wu et. al., FPGA-Accelerated 3rd Generation DNA Sequencing, in IEEE Transactions on Biomedical Circuits and Systems, vol. 14, Issue 1, Feb. 2020, pp. 65-74.
Prabhakar et. al., Plasticine: A Reconfigurable Architecture for Parallel Patterns, ISCA '17, Jun. 24-28, 2017, Toronto, ON, Canada.
Lin et. al., Network in Network, in Proc. of ICLR, 2014.
Sifre, Rigid-motion Scattering for Image Classification, Ph.D. thesis, 2014.
Sifre et. al., Rotation, Scaling and Deformation Invariant Scattering for Texture Discrimination, in Proc. of CVPR, 2013.
Chollet, Xception: Deep Learning with Depthwise Separable Convolutions, in Proc. of CVPR, 2017. 8 pages.
Zhang et. al., ShuffleNet: An Extremely Efficient Convolutional Neural Network for Mobile Devices, 2017.
He et. al., Deep Residual Learning for Image Recognition, in Proc. of CVPR, 2016.
Xie et. al., Aggregated Residual Transformations for Deep Neural Networks, in Proc. of CVPR, 2017.
Howard et. al., Mobilenets: Efficient Convolutional Neural Networks for Mobile Vision Applications, 2017.
Sandler et. al., MobileNetV2: Inverted Residuals and Linear Bottlenecks, 2018.
Qin et. al., FD-MobileNet: Improved MobileNet with a Fast Downsampling Strategy, 2018.
Chen et. al., Rethinking atrous convolution for semantic image segmentation, 2017.
Huang et. al., Speed/accuracy trade-offs for modern convolutional detectors, 2016.
Oord, Dieleman et. al., WAVENET: A Generative Model for Raw Audio, 2016.
Arik et. al., Deep Voice: Real-time Neural Text-to-Speech, 2017.
Yu et. al., Multi-Scale Context Aggregation by Dilated Convolutions, 2016.
He et. al., Deep Residual Learning for Image Recognition, 2015.
Srivastava et. al., Highway Networks, 2015.
Huang et. al., Densely Connected Convolutional Networks, 2017.
Szegedy et. al., Going Deeper with Convolutions, 2014.
Ioffe et. al., Batch Normalization Accelerating Deep Network Training by Reducing Internal Covariate Shift, 2015.
Wolterink et. al., Dilated Convolutional Neural Networks for Cardiovascular MR Segmentation in Congenital Heart Disease, 2017.
Piqueras, Autoregressive Model Based on a Deep Convolutional Neural Network for Audio Generation, Tampere University of Technology, 2016.
Wu, Introduction to Convolutional Neural Networks, Nanjing University, 2017.
Illumina CMOS Chip and One-Channel SBS Chemistry, Illumina Inc, 2018, 4 pages.
Scikit-image/peak.py at master, Github, retrieved on Jun. 8, 2021, 10 pages, Retrieved from the internet <URL: https://github.com/scikit-image/scikit-image/blob/main/skimage/feature/peak.py>.
3.3.9.11.Watershed and random walker for segmentation, Scipy lecture notes, 2 pages, [retrieved on Jun. 8, 2021] Retrieved from the internet <URL: http:scipy-lectures.org/packages/scikit-image/auto_examples/plot_segmentations.html>.
Mordvintsev et. al., Image Segmentation with Watershed Algorithm, Revision 43532856, 2013, 6 pages, [retrieved on Jun. 8, 2021] Retrieved from the Internet <URL: https://opencv-python-tutroals.readthedocs.io/en/latest/py_tutorials/py_imgproc/py_watershed/py_watershed.html>.
Mzur, Watershed.py, Github, 3 pages, [retrieved on Jun. 8, 2021] Retrieved from the internet <URL: https://github.com/mzur/watershed/blob/master/Watershed.py>.
Thakur et. al., A Survey of Image Segmentation Techniques, International Journal of Research in Computer Applications and Robotics, vol. 2, Issue 4, Apr. 2014, p. 158-165.
Long et. al., Fully Convolutional Networks for Semantic Segmentation, IEEE Transactions on Pattern Analysis and Machine Intelligence, vol. 39, Issue 4, Apr. 1, 2017, 12 pages.
Ronneberger et. al., U-net: Convolutional networks for biomedical image segmentation, in International Conference on Medical Image computing and computer assisted intervention, May 18, 2015, 8 pages.
Xie et. al., Microscopy cell counting and detection with fully convolutional regression networks, Computer methods in biomechanics and biomedical engineering, Imaging and Visualization, 6(3), pp. 283-292, 2018.
Xie, Y., et. al., Beyond classification: structured regression for robust cell detection using convolutional neural network, International conference on medical image computing and computer assisted intervention, Oct. 2015, 12 pages.
Snuverink, Deep Learning for Pixelwise Classification of Hyperspectral Images, Master of Science Thesis, Delft University of Technology, Nov. 23, 2017, 128 pages.
Shevchenko, Keras weighted categorical_crossentropy, Github, [retrieved on Jun. 12, 2021], Retrieved from the internet <URL: https://gist.github.com/skeeet/cad06d584548fb45eece1d4e28cfa98b >, 2 pages.
Assem, Predicting periodic and chaotic signals using Wavenets, Master of Science thesis, Delft University of Technology, Aug. 18, 2017, pp. 3-38.
Goodfellow et. al., Convolutional Networks, Deep Learning, MIT Press, 2016.
Gu et. al., Recent Advances in Convolutional Neural Networks, 2017.
Illumina, "Indexed Sequencing Overview Guide", Document No. 15057455, v. 5, Mar. 2019.
PCT/US2020/024090 International Preliminary Report on Patentability, dated Apr. 13, 2021, 20 pages.

(56) References Cited

OTHER PUBLICATIONS

PCT/US2020/024090 Written Opinion of the International Preliminary Examining Authority, dated Dec. 22, 2020, 11 pages.
PCT/US2020/024090 PCT Direct Letter, filed Mar. 21, 2020, 5 pages.
PCT/US2020/024090 International Search Report, dated Aug. 31, 2020, 8 pages.
Carter, H., Douville, C., Stenson, P. D., Cooper, D. N., & Karchin, R. Identifying Mendelian disease genes with the variant effect scoring tool. BMC Genom, (2013), 13 pages.
Choi, Y., Sims, G. E., Murphy, S., Miller, J. R., & Chan, A. P. Predicting the functional effect of amino acid substitutions and indels PLoS One 7, e46688 (2012).
Gulko, B., Hubisz, M. J., Gronau, I., & Siepel, A. A method for calculating probabilities of fitness consequences for point mutations across the human genome. Nat. Genet. 47, 276-283 (2015).
Shihab, H. A. et al. An integrative approach to predicting the functional effects of non-coding and coding sequence variation. Bioinformatics 31, 1536-1543 (2015).
Bell, C. J. et al. Comprehensive carrier testing for severe childhood recessive diseases by next generation sequencing. Sci. Transl. Med. 3, Jan. 12, 2011, 28 pages.
Smedley, D. et al. A whole-genome analysis framework for effective identification of pathogenic regulatory variants in mendelian disease. Am. J. Hum. Genet. 99, 595-606 (2016).
Jagadeesh, K. A. et al. M-CAP eliminates a majority of variants of uncertain significance in clinical exomes at high sensitivity. Nat. Genet. 48, 1581-1586 (2016).
Grimm, D. G. The evaluation of tools used to predict the impact of missense variants is hindered by two types of circularity. Human. Mutat. 36, 513-523 (2015).
Hefferman, R. et al. Improving prediction of secondary structure, local backbone angles, and solvent accessible surface area of proteins by iterative deep learning. Sci. Rep. 5, 11476 (2015) 11 pages.
Wang, S., Peng, J., Ma, J. & Xu, J. Protein secondary structure prediction using deep convolutional neural fields. Sci. Rep. 6, 18962-18962 (2016).
Harpak, A., Bhaskar, A., & Pritchard, J. K. Mutation rate variation is a primary determinant of the distribution of allele frequencies in humans. PLoS Genet. Dec. 15, 2016, 22pgs.
Payandeh, J., Scheuer, T., Zheng, N. & Catterall, W. A. The crystal structure of a voltage-gated sodium channel. Nature 475, 353-358 (2011).
Shen, H. et al. Structure of a eukaryotic voltage-gated sodium channel at near-atomic resolution. Science 355, eaal4326 (2017), 19 pages.
Nakamura, K. et al. Clinical spectrum of SCN2A mutations expanding to Ohtahara syndrome. Neurology 81, 992-998 (2013).
Ioannidis, Nilah M., et al., "REVEL—An Ensemble Method for Predicting the Pathogenicity of Rare Missense Variants", Oct. 5, 2016, 9 pages.
Quang Daniel, et al., "DANN—a deep learning approach for annotating the pathogenicity of genetic variants", Oct. 22, 2014, 3 pages.
Sundaram, et. al., "Predicting the clinical impact of human mutation with deep neural networks", Aug. 2018, 15pgs.
Xiong, et. al., "The human splicing code reveals new insights into the genetic determinants of disease", Jan. 9, 2015, 20pgs.
Yue, et. al., "Deep Learning for Genomics—A Concise Overview from internet", May 8, 2018, 40pgs.
Yuen, et. al., "Genome wide characteristics of de novo mutations in autism", Jun. 1, 2016, 10pgs.
Libbrecht, et. al., "Machine learning in genetics and genomics", Jan. 2, 2017, 30pgs.
Min, et. al., "Deep Learning in Bioinformatics", Jul. 25, 2016, 19 pgs.
Torng, Wen, et al., "3D deep convolutional neural networks for amino acid environment similarity analysis", 2017, 23pages.
Chen, Kathleen M., et. al., "Selene—a PyTorch based deep learning library for sequence level data", Oct. 10, 2018, 15pages.
Grob, C., et. al., "Predicting variant deleteriousness in non human species Applying the CADD approach in mouse", 2018, 11 pages.
Li, et. al., "FoldingZero—Protein Folding from Scratch in Hydrophobic Polar Model", Dec. 3, 2018, 10 pages.
Rentzsch, et. al., "CADD—predicting the deleteriousness of variants throughout the human genome", Oct. 11, 2018, 9 pages.
Zou, etal, "A primer on deep learning in genomics", Nov. 26, 2018, 7pages.
Alberts, Bruce, et al., "Molecular biology of the cell", Sixth Edition, 2015, 3 pages.
PCT/US2018/055840—International Search Report and Written Opinion dated Jan. 25, 2019, 18 pages.
Wei etal_The Role of Balanced Training and Testing Data Sets for Binary Classifiers in Bioinformatics dated Jul. 9, 2013 12 pages.
PCT/US2018/055878—International Search Report and Written Opinion dated Jan. 22, 2019, 20 pages.
PCT/US2018/055881—International Search Report and Written Opinion dated Jan. 25, 2019, 17 pages.
Duggirala, Ravindranath, et.al., "Genome Mapping and Genomics in Human and Non Human Primate", 2015, 306pgs.
Brookes, Anthony J., "The essence of SNPs", 1999, pp. 177-186.
UniProtKB P04217 A1BG Human [retrieved on Mar. 13, 2019 from (www.uniprot.org/uniprot/P04217), 12pages.
Bahar, Protein Actions Principles and Modeling, Chapter 7, 2017 pp. 165-166.
Dunbrack, Roland L., Re Question about your Paper titled "The Role of Balanced Training and Testing Data Sets for Binary Classifiers in Bioinformatics", Message to Sikander Mohammed Khan, Feb. 3, 2019, E-mailm, 3pgs.
DbSNP rs2241788 [Retrieved on Mar. 13, 2019], Retrieved from the Internet<www.ncbi.nlm.nih.gov/snp/rs2241788>, 5 pages.
Wei, et. al., "Prediction of phenotypes of missense mutations in human proteins from biological assemblies", Feb. 2013, 28 pages.
Zhang, Jun, and Bin Liu. "PSFM-DBT—identifying DNA-binding proteins by combing position specific frequency matrix and distance-bigram transformation." International journal of molecular sciences 18.9 (2017) 1856.
Gao, Tingting, et al. "Identifying translation initiation sites in prokaryotes using support vector machine." Journal of theoretical biology 262.4 (2010) 644-649. (Year 2010).
Bi, Yingtao, et al. "Tree-based position weight matrix approach to model transcription factor binding site profiles." PloS one6.9 (2011) e24210.
Korhonen, Janne H., et al. "Fast motif matching revisited—high-order PWMs, SNPs and indels." Bioinformatics 33.4 (2016) 514-521.
Wong, Sebastien C., et al. "Understanding data augmentation for classification—when to warp?." 2016 international conference on digital image computing—techniques and applications (DICTA) IEEE, 2016.
Chang, Chia-Yun, et al. "Oversampling to overcome overfitting—exploring the relationship between data set composition, molecular descriptors, and predictive modeling methods." Journal of chemical information and modeling 53.4 (2013) 958-971.
Li, Gangmin, and Bei Yao. "Classification of Genetic Mutations for Cancer Treatment with Machine Learning Approaches." International Journal of Design, Analysis and Tools for Integrated Circuits and Systems 7.1 (2018) pp. 63-67.
Martin-Navarro, Antonio, et al. "Machine learning classifier for identification of damaging missense mutations exclusive to human mitochondrial DNA-encoded polypeptides." BMC bioinformatics 18.1 (2017) p. 158.
Krizhevsky, Alex, et al, ImageNet Classification with Deep Convolutional Neural Networks, 2012, 9 Pages.
Geeks for Geeks, "Underfitting and Overfilling in Machine Learning", [retrieved on Aug. 26, 2019]. Retrieved from the Internet <www.geeksforgeeks.org/underfitting-and-overfitting-in-machine--learning/>, 2 pages.
Despois, Julien, "Memorizing is not learning!—6 tricks to preventoverfitting in machine learning", Mar. 20, 2018, 17 pages.

(56) References Cited

OTHER PUBLICATIONS

Bhande, Anup What is underfitting and overfitting in machine learning and how to deal with it, Mar. 11, 2018, 10pages.
PCT/US2019031621—International Search Report and Written Opinion dated Aug. 7, 2019, 17 pages.
Carter et al., "Cancer-specific high-throughput annotation of somatic mutations—computational prediction of driver missense mutations," Cancer research 69, No. 16 (2009) pp. 6660-6667.
Min, et. al., "Deep Learning in Bioinformatics", Jun. 19, 2016, 46pgs.
Jiminez et. al., DeepSite—protein binding site predictor using 3D CNNs, dated Oct. 1, 2017, 7 pages.
Pu et. al., "DeepDrug3D: Classification of ligand-binding pockets in proteins with a convolutional neural network", dated Feb. 4, 2019, 23 pages.
Adam, "Deep learning, 3D technology to improve structure modeling for protein interactions, create better drugs", dated Jan. 9, 2020, 4 pages.
Varela, "Ligvoxel: A Deep Learning Pharmacore-Field Predictor", dated Mar. 19, 2019, 5 pages.
Li et. al., "Predicting changes in protein thermostability upon mutation with deep 3D convolutional neural networks", dated Feb. 28, 2020, 21 pages.
Raschka et. al., "Machine Learning and AI-based approaches for bioactive ligand discovery and GPCR-ligand recognition", dated Jun. 6, 2020, 33 pages.
Torng et. al., "3D deep convolutional neural networks for amino acid environment similarity analysis", dated 2017, 23 pages.
Morrone et. al., "Combining docking pose rank and structure with deep learning improves protein-ligand binding mode prediction", dated Oct. 7, 2019, 13 pages.
Li, "Machine Learning Methods for Medical and Biological Image Computing", dated Summer 2016, 113 pages.
Rivera et. al., "A Deep Learning Approach to Protein Structure Prediction", dated Apr. 24, 2019, 22 pages.
Aritake et. al., "Single-molecule localization by voxel-wise regression using convolutional neural network", dated Nov. 3, 2020, 11 pages.
Townshend et. al., "End-to-End Learning on 3D Protein Structure for Interface Prediction", dated 2019, 10 pages.
Amidi et. al., "EnzyNet: enzyme classification using 3D convolutional neural networks on spatial representation", dated Jul. 25, 2017, 18 pages.
Luna, "Machine Learning in structural biology and chemoinformatics", dated 2019, 106 pages.
Anonymous, "Transferrable end-to-end learning for protein interface prediction", dated 2019, 12 pages.
Eraslan et. al., "Deep Learning: New computational modelling techniques for genomics", dated Jul. 2019, 15 pages.
Dias et. al., "Artificial intelligence in clinical and genomic diagnostics", dated 2019, 12 pages.
Luna et. al., "A Deep-Learning Approach toward Rational Molecular Docking Protocol Selection", dated May 27, 2020, 12 pages.
Li et. al., "DeepAtom: A Framework for Protein-Ligand Binding Affinity Prediction", dated 2019, 8 pages.
Zhang et. al., "Template-based prediction of protein structure with deep learning", dated Jun. 2, 2020, 16 pages.
Wallach et. al., AtomNet: A Deep Convolutional Neural Network for Bioactivity Prediction in Structure-based Drug Discovery, dated Oct. 10, 2015, 11 pages.
Illumina, Two-Channel SBS Sequencing Technology, 2016, 2 pages.
Illumina, Low-diversity sequencing on the Illumina HiSeq Platform, 2014, 2 pages.
Hedegaard, An introduction to "Next Generation" DNA Sequencing, dated Nov. 26, 2017, 63 pages.
Jordan, An overview of semantic image segmentation, dated May 21, 2018, 28 pages retrieved on Jul. 21, 2021. Retrieved from the internet [URL: https://www.jeremyjordan.me/semantic-segmentation/ ].
Lanchantin, Deep Motif Dashboard: Visualizing and Understanding Genomic Sequences Using Deep Neural Networks, Oct. 18, 2016, 11 pages.
Thalles Silva, Deeplab Image Semantic Segmentation Network, dated Jan. 29, 2018, 19 pages, retrieved on Jul. 21, 2021. Retrieved from [URL: https://sthalles.github.io/deep_segmentation_network/].
James Le, How to do Semantic Segmentation using Deep Learning, dated May 3, 2018, 17 pages, retrieved on Jul. 21, 2021. Retrieved from [URL: https://medium.com/nanonets/how-to-do-image-segmentation-using-deep-learning-c673cc5862ef].
Townley, Illumina Primary and Secondary Analysis, Illumina UK, 2010, 33 pages.
Silver, Literature Review: Fully Convolutional Networks, dated Jun. 12, 2017, 5 pages, retrieved on Jul. 21, 2021. Retrieved from [URL: https://medium.com/self-driving-cars/literature-review-fully-convolutional-networks-d0a11fe0a7aa ].
Bowen, Nanotechnology for a Genomic Revolution, Illumina, dated Dec. 14, 2016, 40 pages.
Han, Deconvolutions in Convolutional Neural Networks, Postech Computer Vision Lab, 2015, 20 pages.
Illumina, Illumina's Genotyping Data Normalization Methods, 2006, 6 pages.
Illumina, Quality Scores for Next-Generation Sequencing—Assessing sequencing accuracy using Phred quality scoring, 2011, 2 pages.
Restrepo, A Gentle Introduction to Semantic Segmentation—Inputs, Labels and Outputs, 2 pages, retrieved on Jul. 21, 2021. Retrieved from [URL: http://ronny.rest/tutorials/module/seg_01/segmentation_03_inputs_outputs/].
Semantic Segmentation Examples—MATLAB and Simulink, 22 pages, retrieved from [URL: https://www.mathworks.com/help/vision/ug/semantic-segmentation-examples.html ].
Illumina, An Introduction to Next-Generation Sequencing Technology, 2017, 16 pages.
Supplementary Information, Nature, 55 pages, retrieved from [URL: https://media.nature.com/original/nature-assets/nature/journal/v456/n7218/extref/nature07517-s1.pdf ].
Belanovic, Library of Parameterized Hardware Modules for Floating-Point Arithmetic with an Example Application, Northeastern University, Boston, MA, May 2002, 83 pages.
Massingham, Base Calling: methods, problems and alternatives, EMBL Advanced Course in Analysis of Short Read Sequencing Data, Jun. 8, 2009-Jun. 10, 2009, 84 pages.
Thoma, A Survey of Semantic Segmentation, dated May 11, 2016, 16 pages.
Rodriguez-Ezpeleta, Bioinformatics for High Throughput Sequencing, Springer, 2012, 266 pages.
Illumina, Optimizing Cluster Density on Illumina Sequencing Systems, 2016, 12 pages.
Boza et. al., DeepNano: Deep recurrent neural networks for base calling in MinION nanopore reads, PLOS ONE, dated Jun. 5, 2017, 13 pages.
Kircher, Understanding and Improving high-throughput sequencing data production and analysis, Leipzig University, 2011, 216 pages.
Baek et. al., LncRNAnet: long non-coding RNA identification using deep learning, Bioinformatics, vol. 34 (22), 2018, pp. 3889-3897, 9 pages.
Evans et. al., Estimating Change-Points in Biological Sequences via the Cross-Entropy Method, dated Sep. 20, 2010, 17 pages.
Shen et. al., ParticleCall: A particle filter for base calling in next-generation sequencing systems, BMC Bioinformatics, 2012, 10 pages.
Peresini et. al., Nanopore Base Calling on the Edge, dated Nov. 9, 2020, 15 pages.
Liang et. al., Bayesian Basecalling for DNA Sequence Analysis Using Hidden Markov Models, IEEE Transactions on Computational Biology and Bioinformatics, vol. 4, No. 3, Jul.-Sep. 2007, 11 pages.
Wang et. al., DeepDNA: a hybrid convolutional and recurrent neural network for compressing human mitochondrial genomes, IEEE International Conference on Bioinformatics and Biomedicine, 2018, 5 pages.

(56) References Cited

OTHER PUBLICATIONS

PCT/US2020/024092, International Preliminary Report on Patentability (IPRP), dated Jun. 30, 2021, 30 pages.
PCT/US2020/024091 International Preliminary Report and Patentability (IPRP), dated Jun. 30, 2021, 32 pages.
PCT/US2020/024088 International Preliminary Report on Patentability (IPRP), dated Jun. 30, 2021, 35 pages.
PCT/US2020/024087 International Preliminary Report on Patentability (IPRP), dated Jun. 30, 2021, 26 pages.
PCT/US2021/018917 Internation Search Report and Written Opinion, dated Jul. 1, 2021, 15 pages.
Anonymous, Vanishing Gradient Problem, Wikipedia, dated Jun. 16, 2018, retrieved on Jan. 12, 2020. Retrieved from [URL: https://en.wikipedia.org/w/index.php?title=Vanishing_gradient_problem&oldid=846115335 ].
PCT/US2020/033281, Second Article 34 Amendment Letter in response to Second Written Opinion, dated Jul. 10, 2021, 4 pages.
NL 2023310 NL Search Report, dated Mar. 5, 2020, 17 pages.
NL 2023311 NL Search Report, dated Mar. 24, 2020, 15 pages.
NL 2023312, NL Search Report, dated Mar. 24, 2020, 22 pages.
NL 2023317, NL Search Report, dated Mar. 24, 2020, 16 pages.
NL 2023316, NL Search Report, dated Mar. 23, 2020, 15 pages.
MX/a/2020/014288 First Office Action, dated Mar. 10, 2021, 2 pages.
MX/a/2020/014288 Response to First Office Action, dated May 5, 2021, 390 pages.
PCT/US2021/018422—Article 34 Amendment, dated Dec. 20, 2021, 7 pages.
PCT/US/2021/018427—Second Written Opinion, dated Feb. 4, 2022, 9 pages.
PCT/US/2021/018427—Article 34 Amendment, filed Dec. 19, 2021, 7 pages.
PCT/US2021/018913—Second Written Opinion, dated Feb. 4, 2022, 8 pages.
Ye et al., BlindCall: ultra-fast base-calling of high-throughput sequencing data by blind deconvolution, Bioinformatics, vol. 30, No. 9, dated Jan. 9, 2014, pp. 1214-1219, 6 pages.
Wang et al., Achieving Accurate and Fast Base-calling by a Block model of the Illumina Sequencing Data, Science Direct, vol. 48, No. 28, dated Jan. 1, 2015, pp. 1462-1465, 4 pages.
PCT/US2021/018913—Article 34 Amendment, filed Dec. 19, 2021, 18 pages.
PCT/US2021/018915—Second Written Opinion, dated Feb. 4, 2022, 9 pages.
PCT/US2021/018915—Article 34 Amendment, filed Dec. 19, 2021, 7 pages.
PCT/US2021/018917—Second Written Opinion, dated Feb. 4, 2022, 7 pages.
PCT/US2021/018917—Article 34 Amendment, filed Dec. 19, 2021, 6 pages.
U.S. Appl. No. 17/468,411—Office Action, dated Feb. 24, 2022, 36 pages.
Gao et al., Deep Learning in Protein Structural Modeling and Design, Patterns—CelPress, dated Dec. 11, 2020, 23 pages.
Pejaver et al., Inferring the molecular and phenotypic impact of amino acid variants with MutPred2—with Supplementary Information, Nature Communications, dated 2020, 59 pages.
Pakhrin et al., Deep learning based advances in protein structure prediction, International Journal of Molecular sciences, published May 24, 2021, 30 pages.
Wang et al. Predicting the impacts of mutations on protein-ligand binding affinity based on molecular dynamics simulations and machine learning methods, Computational and Structural Biotechnology Journal 18, dated Feb. 20, 2022, pp. 439-454, 16 pages.
Iqbal et al., Comprehensive characterization of amino acid positions in protein structures reveals molecular effects of missense variants, and supplemental information, PNAS, vol. 117, No. 45, dated Nov. 10, 2020, 35 pages.

Forghani et al., Convolutional Neural Network Based Approach to In Silica Non-Anticipating Prediction of Antigenic Distance for Influenza Virus, Viruses, published Sep. 12, 2020, vol. 12, 20 pages.
Jing et al., Learning from protein structure with geometric vector perceptrons, Arxiv: 2009: 01411v2, dated Dec. 31, 2020, 18 pages.
Hacteria Wiki, HiSeq2000—Next Level Hacking—Hackteria Wiki, retrieved on Apr. 12, 2021, retrieved from the internet [URL: https://www.hackteria.org/wiki/HiSeq2000_-_Next_Level_Hacking ], 42 pages.
Pei et al., A Topological Measurement for Weighted Protein Interaction Network, IEEE Computational Systems Bioinformatics Conference dated 2005, 11 pages.
Assfalg et. al., "3DString, A Feature String Kernel for 3D Object Classification on Voxelized Data", dated Nov. 6, 2006, 10 pages.
"MiSEQ: Imaging and Base Calling: Illumina, Inc. Online Training Course", Jan. 1, 2013, 13 pages.
Bentley , et al., "Accurate whole human genome sequencing using reversible terminator chemistry", Supplementary Information, Nature, 2008, 55 pages.
Bentley , et al., "Accurate whole human genome sequencing using reversible terminator chemistry", doi: 10.1038/nature07517, vol. 456, Nov. 6, 2008, pp. 53-59, including supplemental information pp. 1-55, Nov. 6, 2008, pp. 53-59, including supplemental information pp. 1-55.
Sifre, Laurent , "Rigid-Motion Scattering for Image Classification", Oct. 6, 2014, 128 pages.
U.S. Appl. No. 16/825,987, filed Mar. 20, 2020, U.S. Pat. No. 11,347,965, publushed May 31, 2022, Issued.
U.S. Appl. No. 16/825,991, filed Mar. 20, 2020, U.S. Pat. No. 11,210,554, published Dec. 28, 2021, Issued.
U.S. Appl. No. 16/826,126, filed Mar. 20, 2020, US-2020-0302297-A1, published Sep. 24, 2020, Pending.
U.S. Appl. No. 16/826,168, filed Mar. 21, 2020, US-2020-0302224-A1, published Sep. 24, 2020, Allowed.
U.S. Appl. No. 17/529,222, filed Nov. 17, 2021, US-2022-0147760-A1, published May 12, 2022, Pending.
U.S. Appl. No. 17/827,612, filed May 27, 2022, Pending.
U.S. Appl. No. 16/874,633, filed May 14, 2020, US-2020-0364565-A1, published Nov. 19, 2020, Allowed.
U.S. Appl. No. 17/703,975, filed Mar. 24, 2022, Pending.
U.S. Appl. No. 17/175,546, filed Feb. 12, 2021, US-2021-0265009-A1, published Aug. 26, 2021, Pending.
U.S. Appl. No. 17/180,542, filed Feb. 19, 2021, US-2021-0265017-A1, published Aug. 26, 2021, Pending.
U.S. Appl. No. 17/176,151, filed Feb. 15, 2021, US-2021-0265018-A1, published Aug. 26, 2021, Pending.
U.S. Appl. No. 17/411,980, filed Aug. 25, 2021, US-2022-0067489-A1, published Mar. 3, 2022, Pending.
U.S. Appl. No. 17/687,551, filed Mar. 4, 2022, Pending.
U.S. Appl. No. 17/687,583, filed Mar. 4, 2022, Pending.
U.S. Appl. No. 17/176,147, filed Feb. 15, 2021, US-2021-0265015-A1, published Aug. 26, 2021, Pending.
U.S. Appl. No. 17/179,395, filed Feb. 18, 2021, US-2021-0265016-A1, published Aug. 26, 2021, Pending.
U.S. Appl. No. 17/180,480, filed Feb. 19, 2021, US-2021-0264266-A1, published Aug. 26, 2021, Pending.
U.S. Appl. No. 17/180,513, filed Feb. 19, 2021, US-2021-0264267-A1, published Aug. 26, 2021, Pending.
U.S. Appl. No. 17/687,586, filed Mar. 4, 2022, Pending.
U.S. Appl. No. 17/232,056, filed Apr. 15, 2021, Pending.
U.S. Appl. No. 17/468,411, filed Sep. 7, 2021, Pending.
U.S. Appl. No. 17/830,287, filed Jun. 1, 2022, Pending.
U.S. Appl. No. 17/830,316, filed Jun. 1, 2022, Pending.
U.S. Appl. No. 17/839,331, filed Jun. 13, 2022, Pending.
U.S. Appl. No. 17/703,935, filed Mar. 24, 2022, Pending.
U.S. Appl. No. 17/703,958, filed Mar. 24, 2022, Pending.
PCT/US2020/024090, filed Mar. 21, 2020, WO 2020/191389, published Sep. 24, 2020, Nationalized.
PCT/US2020/024087, filed Mar. 21, 2020, WO 2020/205296, published Oct. 8, 2020, Nationalized.
PCT/US2020/024088, filed Mar. 21, 2020, WO 2020/191387, published Sep. 24, 2020, Nationalized.

(56) References Cited

OTHER PUBLICATIONS

PCT/US2020/024091, filed Mar. 21, 2020, WO 2020/191390, published Sep. 24, 2020, Nationalized.
PCT/US2020/024092, filed Mar. 22, 2020, WO 2020/191391, published Sep. 24, 2020, Nationalized.
PCT/US2020/033280, filed May 15, 2020, WO 2020/232409, published Nov. 19, 2020, Nationalized.
PCT/US2020/033281, filed May 15, 2020, WO 2020/232410, Nov. 19, 2020, Nationalized.
PCT/US2021/018258, filed Feb. 16, 2021, Pending.
PCT/US2021/018910, filed Feb. 19, 2021, Pending.
PCT/US2021/018422, filed Feb. 17, 2021, Pending.
PCT/US2021/047763, filed Aug. 26, 2021, Pending.
PCT/US2022/020460, filed Mar. 15, 2022, Pending.
PCT/US2022/020462, filed Mar. 15, 2022, Pending.
PCT/US2021/018427, filed Feb. 17, 2021, Pending.
PCT/US2021/018913, filed Feb. 19, 2021, Pending.
PCT/US2021/018915, filed Feb. 19, 2021, Pending.
PCT/US2021/018917, filed Feb. 19, 2021, Pending.
PCT/US2022/021814, filed Mar. 24, 2022, Pending.
PCT/US2022/24911, filed Apr. 14, 2022, Pending.
PCT/US2022/24913, filed Apr. 14, 2022, Pending.
PCT/US2022/035564, filed Jun. 29, 2022, Pending.
PCT/US2022/035567, filed Jun. 29, 2022, Pending.
PCT/US2022/035847, filed Jun. 30, 2022, Pending.
PCT/US2022/24916, filed Apr. 14, 2022, Pending.
PCT/US2022/24918, filed Apr. 14, 2022, Pending.
Lutteropp, Error-Profile-Aware Correction of Next Generation Sequencing Reads, Karlsruhe Institute of Technology, dated Mar. 31, 2017, 96 pages.
Illumina, GA Bootcamp, Sequencing Module 3: Overview, Broad Institute, 73 pages.
Illumina, HCS 1.4/RTA 1.12 Theory of Operation, 2010, 32 pages.
Cacho, Base-Calling of High-throughput Sequencing Data Using a Random Effects Mixture Model, UC Riverside, Dec. 2016, 102 pages.
Zhou et. al., Incorporating Side-Channel Information into Convolutional Neural Networks for Robotic Tasks, 2017, 7 pages.
Linder, Modeling the intronic regulation of Alternative Splicing using Deep Convolutional Neural Nets, KTH Institute of Technology, dated Jun. 14, 2015, 53 pages.
Grange, NGS: the basics, Institut Jacques Monod, 59 pages.
Bentley et. al., Accurate Whole Human Genome Sequencing using Reversible Terminator Chemistry, Nature, Nov. 2008, 21 pages.
Illumina, Calculating Percent Passing Filter for Patterned and Nonpatterned Flow Cells, 2017, 2 pages.
Frritzilas, An Overview of Illumina's Sequencing Technology and its Applications, University of Primorska, dated Mar. 4, 2011, 47 pages.
Python Implementation of the color map function for the PASCAL VOC data set, Github, 4 pages, retrieved on Jul. 23, 2021. Retrieved from [URL: https://gist.github.com/wllhf/a4533e0adebe57e3ed06d4b50c8419ae ].
Illumina, Quality Score Encoding, 2 pages, retrieved on Jul. 23, 2021. Retrieved from [URL: https://support.illumina.com/help/BaseSpace_OLH_009008/Content/Source/Informatics/BS/QualityScoreEncoding_swBS.htm ].
Illumina, Reducing Whole-Genome Data Storage Footprint, Illumina Whitepaper, 2010-2014, 4 pages.
Badrinarayanan et. al., SegNet: A Deep Convolutional Encoder-Decoder Architecture for Image Segmentation, dated Oct. 10, 2016, 14 pages.
Li et. al., CS231 Lecture 13 Segmentation and Attention, Stanford University, dated Feb. 24, 2016, 133 pages.
Whiteford et. al., Swift: Primary data analysis for the Illumina Solexa sequencing platform, Bioinformatics, vol. 25, No. 17, 2009, pp. 2194-2199, 7 pages.
Schilling, The Effect of Batch Normalization on Deep Convolutional Neural Networks, KTH Royal Institute of Technology, 2016, 113 pages.
Tutorial Image Segmentation, BoofCV, 6 pages, retrieved on Jul. 23 2021. Retrieved from [URL: https://boofcv.org/index.php?title=Tutorial_Image_Segmentation ].
Illumina, Understanding Illumina Quality Scores, dated Apr. 23, 2014, 2 pages.
Yue et. al., Deep Learning for Genomics: A Concise Overview, dated May 8, 2018, 40 pages.
Zhang et. al., Estimating Phred scores of Illumina base calls by logistic regression and sparse modeling, Bio Med Central Bioinformatics, 2017, 14 pages.
Renaud et. al., freelbis: an efficient base caller with calibrated quality scores for Illumina sequencers, dated Mar. 6, 2013, 2 pages.
Kircher, Improving data quality of the Illumina Genome Analyzer platform, Max Planck Institute for Evolutionary Anthropology, dated Oct. 24, 2009, 46 pages.
Mitra et. al., Strategies for Achieving High Sequencing Accuracy for Low Diversity Samples and Avoiding Sample Bleeding Using Illumina Platform, PLOS One, published Apr. 10, 2015, 21 pages.
Datta et. al., Statistical Analyses of Next Generation Sequence Data: A Partial Overview, Journal of Proteomics and Bioinformatics, vol. 3, Issue 6, 2010, 8 pages.
Erlich et. al., Alta-Cyclic: a self-optimizing base-caller for next generation sequencing, Nature Methods, Aug. 2008, 7 pages.
Kao et. al., Algorithms for Next-Generation High-Throughput Sequencing Technologies, University of California, Berkeley, 2011, 106 pages.
Kircher et. al., Addressing challenges in the production and analysis of Illumina sequencing data, published Jul. 29, 2011, retrieved on Jul. 24, 2021, 25 pages. Retrieved from [URL: https://www.ncbi.nlm.nih.gov/pmc/articles/PMC3163567/ ].
Teng et. al., Chiron: translating nanopore raw signal directly into nucleotide sequence using deep learning, GigaScience, 7, 2018, 9 pages.
Ratkovic, Deep Learning Model for Base Calling of MinION Nanopore Reads, dated Jun. 2017, 48 pages.
Teng et. al., Chiron: translating nanopore raw signal directly into nucleotide sequence using deep learning, dated Aug. 23, 2017, 10 pages.
Stoiber et. al., BasecRAWller. Streaming Nanopore Basecalling Directly from Raw Signal, dated May 1, 2017, 15 pages.
Li et. al., DeepSimulator: a deep simulator for Nanopore sequencing, Bioinformatics 34(17), 2018, pp. 2899-2908, 10 pages.
Wick et. al., Performance of neural network basecalling tools for Oxford Nanopore sequencing, dated Feb. 7, 2019, 14 pages.
Ledergerber et. al., Base-calling for next-generation sequencing platforms, Briefings in Bioinformatics vol. 12, No. 5, pp. 489-497, dated Jan. 18, 2011, 9 pages.
Sheikh et. al., Chapter 5 Base-Calling for Bioinformaticians, 2012, 17 pages.
Kriseman et. al., BING: Biomedical informatics pipeline for Next Generation Sequencing, Journal of Biomedical Informatics, vol. 43, 2010, pp. 428-434, 7 pages.
Das et. al., Model-based sequential base calling for Illumina sequencing, IEEE, 2010, 4 pages.
Shamaiah et. al., Base calling error rates in next-generation DNA sequencing, IEEE Statistical Signal Processing Workshop, 2012, 4 pages.
Ye et. al., BlindCall: ultra-fast base-calling of high-throughput sequencing data by blind deconvolution, Bioinformatics, vol. 30, No. 9, 2014, pp. 1214-1219, 6 pages.
Wolowski, High-quality, high-throughput measurement of protein-DNA binding using HiTS-FLIP, Ludwig Maxmilian University, 2016, 251 pages.
Bravo et. al., Model-Based Quality Assessment and Base-Calling for Second-Generation Sequencing Data, Biometrics, 2009, 10 pages.
Maassignham et. al., All Your Base: a fast and accurate probabilistic approach to base calling, European Bioinformatics Institute, 22 pages.
Illumina, RTA Theory of Operation, 2009, 8 pages.
Dash et. al., Artificial Intelligence and Evolutionary Computations in Engineering Systems, Advances in Intelligent Systems and Computing, vol. 1056, Springer 2020, 781 pages.

(56) References Cited

OTHER PUBLICATIONS

Ahmed, SIGNET: A Neural Network Architecture for Predicting Protein-Protein Interactions, The University of Western Ontario, dated May 7, 2017, 84 pages.
Deepa J, Development of Fully Automated Image Analysis Method for High Density cDNA and array CGH Microarray based genomic studies, Cochin University of Science and Technology, Mar. 2013, 232 pages.
Zhang et. al., Nanopore basecalling from a perspective of instance segmentation, BMC Bioinformatics, 2020, 9 pages.
Kao et. al., naiveBayesCall: An Efficient Model-Based Base-Calling Algorithm for High-Throughput Sequencing, Journal of Computational Biology, dated Mar. 2011, 16 pages.
Wick et. al., Performance of neural network basecalling tools for Oxford Nanopore sequencing, Genome Biology, 2019, 10 pages.
Gilissen, C. et al. Genome sequencing identifies major causes of severe intellectual disability. Nature 511, 344-347 (2014).
Lelieveld, S. H. et al. Meta-analysis of 2,104 trios provides support for 10 new genes for intellectual disability. Nat. Neurosci. 19, 1194-1196 (2016).
Famiglietti, M. L. et al. Genetic variations and diseases in UniProtKB Swiss-Prot—the ins and outs of expert manual curation. Human. Mutat. 35, 927-935 (2014).
Horaitis, O., Talbot, C. C.Jr., Phommarinh, M., Phillips, K. M., & Cotton, R. G. A database of locus-specific databases. Nat. Genet. 39, 425 (2007).
Stenson, P. D. et al. The Human Gene Mutation Database—building a comprehensive mutation repository for clinical and molecular genetics, diagnostic testing and personalized genomic medicine. Hum. Genet. 133, 1-9 (2014).
Alipanahi, et. al., "Predicting the Sequence Specificities of DNA and RNA Binding Proteins by Deep Learning", Aug. 2015, 9pgs.
Angermueller, et. al., "Accurate Prediction of Single Cell DNA Methylation States Using Deep Learning", Apr. 11, 2017, 13pgs.
Ching, et. al., "Opportunities and Obstacles for Deep Learning in Biology and Medicine", Jan. 19, 2018, 123pgs.
Ching, et. al., "Opportunities and Obstacles for Deep Learning in Biology and Medicine", May 26, 2017, 47pgs.
Gu, et. al., "Recent Advances in Convolutional Neural Networks", Jan. 5, 2017, 37pgs.
Leung, et. al., "Deep learning of the tissue regulated splicing code", 2014, 9pgs.
Leung, et. al., "Inference of the Human Polyadenylation Code", Apr. 27, 2017, 13pgs.
Leung, et. al., "Machine Learning in Genomic Medicine", Jan. 1, 2016, 22pgs.
Park, et. al., "Deep Learning for Regulatory Genomics", Aug. 2015, 2pgs.
MacArthur, D. G. et al. Guidelines for investigating causality of sequence variants in human disease. Nature 508, 469-476 (2014).
Rehm, H. L. et al. ClinGen—the Clinical Genome Resource. N. Engl. J. Med. 372, 2235-2242 (2015).
Bamshad, M. J. et al. Exome sequencing as a tool for Mendelian disease gene discovery. Nat. Rev. Genet. 12, 745-755 (2011).
Rehm, H. L. Evolving health care through personal genomics. Nat. Rev. Genet. 18, 259-267 (2017).
Richards, S. et al. Standards and guidelines for the interpretation of sequence variants—a joint consensus recommendation of the American College of Medical Genetics and Genomics and the Association for Molecular Pathology. Genet. Med. 17, 405-424 (2015).
Lek, M. et al. Analysis of protein-coding genetic variation in 60,706 humans. Nature 536, 285-291 (2016).
Mallick, S. et al. The Simons Genome Diversity Project—300 genomes from 142 diverse populations. Nature 538, 201-206 (2016).
Genomes Project Consortium. et al. A global reference for human genetic variation. Nature 526, 68-74 (2015).
Liu, X., Jian, X. & Boerwinlde, E. dbNSFP—a lightweight database of human nonsynonyrnous SNPs and their functional predictions. Human. Mutat. 32, 894-899 (2011).
Chimpanzee Sequencing Analysis Consortium. Initial sequence of the chimpanzee genome and comparison with the human genome. Nature 437, 69-87 (2005).
Takahata, N. Allelic genealogy and human evolution. Mol. Biol. Evol. 10, 2-22 (1993).
Asthana, S., Schmidt, S., & Sunyaev, S. A limited role for balancing selection. Trends Genet. 21, 30-32 (2005).
Leffler, E. M. et al. Multiple instances of ancient balancing selection shared between humans and chimpanzees. Science 339, 12 pages (2013).
Samocha, K. E. et al. A framework for the interpretation of de novo mutation in human disease. Nat. Genet. 46, 944-950 (2014).
Ohta, T. Slightly deleterious mutant substitutions in evolution. Nature 246, 96-98 (1973).
Reich, D. E. & Lander, E. S. On the allelic spectrum of human disease. Trends Genet. 17, 502-510 (2001).
Whiffin, N. et al. Using high-resolution variant frequencies to empower clinical genome interpretation. Genet. Med. 19, 1151-1158(2017).
Prado-Martinez, J. et al. Great ape genome diversity and population history. Nature 499, 471-475 (2013).
Klein, J., Satta, Y., O'HUigin, C., & Takahata, N. The molecular descent of the major histocompatibility complex. Annu. Rev. Immunol. 11, 269-295 (1993).
de Manuel, M. et al. Chimpanzee genomic diversity reveals ancient admixture with bonobos. Science 354, 477-481 (2016).
Locke, D. P. et al. Comparative and demographic analysis of orang-utan genomes. Nature 469, 529-533 (2011).
Rhesus Macaque Genome Sequencing Analysis Consortium. Evolutionary and biomedical insights from the rhesus macaque genome. Science 316, 222-234 (2007).
Worley, K. C. et al. The common marmoset genome provides insight into primate biology and evolution. Nat. Genet. 46, 850-857 (2014).
Sherry, S. T. et al. dbSNP—the NCBI database of genetic variation. Nucleic Acids Res. 29, 308-211 (2001).
Schrago, C. G., & Russo, C. A. Timing the origin of New World monkeys. Mol. Biol. Evol. 20, 1620-1625 (2003).
Landrum, M. J. et al. ClinVar—public archive of interpretations of clinically relevant variants. Nucleic Acids Res. 44, D862-868 (2016).
Brandon, E. P., Idzerda, R. L. & McKnight, G. S. Targeting the mouse genome—a compendium of knockouts (Part II). Curr. Biol. 5, 758-765 (1995).
Lieschke, J. G. & Currie, P. D. Animal models of human disease—zebrafish swim into view. Nat. Rev. Genet. 8, 353-367 (2007).
Sittig, L. J. et al. Genetic background limits generalizability of genotype-phenotype relationships. Neuron 91, 1253-1259 (2016).
Bazykin, G. A. et al. Extensive parallelism in protein evolution. Biol. Direct 2, 20, 13 pages (2007).
Ng, P. C., & Henikoff, S. Predicting deleterious amino acid substitutions. Genome Res. 11, 863-874 (2001).
Adzhubei, I. A. et al. A method and server for predicting damaging missense mutations. Nat. Methods 7, 248-249 (2010).
Chun, S. & Fay, J. C. Identification of deleterious mutations within three human genomes. Genome Res. 19, 1553-1561 (2009).
Schwarz, J. M., Rodelsperger, C., Schuelke, M. & Seelow, D. MutationTaster evaluates disease-causing potential of sequence alterations. Nat. Methods 7, 575-576 (2010).
Reva, B., Antipin, Y., & Sander, C. Predicting the functional impact of protein mutations—application to cancer genomics. Nucleic Acids Res. 39, e118 (2011), 14pgs.
Jong, C. et al. Comparison and integration of deleteriousness prediction methods for nonsynonymous SNVs in whole exome sequencing studies. Hum. Mol. Genet. 24, 2125-2137 (2015).

\* cited by examiner

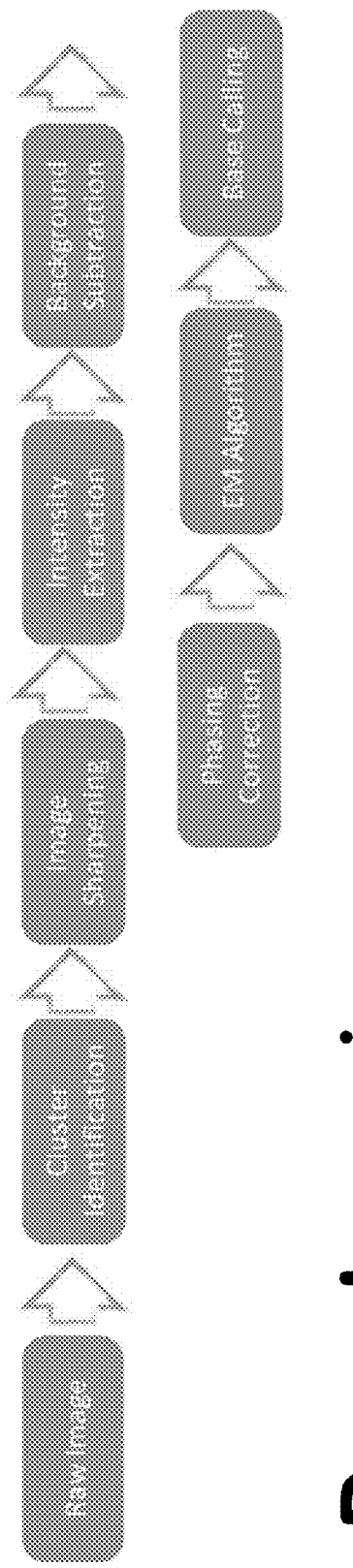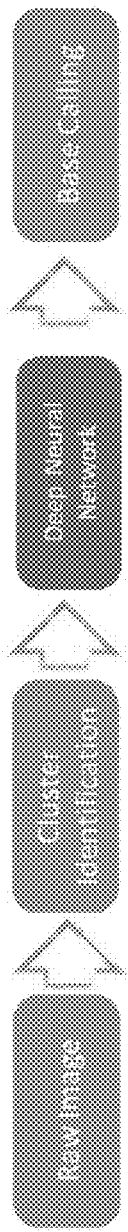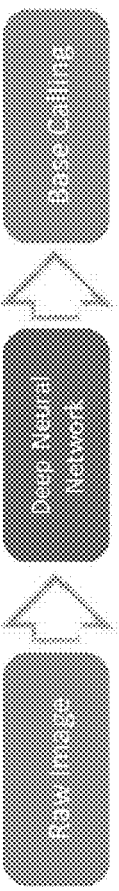
Figure 1

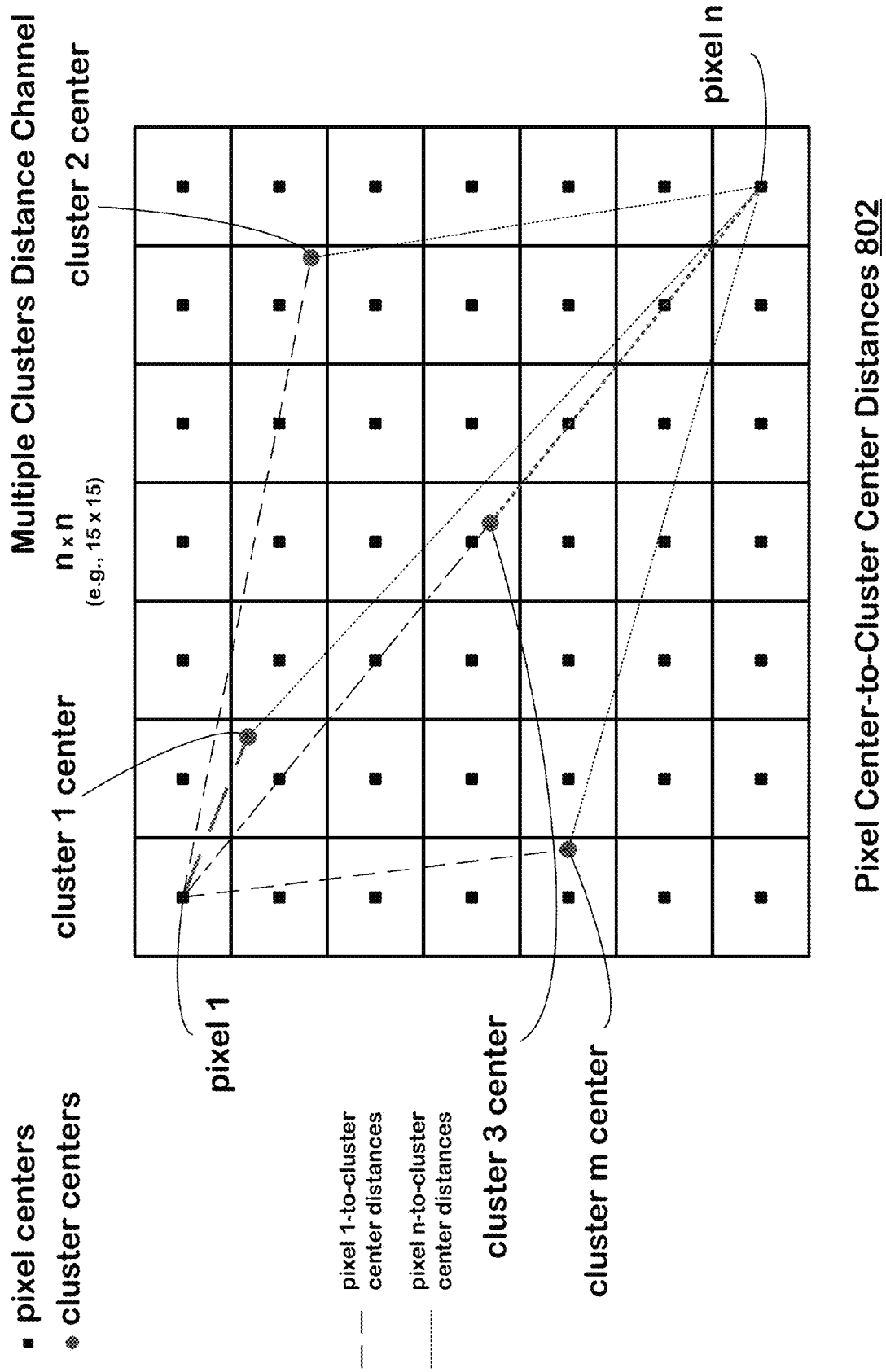

Multiple Clusters Distance Channel n x n
(e.g., 15 x 15)

| d1 | d2 | d3 | | | | |
|---|---|---|---|---|---|---|
| d8 | d9 | d10 | | d13 | d14 | |
| | | | dc | d20 | d21 | |
| | | | d26 | d27 | | |
| | | | d32 | d33 | | |
| d29 | d30 | d31 | | | | |
| d36 | d37 | d38 | | | | dn | center pixel → dc pixel n → dn pixel 1 → d1

Pixel-Wise Encoding of Distances 902

Figure 9

Pixel-to-Cluster Classification 1002

Pixel Centers-to-Assigned Cluster Center Distances 1102

Multiple Clusters, Shape-Based Distance Channel
n x n
(e.g., 15 x 15)

| | d7 | d14 | d21 | d28 | d35 | | |
|---|---|---|---|---|---|---|---|
| | d6 | d13 | d20 | d27 | d34 | | |
| | d5 | d12 | d19 | d26 | d33 | | |
| | | d18 | d25 | d32 | d39 | | |
| d3 | d10 | d17 | d24 | d31 | d38 | | |
| d2 | d9 | | d23 | d30 | d37 | | |
| | | | d22 | d29 | d36 | | | center pixel pixel n pixel 1

Pixel-Wise Encoding of Distances 1202

Figure 12

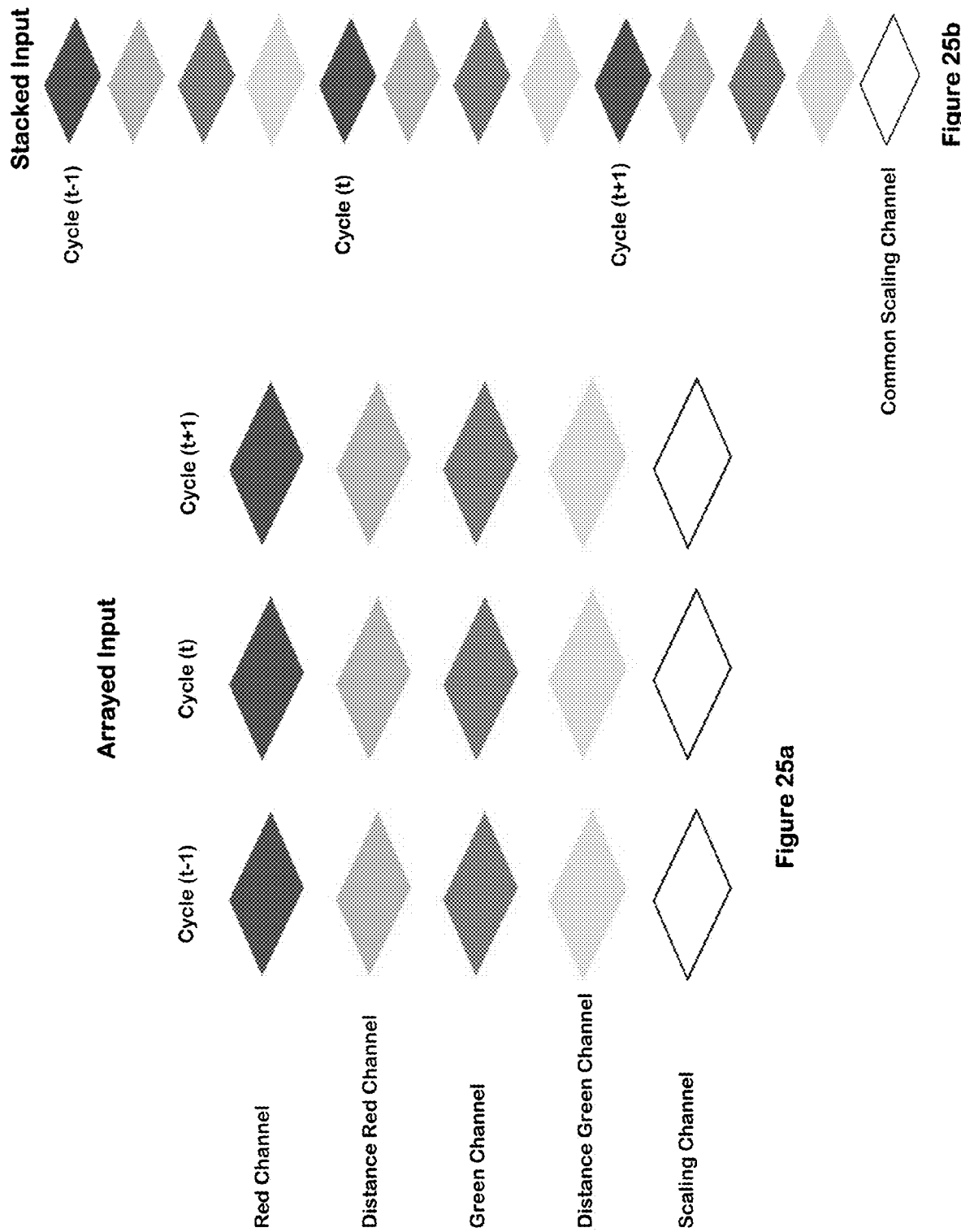

Reframing 2600a

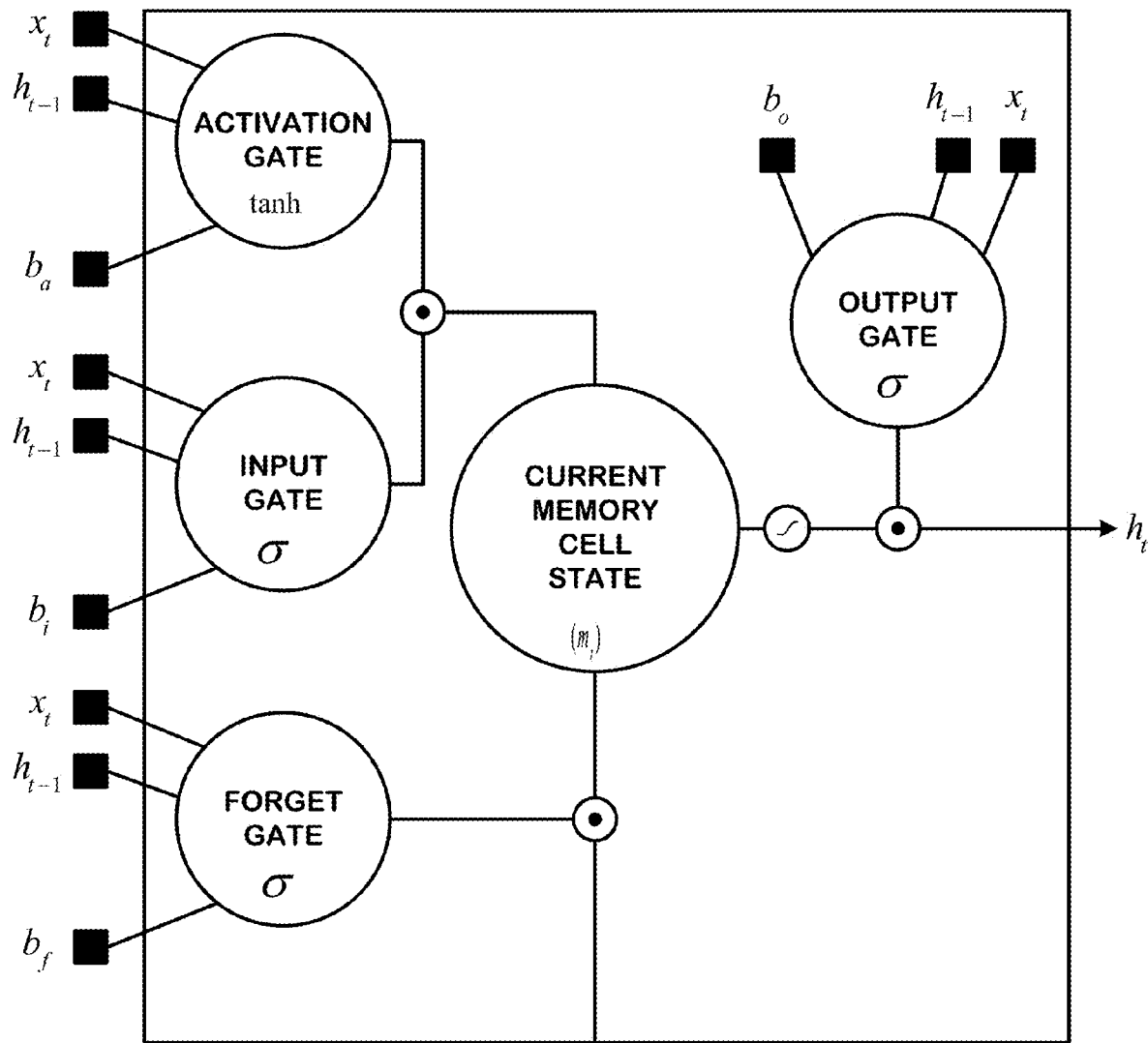
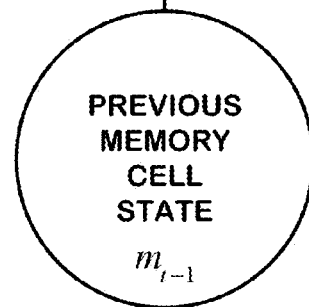
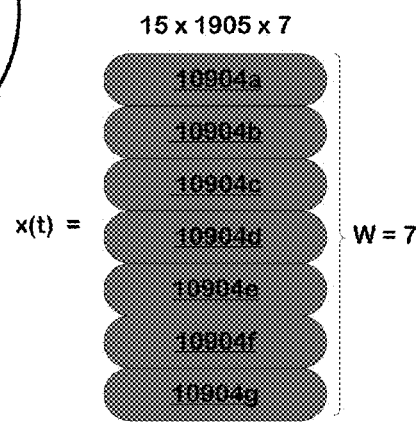
LSTM with 3D CONV 3500b
Figure 35b

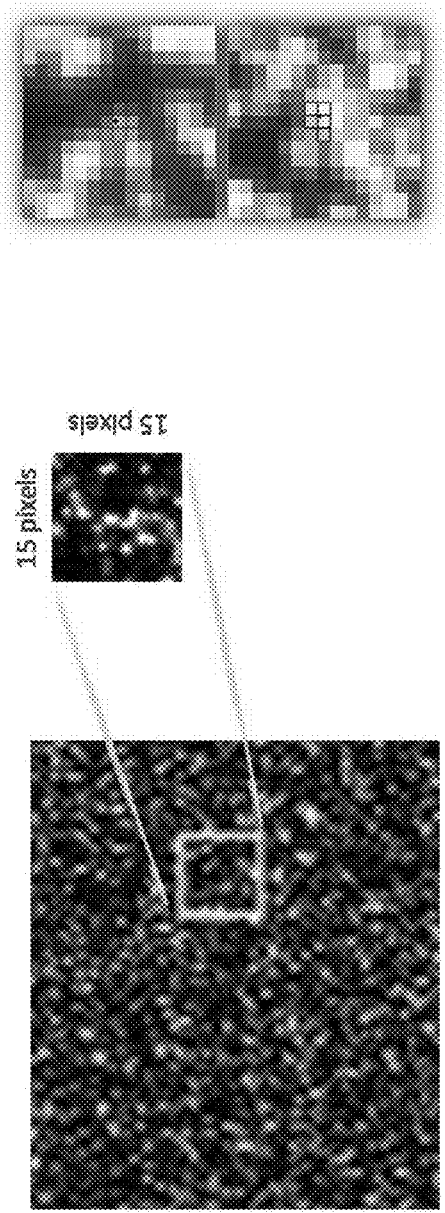
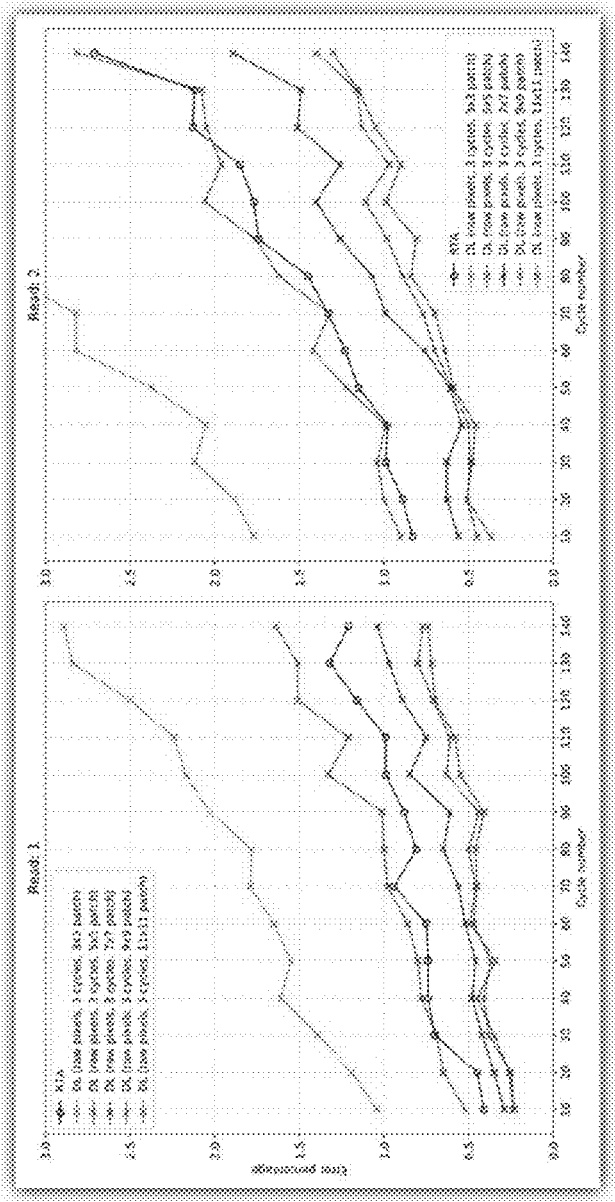
Figure 41

Hardware

- Inference Engines such as:
  - Jetson (Nvidia)
  - Mythic
- Software based enhancements:
  - Works with all platforms including FPGA
  - Collaboration with UCSD
  - Available FPGA capacity on instrument
- Cloud based solutions
  - Firefly / Dragonfly
- Memory

Quality Score Correspondence 5900

Quality Score Correspondence Scheme 5900a

| Quality Score | Softmax Score |
|---|---|
| Q10 | 0.90 |
| Q20 | 0.99 |
| Q30 | 0.999 |
| Q40 | 0.9999 |
| Q50 | 0.99999 |
| Q60 | 0.999999 |

Figure 59a

Quality Score Correspondence Scheme 5900b

| Binned Quality Score | Softmax Score |
|---|---|
| Q2-Q9 -> Q06 | 0.80 |
| Q10-Q19 -> Q15 | 0.95 |
| Q20-Q24 -> Q22 | 0.993 |
| Q25-Q29 -> Q27 | 0.997 |
| Q30-Q34 -> Q33 | 0.9991 |
| Q35-Q39 -> Q37 | 0.9995 |
| Q40 or > Q40 -> Q40 | 0.9999 |

Figure 59b

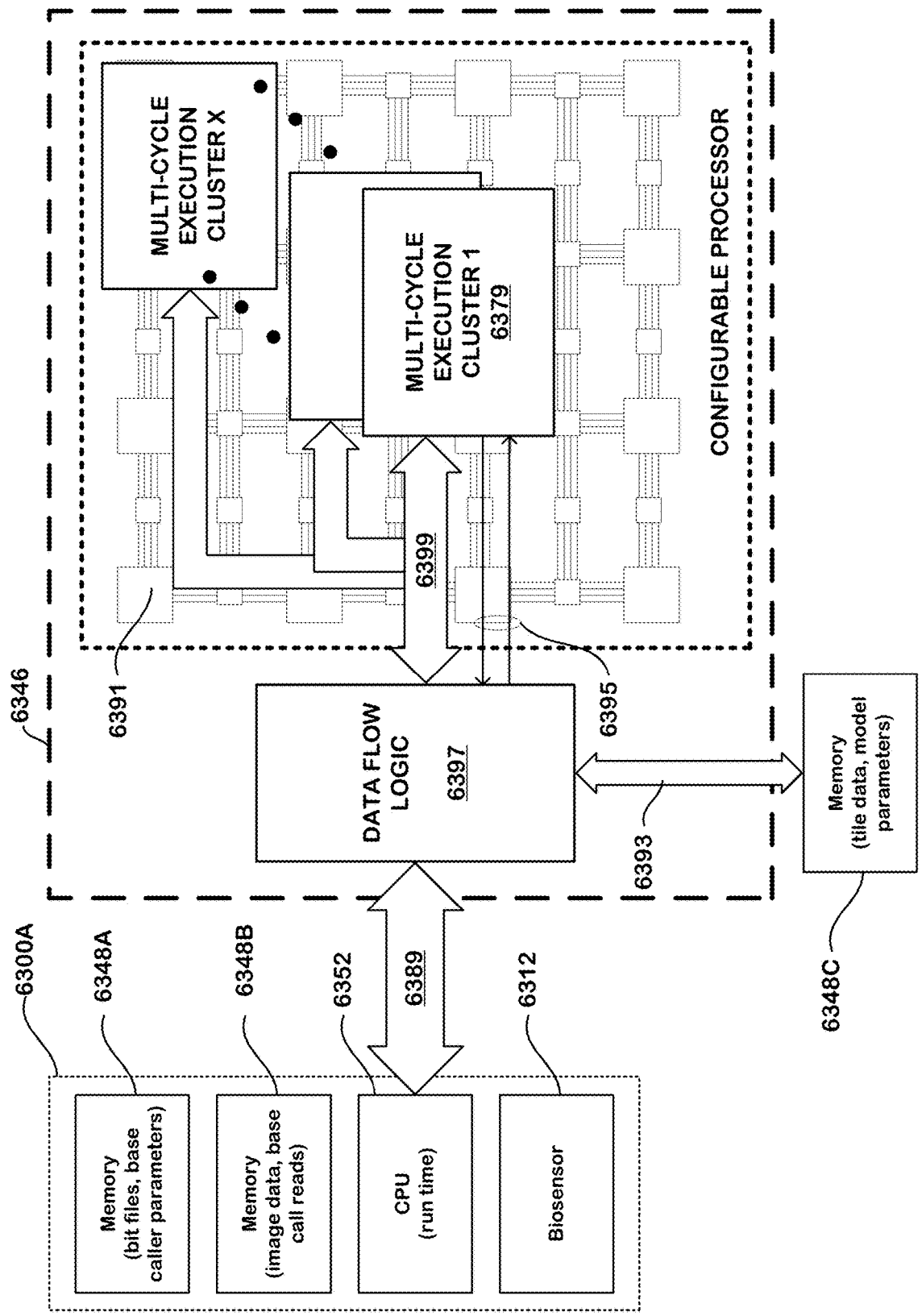

ARTIFICIAL INTELLIGENCE-BASED QUALITY SCORING

PRIORITY APPLICATIONS

This application claims priority to or the benefit of the following applications:

U.S. Provisional Patent Application No. 62/821,602, entitled "Training Data Generation for Artificial Intelligence-Based Sequencing," filed 21 Mar. 2019;

U.S. Provisional Patent Application No. 62/821,618, entitled "Artificial Intelligence-Based Generation of Sequencing Metadata," filed 21 Mar. 2019;

U.S. Provisional Patent Application No. 62/821,681, entitled "Artificial Intelligence-Based Base Calling," filed 21 Mar. 2019;

U.S. Provisional Patent Application No. 62/821,724, entitled "Artificial Intelligence-Based Quality Scoring," filed 21 Mar. 2019;

U.S. Provisional Patent Application No. 62/821,766, entitled "Artificial Intelligence-Based Sequencing," filed 21 Mar. 2019;

NL Application No. 2023310, entitled "Training Data Generation for Artificial Intelligence-Based Sequencing," filed 14 Jun. 2019;

NL Application No. 2023311, entitled "Artificial Intelligence-Based Generation of Sequencing Metadata," filed 14 Jun. 2019;

NL Application No. 2023312, entitled "Artificial Intelligence-Based Base Calling," filed 14 Jun. 2019;

NL Application No. 2023314, entitled "Artificial Intelligence-Based Quality Scoring," filed 14 Jun. 2019; and NL Application No. 2023316, entitled "Artificial Intelligence-Based Sequencing," filed 14 Jun. 2019.

The priority applications are hereby incorporated by reference for all purposes as if fully set forth herein.

INCORPORATIONS

The following are incorporated by reference for all purposes as if fully set forth herein:

US Non-Provisional Applications

U.S. patent application Ser. No. 16/825,987, entitled "Training Data Generation for Artificial Intelligence-Based Sequencing," filed 20 Mar. 2020;

U.S. patent application Ser. No. 16/825,991, entitled "Artificial Intelligence-Based Generation of Sequencing Metadata," filed 20 Mar. 2020;

U.S. patent application Ser. No. 16/826,126, entitled "Artificial Intelligence-Based Base Calling," filed 20 Mar. 2020;

U.S. patent application Ser. No. 16/826,168, entitled "Artificial Intelligence-Based Sequencing," filed 21 Mar. 2020;

PCT Applications

PCT Patent Application No. PCT/US2020/024090, titled "Training Data Generation for Artificial Intelligence-Based Sequencing," filed 21 Mar. 2020;

PCT Patent Application No. PCT/US2020/24087, titled "Artificial Intelligence-Based Generation of Sequencing Metadata," filed 21 Mar. 2020;

PCT Patent Application No. PCT/US2020/024088, titled "Artificial Intelligence-Based Base Calling," filed 21 Mar. 2020;

PCT Patent Application No. PCT/US2020/24091, titled "Artificial Intelligence-Based Quality Scoring," filed 21 Mar. 2020;

PCT Patent Application No. PCT/US2020/24092, titled "Artificial Intelligence-Based Sequencing," filed 22 Mar. 2020;

U.S. Provisional Patent Application No. 62/849,091, entitled, "Systems and Devices for Characterization and Performance Analysis of Pixel-Based Sequencing," filed May 16, 2019;

U.S. Provisional Patent Application No. 62/849,132, entitled, "Base Calling Using Convolutions," filed May 16, 2019;

U.S. Provisional Patent Application No. 62/849,133, entitled, "Base Calling Using Compact Convolutions," filed May 16, 2019;

U.S. Provisional Patent Application No. 62/979,384, entitled, "Artificial Intelligence-Based Base Calling of Index Sequences," filed Feb. 20, 2020;

U.S. Provisional Patent Application No. 62/979,414, entitled, "Artificial Intelligence-Based Many-To-Many Base Calling," filed Feb. 20, 2020;

U.S. Provisional Patent Application No. 62/979,385, entitled, "Knowledge Distillation-Based Compression of Artificial Intelligence-Based Base Caller," filed Feb. 20, 2020;

U.S. Provisional Patent Application No. 62/979,412, entitled, "Multi-Cycle Cluster Based Real Time Analysis System," filed Feb. 20, 2020;

U.S. Provisional Patent Application No. 62/979,411, entitled, "Data Compression for Artificial Intelligence-Based Base Calling," filed Feb. 20, 2020;

U.S. Provisional Patent Application No. 62/979,399, entitled, "Squeezing Layer for Artificial Intelligence-Based Base Calling," filed Feb. 20, 2020;

Liu P, Hemani A, Paul K, Weis C, Jung M, Wehn N. 3D-Stacked Many-Core Architecture for Biological Sequence Analysis Problems. Int J Parallel Prog. 2017; 45(6):1420-60;

Z. Wu, K. Hammad, R. Mittmann, S. Magierowski, E. Ghafar-Zadeh, and X. Zhong, "FPGA-Based DNA Basecalling Hardware Acceleration," in Proc. IEEE 61st Int. Midwest Symp. Circuits Syst., August 2018, pp. 1098-1101;

Z. Wu, K. Hammad, E. Ghafar-Zadeh, and S. Magierowski, "FPGA-Accelerated 3rd Generation DNA Sequencing," in IEEE Transactions on Biomedical Circuits and Systems, Volume 14, Issue 1, February 2020, pp. 65-74;

Prabhakar et al., "Plasticine: A Reconfigurable Architecture for Parallel Patterns," ISCA '17, Jun. 24-28, 2017, Toronto, ON, Canada;

M. Lin, Q. Chen, and S. Yan, "Network in Network," in Proc. of ICLR, 2014;

L. Sifre, "Rigid-motion Scattering for Image Classification, Ph.D. thesis, 2014;

L. Sifre and S. Mallat, "Rotation, Scaling and Deformation Invariant Scattering for Texture Discrimination," in Proc. of CVPR, 2013;

F. Chollet, "Xception: Deep Learning with Depthwise Separable Convolutions," in Proc. of CVPR, 2017;

X. Zhang, X. Zhou, M. Lin, and J. Sun, "ShuffleNet: An Extremely Efficient Convolutional Neural Network for Mobile Devices," in arXiv:1707.01083, 2017;

K. He, X. Zhang, S. Ren, and J. Sun, "Deep Residual Learning for Image Recognition," in Proc. of CVPR, 2016;

S. Xie, R. Girshick, P. Dollar, Z. Tu, and K. He, "Aggregated Residual Transformations for Deep Neural Networks," in Proc. of CVPR, 2017;

A. G. Howard, M. Zhu, B. Chen, D. Kalenichenko, W. Wang, T. Weyand, M. Andreetto, and H. Adam, "Mobilenets: Efficient Convolutional Neural Networks for Mobile Vision Applications," in arXiv:1704.04861, 2017;

M. Sandler, A. Howard, M. Zhu, A. Zhmoginov, and L. Chen, "MobileNetV2: Inverted Residuals and Linear Bottlenecks," in arXiv:1801.04381v3, 2018;

Z. Qin, Z. Zhang, X. Chen, and Y. Peng, "FD-MobileNet: Improved MobileNet with a Fast Downsampling Strategy," in arXiv:1802.03750, 2018;

Liang-Chieh Chen, George Papandreou, Florian Schroff, and Hartwig Adam. Rethinking atrous convolution for semantic image segmentation. CoRR, abs/1706.05587, 2017;

J. Huang, V. Rathod, C. Sun, M. Zhu, A. Komttikara, A. Fathi, I. Fischer, Z. Wojna, Y. Song, S. Guadarrama, et al. Speed/accuracy trade-offs for modern convolutional object detectors. arXiv preprint arXiv:1611.10012, 2016;

S. Dieleman, H. Zen, K. Simonyan, O. Vinyals, A. Graves, N. Kalchbrenner, A. Senior, and K. Kavukcuoglu, "WAVENET: A GENERATIVE MODEL FOR RAW AUDIO," arXiv:1609.03499, 2016;

S. Ö. Arik, M. Chrzanowski, A. Coates, G. Diamos, A. Gibiansky, Y. Kang, X. Li, J. Miller, A. Ng, J. Raiman, S. Sengupta and M. Shoeybi, "DEEP VOICE: REAL-TIME NEURAL TEXT-TO-SPEECH," arXiv:1702.07825, 2017;

F. Yu and V. Koltun, "MULTI-SCALE CONTEXT AGGREGATION BY DILATED CONVOLUTIONS," arXiv:1511.07122, 2016;

K. He, X Zhang, S. Ren, and J. Sun, "DEEP RESIDUAL LEARNING FOR IMAGE RECOGNITION," arXiv:1512.03385, 2015;

R. K. Srivastava, K. Greff, and J. Schmidhuber, "HIGHWAY NETWORKS," arXiv: 1505.00387, 2015;

G. Huang, Z. Liu, L. van der Maaten and K. Q. Weinberger, "DENSELY CONNECTED CONVOLUTIONAL NETWORKS," arXiv:1608.06993, 2017;

C. Szegedy, W. Liu, Y. Jia, P. Sermanet, S. Reed, D. Anguelov, D. Erhan, V. Vanhoucke, and A. Rabinovich, "GOING DEEPER WITH CONVOLUTIONS," arXiv: 1409.4842, 2014;

S. Ioffe and C. Szegedy, "BATCH NORMALIZATION: ACCELERATING DEEP NETWORK TRAINING BY REDUCING INTERNAL COVARIATE SHIFT," arXiv: 1502.03167, 2015;

J. M. Wolterink, T. Leiner, M. A. Viergever, and I. Išgum, "DILATED CONVOLUTIONAL NEURAL NETWORKS FOR CARDIOVASCULAR MR SEGMENTATION IN CONGENITAL HEART DISEASE," arXiv:1704.03669, 2017;

L. C. Piqueras, "AUTOREGRESSIVE MODEL BASED ON A DEEP CONVOLUTIONAL NEURAL NETWORK FOR AUDIO GENERATION," Tampere University of Technology, 2016;

J. Wu, "Introduction to Convolutional Neural Networks," Nanjing University, 2017;

"Illumina CMOS Chip and One-Channel SBS Chemistry", Illumina, Inc. 2018, 2 pages;

"skikit-image/peak.py at master", GitHub, 5 pages, [retrieved on 2018 Nov. 16]. Retrieved from the Internet <URL: https://github.com/scikit-image/scikit-image/blob/master/skimage/feature/peak.py#L25>;

"3.3.9.11. Watershed and random walker for segmentation", Scipy lecture notes, 2 pages, [retrieved on 2018 Nov. 13]. Retrieved from the Internet <URL: http://scipy-lectures.org/packages/scikit-image/auto_examples/plot_segmentations.html>;

Mordvintsev, Alexander and Revision, Abid K., "Image Segmentation with Watershed Algorithm", Revision 43532856, 2013, 6 pages [retrieved on 2018 Nov. 13]. Retrieved from the Internet <URL: https://opencv-python-tutroals.readthedocs.io/en/latest/py_tutorials/py_imgproc/py_watershed/py_watershed.html>;

Mzur, "Watershed.py", 25 Oct. 2017, 3 pages, [retrieved on 2018 Nov. 13]. Retrieved from the Internet <URL: https://github.com/mzur/watershed/blob/master/Watershed.py>;

Thakur, Pratibha, et. al. "A Survey of Image Segmentation Techniques", International Journal of Research in Computer Applications and Robotics, Vol. 2, Issue. 4, April 2014, Pg.: 158-165;

Long, Jonathan, et. al., "Fully Convolutional Networks for Semantic Segmentation", IEEE Transactions on Pattern Analysis and Machine Intelligence, Vol 39, Issue 4, 1 Apr. 2017, 10 pages;

Ronneberger, Olaf, et al., "U-net: Convolutional networks for biomedical image segmentation." In *International Conference on Medical image computing and computer-assisted intervention,* 18 May 2015, 8 pages;

Xie, W., et. al., "Microscopy cell counting and detection with fully convolutional regression networks", *Computer methods in biomechanics and biomedical engineering: Imaging & Visualization,* 6(3), pp. 283-292, 2018;

Xie, Yuanpu, et al., "Beyond classification: structured regression for robust cell detection using convolutional neural network", *International Conference on Medical Image Computing and Computer-Assisted Intervention.* October 2015, 12 pages;

Snuverink, I. A. F., "Deep Learning for Pixelwise Classification of Hyperspectral Images", Master of Science Thesis, Delft University of Technology, 23 Nov. 2017, 19 pages;

Shevchenko, A., "Keras weighted categorical_crossentropy", 1 page, [retrieved on 2019 Jan. 15]. Retrieved from the Internet <URL: https://gist.github.com/skeeet/cad06d584548fb45 eece1d4e28cfa98b>;

van den Assem, D. C. F., "Predicting periodic and chaotic signals using Wavenets", Master of Science Thesis, Delft University of Technology, 18 Aug. 2017, pages 3-38;

I. J. Goodfellow, D. Warde-Farley, M. Mirza, A. Courville, and Y. Bengio, "CONVOLUTIONAL NETWORKS", Deep Learning, MIT Press, 2016; and J. Gu, Z. Wang, J. Kuen, L. Ma, A. Shahroudy, B. Shuai, T. Liu, X. Wang, and G. Wang, "RECENT ADVANCES IN CONVOLUTIONAL NEURAL NETWORKS," arXiv: 1512.07108, 2017.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep neural networks such as deep convolutional neural networks for analyzing data.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Deep neural networks are a type of artificial neural networks that use multiple nonlinear and complex transforming layers to successively model high-level features. Deep neural networks provide feedback via backpropagation which carries the difference between observed and predicted output to adjust parameters. Deep neural networks have evolved with the availability of large training datasets, the power of parallel and distributed computing, and sophisticated training algorithms. Deep neural networks have facilitated major advances in numerous domains such as computer vision, speech recognition, and natural language processing.

Convolutional neural networks (CNNs) and recurrent neural networks (RNNs) are components of deep neural networks. Convolutional neural networks have succeeded particularly in image recognition with an architecture that comprises convolution layers, nonlinear layers, and pooling layers. Recurrent neural networks are designed to utilize sequential information of input data with cyclic connections among building blocks like perceptrons, long short-term memory units, and gated recurrent units. In addition, many other emergent deep neural networks have been proposed for limited contexts, such as deep spatio-temporal neural networks, multi-dimensional recurrent neural networks, and convolutional auto-encoders.

The goal of training deep neural networks is optimization of the weight parameters in each layer, which gradually combines simpler features into complex features so that the most suitable hierarchical representations can be learned from data. A single cycle of the optimization process is organized as follows. First, given a training dataset, the forward pass sequentially computes the output in each layer and propagates the function signals forward through the network. In the final output layer, an objective loss function measures error between the inferenced outputs and the given labels. To minimize the training error, the backward pass uses the chain rule to backpropagate error signals and compute gradients with respect to all weights throughout the neural network. Finally, the weight parameters are updated using optimization algorithms based on stochastic gradient descent. Whereas batch gradient descent performs parameter updates for each complete dataset, stochastic gradient descent provides stochastic approximations by performing the updates for each small set of data examples. Several optimization algorithms stem from stochastic gradient descent. For example, the Adagrad and Adam training algorithms perform stochastic gradient descent while adaptively modifying learning rates based on update frequency and moments of the gradients for each parameter, respectively.

Another core element in the training of deep neural networks is regularization, which refers to strategies intended to avoid overfitting and thus achieve good generalization performance. For example, weight decay adds a penalty term to the objective loss function so that weight parameters converge to smaller absolute values. Dropout randomly removes hidden units from neural networks during training and can be considered an ensemble of possible subnetworks. To enhance the capabilities of dropout, a new activation function, maxout, and a variant of dropout for recurrent neural networks called rnnDrop have been proposed. Furthermore, batch normalization provides a new regularization method through normalization of scalar features for each activation within a mini-batch and learning each mean and variance as parameters.

Given that sequenced data are multi- and high-dimensional, deep neural networks have great promise for bioinformatics research because of their broad applicability and enhanced prediction power. Convolutional neural networks have been adapted to solve sequence-based problems in genomics such as motif discovery, pathogenic variant identification, and gene expression inference. Convolutional neural networks use a weight-sharing strategy that is especially useful for studying DNA because it can capture sequence motifs, which are short, recurring local patterns in DNA that are presumed to have significant biological functions A hallmark of convolutional neural networks is the use of convolution filters.

Unlike traditional classification approaches that are based on elaborately-designed and manually-crafted features, convolution filters perform adaptive learning of features, analogous to a process of mapping raw input data to the informative representation of knowledge. In this sense, the convolution filters serve as a series of motif scanners, since a set of such filters is capable of recognizing relevant patterns in the input and updating themselves during the training procedure. Recurrent neural networks can capture long-range dependencies in sequential data of varying lengths, such as protein or DNA sequences.

Therefore, an opportunity arises to use a principled deep learning-based framework for template generation and base calling.

In the era of high-throughput technology, amassing the highest yield of interpretable data at the lowest cost per effort remains a significant challenge. Cluster-based methods of nucleic acid sequencing, such as those that utilize bridge amplification for cluster formation, have made a valuable contribution toward the goal of increasing the throughput of nucleic acid sequencing. These cluster-based methods rely on sequencing a dense population of nucleic acids immobilized on a solid support, and typically involve the use of image analysis software to deconvolve optical signals generated in the course of simultaneously sequencing multiple clusters situated at distinct locations on a solid support.

However, such solid-phase nucleic acid cluster-based sequencing technologies still face considerable obstacles that limit the amount of throughput that can be achieved. For example, in cluster-based sequencing methods, determining the nucleic acid sequences of two or more clusters that are physically too close to one another to be resolved spatially, or that in fact physically overlap on the solid support, can pose an obstacle. For example, current image analysis software can require valuable time and computational resources for determining from which of two overlapping clusters an optical signal has emanated. As a consequence, compromises are inevitable for a variety of detection platforms with respect to the quantity and/or quality of nucleic acid sequence information that can be obtained.

High density nucleic acid cluster-based genomics methods extend to other areas of genome analysis as well. For example, nucleic acid cluster-based genomics can be used in sequencing applications, diagnostics and screening, gene expression analysis, epigenetic analysis, genetic analysis of polymorphisms, and the like. Each of these nucleic acid cluster-based genomics technologies, too, is limited when there is an inability to resolve data generated from closely proximate or spatially overlapping nucleic acid clusters.

Clearly there remains a need for increasing the quality and quantity of nucleic acid sequencing data that can be obtained rapidly and cost-effectively for a wide variety of uses, including for genomics (e.g., for genome characterization of any and all animal, plant, microbial or other biological species or populations), pharmacogenomics, transcriptomics, diagnostics, prognostics, biomedical risk assessment, clinical and research genetics, personalized medicine, drug efficacy and drug interactions assessments, veterinary medicine, agriculture, evolutionary and biodiversity studies, aquaculture, forestry, oceanography, ecological and environmental management, and other purposes.

The technology disclosed provides neural network based methods and systems that address these and similar needs, including increasing the level of throughput in high-throughput nucleic acid sequencing technologies, and offers other related advantages.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab.

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 1 shows the processing stages used by the RTA base caller for base calling, according to one implementation.

FIG. 8a depicts one implementation of determining distance values for a distance channel when multiple target clusters are being simultaneously base called by the neural network-based base caller.

FIG. 9 shows one implementation of pixel-wise encoding the minimum distance values that are calculated between the pixels and the nearest one of the clusters.

FIG. 12 shows one implementation of pixel-wise encoding the distance values that are calculated between the pixels and the assigned clusters.

FIG. 25a depicts an example arrayed input configuration the multi-cycle input data.

FIG. 25b shows an example stacked input configuration the multi-cycle input data.

FIG. 35b shows one implementation of processing a 3D input volume x(t), which comprises groups of flattened mixed representations, through an input gate, an activation gate, a forget gate, and an output gate of a long short-term memory (LSTM) network that applies the 3D convolutions. The LSTM network is part of the recurrent module of the hybrid neural network.

FIG. 41 shows how different sizes of the image patches fed as input to the neural network-based base caller effect the base calling accuracy.

FIGS. 59a-59b depict one implementation of correspondence between the quality scores and the base call confidence predictions made by the neural network-based base caller.

FIG. 63C is a simplified block diagram of a system for analysis of sensor data from the sequencing system, such as base call sensor outputs.

DETAILED DESCRIPTION

Figure 2:
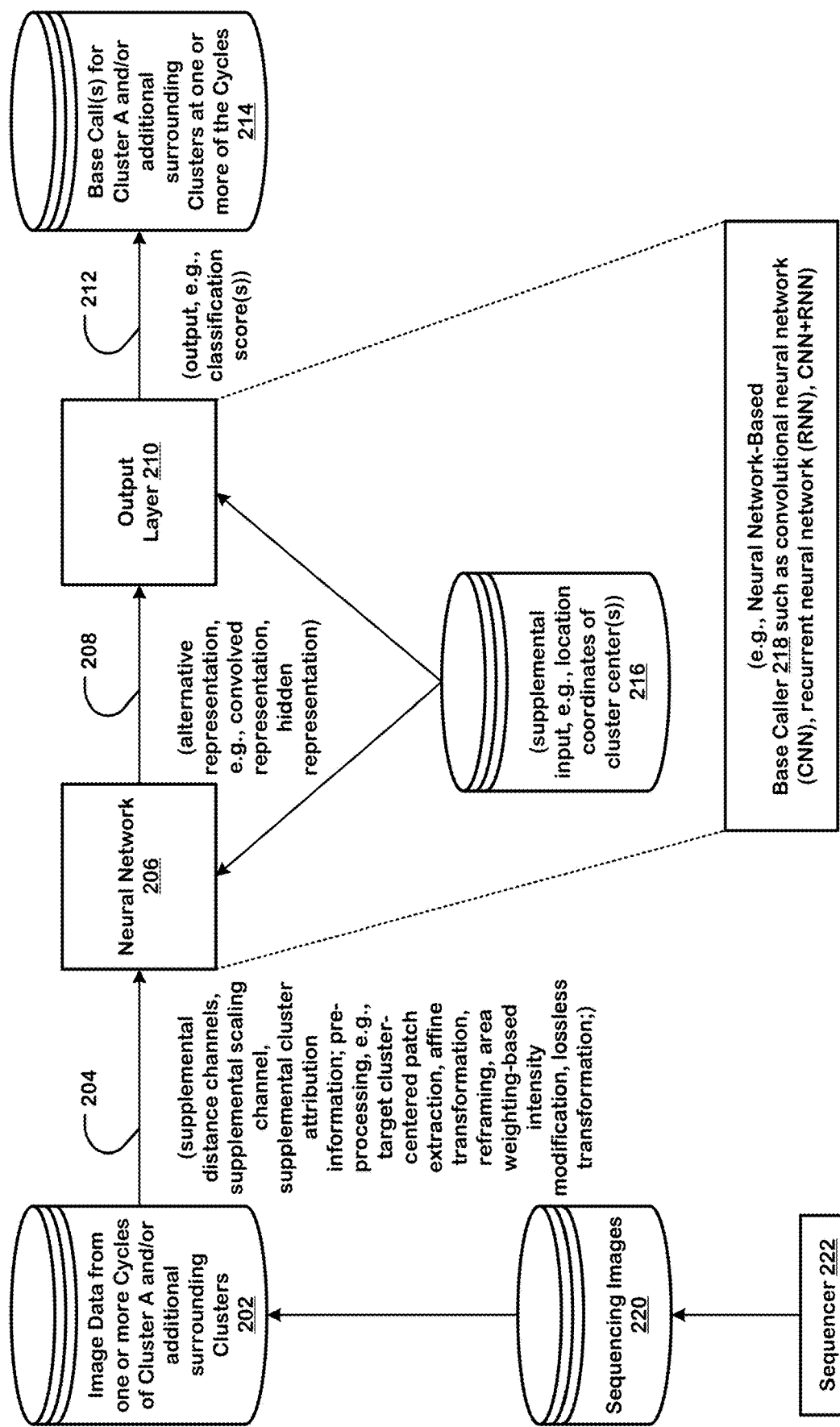
FIG. 2 illustrates one implementation of base calling using the disclosed neural network-based base caller.

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

INTRODUCTION

When bases are classified in sequences of digital images, the neural network processes multiple image channels in a current cycle together with image channels of past and future cycles. In a cluster, some of the strands may run ahead or behind the main course of synthesis, which out-of-phase tagging is known as pre-phasing or phasing. Given the low rates of pre-phasing and post-phasing observed empirically, nearly all of the noise in the signal resulting from pre-phasing and post-phasing can be handled by a neural network that processes digital images in current, past and future cycles, in just three cycles.

Among digital image channels in the current cycle, careful registration to align images within a cycle contributes strongly to accurate base classification. A combination of wavelengths and non-coincident illumination sources, among other sources of error, produces a small, correctable difference in measured cluster center locations. A general affine transformation, with translation, rotation and scaling, can be used to bring the cluster centers across an image tile into precise alignment. An affine transformation can be used to reframe image data and to resolve offsets for cluster centers.

Reframing image data means interpolating image data, typically by applying an affine transformation. Reframing can put a cluster center of interest in the middle of the center pixel of a pixel patch. Or, it can align an image with a template, to overcome jitter and other discrepancies during image collection. Reframing involves adjusting intensity values of all pixels in the pixel patch. Bi-linear and bi-cubic interpolation and weighted area adjustments are alternative strategies.

In some implementations, cluster center coordinates can be fed to a neural network as an additional image channel.

Distance signals also can contribute to base classification. Several types of distance signals reflect separation of regions from cluster centers. The strongest optical signal is deemed to coincide with the cluster center. The optical signal along the cluster perimeter sometimes includes a stray signal from a nearby cluster. Classification has been observed to be more accurate when contribution of signal component is attenuated according to its separation from the cluster center. Distance signals that work include a single cluster distance channel, a multi-cluster distance channel, and a multi-cluster shape based distance channel. A single cluster distance channel applies to a patch with a cluster center in the center pixel. Then, distance of all regions in the patch is a distance from the cluster center in the center pixel. Pixels that do not belong to same cluster as the center pixel can be flagged as background, instead of given a calculated distance. A multi-cluster distance channel pre-calculates distance of each region to the closest cluster center. This has the potential of connecting a region to the wrong cluster center, but that potential is low. A multi-cluster shape-based distance channel associates regions (sub-pixels or pixels) through adjoining regions to a pixel center that produces a same base classification. At some computational expense, this avoids the possibility of measuring a distance to the wrong pixel. The multi-cluster and multi-cluster shape-based approaches to distance signals have the advantage of being subject to pre-calculation and use with multiple clusters in an image.

Shape information can be used by a neural network to separate signal from noise, to improve the signal-to-noise ratio. In the discussion above, several approaches to region classification and to supplying distance channel information were identified. In any of the approaches, regions can be marked as background, as not being part of a cluster, to define cluster edges. A neural network can be trained to take advantage of the resulting information about irregular cluster shapes. Distance information and background classification can be combined or used separately. Separating signals from abutting clusters will be increasingly important as cluster density increases.

One direction for increasing the scale of parallel processing is to increase cluster density on the imaged media. Increasing density has the downside of increasing background noise when reading a cluster that has an adjacent neighbor. Using shape data, instead of an arbitrary patch (e.g., of 3×3 pixels), for instance, helps maintain signal separation as cluster density increases.

Applying one aspect of the technology disclosed, base classification scores also can be leveraged to predict quality. The technology disclosed includes correlating classification scores, directly or through a prediction model, with traditional Sanger or Phred quality Q-scores. Scores such as Q20, Q30 or Q40 are logarithmically related to base classification error probabilities, by $Q=-10 \log_{10} P$. Correlation of class scores with Q scores can be performed using a multi-output neural network or multi-variate regression analysis. An advantage of real time calculation of quality scores, during base classification, is that a flawed sequencing run can be terminated early. Applicant has found that occasional (rare) decisions to terminate runs can be made one-eighth to one-quarter of the way through the analysis sequence. A decision to terminate can be made after 50 cycles or after 25 to 75 cycles. In a sequential process that would otherwise run 300 to 1000 cycles, early termination results in substantial resource savings.

Specialized convolutional neural network (CNN) architectures can be used to classify bases over multiple cycles. One specialization involves segregation among digital image channels during initial layers of processing. Convolution filters stacks can be structured to segregate processing among cycles, preventing cross-talk between digital image sets from different cycles. The motivation for segregating processing among cycles is that images taken at different cycles have residual registration error and are thus misaligned and have random translational offsets with respect to each other. This occurs due to the finite accuracy of the movements of the sensor's motion stage and also because images taken in different frequency channels have different optical paths and wavelengths.

The motivation for using image sets from successive cycles is that the contribution of pre-phasing and post-phasing to signals in a particular cycle is a second order contribution. It follows that it can be helpful for the convolutional neural network to structurally segregate lower layer convolution of digital image sets among image collection cycles.

The convolutional neural network structure also can be specialized in handling information about clustering. Templates for cluster centers and/or shapes provide additional information, which the convolutional neural network combines with the digital image data. The cluster center classification and distance data can be applied repeatedly across cycles.

The convolutional neural network can be structured to classify multiple clusters in an image field. When multiple clusters are classified, the distance channel for a pixel or subpixel can more compactly contain distance information relative to either the closest cluster center or to the adjoining cluster center, to which a pixel or subpixel belongs. Alternatively, a large distance vector could be supplied for each pixel or subpixel, or at least for each one that contains a cluster center, which gives complete distance information from a cluster center to all other pixels that are context for the given pixel.

Some combinations of template generation with base calling can use variations on area weighting to supplant a distance channel. The discussion now turns to how output of the template generator can be used directly, in lieu of a distance channel.

We discuss three considerations that impact direct application of template images to pixel value modification: whether image sets are processed in the pixel or subpixel domain; in either domain, how area weights are calculated; and in the subpixel domain, applying a template image as mask to modify interpolated intensity values.

Performing base classification in the pixel domain has the advantage of not calling for an increase in calculations, such as 16 fold, which results from upsampling. In the pixel domain, even the top layer of convolutions may have sufficient cluster density to justify performing calculations that would not be harvested, instead of adding logic to cancel unneeded calculations. We begin with examples in the pixel domain of directly using template image data without a distance channel.

In some implementations, classification focuses on a particular cluster. In these instances, pixels on the perimeter of a cluster may have different modified intensity values, depending on which adjoining cluster is the focus of classification. The template image in the subpixel domain can indicate that an overlap pixel contributes intensity value to two different clusters. We refer to optical pixel as an "overlap pixel" when two or more adjacent or abutting clusters both overlap the pixel; both contribute to the intensity reading from the optical pixel. Watershed analysis, named after separating rain flows into different watersheds at a ridge line, can be applied to separate even abutting clusters. When data is received for classification on a cluster-by-cluster basis, the template image can be used to modify intensity data for overlap pixels along the perimeter of clusters. The overlap pixels can have different modified intensities, depending on which cluster is the focus of classification.

The modified intensity of a pixel can be reduced based on subpixel contribution in the overlap pixel to a home cluster (i.e., the cluster to which the pixel belongs or the cluster whose intensity emissions the pixel primarily depicts), as opposed to an away cluster (i.e., the non-home cluster whose intensity emissions the pixel depicts). Suppose that 5 subpixels are part of the home cluster and 2 subpixels are part of the away cluster. Then, 7 subpixels contribute intensity to the home or away cluster. During focus on the home cluster, in one implementation the overlap pixel is reduced in intensity by $7/16$, because 7 of the 16 subpixels contribute intensity to the home or away cluster. In another implementation, intensity is reduced by $5/16$, based on the area of subpixels contributing to the home cluster divided by the total number of subpixels. In a third implementation, intensity is reduced by $5/7$, based on the area of subpixels contributing to the home cluster divided by the total area of contributing subpixels. The latter two calculations change when the focus turns to the away cluster, producing fractions with "2" in the numerator.

Of course, further reduction in intensity can be applied if a distance channel is being considered along with a subpixel map of cluster shapes.

Once the pixel intensities for a cluster that is the focus of classification have been modified using the template image, the modified pixel values are convolved through layers of a neural network-based classifier to produce modified images. The modified images are used to classify bases in successive sequencing cycles.

Alternatively, classification in the pixel domain can proceed in parallel for all pixels or all clusters in a chunk of an image. Only one modification of a pixel value can be applied in this scenario to assure reusability of intermediate calculations. Any of the fractions given above can be used to modify pixel intensity, depending on whether a smaller or larger attenuation of intensity is desired.

Once the pixel intensities for the image chunk have been modified using the template image, pixels and surrounding context can be convolved through layers of a neural network-based classifier to produce modified images. Performing convolutions on an image chunk allows reuse of intermediate calculations among pixels that have shared context. The modified images are used to classify bases in successive sequencing cycles.

This description can be paralleled for application of area weights in the subpixel domain. The parallel is that weights can be calculated for individual subpixels. The weights can, but do not need to, be the same for different subpixel parts of an optical pixel. Repeating the scenario above of home and away clusters, with 5 and 2 subpixels of the overlap pixel, respectively, the assignment of intensity to a subpixel belonging to the home cluster can be $7/16$, $5/16$ or $5/7$ of the pixel intensity. Again, further reduction in intensity can be applied if a distance channel is being considered along with a subpixel map of cluster shapes.

Once the pixel intensities for the image chunk have been modified using the template image, subpixels and surrounding context can be convolved through layers of a neural network-based classifier to produce modified images. Performing convolutions on an image chunk allows reuse of intermediate calculations among subpixels that have shared context. The modified images are used to classify bases in successive sequencing cycles.

Another alternative is to apply the template image as a binary mask, in the subpixel domain, to image data interpolated into the subpixel domain. The template image can either be arranged to require a background pixel between clusters or to allow subpixels from different clusters to abut. The template image can be applied as a mask. The mask determines whether an interpolated pixel keeps the value assigned by interpolation or receives a background value (e.g., zero), if it is classified in the template image as background.

Again, once the pixel intensities for the image chunk have been masked using the template image, subpixels and surrounding context can be convolved through layers of a neural network-based classifier to produce modified images. Performing convolutions on an image chunk allows reuse of intermediate calculations among subpixels that have shared context. The modified images are used to classify bases in successive sequencing cycles.

Features of the technology disclosed are combinable to classify an arbitrary number of clusters within a shared context, reusing intermediate calculations. At optical pixel resolution, in one implementation, about ten percent of pixels hold cluster centers to be classified. In legacy systems, three by three optical pixels were grouped for analysis as potential signal contributors for a cluster center, given observation of irregularly shaped clusters. Even one 3-by-3 filter away from the top convolution layer, cluster densities are likely to roll up into pixels at cluster centers optical signals from substantially more than half of the optical pixels. Only at super sampled resolution does cluster center density for the top convolution layer drop below one percent.

Shared context is substantial in some implementations. For instance, 15-by-15 optical pixel context may contribute to accurate base classification. An equivalent 4× up sampled context would be 60-by-60 sub pixels. This extent of context helps the neural network recognize impacts of non-uniform illumination and background during imaging.

The technology disclosed uses small filters at a lower convolution layer to combine cluster boundaries in template input with boundaries detected in digital image input. Cluster boundaries help the neural network separate signal from background conditions and normalize image processing against the background.

The technology disclosed substantially reuses intermediate calculations. Suppose that 20 to 25 cluster centers appear within a context area of 15-by-15 optical pixels. Then, first layer convolutions stand to be reused 20 to 25 times in blockwise convolution roll-ups. The reuse factor is reduced layer-by-layer until the penultimate layer, which is the first time that the reuse factor at optical resolution drops below 1×.

Blockwise roll-up training and inference from multiple convolution layers applies successive roll-ups to a block of pixels or sub pixels. Around a block perimeter, there is an overlap zone in which data used during roll-up of a first data block overlaps with and can be reused for a second block of roll-ups. Within the block, in a center area surrounded by the overlap zone, are pixel values and intermediate calculations that can be rolled up and that can be reused. With an overlap zone, convolution results that progressively reduce the size of a context field, for instance from 15-by-15 to 13-by-13 by application of a 3-by-3 filter, can be written into the same memory block that holds the values convolved, conserving memory without impairing reuse of underlying calculations within the block. With larger blocks, sharing intermediate calculations in the overlap zone, requires less resources. With smaller blocks, it can be possible to calculate multiple blocks in parallel, to share the intermediate calculations in the overlap zones.

Larger filters and dilations would reduce the number of convolution layers, which may be speed calculation without impairing classification, after lower convolution layers have reacted to cluster boundaries in the template and/or digital image data.

The input channels for template data can be chosen to make the template structure consistent with classifying multiple cluster centers in a digital image field. Two alternatives described above do not satisfy this consistency criteria: reframing and distance mapping over an entire context. Reframing places the center of just one cluster in the center of an optical pixel. Better for classifying multiple clusters is supplying center offsets for pixels classified as holding cluster centers.

Distance mapping, if provided, is difficult to perform across a whole context area unless every pixel has its own distance map over a whole context. Simpler distance maps provide the useful consistency for classifying multiple clusters from a digital image input block.

A neural network can learn from classification in a template of pixels or sub pixels at the boundary of a cluster, so a distance channel can be supplanted by a template that supplies binary or ternary classification, accompanied by a cluster center offset channel. When used, a distance map can give a distance of a pixel from a cluster center to which the pixel (or subpixel) belongs. Or the distance map can give a distance to the closest cluster center. The distance map can encode binary classification with a flag value assigned to background pixels or it can be a separate channel from pixel classification. Combined with cluster center offsets, the distance map can encode ternary classification. In some implementations, particularly ones that encode pixel classifications with one or two bits, it may be desirable, at least during development, to use separate channels for pixel classification and for distance.

The technology disclosed can include reduction of calculations to save some calculation resources in upper layers. The cluster center offset channel or a ternary classification map can be used to identify centers of pixel convolutions that do not contribute to an ultimate classification of a pixel center. In many hardware/software implementations, performing a lookup during inference and skipping a convolution roll up can be more efficient in upper layer(s) than performing even nine multiplies and eight adds to apply a 3-by-3 filter. In custom hardware that pipelines calculations for parallel execution, every pixel can be classified within the pipeline. Then, the cluster center map can be used after the final convolution to harvest results for only pixels that coincide with cluster centers, because an ultimate classification is only desired for those pixels. Again, in the optical pixel domain, at currently observed cluster densities, rolled up calculations for about ten percent of the pixels would be harvested. In a 4× up sampled domain, more layers could benefit from skipped convolutions, on some hardware, because less than one percent of the sub pixel classifications in the top layer would be harvested.

Neural Network-Based Base Calling

FIG. 1 shows the processing stages used by the RTA base caller for base calling, according to one implementation. FIG. 1 also shows the processing stages used by the disclosed neural network-based base caller for base calling, according to two implementations. As shown in FIG. 1, the neural network-based base caller 218 can streamline the base calling process by obviating many of the processing stages used by the RTA base caller. The streamlining improves base calling accuracy and scale. In a first implementation of the neural network-based base caller 218, it performs base calling using location/position information of cluster centers identified from the output of the neural network-based template generator 1512. In a second implementation, the neural network-based base caller 218 does not use the location/position information of the cluster centers for base calling. The second implementation is used when a patterned flow cell design is used for cluster generation. The patterned flow cell contains nanowells that are precisely positioned relative to known fiducial locations and provide prearranged cluster distribution on the patterned flow cell. In other implementations, the neural network-based base caller 218 base calls clusters generated on random flow cells.

The discussion now turns to the neural network based base calling in which a neural network is trained to map sequencing images to base calls. The discussion is organized as follows. First, the inputs to the neural network are described. Then, the structure and form of the neural network are described. Finally, the outputs of the neural network are described.

Input

FIG. 2 illustrates one implementation of base calling using the neural network 206.

Main Input: Image Channels

The main input to the neural network 206 is image data 202. The image data 202 is derived from the sequencing images 108 produced by the sequencer 222 during a sequencing run. In one implementation, the image data 202 comprises n×n image patches extracted from the sequencing images 222, where n is any number ranging from 1 and 10,000. The sequencing run produces m image(s) per sequencing cycle for corresponding m image channels, and an image patch is extracted from each of the m image(s) to prepare the image data for a particular sequencing cycle. In different implementations such as 4-, 2-, and 1-channel chemistries, m is 4 or 2. In other implementations, m is 1, 3, or greater than 4. The image data 202 is in the optical, pixel domain in some implementations, and in the upsampled, subpixel domain in other implementations.

The image data 202 comprises data for multiple sequencing cycles (e.g., a current sequencing cycle, one or more preceding sequencing cycles, and one or more successive sequencing cycles). In one implementation, the image data 202 comprises data for three sequencing cycles, such that data for a current (time t) sequencing cycle to be base called is accompanied with (i) data for a left flanking/context/previous/preceding/prior (time t−1) sequencing cycle and (ii) data for a right flanking/context/next/successive/subsequent (time t+1) sequencing cycle. In other implementations, the image data 202 comprises data for a single sequencing cycle.

The image data 202 depicts intensity emissions of one or more clusters and their surrounding background. In one implementation, when a single target cluster is to be base called, the image patches are extracted from the sequencing images 108 in such a way that each image patch contains the center of the target cluster in its center pixel, a concept referred to herein as the "target cluster-centered patch extraction".

The image data 202 is encoded in the input data 204 using intensity channels (also called image channels). For each of the m images obtained from the sequencer 222 for a particular sequencing cycle, a separate image channel is used to encode its intensity data. Consider, for example, that the sequencing run uses the 2-channel chemistry which produces a red image and a green image at each sequencing cycle, then the input data 204 comprises (i) a first red image channel with n×n pixels that depict intensity emissions of the one or more clusters and their surrounding background captured in the red image and (ii) a second green image channel with n×n pixels that depict intensity emissions of the one or more clusters and their surrounding background captured in the green image.

In one implementation, a biosensor comprises an array of light sensors. A light sensor is configured to sense information from a corresponding pixel area (e.g., a reaction site/well/nanowell) on the detection surface of the biosensor. An analyte disposed in a pixel area is said to be associated with the pixel area, i.e., the associated analyte. At a sequencing cycle, the light sensor corresponding to the pixel area is configured to detect/capture/sense emissions/photons from the associated analyte and, in response, generate a pixel signal for each imaged channel. In one implementation, each imaged channel corresponds to one of a plurality of filter wavelength bands. In another implementation, each imaged channel corresponds to one of a plurality of imaging events at a sequencing cycle. In yet another implementation, each imaged channel corresponds to a combination of illumination with a specific laser and imaging through a specific optical filter.

Pixel signals from the light sensors are communicated to a signal processor coupled to the biosensor (e.g., via a communication port). For each sequencing cycle and each imaged channel, the signal processor produces an image whose pixels respectively depict/contain/denote/represent/characterize pixel signals obtained from the corresponding light sensors. This way, a pixel in the image corresponds to: (i) a light sensor of the biosensor that generated the pixel signal depicted by the pixel, (ii) an associated analyte whose emissions were detected by the corresponding light sensor and converted into the pixel signal, and (iii) a pixel area on the detection surface of the biosensor that holds the associated analyte.

Consider, for example, that a sequencing run uses two different imaged channels: a red channel and a green channel. Then, at each sequencing cycle, the signal processor produces a red image and a green image. This way, for a series of k sequencing cycles of the sequencing run, a sequence with k pairs of red and green images is produced as output.

Pixels in the red and green images (i.e., different imaged channels) have one-to-one correspondence within a sequencing cycle. This means that corresponding pixels in a pair of the red and green images depict intensity data for the same associated analyte, albeit in different imaged channels. Similarly, pixels across the pairs of red and green images have one-to-one correspondence between the sequencing cycles. This means that corresponding pixels in different pairs of the red and green images depict intensity data for the same associated analyte, albeit for different acquisition events/timesteps (sequencing cycles) of the sequencing run.

Corresponding pixels in the red and green images (i.e., different imaged channels) can be considered a pixel of a "per-cycle image" that expresses intensity data in a first red channel and a second green channel. A per-cycle image whose pixels depict pixel signals for a subset of the pixel areas, i.e., a region (tile) of the detection surface of the biosensor, is called a "per-cycle tile image." A patch extracted from a per-cycle tile image is called a "per-cycle image patch." In one implementation, the patch extraction is performed by an input preparer.

The image data comprises a sequence of per-cycle image patches generated for a series of k sequencing cycles of a sequencing run. The pixels in the per-cycle image patches contain intensity data for associated analytes and the intensity data is obtained for one or more imaged channels (e.g., a red channel and a green channel) by corresponding light sensors configured to detect emissions from the associated analytes. In one implementation, when a single target cluster is to be base called, the per-cycle image patches are centered at a center pixel that contains intensity data for a target associated analyte and non-center pixels in the per-cycle image patches contain intensity data for associated analytes adjacent to the target associated analyte. In one implementation, the image data is prepared by an input preparer.

Non-Image Data

In another implementation, the input data to the neural network-based base caller 218 and the neural network-based quality scorer 6102 is based on pH changes induced by the release of hydrogen ions during molecule extension. The pH changes are detected and converted to a voltage change that is proportional to the number of bases incorporated (e.g., in the case of Ion Torrent).

In yet another implementation, the input data to the neural network-based base caller 218 and the neural network-based quality scorer 6102 is constructed from nanopore sensing that uses biosensors to measure the disruption in current as an analyte passes through a nanopore or near its aperture while determining the identity of the base. For example, the Oxford Nanopore Technologies (ONT) sequencing is based on the following concept: pass a single strand of DNA (or RNA) through a membrane via a nanopore and apply a voltage difference across the membrane. The nucleotides present in the pore will affect the pore's electrical resistance, so current measurements over time can indicate the sequence of DNA bases passing through the pore. This electrical current signal (the 'squiggle' due to its appearance when plotted) is the raw data gathered by an ONT sequencer. These measurements are stored as 16-bit integer data acquisition (DAC) values, taken at 4 kHz frequency (for example). With a DNA strand velocity of ~450 base pairs per second, this gives approximately nine raw observations per base on average. This signal is then processed to identify breaks in the open pore signal corresponding to individual reads. These stretches of raw signal are base called the process of converting DAC values into a sequence of DNA bases. In some implementations, the input data comprises normalized or scaled DAC values.

Supplemental Input: Distance Channels

The image data 202 is accompanied with supplemental distance data (also called distance channels). Distance channels supply additive bias that is incorporated in the feature maps generated from the image channels. This additive bias contributes to base calling accuracy because it is based on pixel center-to-cluster center(s) distances, which are pixel-wise encoded in the distance channels.

In a "single target cluster" base calling implementation, for each image channel (image patch) in the input data 204, a supplemental distance channel identifies distances of its pixels' centers from the center of a target cluster containing its center pixel and to be base called. The distance channel thereby indicates respective distances of pixels of an image patch from a center pixel of the image patch.

In a "multi-cluster" base calling implementation, for each image channel (image patch) in the input data 204, a supplemental distance channel identifies each pixel's center-to-center distance from a nearest one of the clusters selected based on center-to-center distances between the pixel and each of the clusters.

In a "multi-cluster shape-based" base calling implementation, for each image channel (image patch) in the input data 204, a supplemental distance channel identifies each cluster pixel's center-to-center distance from an assigned cluster selected based on classifying each cluster pixel to only one cluster.

Supplemental Input: Scaling Channel

The image data 202 is accompanied with supplemental scaling data (also called scaling channel) that accounts for different cluster sizes and uneven illumination conditions. Scaling channel also supplies additive bias that is incorporated in the feature maps generated from the image channels. This additive bias contributes to base calling accuracy because it is based on mean intensities of central cluster pixel(s), which are pixel-wise encoded in the scaling channel.

Supplemental Input: Cluster Center Coordinates

In some implementations, the location/position information 216 (e.g., x-y coordinates) of cluster center(s) identified from the output of the neural network based template generator 1512 is fed as supplemental input to the neural network 206.

Supplemental Input: Cluster Attribution Information

In some implementations, the neural network 206 receives, as supplemental input, cluster attribution information that classifies which pixels or subpixels are: background pixels or subpixels, cluster center pixels or subpixels, and cluster/cluster interior pixels or subpixels depicting/contributing to/belonging to a same cluster. In other implementations, the decay map, the binary map, and/or the ternary map or a variation of those is fed as supplemental input to the neural network 206.

Pre-Processing: Intensity Modification

In some implementations, the input data 204 does not contain the distance channels, but instead the neural network 206 receives, as input, modified image data that is modified based on the output of the neural network-based template generator 1512 1512, i.e., the decay map, the binary map, and/or the ternary map. In such implementations, the intensities of the image data 202 are modified to account for the absence of distance channels.

In other implementations, the image data 202 is subjected to one or more lossless transformation operations (e.g., convolutions, deconvolutions, Fourier transforms) and the resulting modified image data is fed as input to the neural network 206.

Network Structure and Form

The neural network 206 is also referred to herein as the "neural network-based base caller" 218. In one implementation, the neural network-based base caller 218 is a multi-layer perceptron (MLP). In another implementation, the neural network-based base caller 218 is a feedforward neural network. In yet another implementation, the neural network based base caller 218 is a fully-connected neural network. In a further implementation, the neural network-based base caller 218 is a fully convolutional neural network. In yet further implementation, the neural network-based base caller 218 is a semantic segmentation neural network.

In one implementation, the neural network-based base caller 218 is a convolutional neural network (CNN) with a plurality of convolution layers. In another implementation, it is a recurrent neural network (RNN) such as a long short-term memory network (LSTM), bi-directional LSTM (Bi-LSTM), or a gated recurrent unit (GRU). In yet another implementation, it includes both a CNN and a RNN.

In yet other implementations, the neural network-based base caller 218 can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous SGD. It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tan h)), batch normalization layers, regularization layers, dropout, pooling layers (e.g., max or average pooling), global average pooling layers, and attention mechanisms.

The neural network-based base caller 218 processes the input data 204 and produces an alternative representation 208 of the input data 204. The alternative representation 208 is a convolved representation in some implementations and a hidden representation in other implementations. The alternative representation 208 is then processed by an output layer 210 to produce an output 212. The output 212 is used to produce the base call(s), as discussed below.

Output

In one implementation, the neural network-based base caller 218 outputs a base call for a single target cluster for a particular sequencing cycle. In another implementation, it outputs a base call for each target cluster in a plurality of target clusters for the particular sequencing cycle. In yet another implementation, it outputs a base call for each target cluster in a plurality of target clusters for each sequencing cycle in a plurality of sequencing cycles, thereby producing a base call sequence for each target cluster.

Distance Channel Calculation

The discussion now turns to how appropriate location/position information (e.g., x-y coordinates) of cluster center(s) is obtained for use in calculating distance values of the distance channels.

Downscaling of Coordinates

Figure 3:
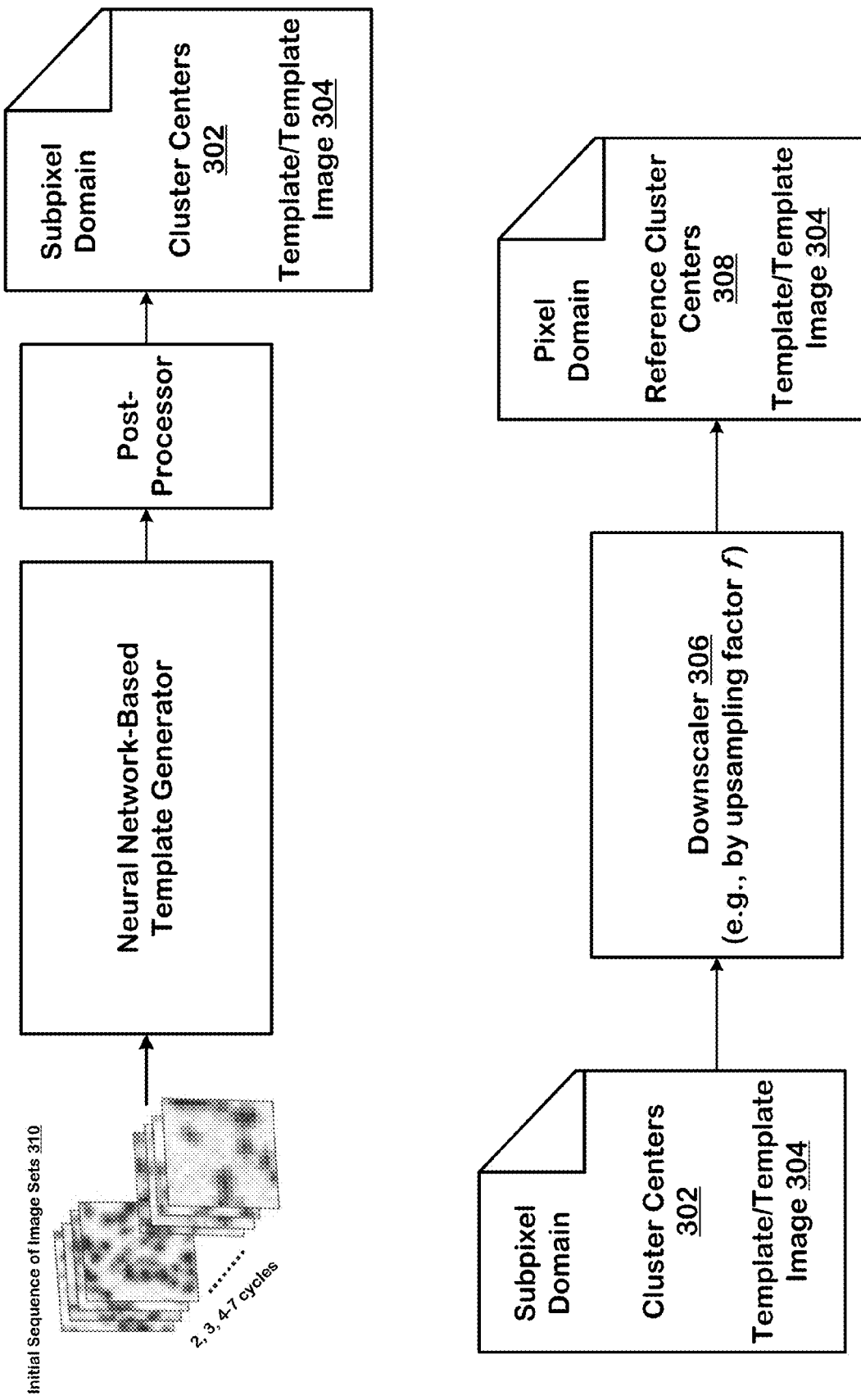
FIG. 3 is one implementation of transforming, from subpixel domain to pixel domain, location/position information of cluster centers identified from the output of the neural network-based template generator.

FIG. 3 is one implementation of transforming, from subpixel domain to pixel domain, location/position information of cluster centers identified from the output of the neural network-based template generator 1512.

Cluster center location/position information is used for the neural network based base calling at least (i) to construct the input data by extracting image patches from the sequencing images 108 that contain the centers of target clusters to be base called in their center pixels, (ii) to construct the distance channel that identifies distances of an image patch's pixels' centers from the center of a target cluster contained its center pixel, and/or (iii) as supplemental input 216 to the neural network-based base caller 218.

In some implementations, the cluster center location/position information is identified from the output of the neural network-based template generator 1512 in the upsampled, subpixel resolution. However, in some implementations, the neural network-based base caller 218 operates on image data that is in optical, pixel-resolution. Therefore, in one implementation, the cluster center location/position information is transformed into the pixel domain by downscaling coordinates of the cluster centers by the same upsampling factor used to upsample image data fed as input to the neural network-based template generator 1512.

Consider, for example, that the image patches data fed as input to the neural network-based template generator 1512 are derived by upsampling sequencing images 108 from some initial sequencing cycles by an upsampling factor f. Then, in one implementation, the coordinates of the cluster centers 302, produced by the neural network-based template generator 1512 by the post-processor 1814 and stored in the template/template image 304, are divided by f (the divisor). These downscaled cluster center coordinates are referred to herein as the "reference cluster centers" 308 and stored in the template/template image 304. In one implementation, the downscaling is performed by a downscaler 306.

Transformation of Coordinates

Figure 4:
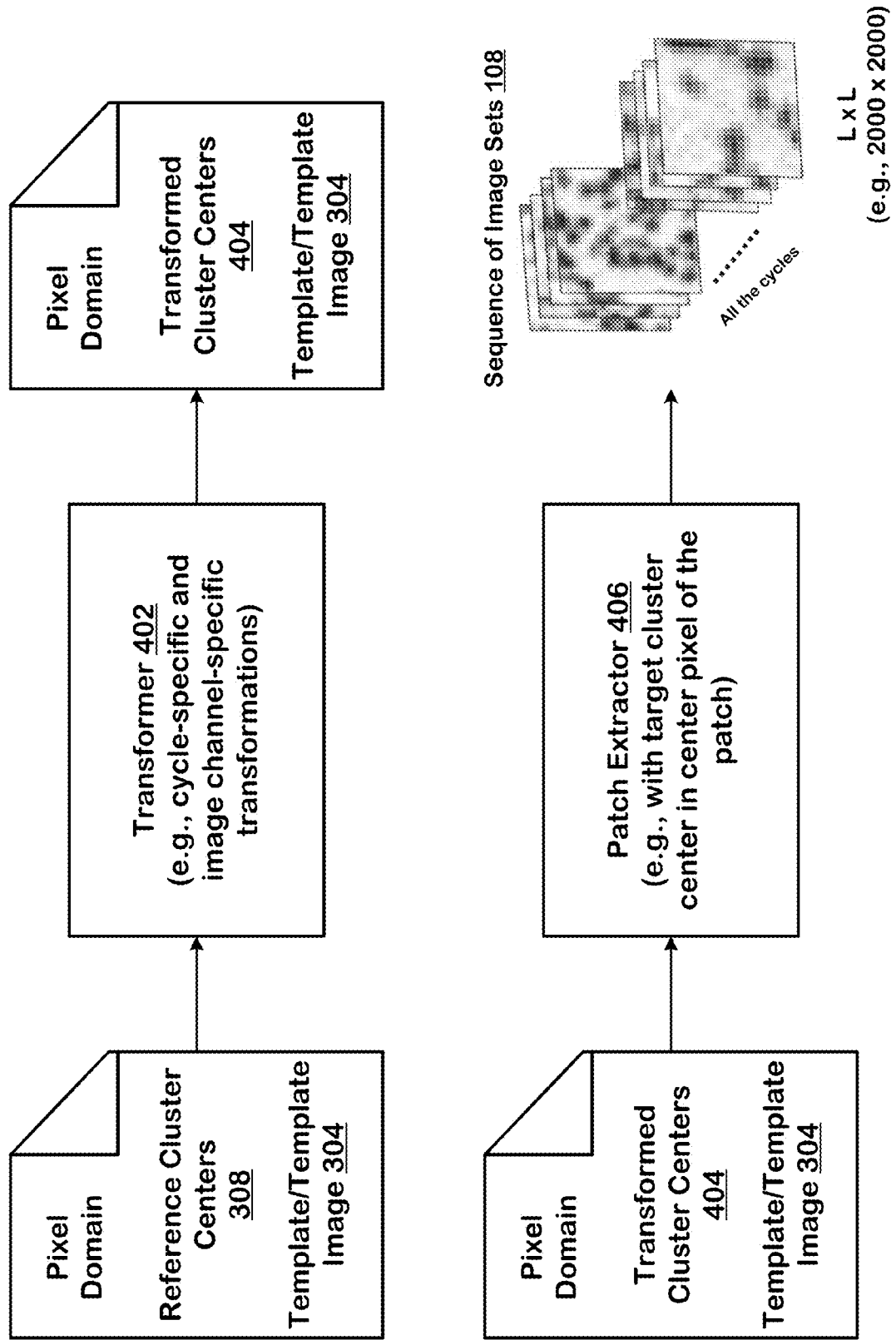
FIG. 4 is one implementation of using cycle-specific and image channel-specific transformations to derive the so-called "transformed cluster centers" from the reference cluster centers.

FIG. 4 is one implementation of using cycle-specific and image channel-specific transformations to derive the so-called "transformed cluster centers" 404 from the reference cluster centers 308. The motivation for doing so is discussed first.

Sequencing images taken at different sequencing cycles are misaligned and have random translational offsets with respect to each other. This occurs due to the finite accuracy of the movements of the sensor's motion stage and also because images taken in different image/frequency channels have different optical paths and wavelengths. Consequently, an offset exists between the reference cluster centers and locations/positions of the cluster centers in the sequencing images. This offset varies between images captured at different sequencing cycles and within images captured at a same sequencing cycle in different image channels.

To account for this offset, cycle-specific and image channel-specific transformations are applied to the reference cluster centers to produce respective transformed cluster centers for image patches of each sequencing cycle. The cycle-specific and image channel-specific transformations are derived by an image registration process that uses image correlation to determine a full six-parameter affine transformation (e.g., translation, rotation, scaling, shear, right reflection, left reflection) or a Procrustes transformation (e.g., translation, rotation, scaling, optionally extended to aspect ratio), additional details of which can be found in Appendices 1, 2, 3, and 4.

Consider, for example, that the reference cluster centers for four cluster centers are $(x_1, y_1)$; $(x_2, y_2)$; $(x_3, y_3)$; $(x_4, y_4)$ and the sequencing run uses 2-channel chemistry in which a red image and a green image are produced at each sequencing cycle. Then, for example sequencing cycle 3, the cycle-specific and image channel-specific transformations are $\{\alpha_r^3, \beta_r^3, \chi_r^3, \delta_r^3, \varepsilon_r^3, \phi_r^3\}$ for the red image and $\{\alpha_g^3, \beta_g^3, \chi_g^3, \delta_g^3, \varepsilon_g^3, \phi_g^3\}$ for the green image.

Similarly, for example sequencing cycle 9, the cycle-specific and image channel-specific transformations are $\{\alpha_r^9, \beta_r^9, \chi_r^9, \delta_r^9, \varepsilon_r^9, \phi_r^9\}$ for the red image and $\{\alpha_g^9, \beta_g^9, \chi_g^9, \delta_g^9, \varepsilon_g^9, \phi_g^9\}$ for the green image.

Then, the transformed cluster centers for the red image of sequencing cycle 3 $(\hat{x}_1, \hat{y}_1); \hat{x}_2, \hat{y}_2), (\hat{x}_3, \hat{y}_3), (\hat{x}_4, \hat{y}_4)$ are derived by applying the transformation $\{\alpha_r^3, \beta_r^3, \chi_r^3, \delta_r^3, \varepsilon_r^3, \phi_r^3\}$ to the reference cluster centers $(x_1, y_1); (x_2, y_2); (x_3, y_3); (x_4, y_4)$, and the transformed cluster centers for the green image of sequencing cycle 3 $(\tilde{x}_1, \tilde{y}_1); (\tilde{x}_2, \tilde{y}_2); (\tilde{x}_3, \tilde{y}_3); (\tilde{x}_4, \tilde{y}_4)$ are derived by applying the transformation $\{\alpha_g^3, \beta_g^3, \chi_g^3, \delta_g^3, \varepsilon_g^3, \phi_g^3\}$ to the reference cluster centers $(x_1, y_1); (x_2, y_2); (x_3, y_3); (x_4, y_4)$.

Similarly, the transformed cluster centers for the red image of sequencing cycle 9 $(\vec{x}_1, \vec{y}_1); (\vec{x}_2, \vec{y}_2); (\vec{x}_3, \vec{y}_3); (\vec{x}_4, \vec{y}_4)$ are derived by applying the transformation $\{\alpha_r^9, \beta_r^9, \chi_r^9, \delta_r^9, \varepsilon_r^9, \phi_r^9\}$ to the reference cluster centers $(x_1, y_1); (x_2, y_2); (x_3, y_3); (x_4, y_4)$, and the transformed cluster centers for the green image of sequencing cycle 9 $(\tilde{x}_1, \tilde{y}_1); (\tilde{x}_2, \tilde{y}_2); (\tilde{x}_3, \tilde{y}_3); (\tilde{x}_4, \tilde{y}_4)$ are derived by applying the transformation $\{\alpha_g^9, \beta_g^9, \chi_g^9, \delta_g^9, \varepsilon_g^9, \phi_g^9\}$ to the reference cluster centers $(x_1, y_1); (x_2, y_2); (x_3, y_3); (x_4, y_4)$.

In one implementation, the transformations are performed by a transformer 402.

The transformed cluster centers 404 are the stored in the template/template image 304 and respectively used (i) to do the patch extraction from corresponding sequencing images 108 (e.g., by a patch extractor 406), (ii) in the distance formula $d=(x_2-x_1)^2+(y_2-y_1)^2$) to calculate the distance channels for corresponding image patches, and (iii) as supplemental input to the neural network-based base caller 218 for the corresponding sequencing cycle being base called. In other implementations, a different distance formula can be used such as distance squared, $e^\wedge$-distance, and $e^\wedge$-distance squared.

Image Patch

Figure 5:
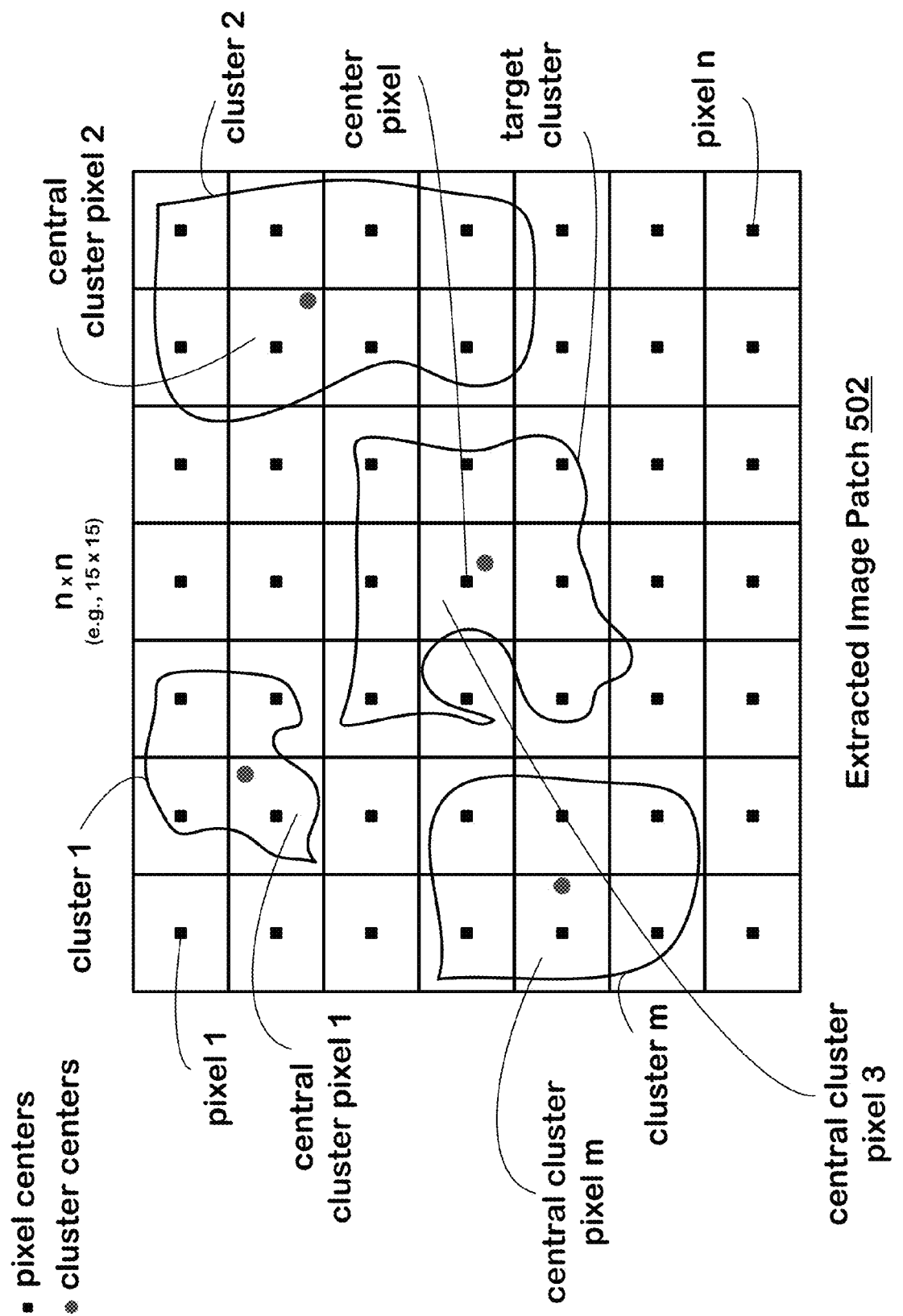
FIG. 5 illustrates an image patch that is part of the input data fed to the neural network-based base caller.

FIG. 5 illustrates an image patch 502 that is part of the input data fed to the neural network-based base caller 218. The input data includes a sequence of per-cycle image patch sets generated for a series of sequencing cycles of a sequencing run. Each per-cycle image patch set in the sequence has an image patch for a respective one of one or more image channels.

Consider, for example, that the sequencing run uses the 2-channel chemistry which produces a red image and a green image at each sequencing cycle, and the input data comprises data spanning a series of three sequencing cycles of the sequencing run: a current (time t) sequencing cycle to be base called, a previous (time t−1) sequencing cycle, and a next (time t+1) sequencing cycle.

Then, the input data comprises the following sequence of per-cycle image patch sets: a current cycle image patch set with a current red image patch and a current green image patch respectively extracted from the red and green sequencing images captured at the current sequencing cycle, a previous cycle image patch set with a previous red image patch and a previous green image patch respectively extracted from the red and green sequencing images captured at the previous sequencing cycle, and a next cycle image patch set with a next red image patch and a next green image patch respectively extracted from the red and green sequencing images captured at the next sequencing cycle.

The size of each image patch can be n×n, where n can be any number ranging from 1 and 10,000. Each image patch can be in the optical, pixel domain or in the upsampled, subpixel domain. In the implementation illustrated in FIG. 5, the extracted image page 502 has pixel intensity data for pixels that cover/depict a plurality of clusters 1-m and their surrounding background. Also, in the illustrated implementation, the image patch 502 is extracted in such a way that is contains in its center pixel the center of a target cluster being base called.

In FIG. 5, the pixel centers are depicted by a black rectangle and have integer location/position coordinates, and the cluster centers are depicted by a purple circle and have floating-point location/position coordinates.

Distance Calculation for a Single Target Cluster

Figure 6:
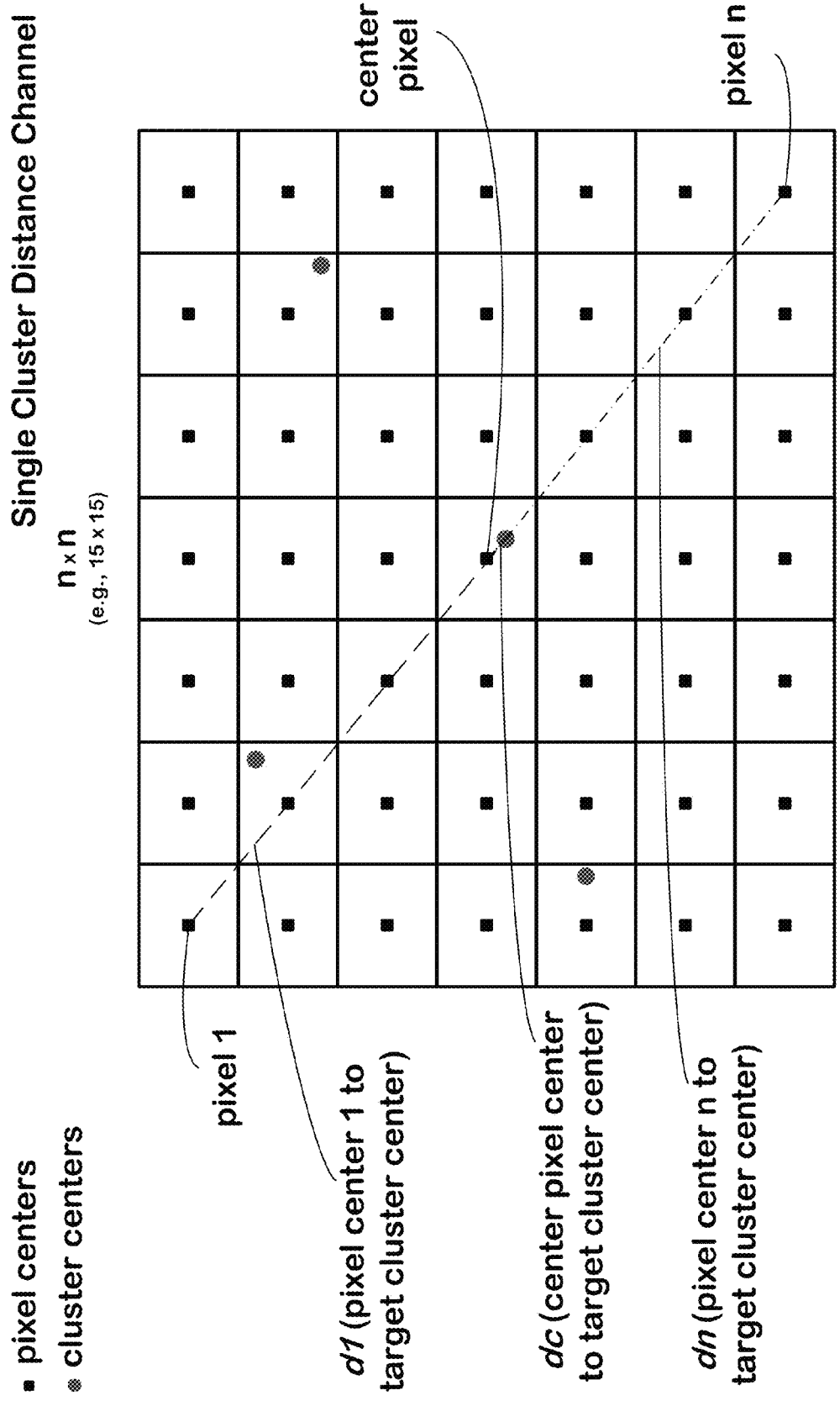
FIG. 6 depicts one implementation of determining distance values for a distance channel when a single target cluster is being base called by the neural network-based base caller.

FIG. 6 depicts one implementation of determining distance values 602 for a distance channel when a single target cluster is being base called by the neural network-based base caller 218. The center of the target cluster is contained in the center pixels of the image patches that are fed as input to the neural network based base caller 218. The distance values are calculated on a pixel-by-pixel basis, such that, for each pixel, the distance between its center and the center of the target cluster is determined. Accordingly, a distance value is calculated for each pixel in each of the image patches that are part of the input data.

FIG. 6 shows three distance values dl, dc, and do for a particular image patch. In one implementation, the distance values 602 are calculated using the following distance formula: $d=\sqrt{(x_2-x_1)^2+(y_2-y_1)^2}$, which operates on the transformed cluster centers 404.

In other implementations, a different distance formula can be used such as distance squared, $e^\wedge$-distance, and $e^\wedge$-distance squared.

In other implementations, when the image patches are in the upsampled, subpixel resolution, the distance values 602 are calculated in the subpixel domain.

Thus, in the single target cluster base calling implementation, the distance channels are calculated only with respect to the target cluster being base called.

Figure 7:
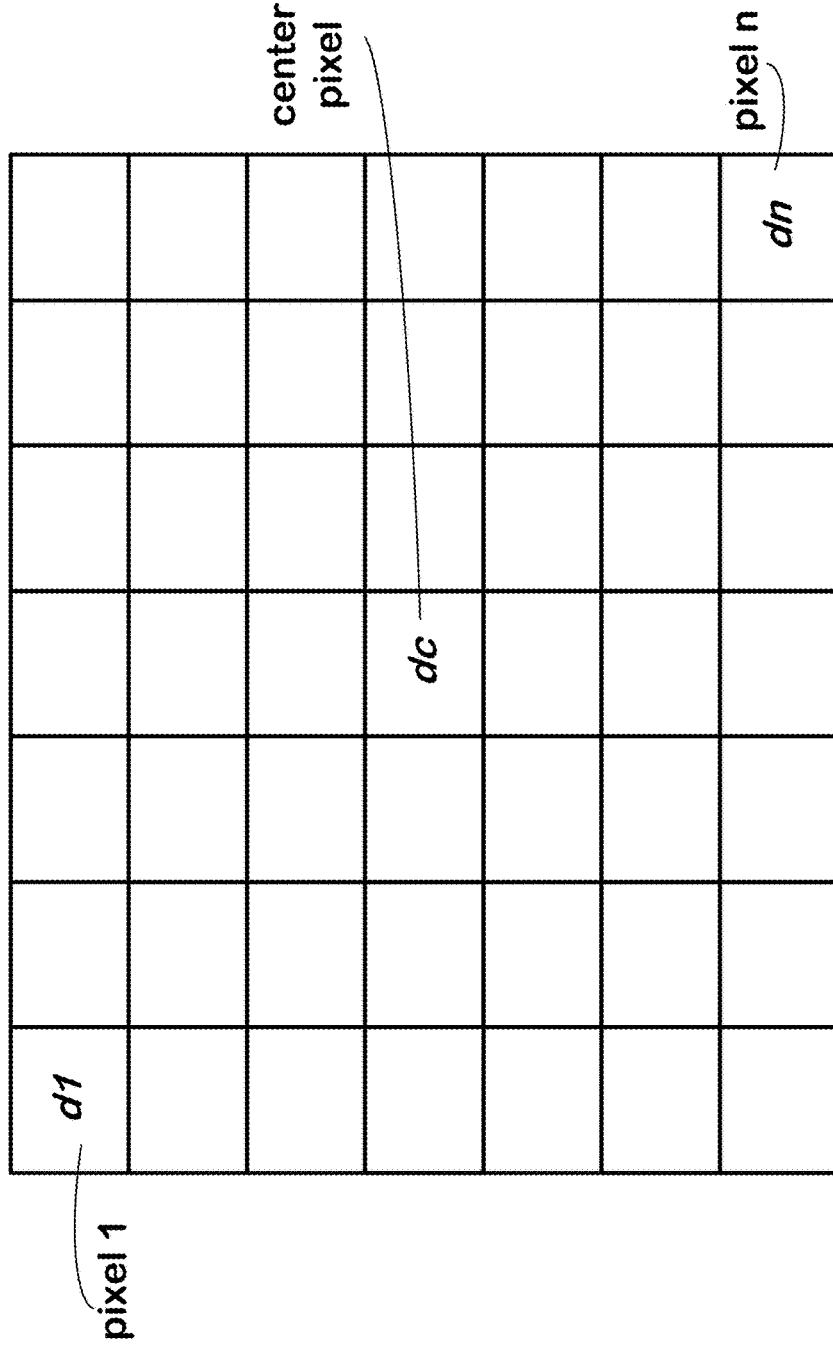
FIG. 7 shows one implementation of pixel-wise encoding the distance values that are calculated between the pixels and the target cluster.

FIG. 7 shows one implementation of pixel-wise encoding 702 the distance values 602 that are calculated between the pixels and the target cluster. In one implementation, in the input data, the distance values 602, as part of the distance channel, supplement each corresponding image channel (image patch) as "pixel distance data". Returning to the example of a red image and a green image being generated per-sequencing cycle, the input data comprises a red distance channel and a green distance channel that supplement the red image channel and the green image channel as pixel distance data, respectively.

In other implementations, when the image patches are in the upsampled, subpixel resolution, the distance channels are encoded on a subpixel-by-subpixel basis.

Distance Calculation for Multiple Target Clusters

FIG. 8a depicts one implementation of determining distance values 802 for a distance channel when multiple target clusters 1-m are being simultaneously base called by the neural network-based base caller 218. The distance values are calculated on a pixel-by-pixel basis, such that, for each pixel, the distance between its center and respective centers of each of the multiple clusters 1-m is determined and the minimum distance value (in red) is assigned to the pixel.

Accordingly, the distance channel identifies each pixel's center-to-center distance from a nearest one of the clusters selected based on center-to-center distances between the pixel and each of the clusters. In the illustrated implementation, FIG. 8a shows pixel center-to-cluster center distances for two pixels and four cluster centers. Pixel 1 is nearest to cluster 1 and pixel n is nearest to cluster 3.

In one implementation, the distance values 802 are calculated using the following distance formula: $d=\sqrt{(x_2-x_1)^2+(y_2-y_1)^2}$, which operates on the transformed cluster centers 404. In other implementations, a different distance formula can be used such as distance squared, $e^\wedge$-distance, and $e^\wedge$-distance squared.

In other implementations, when the image patches are in the upsampled, subpixel resolution, the distance values 802 are calculated in the subpixel domain.

Thus, in the multi-cluster base calling implementation, the distance channels are calculated with respect to the nearest cluster from among a plurality of clusters.

Figure 8B:
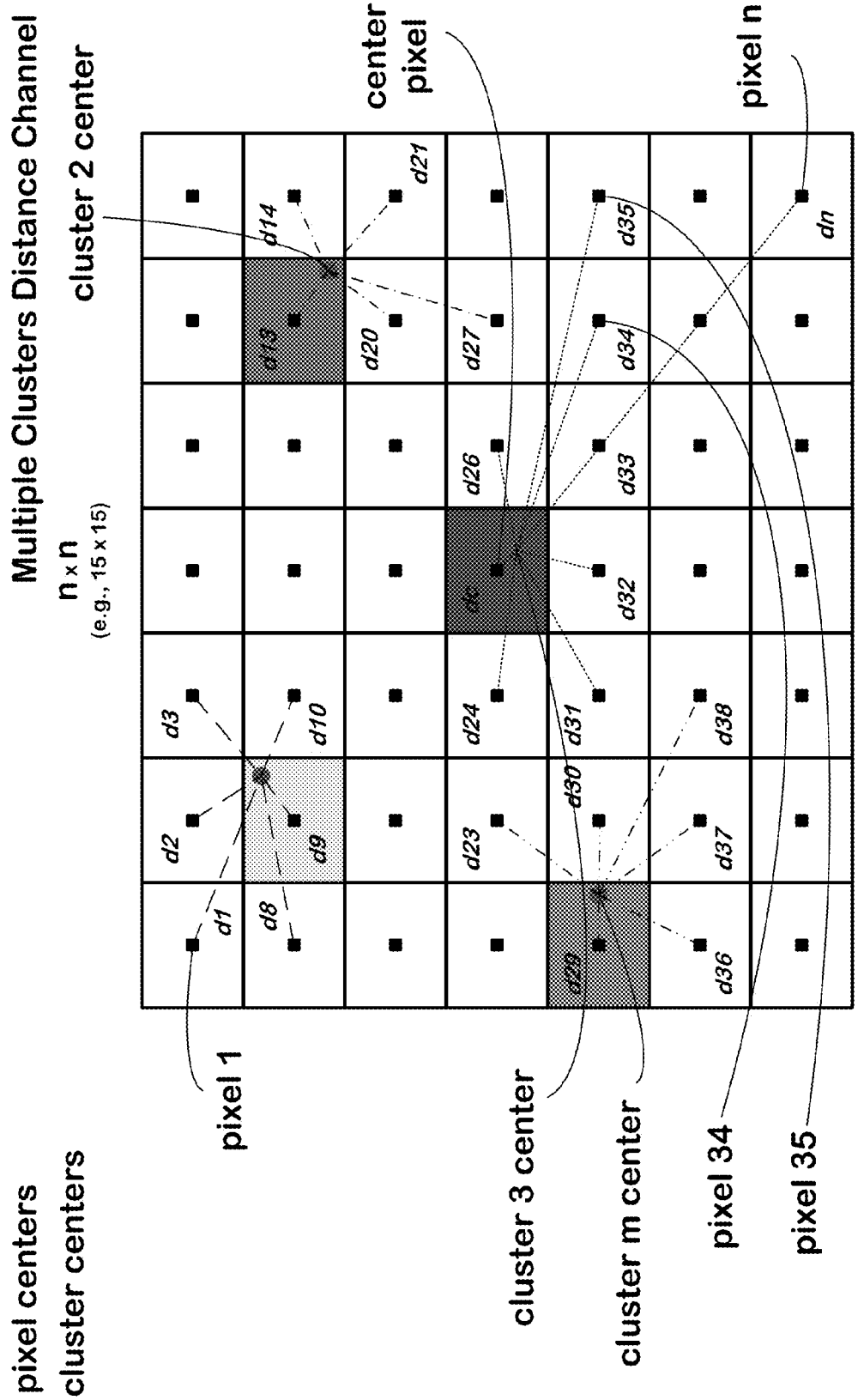
FIG. 8b shows, for each of the target clusters, some nearest pixels determined based on the pixel center-to-nearest cluster center distances.

FIG. 8b shows, for each of the target clusters 1-m, some nearest pixels determined based on the pixel center-to-nearest cluster center distances 804 (d1, d2, d23, d29, d24, d32, dn, d13, d14, and etc.).

FIG. 9 shows one implementation of pixel-wise encoding 902 the minimum distance values that are calculated between the pixels and the nearest one of the clusters. In other implementations, when the image patches are in the upsampled, subpixel resolution, the distance channels are encoded on a subpixel-by-subpixel basis.

Distance Calculation for Multiple Target Clusters Based on Cluster Shapes

Figure 10:
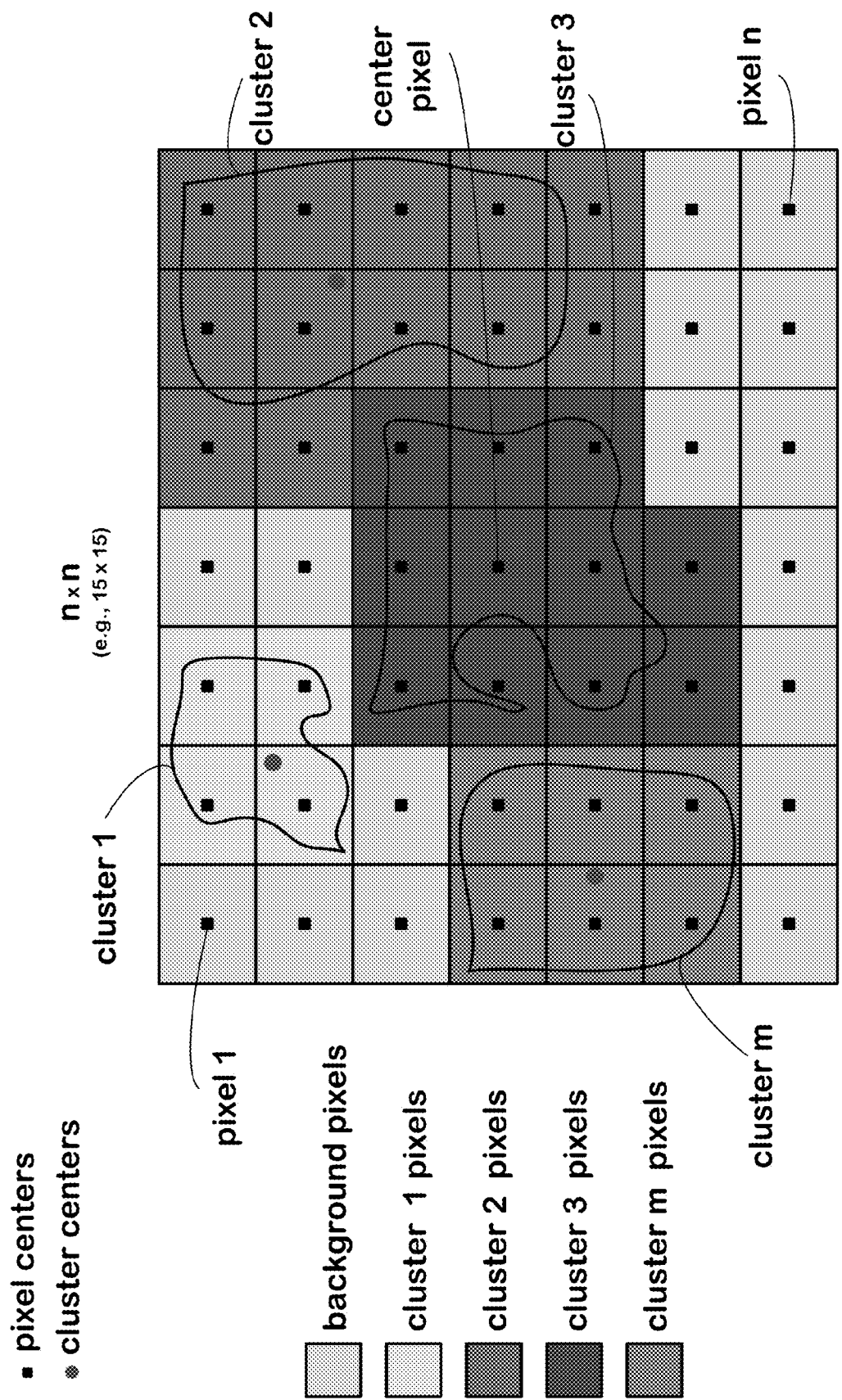
FIG. 10 illustrates one implementation using pixel-to-cluster classification/attribution/categorization, referred to herein as "cluster shape data".

FIG. 10 illustrates one implementation using pixel-to-cluster classification/attribution/categorization 1002, referred to herein as "cluster shape data" or "cluster shape information", to determine cluster distance values 1102 for a distance channel when multiple target clusters 1-m are being simultaneously base called by the neural network-based base caller 218. First, what follows is a brief review of how the cluster shape data is generated.

As discussed above, the output of the neural network-based template generator 1512 is used to classify the pixels as: background pixels, center pixels, and cluster/cluster interior pixels depicting/contributing to/belonging to a same cluster. This pixel-to-cluster classification information is used to attribute each pixel to only one cluster, irrespective of the distances between the pixel centers and the cluster centers, and is stored as the cluster shape data.

In the implementation illustrated in FIG. 10, background pixels are colored in grey, pixels belonging to cluster 1 are colored in yellow (cluster 1 pixels), pixels belonging to cluster 2 are colored in green (cluster 2 pixels), pixels belonging to cluster 3 are colored in red (cluster 3 pixels), and pixels belonging to cluster m are colored in blue (cluster m pixels).

Figure 11:
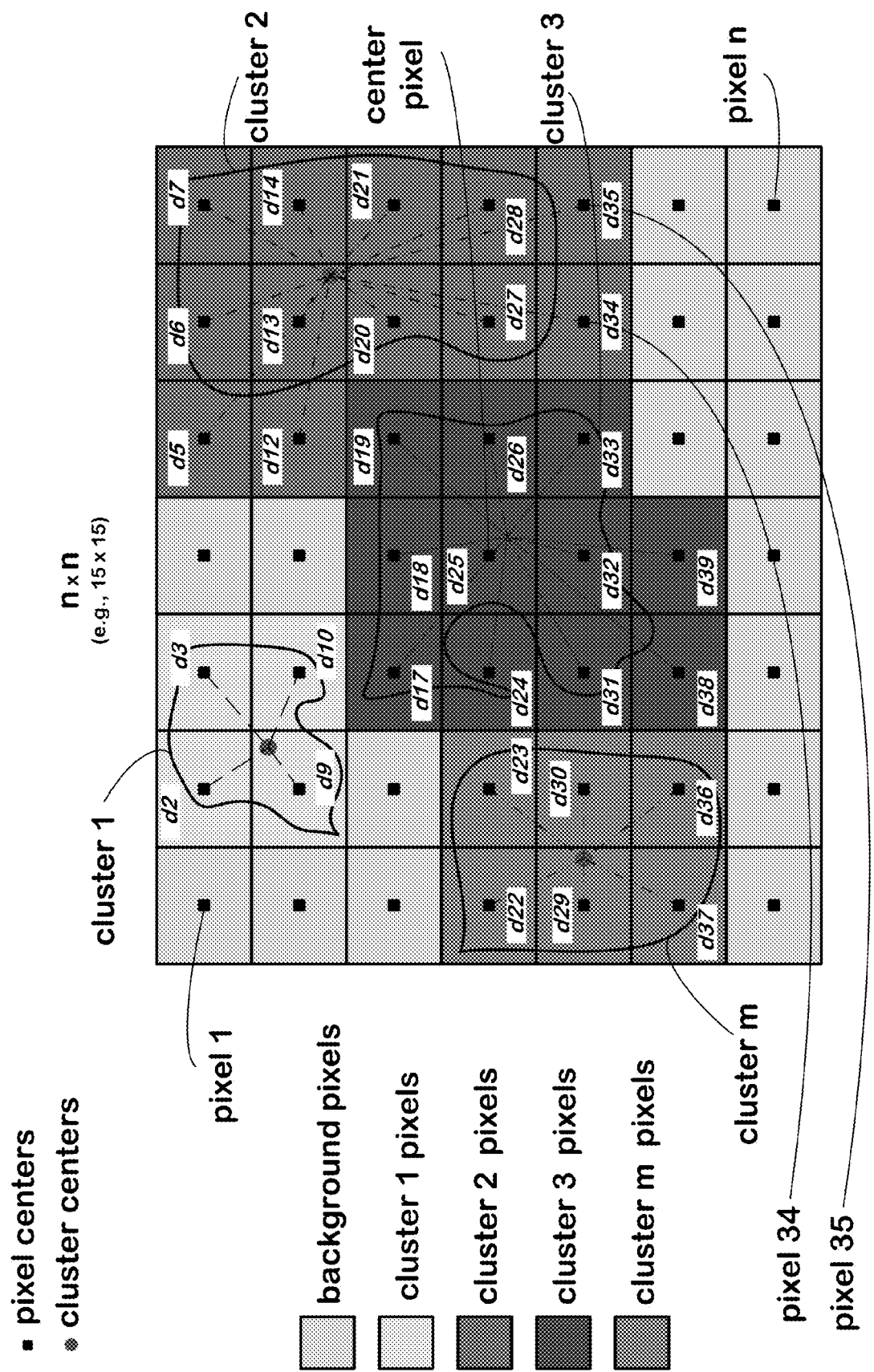
FIG. 11 shows one implementation of calculating the distance values using the cluster shape data.

FIG. 11 shows one implementation of calculating the distance values 1102 using the cluster shape data. First, we explain why distance information calculated without accounting for cluster shapes is prone to error. We then explain how the cluster shape data overcomes this limitation.

In the "multi-cluster" base calling implementation that does not use cluster shape data (FIGS. 8a-b and 9), the center-to-center distance value for a pixel is calculated with respect to the nearest cluster from among a plurality of clusters. Now, consider the scenario when a pixel that belongs to cluster A is further away from the center of cluster A but nearer to the center of cluster B. In such a case, without the cluster shape data, the pixel is assigned a distance value that is calculated with respect to cluster B (to which it does not belong), instead of being assigned a distance value vis-a-vis cluster A (to which it truly belongs).

The "multi-cluster shape-based" base calling implementation avoids this by using the true pixel-to-cluster mapping, as defined in the raw image data and produced by the neural network-based template generator 1512.

Contrast between the two implementations can be seen with regards to pixels 34 and 35. In FIG. 8b, distance values of pixels 34 and 35 are calculated with respect to the nearest center of cluster 3, without accounting for the cluster shape data. However, in FIG. 11, based on the cluster shape data, distance values 1102 of pixels 34 and 35 are calculated with respect to cluster 2 (to which they actually belong).

In FIG. 11, the cluster pixels depict cluster intensities and the background pixels depict background intensities. The cluster distance values identify each cluster pixel's center-to-center distance from an assigned one of the clusters selected based on classifying each cluster pixel to only one of the clusters. In some implementations, the background pixels are assigned a predetermined background distance value, such as 0 or 0.1, or some other minimum value.

In one implementation, as discussed above, the cluster distance values 1102 are calculated using the following distance formula: $d=\sqrt{(x_2-x_1)^2+(y_2-y_1)^2}$, which operates on the transformed cluster centers 404. In other implementations, a different distance formula can be used such as distance squared, $e^\wedge$-distance, and $e^\wedge$-distance squared.

In other implementations, when the image patches are in the upsampled, subpixel resolution, the cluster distance values 1102 are calculated in the subpixel domain and the cluster and background attribution 1002 occurs on a subpixel-by-subpixel basis.

Thus, in the multi-cluster shape-based base calling implementation, the distance channels are calculated with respect to an assigned cluster from among a plurality of clusters. The assigned cluster is selected based on classifying each cluster pixel to only one of the clusters in accordance with the true pixel-to-cluster mapping defined in the raw image data.

FIG. 12 shows one implementation of pixel-wise encoding the distance values 1002 that are calculated between the pixels and the assigned clusters. In other implementations, when the image patches are in the upsampled, subpixel resolution, the distance channels are encoded on a subpixel-by-subpixel basis.

Deep learning is a powerful machine learning technique that uses many-layered neural networks. One particularly successful network structure in computer vision and image processing domains is the convolutional neural network (CNN), where each layer performs a feed-forward convolutional transformations from an input tensor (an image-like, multi-dimensional dense array) to an output tensor of different shape. CNNs are particularly suited for image-like input due the spatial coherence of images and the advent of general purpose graphics processing units (GPUs) which make training fast on arrays up to 3- or 4-D. Exploiting these image-like properties leads to superior empirical performance compared to other learning methods such as support vector machine (SVM) or multi-layer perceptron (MLP).

We introduce a specialized architecture that augments a standard CNN to handle both image data and supplemental distance and scaling data. More details follow.

Specialized Architecture

Figure 13:
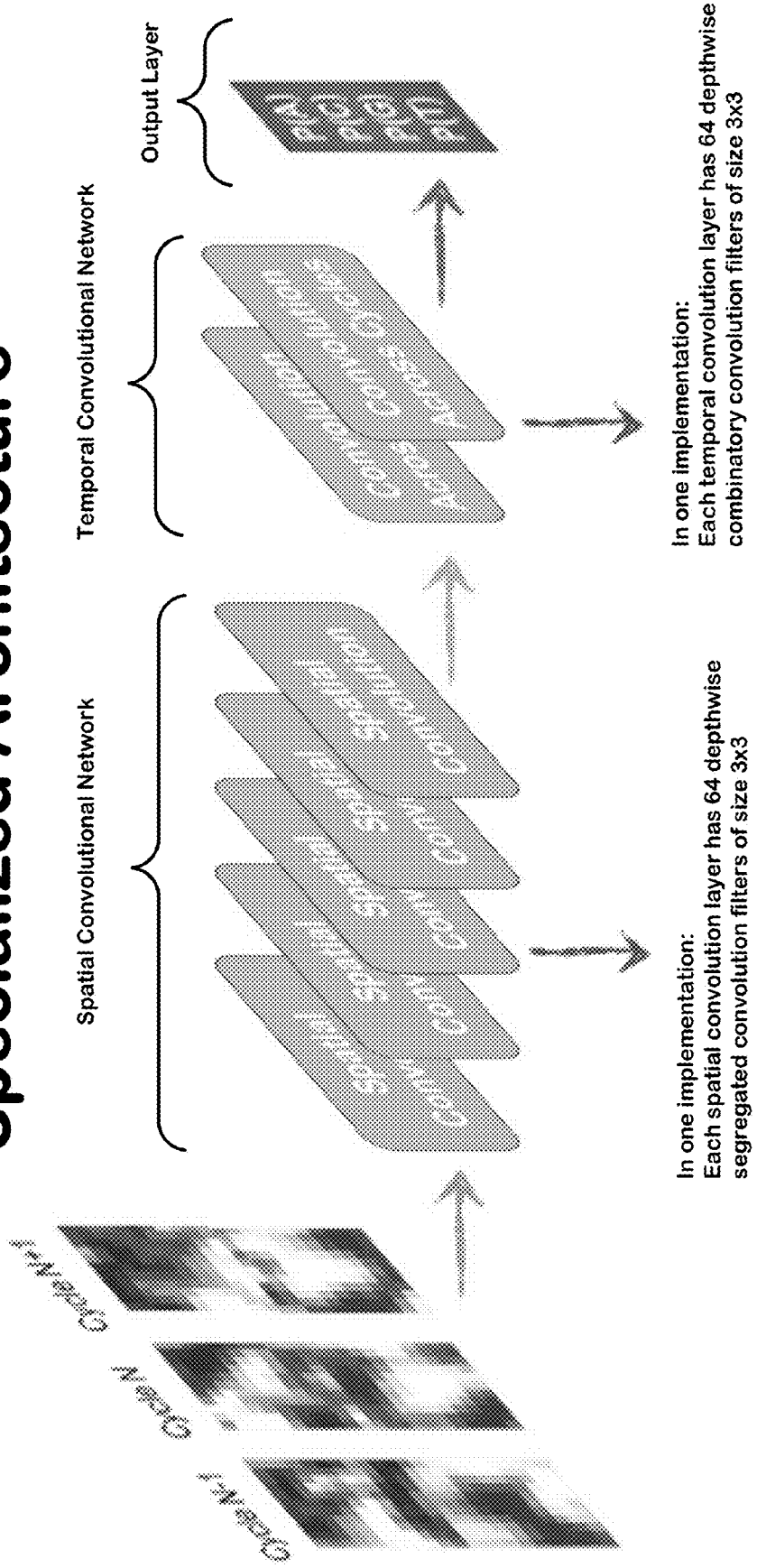
FIG. 13 illustrates one implementation of the specialized architecture of the neural network-based base caller that is used to segregate processing of data for different sequencing cycles.

FIG. 13 illustrates one implementation of the specialized architecture of the neural network-based base caller 218 that is used to segregate processing of data for different sequencing cycles. The motivation for using the specialized architecture is described first.

As discussed above, the neural network-based base caller 218 processes data for a current sequencing cycle, one or more preceding sequencing cycles, and one or more successive sequencing cycles. Data for additional sequencing cycles provides sequence-specific context. The neural network based base caller 218 learns the sequence-specific context during training and base call them. Furthermore, data for pre and post sequencing cycles provides second order contribution of pre-phasing and phasing signals to the current sequencing cycle.

Spatial Convolution Layers

However, as discussed above, images captured at different sequencing cycles and in different image channels are misaligned and have residual registration error with respect to each other. To account for this misalignment, the specialized architecture comprises spatial convolution layers that do not mix information between sequencing cycles and only mix information within a sequencing cycle.

Spatial convolution layers use so-called "segregated convolutions" that operationalize the segregation by independently processing data for each of a plurality of sequencing cycles through a "dedicated, non-shared" sequence of convolutions. The segregated convolutions convolve over data and resulting feature maps of only a given sequencing cycle, i.e., intra-cycle, without convolving over data and resulting feature maps of any other sequencing cycle.

Consider, for example, that the input data comprises (i) current data for a current (time t) sequencing cycle to be base called, (ii) previous data for a previous (time t−1) sequencing cycle, and (iii) next data for a next (time t+1) sequencing cycle. The specialized architecture then initiates three separate data processing pipelines (or convolution pipelines), namely, a current data processing pipeline, a previous data processing pipeline, and a next data processing pipeline. The current data processing pipeline receives as input the current data for the current (time t) sequencing cycle and independently processes it through a plurality of spatial convolution layers to produce a so-called "current spatially convolved representation" as the output of a final spatial convolution layer. The previous data processing pipeline receives as input the previous data for the previous (time t−1) sequencing cycle and independently processes it through the plurality of spatial convolution layers to produce a so-called "previous spatially convolved representation" as the output of the final spatial convolution layer. The next data processing pipeline receives as input the next data for the next (time t+1) sequencing cycle and independently processes it through the plurality of spatial convolution layers to produce a so-called "next spatially convolved representation" as the output of the final spatial convolution layer.

In some implementations, the current, previous, and next processing pipelines are executed in parallel.

In some implementations, the spatial convolution layers are part of a spatial convolutional network (or subnetwork) within the specialized architecture.

Temporal Convolution Layers

The neural network-based base caller 218 further comprises temporal convolution layers that mix information between sequencing cycles, i.e., inter-cycles. The temporal convolution layers receive their inputs from the spatial convolutional network and operate on the spatially convolved representations produced by the final spatial convolution layer for the respective data processing pipelines.

The inter-cycle operability freedom of the temporal convolution layers emanates from the fact that the misalignment property, which exists in the image data fed as input to the spatial convolutional network, is purged out from the spatially convolved representations by the cascade of segregated convolutions performed by the sequence of spatial convolution layers.

Temporal convolution layers use so-called "combinatory convolutions" that groupwise convolve over input channels in successive inputs on a sliding window basis. In one implementation, the successive inputs are successive outputs produced by a previous spatial convolution layer or a previous temporal convolution layer.

In some implementations, the temporal convolution layers are part of a temporal convolutional network (or subnetwork) within the specialized architecture. The temporal convolutional network receives its inputs from the spatial convolutional network. In one implementation, a first temporal convolution layer of the temporal convolutional network groupwise combines the spatially convolved representations between the sequencing cycles. In another implementation, subsequent temporal convolution layers of the temporal convolutional network combine successive outputs of previous temporal convolution layers.

The output of the final temporal convolution layer is fed to an output layer that produces an output. The output is used to base call one or more clusters at one or more sequencing cycles.

What follows is a more detailed discussion of the segregated and combinatory convolutions.

Segregated Convolutions

During a forward propagation, the specialized architecture processes information from a plurality of inputs in two stages. In the first stage, segregation convolutions are used to prevent mixing of information between the inputs. In the second stage, combinatory convolutions are used to mix information between the inputs. The results from the second stage are used to make a single inference for the plurality of inputs.

This is different than the batch mode technique where a convolution layer processes multiple inputs in a batch at the same time and makes a corresponding inference for each input in the batch. In contrast, the specialized architecture maps the plurality of inputs to the single inference. The single inference can comprise more than one prediction, such as a classification score for each of the four bases (A, C, T, and G).

In one implementation, the inputs have temporal ordering such that each input is generated at a different time step and has a plurality of input channels. For example, the plurality of inputs can include the following three inputs: a current input generated by a current sequencing cycle at time step (t), a previous input generated by a previous sequencing cycle at time step (t−1), and a next input generated by a next sequencing cycle at time step (t+1). In another implementation, each input is respectively derived from the current, previous, and next inputs by one or more previous convolution layers and includes k feature maps.

In one implementation, each input can include the following five input channels: a red image channel (in red), a red distance channel (in yellow), a green image channel (in green), a green distance channel (in purple), and a scaling channel (in blue). In another implementation, each input can include k feature maps produced by a previous convolution layer and each feature map is treated as an input channel.

Figure 14:
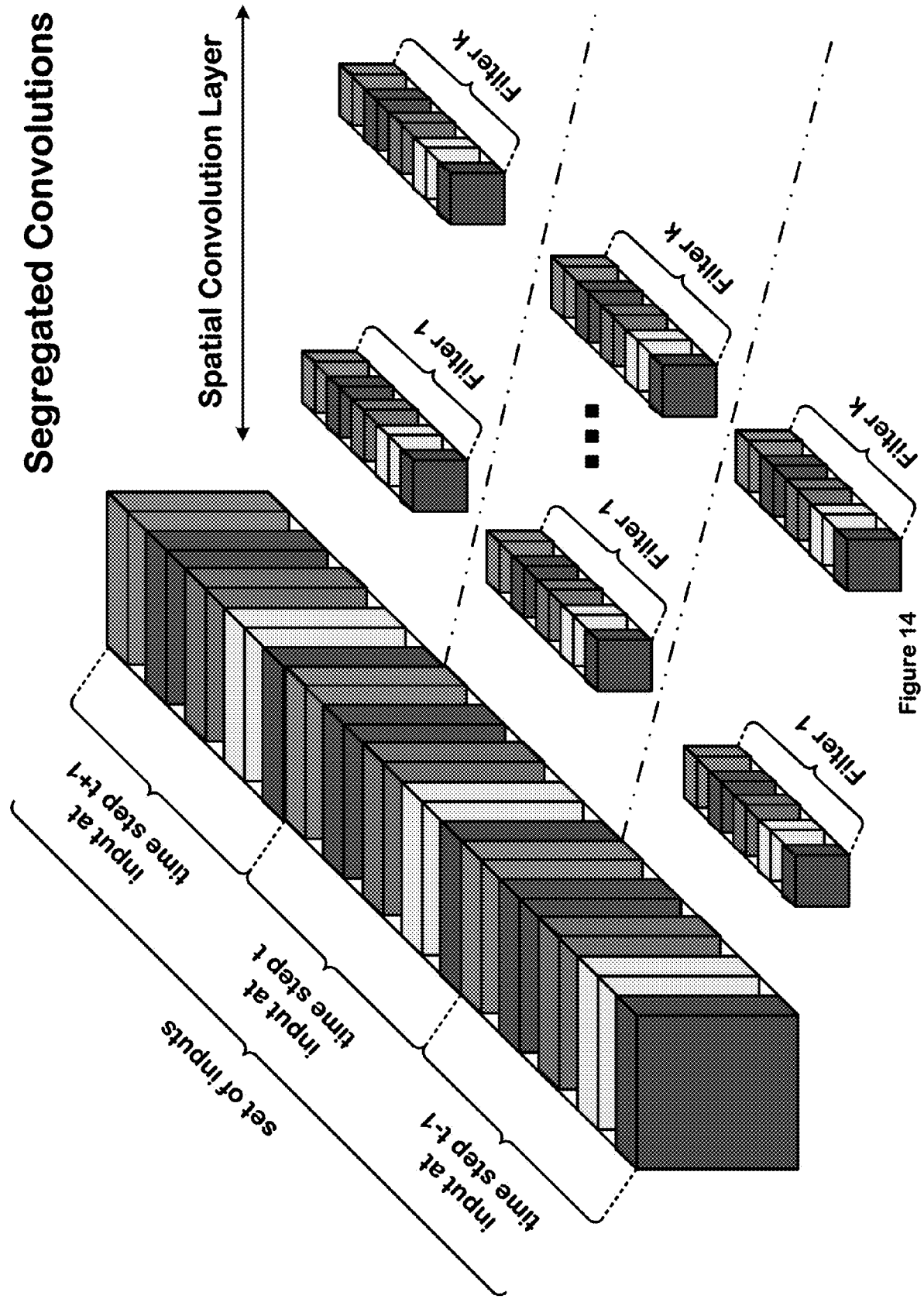
FIG. 14 depicts one implementation of segregated convolutions.

FIG. 14 depicts one implementation of the segregated convolutions. Segregated convolutions process the plurality of inputs at once by applying a convolution filter to each input in parallel. With the segregated convolutions, the convolution filter combines input channels in a same input and does not combine input channels in different inputs. In one implementation, a same convolution filter is applied to each input in parallel. In another implementation, a different convolution filter is applied to each input in parallel. In some implementations, each spatial convolution layer comprises a bank of k convolution filters, each of which applies to each input in parallel.

Combinatory Convolutions

Combinatory convolutions mix information between different inputs by grouping corresponding input channels of the different inputs and applying a convolution filter to each group. The grouping of the corresponding input channels and application of the convolution filter occurs on a sliding window basis. In this context, a window spans two or more successive input channels representing, for instance, outputs for two successive sequencing cycles. Since the window is a sliding window, most input channels are used in two or more windows.

In some implementations, the different inputs originate from an output sequence produced by a preceding spatial or temporal convolution layer. In the output sequence, the different inputs are arranged as successive outputs and therefore viewed by a next temporal convolution layer as successive inputs. Then, in the next temporal convolution layer, the combinatory convolutions apply the convolution filter to groups of corresponding input channels in the successive inputs.

In one implementation, the successive inputs have temporal ordering such that a current input is generated by a current sequencing cycle at time step (t), a previous input is generated by a previous sequencing cycle at time step (t−1), and a next input is generated by a next sequencing cycle at time step (t+1). In another implementation, each successive input is respectively derived from the current, previous, and next inputs by one or more previous convolution layers and includes k feature maps.

In one implementation, each input can include the following five input channels: a red image channel (in red), a red distance channel (in yellow), a green image channel (in green), a green distance channel (in purple), and a scaling channel (in blue). In another implementation, each input can include k feature maps produced by a previous convolution layer and each feature map is treated as an input channel.

The depth B of the convolution filter is dependent upon the number of successive inputs whose corresponding input channels are groupwise convolved by the convolution filter on a sliding window basis. In other words, the depth B is equal to the number of successive inputs in each sliding window and the group size.

Figure 15A:
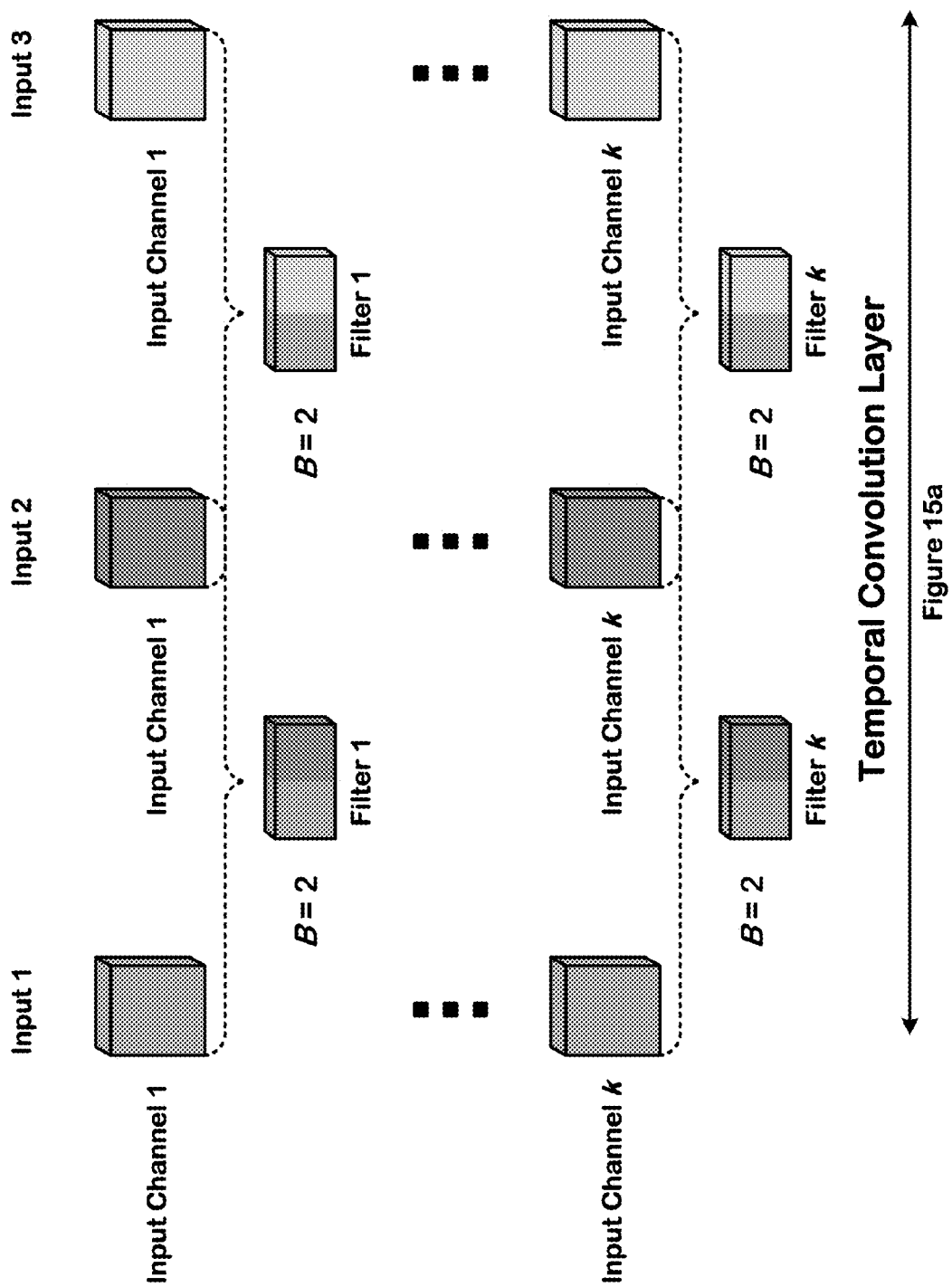
FIG. 15a depicts one implementation of combinatory convolutions.
Figure 15B:
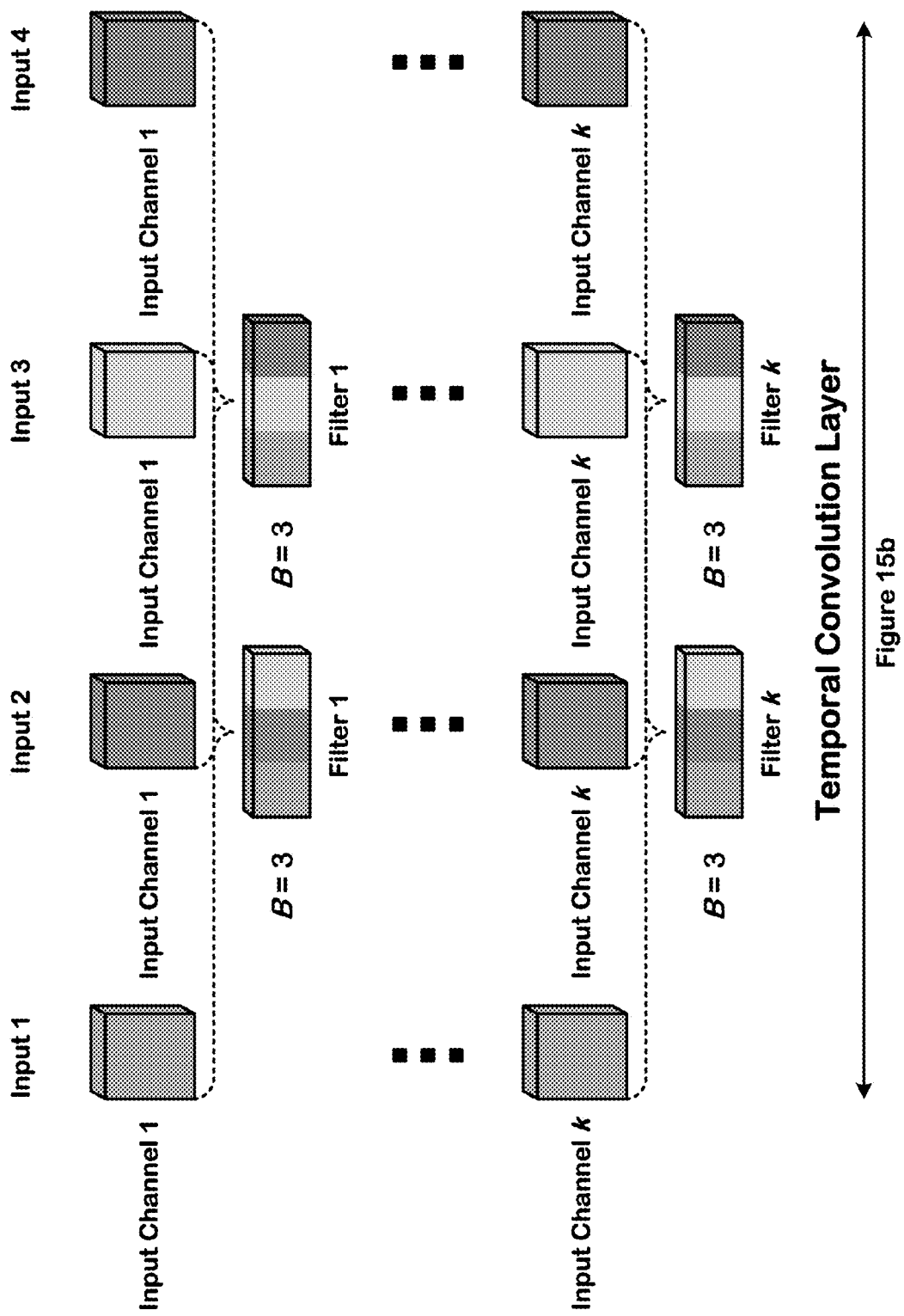
FIG. 15b depicts another implementation of the combinatory convolutions.

In FIG. 15a, corresponding input channels from two successive inputs are combined in each sliding window, and therefore B=2. In FIG. 15b, corresponding input channels from three successive inputs are combined in each sliding window, and therefore B=3.

In one implementation, the sliding windows share a same convolution filter. In another implementation, a different convolution filter is used for each sliding window. In some implementations, each temporal convolution layer comprises a bank of k convolution filters, each of which applies to the successive inputs on a sliding window basis.

Filter Banks

Figure 16:
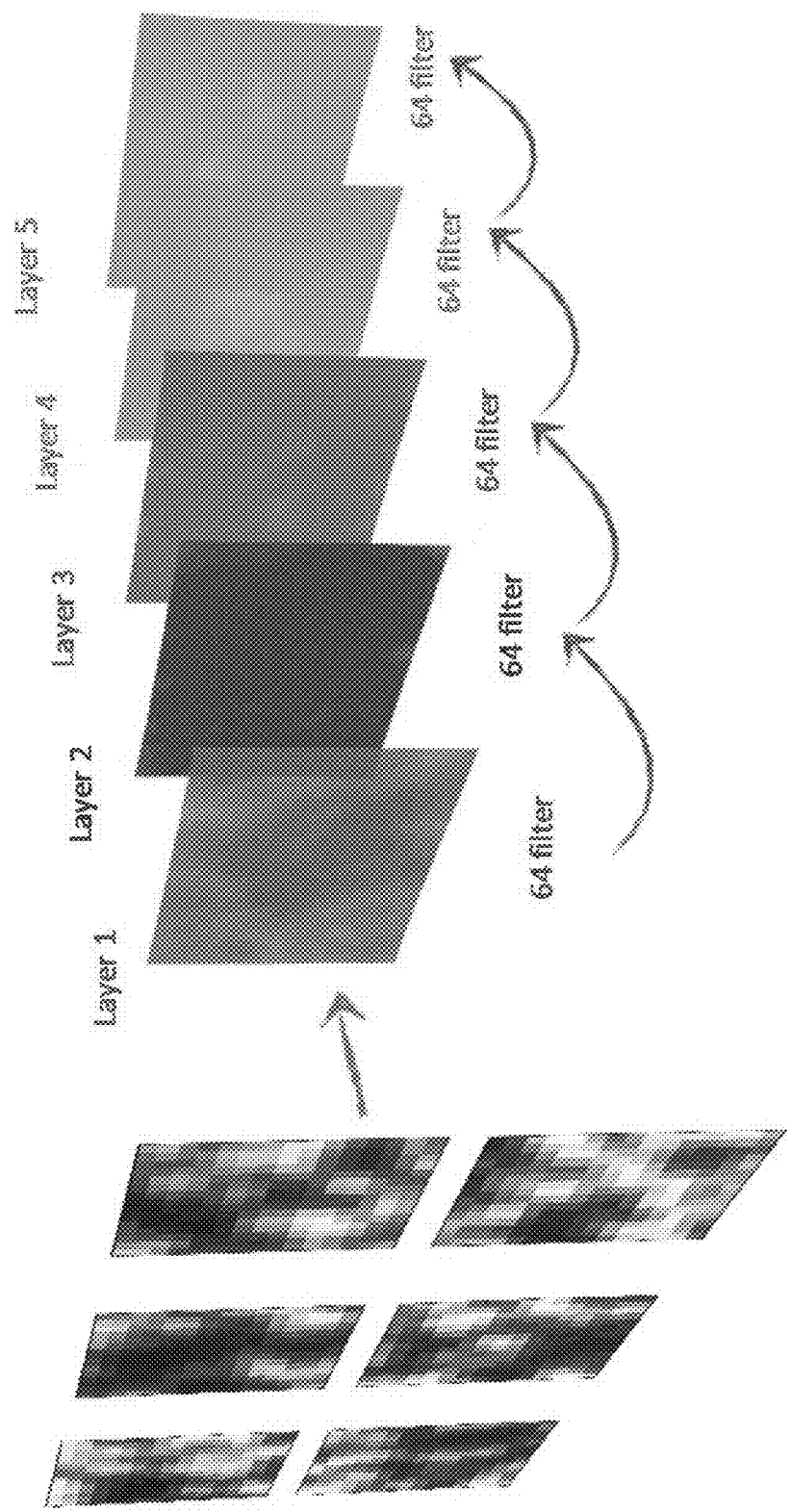
FIG. 16 shows one implementation of convolution layers of the neural network-based base caller in which each convolution layer has a bank of convolution filters.

FIG. 16 shows one implementation of convolution layers of the neural network-based base caller 218 in which each convolution layer has a bank of convolution filters. In FIG. 16, five convolution layers are shown, each of which has a bank of 64 convolution filters. In some implementations, each spatial convolution layer has a bank of k convolution filters, where k can be any number such as 1, 2, 8, 64, 128, 256, and so on. In some implementations, each temporal convolution layer has a bank of k convolution filters, where k can be any number such as 1, 2, 8, 64, 128, 256, and so on.

The discussion now turns to the supplemental scaling channel and how it is calculated.

Scaling Channel

Figure 17:
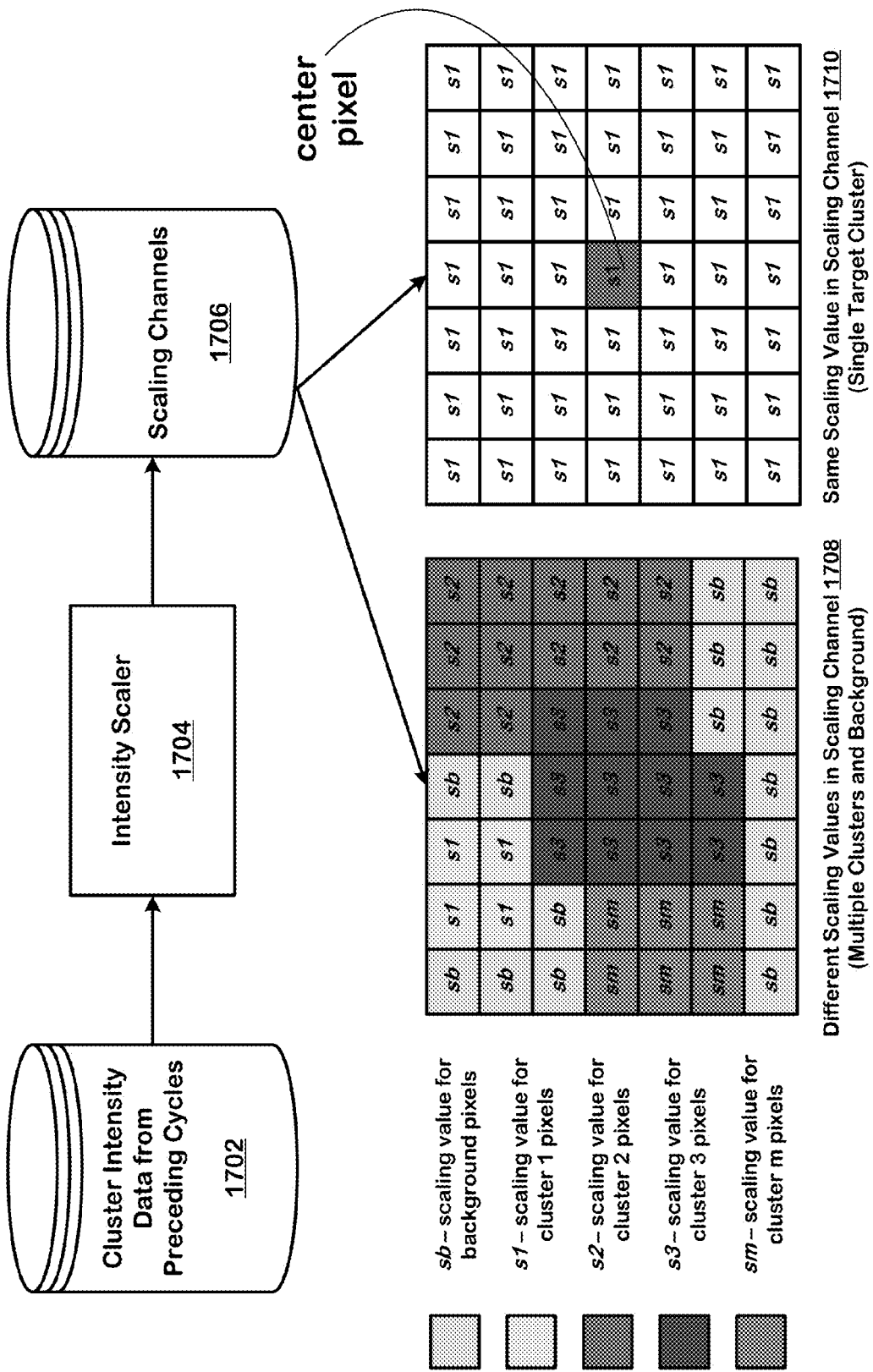
FIG. 17 depicts two configurations of the scaling channel that supplements the image channels.

FIG. 17 depicts two configurations of the scaling channel that supplements the image channels. The scaling channel is pixel-wise encoded in the input data that is fed to the neural network based base caller 218. Different cluster sizes and uneven illumination conditions result in a wide range of cluster intensities being extracted. The additive bias supplied by the scaling channel makes cluster intensities comparable across clusters. In other implementations, when the image patches are in the upsampled, subpixel resolution, the scaling channel is encoded on a subpixel-by-subpixel basis.

When a single target cluster is being base called, the scaling channel assigns a same scaling value to all the pixels. When multiple target clusters are being simultaneously base called, the scaling channels assign different scaling values to groups of pixels based on the cluster shape data.

Scaling channel 1710 has a same scaling value (s1) for all the pixels. Scaling value (s1) is based on a mean intensity of the center pixel that contains the center of the target cluster. In one implementation, the mean intensity is calculated by averaging intensity values of the center pixel observed during two or more preceding sequencing cycles that produced an A and a T base call for the target cluster.

Scaling channel 1708 has different scaling values (s1, s2, s3, sm) for respective pixel groups attributed to corresponding clusters based on the cluster shape data. Each pixel group includes a central cluster pixel that contains a center of the corresponding cluster. Scaling value for a particular pixel group is based on the mean intensity of its central cluster pixel. In one implementation, the mean intensity is calculated by averaging intensity values of the central cluster pixel observe during two or more preceding sequencing cycles that produced an A and a T base call for the corresponding cluster.

In some implementations, the background pixels are assigned a background scaling value (sb), which can be 0 or 0.1, or some other minimum value.

In one implementation, the scaling channels 1706 and their scaling values are determined by an intensity scaler 1704. The intensity scaler 1704 uses cluster intensity data 1702 from preceding sequencing cycles to calculate the mean intensities.

In other implementations, the supplemental scaling channel can be provided as input in a different way, such as prior to or to the last layer of the neural network-based base caller 218, prior to or to the one or more intermediate layers of the neural network-based base caller 218, and as a single value instead of encoding it pixel-wise to match the image size.

The discussion now turns to the input data that is fed to the neural network-based base caller 218

Input Data: Image Channels, Distance Channels, and Scaling Channel

Figure 18A:
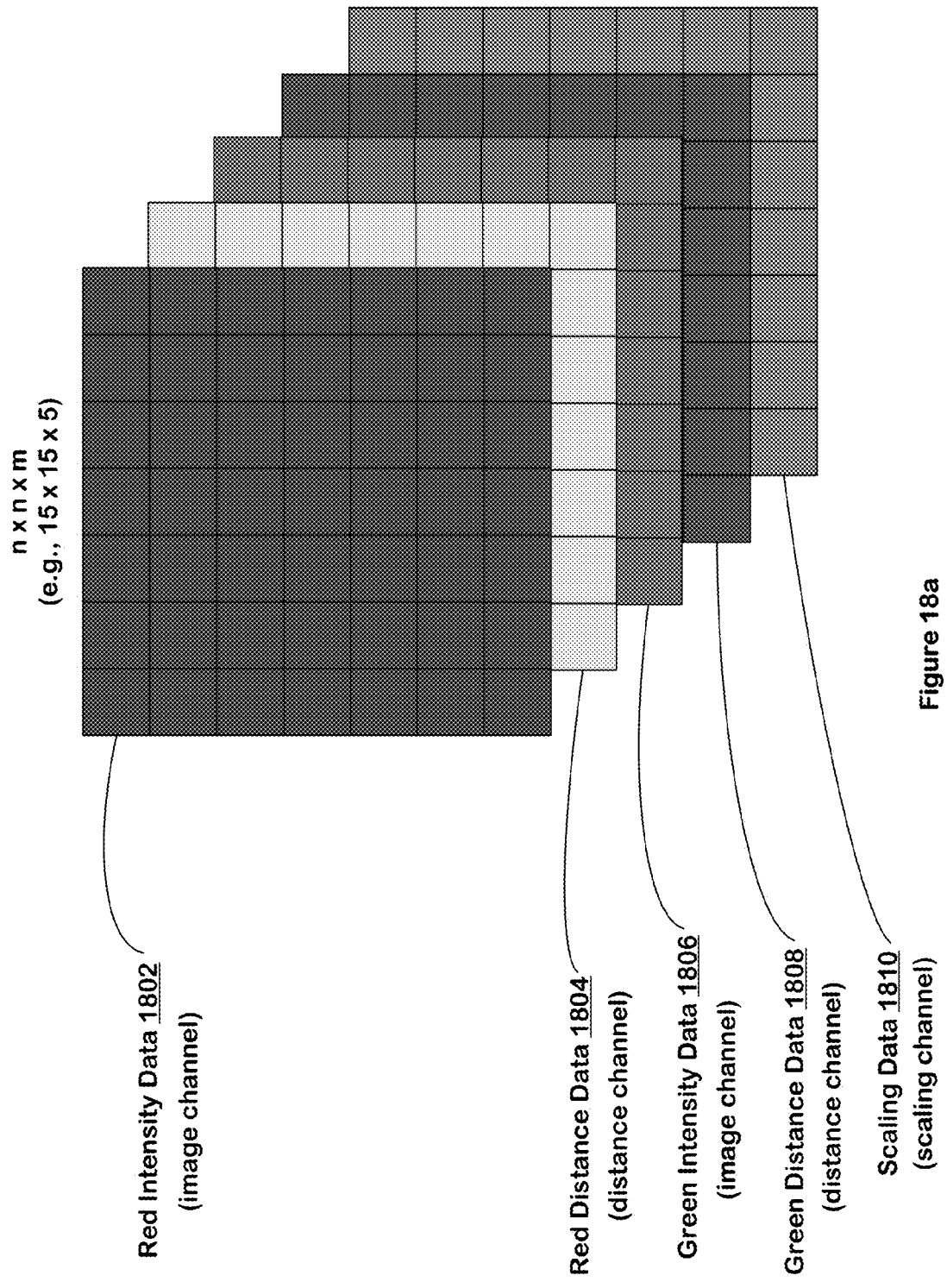
FIG. 18a illustrates one implementation of input data for a single sequencing cycle that produces a red image and a green image.

FIG. 18a illustrates one implementation of input data 1800 for a single sequencing cycle that produces a red image and a green image. The input data 1800 comprises the following:

Red intensity data 1802 (in red) for pixels in an image patch extracted from the red image. The red intensity data 1802 is encoded in a red image channel.

Red distance data 1804 (in yellow) that pixel-wise supplements the red intensity data 1802. The red distance data 1804 is encoded in a red distance channel.

Green intensity data 1806 (in green) for pixels in an image patch extracted from the green image. The green intensity data 1806 is encoded in a green image channel.

Green distance data 1808 (in purple) that pixel-wise supplements the green intensity data 1806. The green distance data 1808 is encoded in a green distance channel.

Scaling data 1810 (in blue) that pixel-wise supplements the red intensity data 1802 and the green intensity data 1806. The scaling data 1810 is encoded in a scaling channel.

In other implementations, the input data can include fewer or greater number of image channels and supplemental distance channels. In one example, for a sequencing run that uses 4-channel chemistry, the input data comprises four image channels for each sequencing cycle and four supplemental distance channels.

The discussion now turns to how the distance channels and the scaling channel contribute to base calling accuracy.

Additive Biasing

Figure 18B:
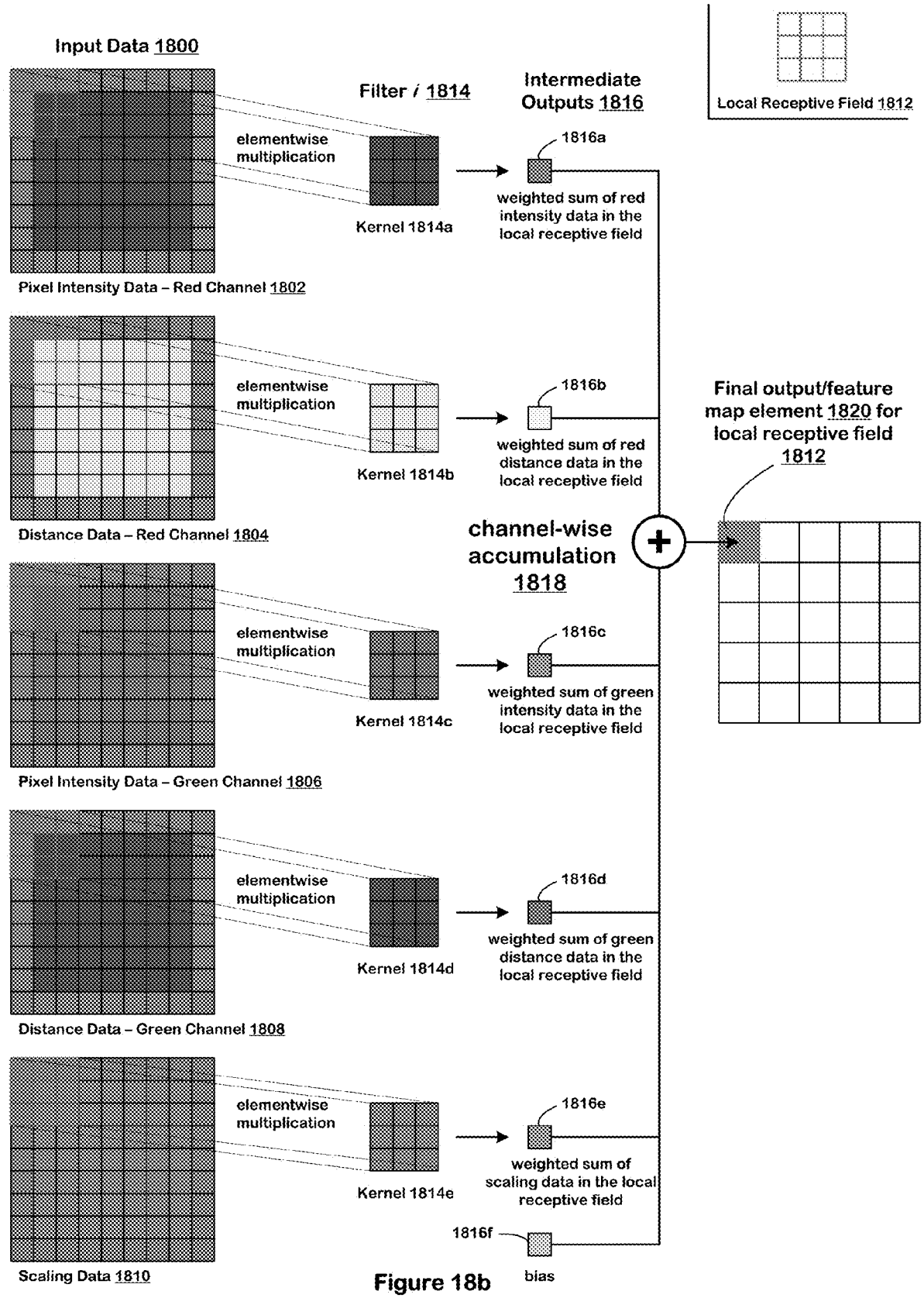
FIG. 18b illustrates one implementation of the distance channels supplying additive bias that is incorporated in the feature maps generated from the image channels.

FIG. 18b illustrates one implementation of the distance channels supplying additive bias that is incorporated in the feature maps generated from the image channels. This additive bias contributes to base calling accuracy because it is based on pixel center-to-cluster center(s) distances, which are pixel-wise encoded in the distance channels.

On average, around 3×3 pixels comprise one cluster. Density at the center of a cluster is expected to be higher than at the fringe because the cluster grows outwards from a substantially central location. Perimeter cluster pixels can contain conflicting signals from nearby clusters. Therefore, the central cluster pixel is considered the maximum intensity region and serves as a beacon that reliably identifies the cluster.

An image patch's pixels depict intensity emissions of a plurality of clusters (e.g., 10 to 200 clusters) and their surround background. Additional clusters incorporate information from a wider radius and contribute to base call prediction by discerning the underlying base whose intensity emissions are depicted in the image patch In other words, intensity emissions from a group of clusters cumulatively create an intensity pattern that can be assigned to a discrete base (A, C, T, or G).

We observe that explicitly communicating to the convolution filters distance of each pixel from the cluster center(s) in the supplemental distance channels results in higher base calling accuracy. The distance channels convey to the convolution filters which pixels contain the cluster centers and which pixels are farther away from the cluster centers. The convolution filters use this information to assign a sequencing signal to its proper source cluster by attending to (a) the central cluster pixels, their neighboring pixels, and feature maps derived from them more than (b) the perimeter cluster pixels, background pixels, and feature maps derived from them. In one example of the attending, the distance channels supply positive additive biases that are incorporated in feature maps resulting from (a), but supply negative additive biases that are incorporated in feature maps resulting from (b).

The distance channels have the same dimensionality as the image channels. This allows the convolution filters to separately evaluate the image channels and the distance channels within a local receptive field and coherently combine the evaluations.

When a single target cluster is being base called, the distance channels identify only one central cluster pixel at the center of the image patches. When multiple target clusters are being simultaneously base called, the distance channels identify multiple central cluster pixels distributed across the image patches.

A "single cluster" distance channel applies to an image patch that contains the center of a single target cluster to be base called in its center pixel. The single cluster distance channel includes center-to-center distance of each pixel in the image patch to the single target cluster. In this implementation, the image patch also includes additional clusters that are adjacent to the single target cluster, but the additional clusters are not base called.

A "multi-cluster" distance channel applies to an image patch that contains the centers of multiple target clusters to be base called in its respective central cluster pixels. The multi-cluster distance channel includes center-to-center distance of each pixel in the image patch to the nearest cluster from among the multiple target clusters. This has the potential of measuring a center-to-center distance to the wrong cluster, but that potential is low.

A "multi-cluster shape-based" distance channel applies to an image patch that contains the centers of multiple target clusters to be base called in its respective central cluster pixels and for which pixel-to-cluster attribution information is known. The multi-cluster distance channel includes center-to-center distance of each cluster pixel in the image patch to the cluster to which it belongs or is attributed to from among the multiple target clusters. Background pixels can be flagged as background, instead of given a calculated distance.

FIG. 18*b* also illustrates one implementation of the scaling channel supplying additive bias that is incorporated in the feature maps generated from the image channels. This additive bias contributes to base calling accuracy because it is based on mean intensities of central cluster pixel(s), which are pixel-wise encoded in the scaling channel. The discussion about additive biasing in the context of the distance channels analogously applies to the scaling channel.

Example of Additive Biasing

FIG. 18*b* further shows an example of how the additive biases are derived from the distance and scaling channels and incorporated into the features maps generated from the image channels.

In FIG. 18*b*, convolution filter i 1814 evaluates a local receptive field 1812 (in magenta) across the two image channels 1802 and 1806, the two distance channels 1804 and 1808, and the scaling channel 1810. Because the distance and scaling channels are separately encoded, the additive biasing occurs when the intermediate outputs 1816*a-e* of each of the channel-specific convolution kernels (or feature detectors) 1816*a-e* (plus bias 18160 are channel-wise accumulated 1818 as the final output/feature map element 1820 for the local receptive field 1812. In this example, the additive biases supplied by the two distance channels 1804 and 1808 are the intermediate outputs 1816*b* and 1816*d*, respectively. The additive bias supplied by the scaling channel 1810 is the intermediate output 1816*e*.

The additive biasing guides the feature map compilation process by putting greater emphasis on those features in the image channels that are considered more important and reliable for base calling, i.e., pixel intensities of central cluster pixels and their neighboring pixels. During training, backpropagation of gradients computed from comparison to the ground truth base calls updates weights of the convolution kernels to produce stronger activations for central cluster pixels and their neighboring pixels.

Consider, for example, that a pixel in the group of adjacent pixels covered by the local receptive field 1812 contains a cluster center, then the distance channels 1804 and 1808 reflect the proximity of the pixels to the cluster center. As a result, when the intensity intermediate outputs 1816*a* and 1816*c* are merged with the distance channel additive biases 1816*b* and 1816*d* at the channelwise accumulation 1818, what results is a positively biased convolved representation 1820 of the pixels.

In contrast, if the pixels covered by the local receptive field 1812 are not near a cluster center, then the distance channels 1804 and 1808 reflect their separation from the cluster center. As a result, when the intensity intermediate outputs 1816*a* and 1816*c* are merged with the distance channel additive biases 1816*b* and 1816*d* at the channelwise accumulation 1818, what results is a negatively biased convolved representation 1820 of the pixels.

Similarly, the scaling channel additive bias 1816*e* derived from the scaling channel 1810 can positively or negatively bias the convolved representation 1820 of the pixels.

For clarity's sake, FIG. 18*b* shows application of a single convolution filter 11814 on the input data 1800 for a single sequencing cycle. One skilled in the art will appreciate that the discussion can be extended to multiple convolution filters (e.g., a filter bank of k filters, where k can be 8, 16, 32, 64, 128, 256, and so on), to multiple convolutional layers (e.g., multiple spatial and temporal convolution layers), and multiple sequencing cycles (e.g., t, t+1, t−1).

In other implementations, the distance and scaling channels, instead of being separately encoded, are directly applied to the image channels to generate modulated pixel multiplication) since the distance and scaling channels and the image channels have the same dimensionality. In further implementations, weights of the convolution kernels are determined based on the distance and image channels so as to detect most important features in the image channels during the elementwise multiplication. In yet other implementations, instead of being fed to a first layer, the distance and scaling channels are provided as auxiliary input to downstream layers and/or networks (e.g., to a fully-connected network or a classification layer). In yet further implementations, the distance and scaling channels are fed to the first layer and re-fed to the downstream layers and/or networks (e.g., via a residual connection).

The discussion above is for 2D input data with k input channels. The extension to 3D input will be appreciated by one skilled in the art. Briefly, volumetric input is a 4D tensor with dimensions k×l×w×h, with l being the additional dimension, length. Each individual kernel is a 4D tensor swept in a 4D tensor, resulting in a 3D tensor (the channel dimension is collapsed because it is not swept across).

In other implementations, when the input data 1800 is in the upsampled, subpixel resolution, the distance and scaling channels are separately encoded on a subpixel-by-subpixel basis and the additive biasing occurs at the subpixel level.

Base Calling Using the Specialized Architecture and the Input Data

The discussion now turns to how the specialized architecture and the input data are used for the neural network based base calling.

Single Cluster Base Calling

Figure 19A:
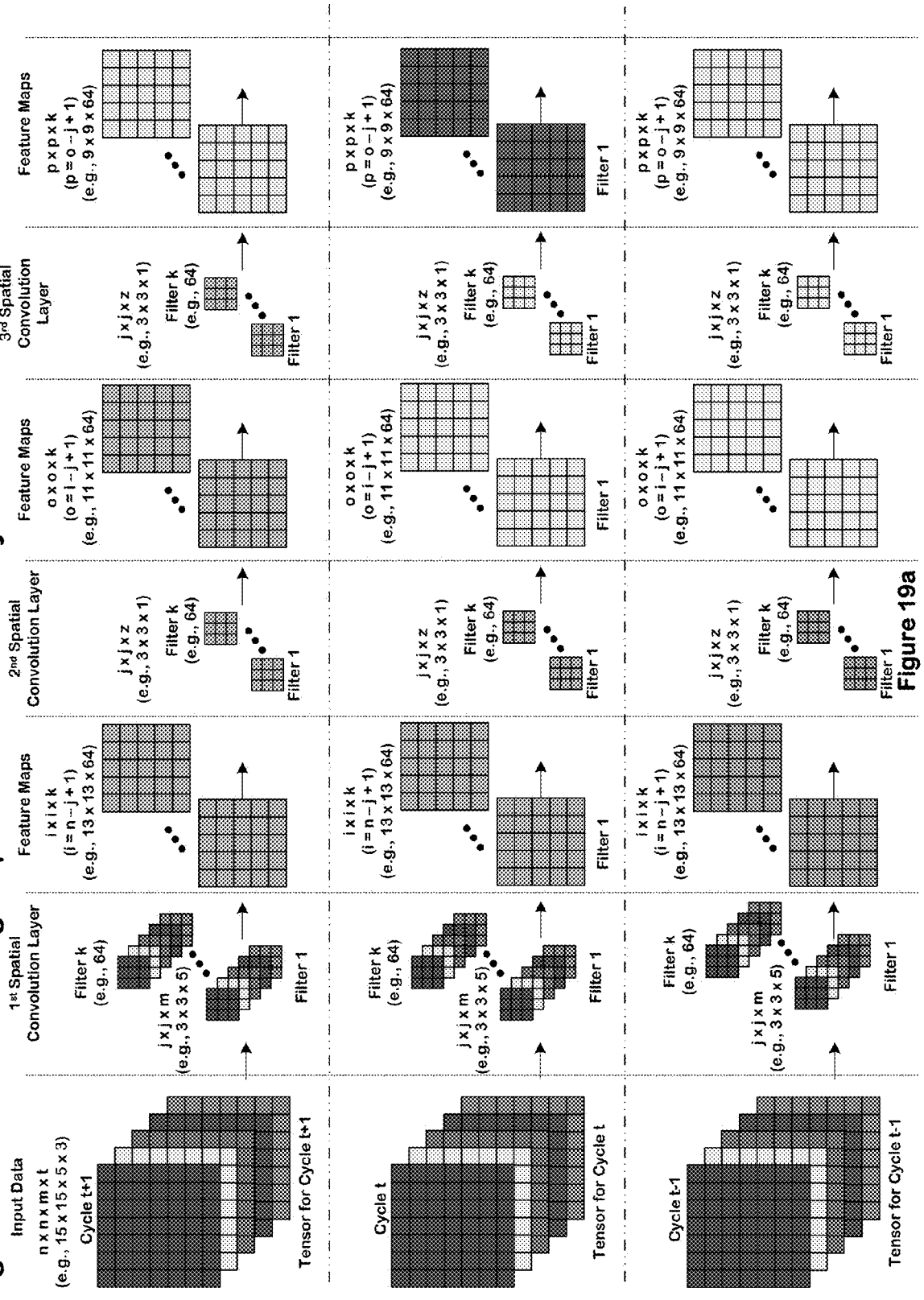
FIGS. 19a, 19b, and 19c depict one implementation of base calling a single target cluster.
Figure 19B:
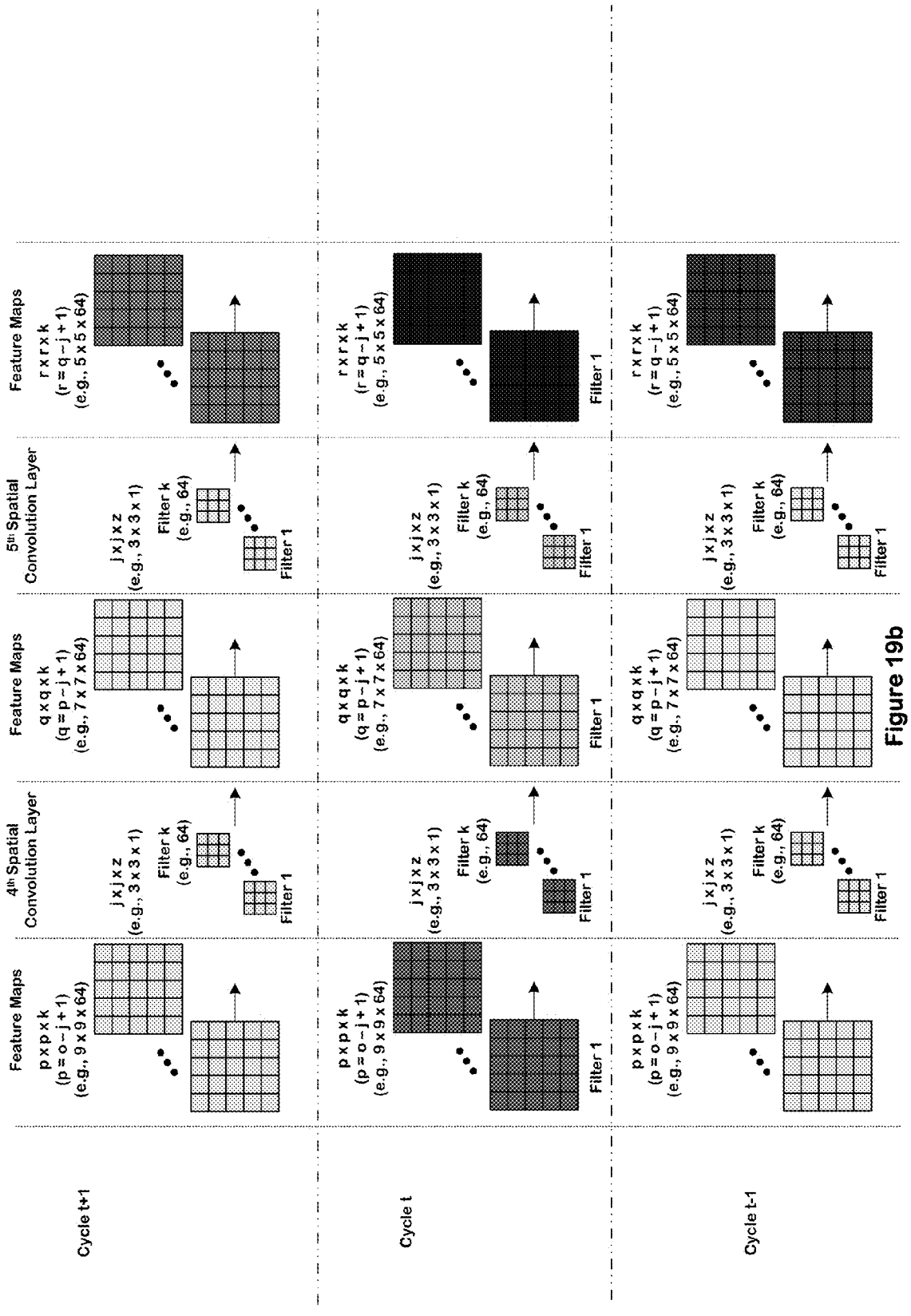
Figure 19C:
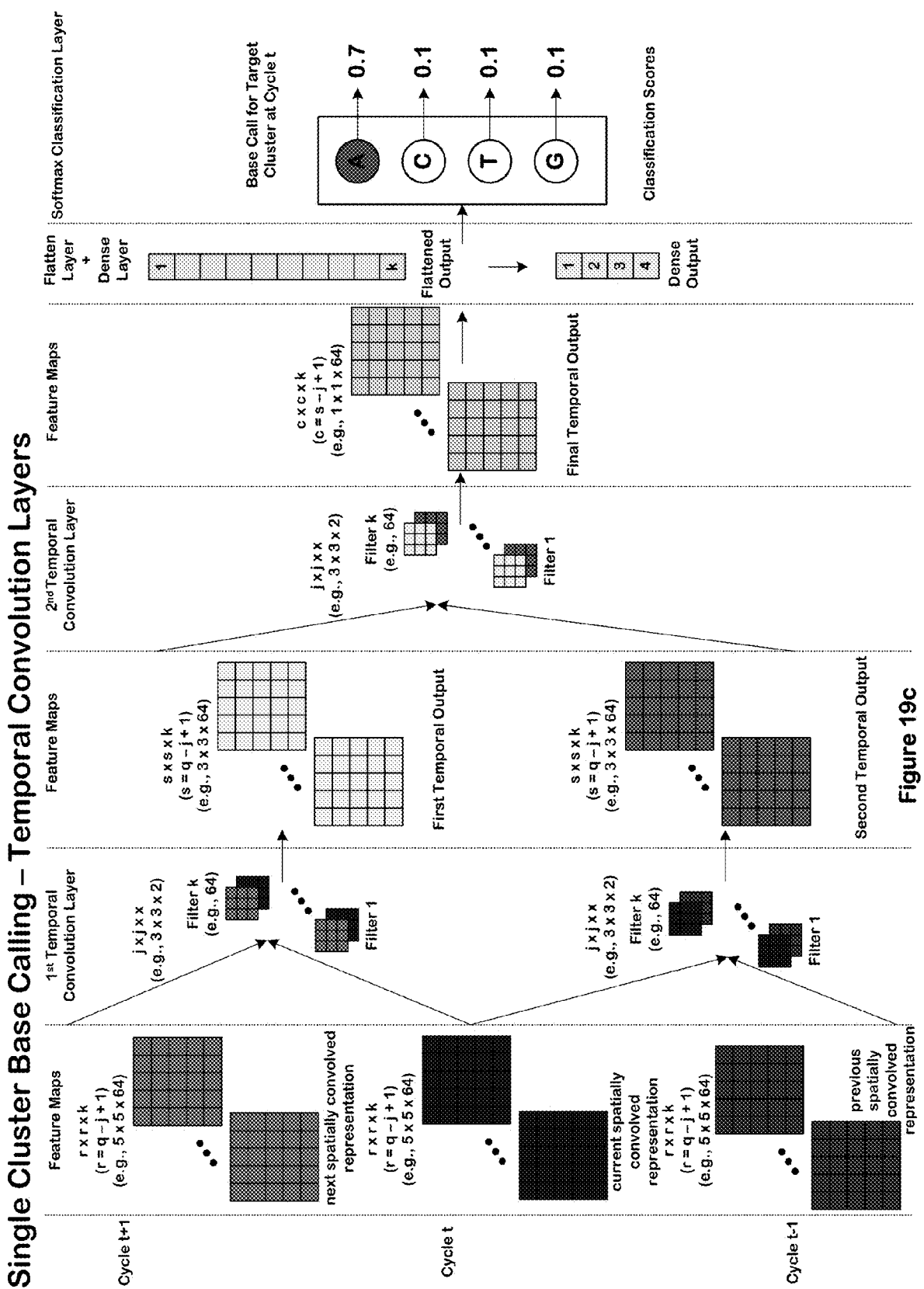

FIGS. 19a, 19b, and 19c depict one implementation of base calling a single target cluster. The specialized architecture processes the input data for three sequencing cycles, namely, a current (time t) sequencing cycle to be base called, a previous (time t−1) sequencing cycle, and a next (time t+1) sequencing cycle and produces a base call for the single target cluster at the current (time t) sequencing cycle.

FIGS. 19a and 19b show the spatial convolution layers. FIG. 19c shows the temporal convolution layers, along with some other non-convolution layers. In FIGS. 19a and 19b, vertical dotted lines demarcate spatial convolution layers from the feature maps and horizontal dashdotted lines demarcate the three convolution pipelines corresponding to the three sequencing cycles.

For each sequencing cycle, the input data includes a tensor of dimensionality n×n×m (e.g., the input tensor 1800 in FIG. 18a), where n represents the width and height of a square tensor and m represents the number of input channels, making the dimensionality of the input data for the three cycles n×n×m×t.

Here, each per-cycle tensor contains, in the center pixel of its image channels, a center of the single target cluster. It also depicts intensity emissions of the single target cluster, of some adjacent clusters, and of their surrounding background captured in each of the image channels at a particular sequencing cycle. In FIG. 19a, two example image channels are depicted, namely, the red image channel and the green image channel.

Each per-cycle tensor also includes distance channels that supplement corresponding image channels (e.g., a red distance channel and a green distance channel). The distance channels identify center-to-center distance of each pixel in the corresponding image channels to the single target cluster. Each per-cycle tensor further includes a scaling channel that pixel-wise scales intensity values in each of the image channels.

The specialized architecture has five spatial convolution layers and two temporal convolution layers. Each spatial convolution layer applies segregated convolutions using a bank of k convolution filters of dimensionality j×j×∂, where j represents the width and height of a square filter and ∂ represents its depth. Each temporal convolution layer applies combinatory convolutions using a bank of k convolution filters of dimensionality j×j×a, where j represents the width and height of a square filter and a represents its depth.

The specialized architecture has pre-classification layers (e.g., a flatten layer and a dense layer) and an output layer (e.g., a softmax classification layer). The pre-classification layers prepare the input for the output layer. The output layer produces the base call for the single target cluster at the current (time t) sequencing cycle.

Consistently Reducing Spatial Dimensionality

FIGS. 19a, 19b, and 19c also show the resulting feature maps (convolved representations or intermediate convolved representations or convolved features or activation maps) produced by the convolution filters. Starting from the per-cycle tensors, the spatial dimensionality of the resulting feature maps reduces by a constant step size from one convolution layer to the next, a concept referred to herein as the "consistently reducing spatial dimensionality". In FIGS. 19a, 19b, and 19c, an example constant step size of two is used for the consistently reducing spatial dimensionality.

The consistently reducing spatial dimensionality is expressed by the following formulation: "current feature map spatial dimensionality=previous feature map spatial dimensionality−convolution filter spatial dimensionality+1". The consistently reducing spatial dimensionality causes the convolution filters to progressively narrow the focus of attention on the central cluster pixels and their neighboring pixels and generate feature maps with features that capture local dependencies among the central cluster pixels and their neighboring pixels. This in turn helps with accurately base calling the clusters whose centers are contained in the central cluster pixels.

The segregated convolutions of the five spatial convolution layers prevent mixing of information between the three sequencing cycles and maintain the three separate convolution pipelines.

The combinatory convolutions of the two temporal convolution layers mix information between the three sequencing cycles. The first temporal convolution layer convolves over the next and current spatially convolved representations respectively produced for the next and current sequencing cycles by a final spatial convolution layer. This yields a first temporal output. The first temporal convolution layer also convolves over the current and previous spatially convolved representations respectively produced for the current and previous sequencing cycles by the final spatial convolution layer. This yields a second temporal output. The second temporal convolution layer convolves over the first and second temporal outputs and produces a final temporal output.

In some implementations, the final temporal output is fed to the flatten layer to produce a flattened output. The flattened output is then fed to the dense layer to produce a dense output. The dense output is processed by the output layer to produce the base call for the single target cluster at the current (time t) sequencing cycle.

In some implementations, the output layer produces likelihoods (classification scores) of a base incorporated in the single target cluster at the current sequencing cycle being A, C, T, and G, and classifies the base as A, C, T, or G based on the likelihoods (e.g., the base with the maximum likelihood is selected, such the base A in FIG. 19a). In such implementations, the likelihoods are exponentially normalized scores produced by a softmax classification layer and sum to unity.

In some implementations, the output layer derives an output pair for the single target cluster. The output pair identifies a class label of a base incorporated in the single target cluster at the current sequencing cycle being A, C, T, or G, and base calls the single target cluster based on the class label. In one implementation, a class label of 1, 0 identifies an A base, a class label of 0, 1 identifies a C base, a class label of 1, 1 identifies a T base, and a class label of 0, 0 identifies a G base. In another implementation, a class label of 1, 1 identifies an A base, a class label of 0, 1 identifies a C base, a class label of 0.5, 0.5 identifies a T base, and a class label of 0, 0 identifies a G base. In yet another implementation, a class label of 1, 0 identifies an A base, a class label of 0, 1 identifies a C base, a class label of 0.5, 0.5 identifies a T base, and a class label of 0, 0 identifies a G base. In yet further implementation, a class label of 1, 2 identifies an A base, a class label of 0, 1 identifies a C base, a class label of 1, 1 identifies a T base, and a class label of 0, 0 identifies a G base.

In some implementations, the output layer derives a class label for the single target cluster that identifies a base incorporated in the single target cluster at the current sequencing cycle being A, C, T, or G, and base calls the single target cluster based on the class label. In one implementation, a class label of 0.33 identifies an A base, a class label of 0.66 identifies a C base, a class label of 1 identifies a T base, and a class label of 0 identifies a G base. In another implementation, a class label of 0.50 identifies an A base, a class label of 0.75 identifies a C base, a class label of 1 identifies a T base, and a class label of 0.25 identifies a G base.

In some implementations, the output layer derives a single output value, compares the single output value against class value ranges corresponding to bases A, C, T, and G, based on the comparison, assigns the single output value to a particular class value range, and base calls the single target cluster based on the assignment. In one implementation, the single output value is derived using a sigmoid function and the single output value ranges from 0 to 1. In another implementation, a class value range of 0-0.25 represents an A base, a class value range of 0.25-0.50 represents a C base, a class value range of 0.50-0.75 represents a T base, and a class value range of 0.75-1 represents a G base.

One skilled in the art will appreciate that, in other implementations, the specialized architecture can process input data for fewer or greater number of sequencing cycles and can comprise fewer or greater number of spatial and temporal convolution layers. Also, the dimensionality of the input data, the per-cycle tensors in the input data, the convolution filters, the resulting feature maps, and the output can be different. Also, the number of convolution filters in a convolution layer can be different. It can use different padding and striding configurations. It can use a different classification function (e.g., sigmoid or regression) and may or may not include a fully-connected layer. It can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous SGD. It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tan h)), batch normalization layers, regularization layers, dropout, pooling layers (e.g., max or average pooling), global average pooling layers, and attention mechanisms.

Having described single cluster base calling, the discussion now turns to multiple clusters base calling.

Multiple Clusters Base Calling

Depending on the size of the input data and cluster density on the flow cell, anywhere between ten to three hundred thousand clusters are simultaneously base called by the neural network based base caller 218 on a per-input basis. Extending this to the data parallelism and/or model parallelism strategies implemented on parallel processors, using a batch or mini-batch of size ten results in hundred to three million clusters being simultaneously base called on a per-batch basis or per-mini-batch basis.

Depending on the sequencing configuration (e.g., cluster density, number of tiles on the flow cell), a tile includes twenty thousand to three hundred thousand clusters. In another implementation, Illumina's NovaSeq sequencer has up to four million clusters per tile. Therefore, a sequencing image of the tile (tile image) can depict intensity emissions from twenty thousand to three hundred thousand clusters and their surrounding background. So, in one implementation, using input data which includes the entire tile image results in three hundred thousand clusters being simultaneously base called on a per-input basis. In another implementation, using image patches of size 15×15 pixels in the input data results in less than hundred clusters being simultaneously base called on a per-input basis. One skilled in the art will appreciate that these numbers can vary depending on the sequencing configuration, the parallelism strategy, the details of the architecture (e.g., based on optimal architecture hypernarameters), and available compute.

Figure 20:
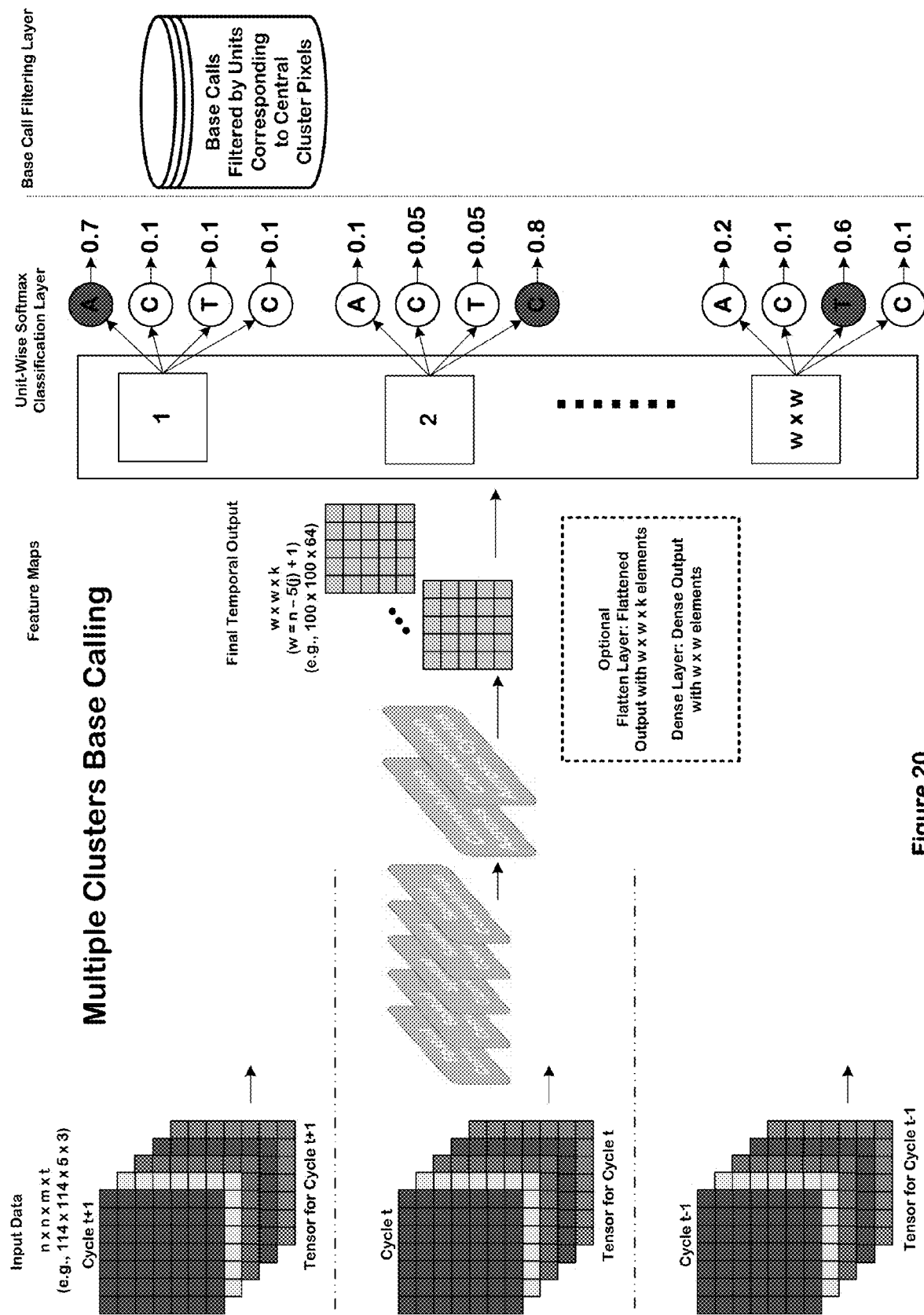
FIG. 20 shows one implementation of simultaneously base calling multiple target clusters.

FIG. 20 shows one implementation of simultaneously base calling multiple target clusters. The input data has three tensors for the three sequencing cycles discussed above. Each per-cycle tensor (e.g., the input tensor 1800 in FIG. 18a) depicts intensity emissions of multiple target clusters to be base called and their surrounding background captured in each of the image channels at a particular sequencing cycle. In other implementations, some additional adjacent clusters, which are not base called, are also included for context.

In the multi-cluster base calling implementation, each per-cycle tensor includes distance channels that supplement corresponding image channels (e.g., a red distance channel and a green distance channel). The distance channels identify center-to-center distance of each pixel in the corresponding image channels to the nearest cluster from among the multiple target clusters.

In the multi-cluster shape-based base calling implementation, each per-cycle tensor includes distance channels that supplement corresponding image channels (e.g., a red distance channel and a green distance channel). The distance channels identify center-to-center distance of each cluster pixel in the corresponding image channels to the cluster to which it belongs or is attributed to from among the multiple target clusters.

Each per-cycle tensor further includes a scaling channel that pixel-wise scales intensity values in each of the image channels.

In FIG. 20, the spatial dimensionality of each per-cycle tensor is great than that shown in FIG. 19a. That is, in the single target cluster base calling implementation in FIG. 19a, the spatial dimensionality of each per-cycle tensor is 15×15, whereas in the multiple cluster base calling implementation in FIG. 20, the spatial dimensionality of each per-cycle tensor is 114×114. Having greater amount of pixelated data that depicts intensity emissions of additional clusters improves the accuracy of base calls simultaneously predicted for the multiple clusters, according to some implementations.

Avoiding Redundant Convolutions

Furthermore, the image channels in each per-cycle tensor are obtained from the image patches extracted from the sequencing images. In some implementations, there are overlapping pixels between extracted image patches that are spatially contiguous (e.g., left, right, top, and bottom contiguous). Accordingly, in one implementation, the overlapping pixels are not subjected to redundant convolutions and results from a prior convolution are reused in later instances when the overlapping pixels are part of the subsequent inputs.

Consider, for example, that a first image patch of size n×n pixels is extracted from a sequencing image and a second image patch of size m×m pixels is also extracted from the same sequencing image, such that the first and second image patches are spatially contiguous and share an overlapping region of o×o pixels. Further consider that the o×o pixels are convolved as part of the first image patch to produce a first convolved representation that is stored in memory. Then, when the second image patch is convolved, the o×o pixels are not convolved again and instead the first convolved representation is retrieved from memory and reused. In some implementations, n=m. In other implementations, they are not equal.

The input data is then processed through the spatial and temporal convolution layers of the specialized architecture to produce a final temporal output of dimensionality w×w×k. Here too, under the consistently reducing spatial dimensionality phenomenon, the spatial dimensionality is reduced by a constant step size of two at each convolution layer. That is, starting with a n×n spatial dimensionality of the input data, a w×w spatial dimensionality of the final temporal output is derived.

Then, based on the final temporal output of spatial dimensionality w×w, an output layer produces a base call for each unit in the w×w set of units. In one implementation, the output layer is a softmax layer that produces four-way classification scores for the four bases (A, C, T, and G) on a unit-by-unit basis. That is, each unit in the w×w set of units is assigned a base call based on the maximum classification score in a corresponding softmax quadruple, as depicted in FIG. 20. In some implementations, the w×w set of units is derived as a result of processing the final temporal output through a flatten layer and a dense layer to produce a flattened output and a dense output, respectively. In such implementations, the flattened output has w×w×k elements and the dense output has w×w elements that form the w×w set of units.

Base calls for the multiple target clusters are obtained by identifying which of the base called units in the w×w set of units coincide with or correspond to central cluster pixels, i.e., pixels in the input data that contain the respective centers of the multiple target clusters. A given target cluster is assigned the base call of the unit that coincides with or corresponds to the pixel that contains the center of the given target cluster. In other words, base calls of units that do not coincide with or correspond to the central cluster pixels are filtered out. This functionality is operationalized by a base call filtering layer, which is part of the specialized architecture in some implementations, or implemented as a post-processing module in other implementations.

In other implementations, base calls for the multiple target clusters are obtained by identifying which groups of base called units in the w×w set of units cover a same cluster, i.e., identifying pixel groups in the input data that depict a same cluster. Then, for each cluster and its corresponding pixel group, an average of classification scores (softmax probabilities) of the respective four base classes (A, C, T, and G) is calculated across pixels in the pixel group and the base class that has the highest average classification score is selected for base calling the cluster.

During training, in some implementations, the ground truth comparison and error computation occurs only for those units that coincide with or correspond to the central cluster pixels, such that their predicted base calls are evaluated against the correct base calls identified as ground truth labels.

Having described multiple clusters base calling, the discussion now turns to multiple clusters and multiple cycles base calling.

Multiple Clusters and Multiple Cycles Base Calling

Figure 21:
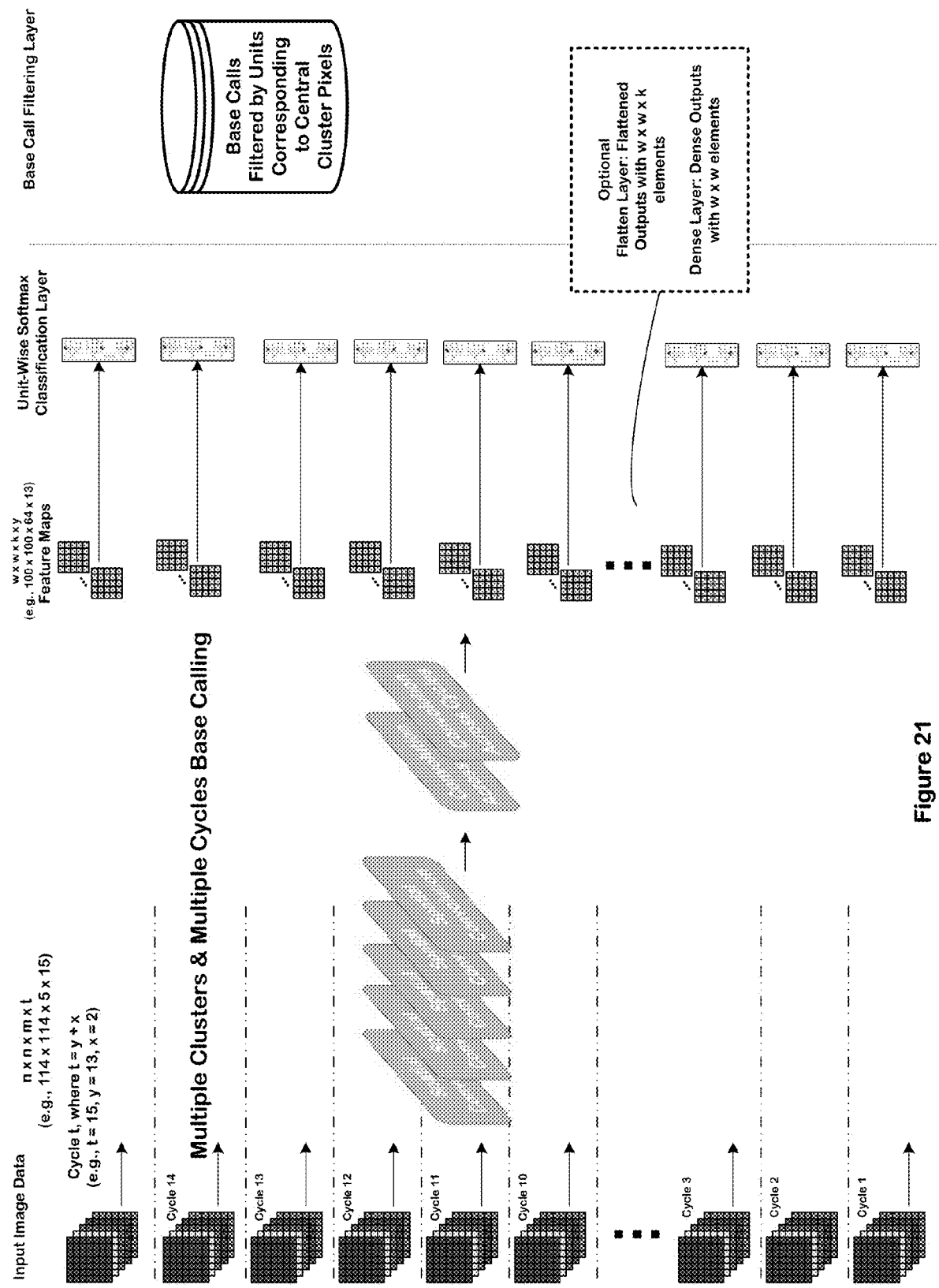
FIG. 21 shows one implementation of simultaneously base calling multiple target clusters at a plurality of successive sequencing cycles, thereby simultaneously producing a base call sequence for each of the multiple target clusters.

FIG. 21 shows one implementation of simultaneously base calling multiple target clusters at a plurality of successive sequencing cycles, thereby simultaneously producing a base call sequence for each of the multiple target clusters.

In the single and multiple base calling implementations discussed above, base call at one sequencing cycle (the current (time t) sequencing cycle) is predicted using data for three sequencing cycles (the current (time t), the previous/left flanking (time t−1), and the next/right flanking (time t+1) sequencing cycles), where the right and left flanking sequencing cycles provide sequence-specific context for base triplet motifs and second order contribution of pre-phasing and phasing signals. This relationship is expressed by the following formulation: "number of sequencing cycles for which data is included in the input data (t)=number of sequencing cycles being base called (y)+number of right and left flanking sequencing cycles (x)."

In FIG. 21, the input data includes t per-cycle tensors for t sequencing cycles, making its dimensionality n×n×m×t, where n=114, m=5, and t=15. In other implementations, these dimensionalities are different. Of the t sequencing cycles, the $t^{th}$ sequencing cycle and the first sequencing cycle serve as right and left flanking contexts x, and y sequencing cycles between them are base called. Thus, y=13, x=2, and t=y+x. Each per-cycle tensor includes image channels, corresponding distance channels, and a scaling channel, such as the input tensor 1800 in FIG. 18a.

The input data with t per-cycle tensors is then processed through the spatial and temporal convolution layers of the specialized architecture to produce y final temporal outputs, each of which corresponds to a respective one of they sequencing cycles being base called. Each of they final temporal outputs has a dimensionality of w×w×k. Here too, under the consistently reducing spatial dimensionality phenomenon, the spatial dimensionality is reduced by a constant step size of two at each convolution layer. That is, starting with a n×n spatial dimensionality of the input data, a w×w spatial dimensionality of each of they final temporal outputs is derived.

Then, each of they final temporal outputs is processed in parallel by an output layer. For each of they final temporal outputs, the output layer produces a base call for each unit in the w×w set of units. In one implementation, the output layer is a softmax layer that produces four-way classification scores for the four bases (A, C, T, and G) on a unit-by-unit basis. That is, each unit in the w×w set of units is assigned a base call based on the maximum classification score in a corresponding softmax quadruple, as depicted in FIG. 20. In some implementations, the w×w set of units is derived for each of they final temporal outputs as a result of respectively processing the later through a flatten layer and a dense layer to produce corresponding flattened outputs and dense outputs. In such implementations, each flattened output has w×w×k elements and each dense output has w×w elements that form the w×w set of units.

For each of they sequencing cycles, base calls for the multiple target clusters are obtained by identifying which of the base called units in the corresponding w×w set of units coincide with or correspond to central cluster pixels, i.e., pixels in the input data that contain the respective centers of the multiple target clusters. A given target cluster is assigned the base call of the unit that coincides with or corresponds to the pixel that contains the center of the given target cluster. In other words, base calls of units that do not coincide with or correspond to the central cluster pixels are filtered out. This functionality is operationalized by a base call filtering layer, which is part of the specialized architecture in some implementations, or implemented as a post-processing module in other implementations.

During training, in some implementations, the ground truth comparison and error computation occurs only for those units that coincide with or correspond to the central cluster pixels, such that their predicted base calls are evaluated against the correct base calls identified as ground truth labels.

On a per-input basis, what results is a base call for each of the multiple target clusters at each of they sequencing cycles, i.e., a base call sequence of lengthy for each of the multiple target clusters. In other implementations, y is 20, 30, 50, 150, 300, and so on. One skilled in the art will appreciate that these numbers can vary depending on the sequencing configuration, the parallelism strategy, the details of the architecture (e.g., based on optimal architecture hyperparameters), and available compute.

End-to-End Dimensionality Diagrams

The following discussion uses dimensionality diagrams to illustrate different implementations of underlying data dimensionality changes involved in producing base calls from image data, together with dimensionality of data operators that effectuate the said data dimensionality changes.

Figure 22:
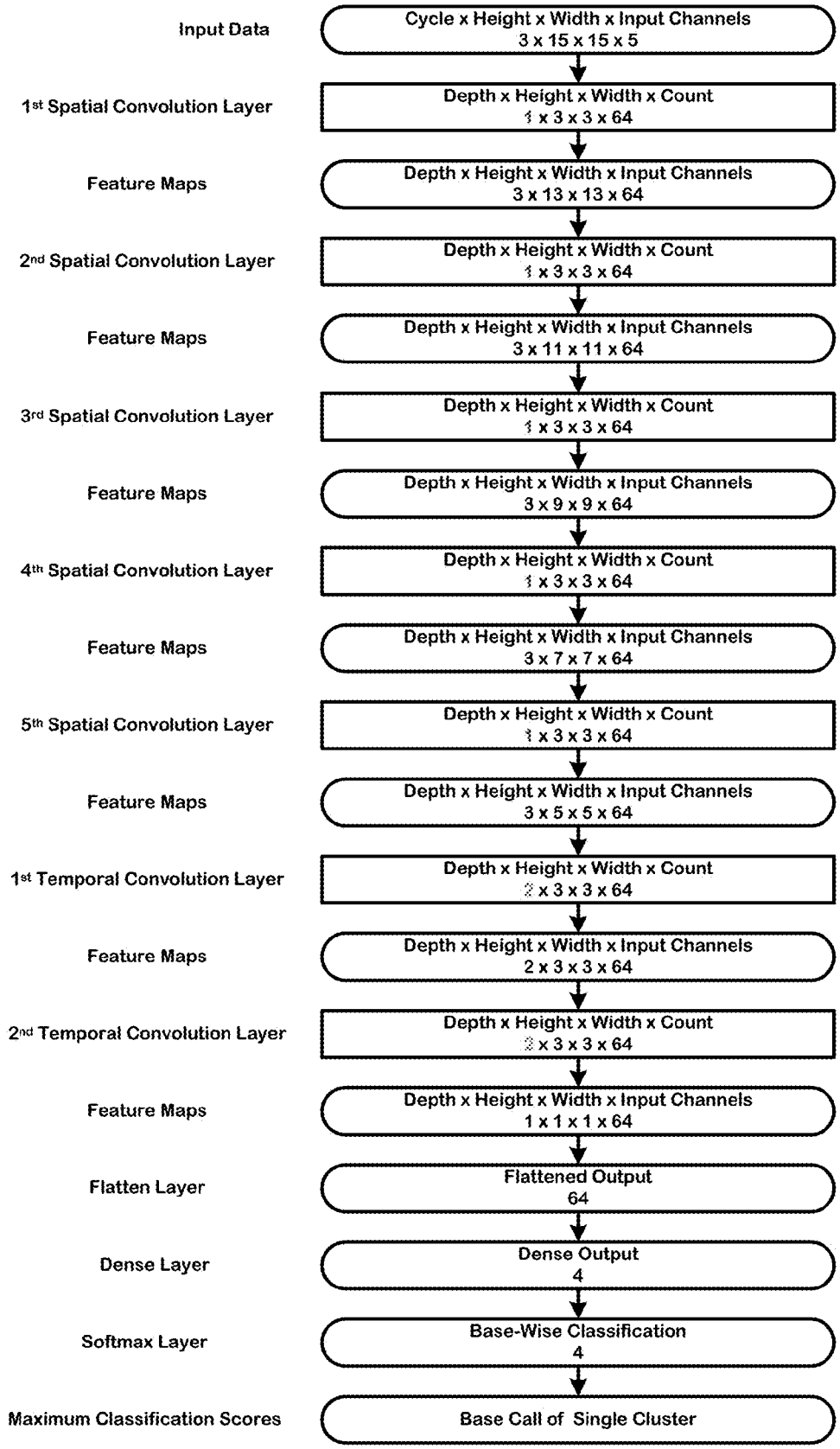
FIG. 22 illustrates the dimensionality diagram for the single cluster base calling implementation.
Figure 23:
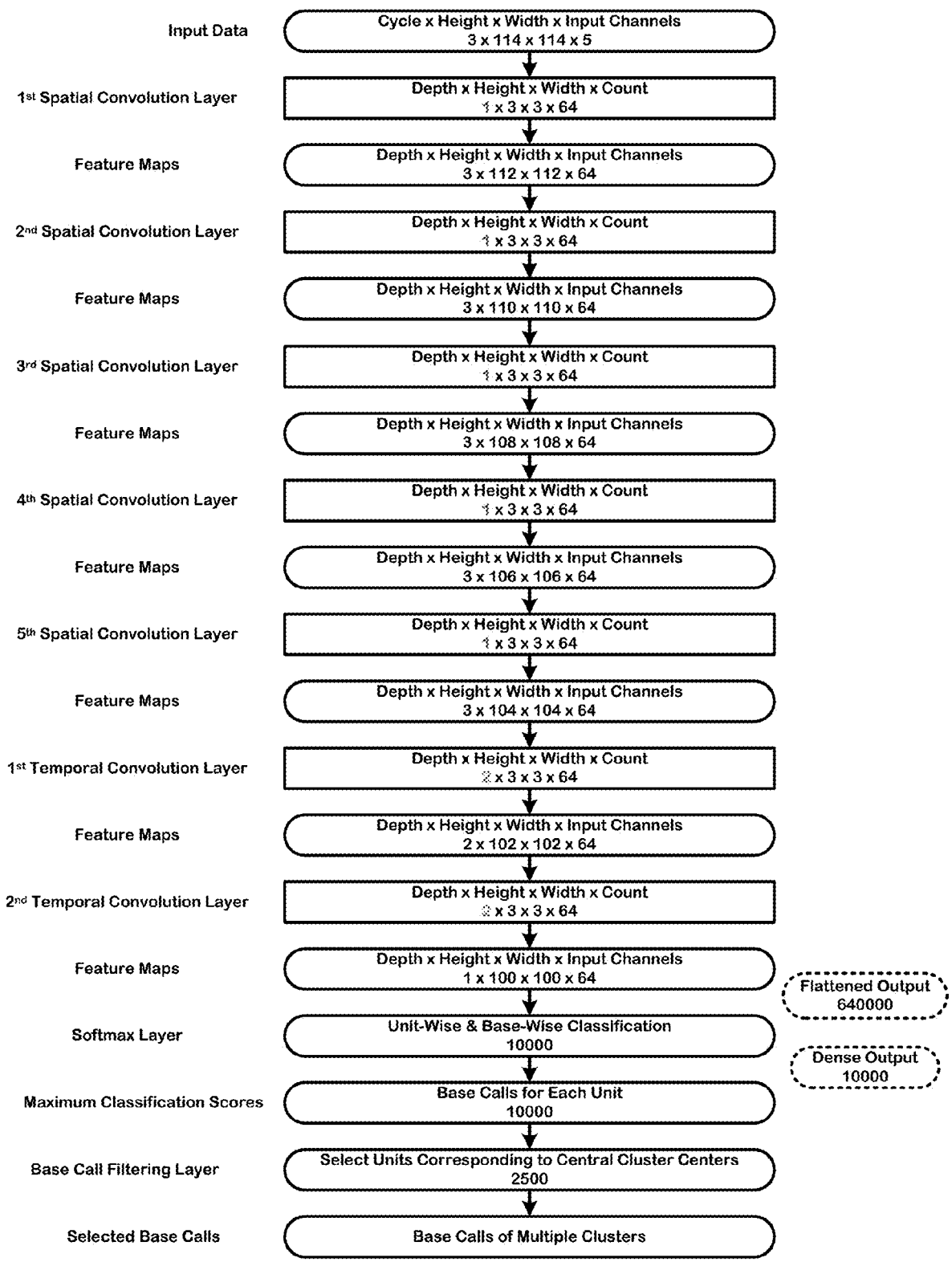
FIG. 23 illustrates the dimensionality diagram for the multiple clusters, single sequencing cycle base calling implementation.
Figure 24:
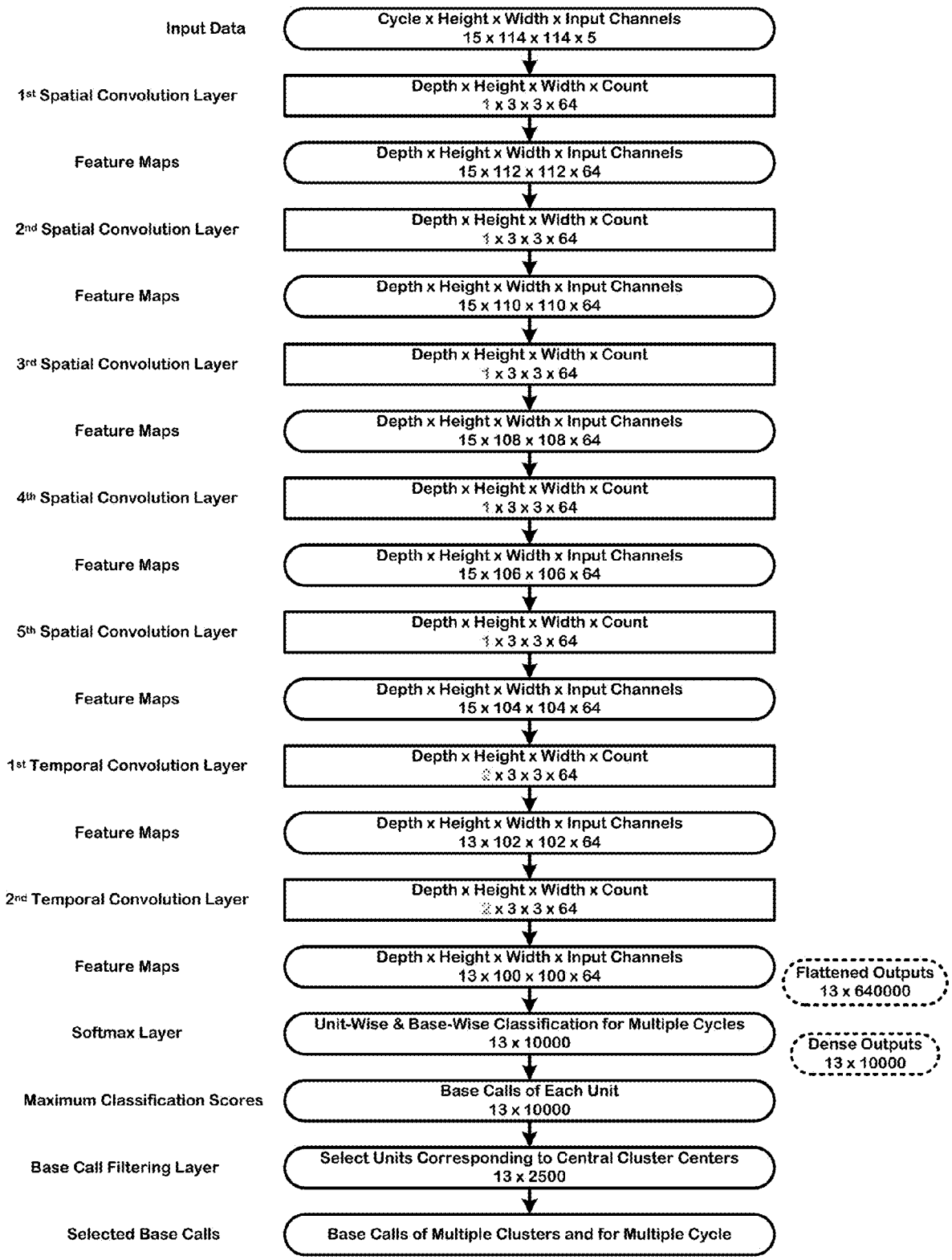
FIG. 24 illustrates the dimensionality diagram for the multiple clusters, multiple sequencing cycles base calling implementation.

In FIGS. 22, 23, and 24, rectangles represent data operators like spatial and temporal convolution layers and softmax classification layer, and rounded corner rectangles represent data (e.g., feature maps) produced by the data operators.

FIG. 22 illustrates the dimensionality diagram 2200 for the single cluster base calling implementation. Note that the "cycle dimension" of the input is three and continues to be that for the resulting feature maps up until the first temporal convolution layer. Cycle dimension of three presents the three sequencing cycles, and its continuity represents that feature maps for the three sequencing cycles are separately generated and convolved upon and no features are mixed between the three sequencing cycles. The segregated convolution pipelines are effectuated by the depth-wise segregated convolution filters of the spatial convolution layers. Note that the "depth dimensionality" of the depth-wise segregated convolution filters of the spatial convolution layers is one. This is what enables the depth-wise segregated convolution filters to convolve over data and resulting feature maps of only a given sequencing cycle, i.e., intra-cycle, and prevents them from convolving over data and resulting feature maps of any other sequencing cycle.

In contrast, note that the depth dimensionality of the depth-wise combinatory convolution filters of the temporal convolution layers is two. This is what enables the depth-wise combinatory convolution filters to groupwise convolve over resulting features maps from multiple sequencing cycles and mix features between the sequencing cycles.

Also note the consistent reduction in the "spatial dimensionality" by a constant step size of two.

Further, a vector with four elements is exponentially normalized by the softmax layer to produce classification scores (i.e., confidence scores, probabilities, likelihoods, softmax scores) for the four bases (A, C, T, and G). The base with the highest (maximum) softmax score is assigned to the single target cluster being base called at the current sequencing cycle.

One skilled in the art will appreciate that, in other implementations, the illustrated dimensionalities can vary depending on the sequencing configuration, the parallelism strategy, the details of the architecture (e.g., based on optimal architecture hyperparameters), and available compute.

FIG. 23 illustrates the dimensionality diagram 2300 for the multiple clusters, single sequencing cycle base calling implementation.

The above discussion about the cycle, depth, and spatial dimensionality with respect to the single cluster base calling applies to this implementation.

Here, the softmax layer operates independently on each of the 10,000 units and produces a respective quadruple of softmax scores for each of the 10,000 units. The quadruple corresponds to the four bases (A, C, T, and G). In some implementations, the 10,000 units are derived from the transformation of 64,0000 flattened units to 10,000 dense units.

Then, from the softmax score quadruple of each of the 10,000 units, the base with the highest softmax score in each quadruple is assigned to a respective one of the 10,000 units.

Then, of the 10,000 units, those 2500 units are selected which correspond the 2,500 central cluster pixels containing respective centers of the 2,500 target clusters being simultaneously base called at the current sequencing cycle. The bases assigned to the selected 2,500 units are in turn assigned to the corresponding ones of the 2,500 target clusters.

One skilled in the art will appreciate that, in other implementations, the illustrated dimensionalities can vary depending on the sequencing configuration, the parallelism strategy, the details of the architecture (e.g., based on optimal architecture hyperparameters), and available compute.

FIG. 24 illustrates the dimensionality diagram 2400 for the multiple clusters, multiple sequencing cycles base calling implementation. The above discussion about the cycle, depth, and spatial dimensionality with respect to the single cluster base calling applies to this implementation.

Further, the above discussion about the softmax-based base call classification with respect to the multiple clusters base calling applies here too. However, here, the softmax-based base call classification of the 2,500 target clusters occurs in parallel for each of the thirteen sequencing cycles base called, thereby simultaneously producing thirteen base calls for each of the 2,500 target clusters.

One skilled in the art will appreciate that, in other implementations, the illustrated dimensionalities can vary depending on the sequencing configuration, the parallelism strategy, the details of the architecture (e.g., based on optimal architecture hyperparameters), and available compute.

Arrayed Input v/s Stacked Input

The discussion now turns to the two configurations in which the multi-cycle input data to the neural network-based caller can be arranged. The first configuration is called "arrayed input" and the second configuration is called "stacked input". The arrayed input is shown in FIG. 25a and is discussed above with respect to FIGS. 19a to 24. The arrayed input encodes each sequencing cycle's input in a separate column/block because image patches in the per-cycle inputs are misaligned with respect to each other due to residual registration error. The specialized architecture is used with the arrayed input to segregate processing of each of the separate columns/blocks. Also, the distance channels are calculated using the transformed cluster centers to account for the misalignments between image patches in a cycle and between image patches across cycles.

In contrast, the stacked input, shown in FIG. 25b, encodes the inputs from different sequencing cycles in a single column/block. In one implementation, this obviates the need of using the specialized architecture because the image patches in the stacked input are aligned with each other through affine transformation and intensity interpolation, which eliminate the inter-cycle and intra-cycle residual registration error. In some implementations, the stacked input has a common scaling channel for all the inputs.

Figure 27:
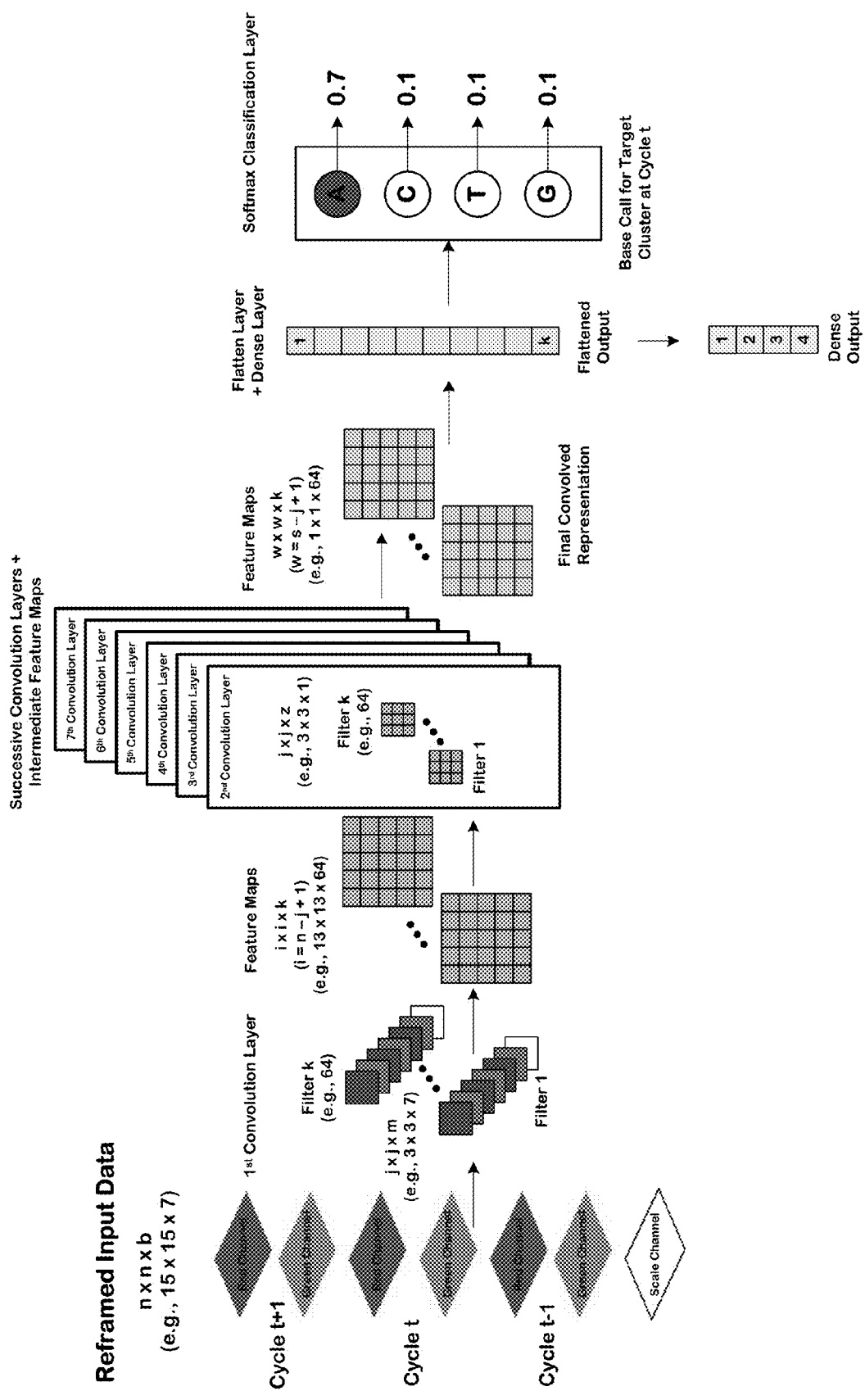
FIG. 27 shows one implementation of base calling a single target cluster at a current sequencing cycle using a standard convolution neural network and the reframed input.

In another implementation, intensity interpolation is used to reframe or shift the image patches such that the center of the center pixel of each image patch coincides with the center of the single target cluster being base called. This obviates the need of using the supplemental distance channels because all the non-center pixels are equidistant from the center of the single target cluster. Stacked input without the distance channels is referred to herein as the "reframed input" and is illustrated in FIG. 27.

Figure 28:
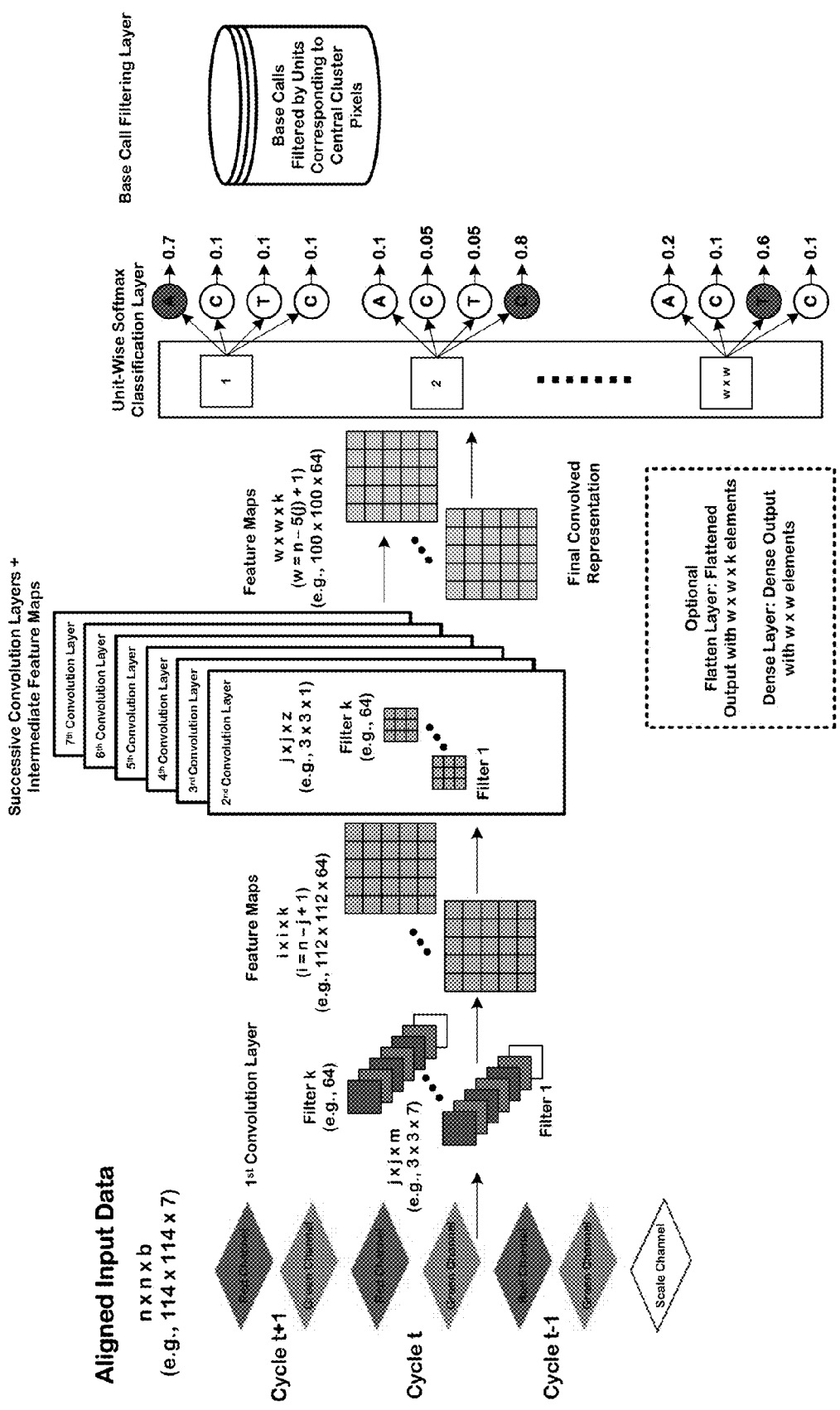
FIG. 28 shows one implementation of base calling multiple target clusters at the current sequencing cycle using the standard convolution neural network and the aligned input.
Figure 29:
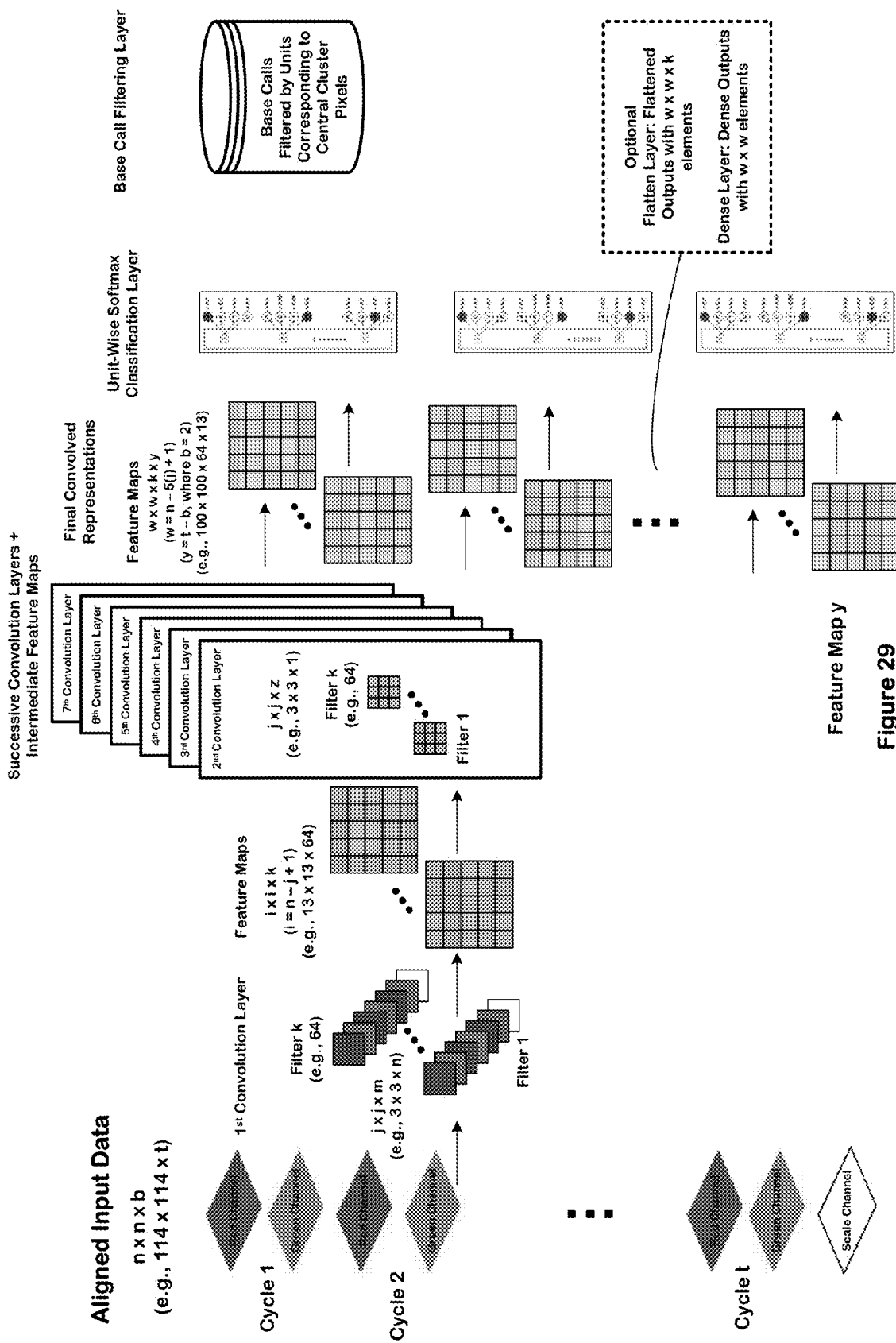
FIG. 29 shows one implementation of base calling multiple target clusters at a plurality of sequencing cycles using the standard convolution neural network and the aligned input.

However, the reframing may not be feasible with base calling implementations involving multiple clusters because there the image patches contain multiple central cluster pixels that are base called. Stacked input without the distance channels and without the reframing is referred to herein as the "aligned input" and is illustrated in FIGS. 28 and 29. Aligned input may be used when calculation of the distance channels is not desired (e.g., due to compute limitations) and reframing is not feasible.

The following section discusses various base calling implementations that do not use the specialized architecture and the supplemental distance channels, and instead using standard convolution layers and filters.

Reframed Input: Aligned Image Patches without the Distance Channels

Figure 26A:
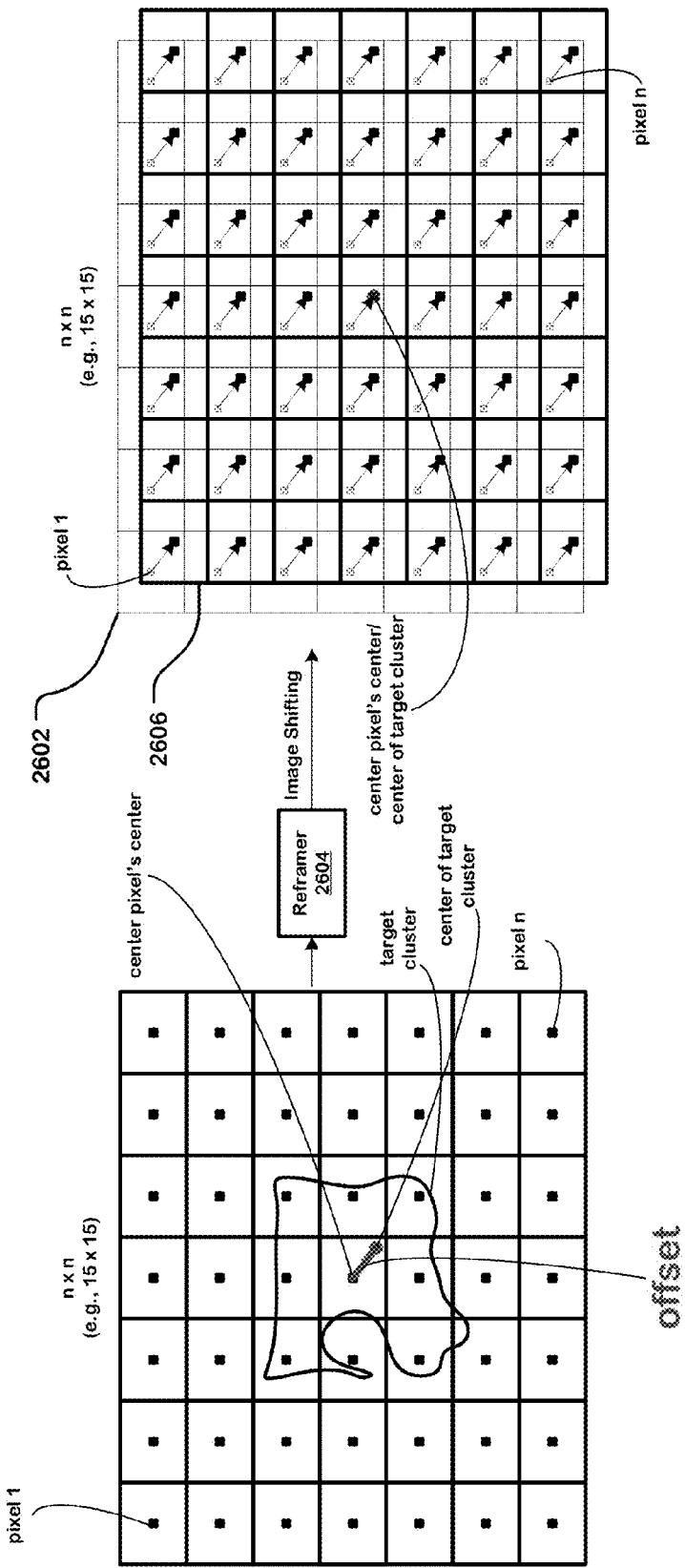
FIG. 26a depicts one implementation of reframing pixels of an image patch to center a center of a target cluster being base called in a center pixel.

FIG. 26a depicts one implementation of reframing 2600a pixels of an image patch 2602 to center a center of a target cluster being base called in a center pixel. The center of the target cluster (in purple) falls within the center pixel of the image patch 2602, but is at an offset (in red) from the center pixel's center, as depicted in FIG. 2600a.

To eliminate the offset, a reframer 2604 shifts the image patch 2602 by interpolating intensity of the pixels to compensate for the reframing and produces a reframed/shifted image patch 2606. In the shifted image patch 2606, the center of the center pixel coincides with the center of the target cluster. Also, the non-center pixels are equidistant from the center of the target cluster. The interpolation can be performed by nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage. These techniques are described in detail in Appendix entitled "Intensity Extraction Methods".

Figure 26B:
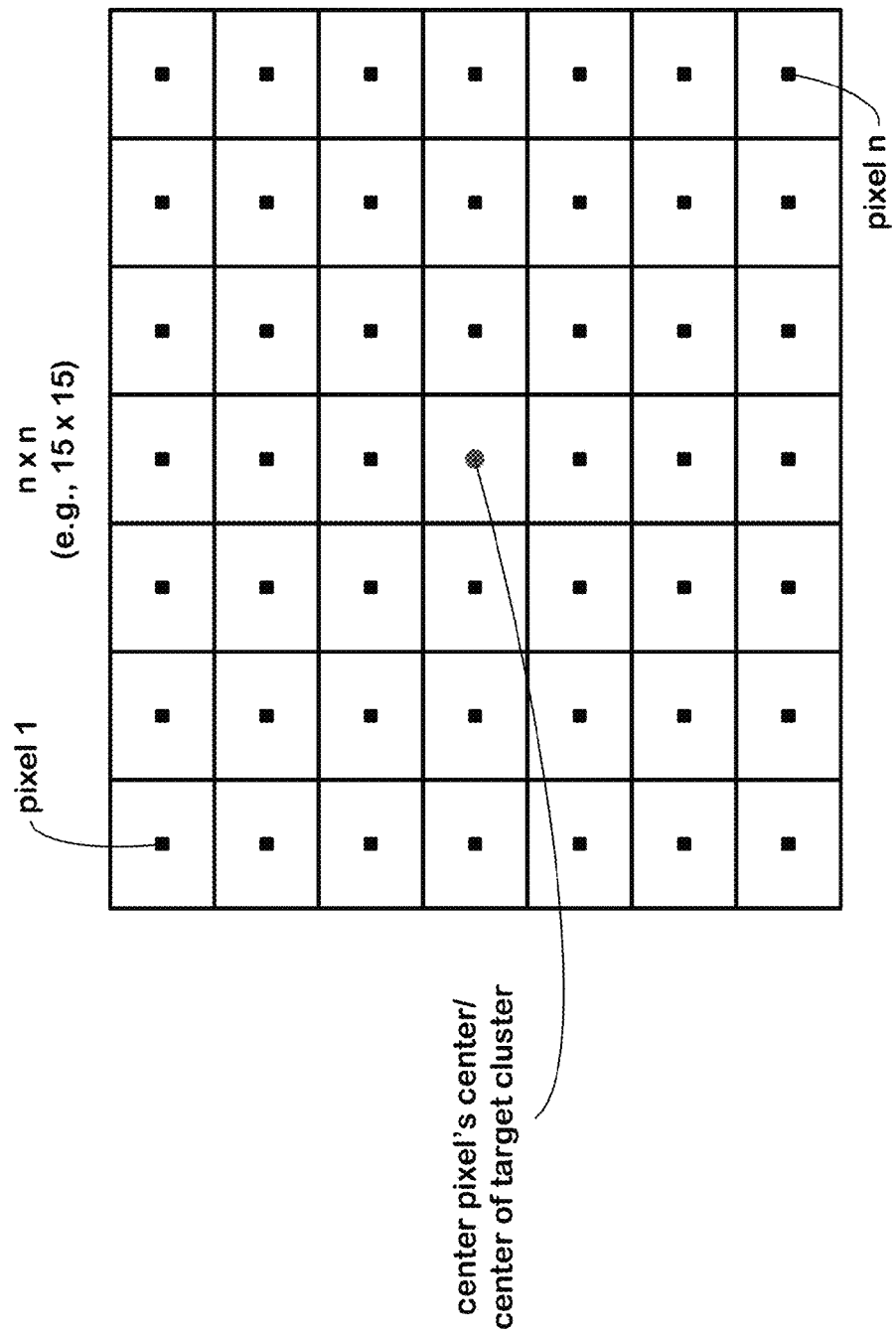
FIG. 26b depicts another example reframed/shifted image patch in which (i) the center of the center pixel coincides with the center of the target cluster and (ii) the non-center pixels are equidistant from the center of the target cluster.

FIG. 26b depicts another example reframed/shifted image patch 2600b in which (i) the center of the center pixel coincides with the center of the target cluster and (ii) the non-center pixels are equidistant from the center of the target cluster. These two factors obviate the need of providing a supplemental distance channel because all the non-center pixels have the same degree of proximity to the center of the target cluster.

FIG. 27 shows one implementation of base calling a single target cluster at a current sequencing cycle using a standard convolution neural network and the reframed input. In the illustrated implementation, the reframed input includes a current image patch set for a current (t) sequencing cycle being base called, a previous image patch set for a previous (t−1) sequencing cycle, and a next image patch set for a next (t+1) sequencing cycle. Each image patch set has an image patch for a respective one of one or more image channels. FIG. 27 depicts two image channels, a red channel and a green channel. Each image patch has pixel intensity data for pixels covering a target cluster being base called, some adjacent clusters, and their surrounding background. The reframed input also includes a common scaling channel.

The reframed input does not include any distance channels because the image patches are reframed or shifted to center at the center the target cluster, as explained above with respect to FIGS. 26a-b. Also, the image patches are aligned with each other to remove inter-cycle and intra-cycle residual registration error. In one implementation, this is done using affine transformation and intensity interpolation, additional details of which can be found in Appendices 1, 2, 3, and 4. These factors obviate the need of using the specialized architecture, and instead a standard convolutional neural network is used with the reframed input.

In the illustrated implementation, the standard convolutional neural network 2700 includes seven standard convolution layers that use standard convolution filters. This means that there are no segregated convolution pipelines to prevent mixing of data between the sequencing cycles (since the data is aligned and can be mixed). In some implementations, the consistently reducing spatial dimensionality phenomenon is used to teach the standard convolution filters to attend to the central cluster center and its neighboring pixels more than to other pixels.

The reframed input is then processed through the standard convolution layers to produce a final convolved representation. Based on the final convolved representation, the base call for the target cluster at the current sequencing cycle is obtained in the similar fashion using flatten, dense, and classification layers as discussed above with respect to FIG. 19c.

In some implementations, the process is iterated over a plurality of sequencing cycles to produce a sequence of base calls for the target cluster.

In other implementations, the process is iterated over a plurality of sequencing cycles for a plurality of target clusters to produce a sequence of base calls for each target cluster in the plurality of target clusters.

Aligned Input: Aligned Image Patches without the Distance Channels and the Reframing FIG. 28 shows one implementation of base calling multiple target clusters at the current sequencing cycle using the standard convolution neural network and the aligned input. The reframing is not feasible here because the image patches contain multiple central cluster pixels that are being base called. As a result, the image patches in the aligned input are not reframed. Further, the supplemental distance channels are not included due to compute considerations, according to one implementation.

The aligned input is then processed through the standard convolution layers to produce a final convolved representation. Based on the final convolved representation, a base call for each of the target clusters is obtained at the current sequencing cycle in the similar fashion using flatten (optional), dense (optional), classification, and base call filtering layers as discussed above with respect to FIG. 20.

FIG. 29 shows one implementation of base calling multiple target clusters at a plurality of sequencing cycles using the standard convolution neural network and the aligned input. The aligned input is processed through the standard convolution layers to produce a final convolved representation for each of they sequencing cycles being base called. Based on they final convolved representations, a base call for each of the target clusters is obtained for each of they sequencing cycles being base called in the similar fashion using flatten (optional), dense (optional), classification, and base call filtering layers as discussed above with respect to FIG. 21.

One skilled in the art will appreciate that, in other implementations, the standard convolutional neural network can process reframed input for fewer or greater number of sequencing cycles and can comprise fewer or greater number of standard convolution layers. Also, the dimensionality of the reframed input, the per-cycle tensors in the reframed input, the convolution filters, the resulting feature maps, and the output can be different. Also, the number of convolution filters in a convolution layer can be different. It can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous SGD. It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tan h)), batch normalization layers, regularization layers, dropout, pooling layers (e.g., max or average pooling), global average pooling layers, and attention mechanisms.

Training

Figure 30:
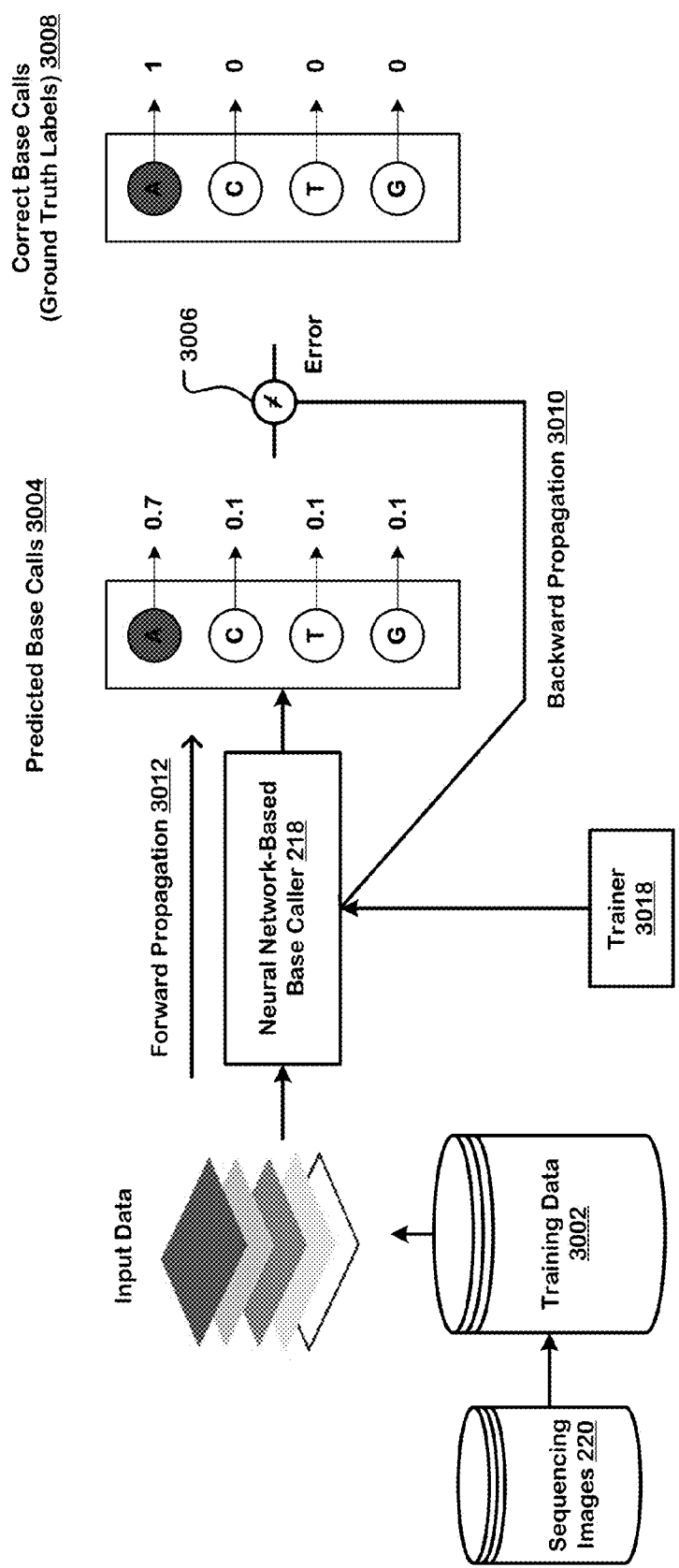
FIG. 30 shows one implementation of training the neural network-based base caller.

FIG. 30 shows one implementation of training 3000 the neural network-based base caller 218. With both the specialized and standard architectures, the neural network-based base caller 218 is trained using a backpropagation-based gradient update technique that compares the predicted base calls 3004 against the correct base calls 3008 and computes an error 3006 based on the comparison. The error 3006 is then used to calculate gradients, which are applied to the weights and parameters of the neural network-based base caller 218 during backward propagation 3010. The training 3000 is operationalized by the trainer 1510 using a stochastic gradient update algorithm such as ADAM.

The trainer 1510 uses training data 3002 (derived from the sequencing images 108) to train the neural network-based base caller 218 over thousands and millions of iterations of the forward propagation 3012 that produces the predicted base calls 3004 and the backward propagation 3010 that updates the weights and parameters based on the error 3006. Additional details about the training 3000 can be found in Appendix entitled "Deep Learning Tools".

CNN-RNN-Based Base Caller

Hybrid Neural Network

Figure 31A:
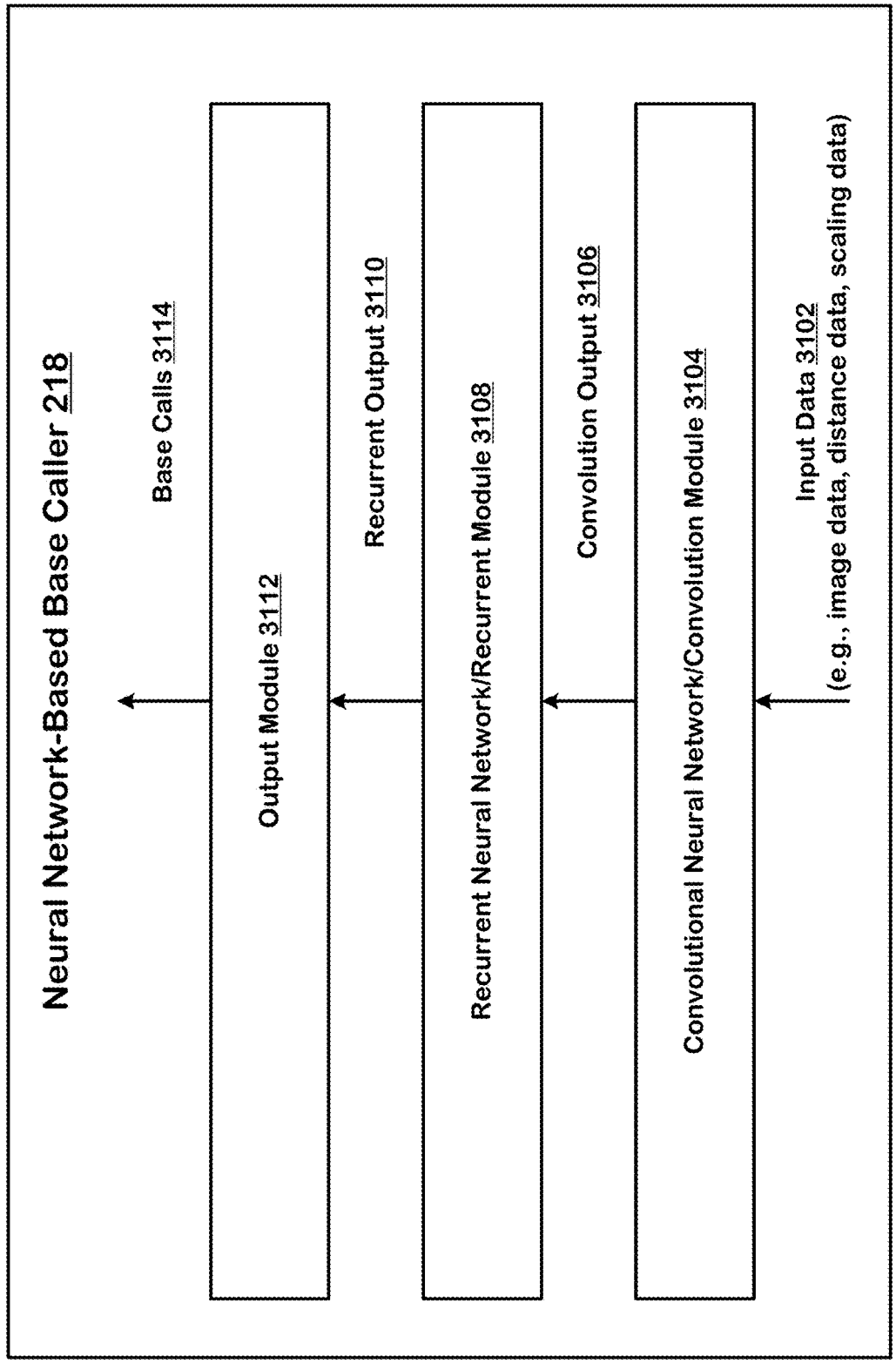
FIG. 31a depicts one implementation of a hybrid neural network that is used as the neural network based base caller.

FIG. 31a depicts one implementation of a hybrid neural network 3100a that is used as the neural network-based base caller 218. The hybrid neural network 3100a comprises at least one convolution module 3104 (or convolutional neural network (CNN)) and at least one recurrent module 3108 (or recurrent neural network (RNN)). The recurrent module 3108 uses and/or receives inputs from the convolution module 3104.

The convolution module 3104 processes input data 3102 through one or more convolution layers and produces convolution output 3106. In one implementation, the input data 3102 includes only image channels or image data as the main input, as discussed above in the Section entitled "Input". The image data fed to the hybrid neural network 3100a can be the same as the image data 202 described above.

In another implementation, the input data 3102, in addition to the image channels or the image data, also includes supplemental channels such as the distance channels, the scaling channel, the cluster center coordinates, and/or cluster attribution information, as discussed above in the Section entitled "Input".

The image data (i.e., the input data 3102) depicts intensity emissions of one or more clusters and their surrounding background. The convolution module 3104 processes the image data for a series of sequencing cycles of a sequencing run through the convolution layers and produces one or more convolved representations of the image data (i.e., the convolved output 3106).

The series of sequencing cycles can include image data for t sequencing cycles that are to be base called, where t is any number between 1 and 1000. We observe accurate base calling results when t is between fifteen and twenty-one.

The recurrent module 3110 convolves the convolved output 3106 and produces recurrent output 3110. In particular, the recurrent module 3110 produces current hidden state representations (i.e., the recurrent output 3110) based on convolving the convolved representations and previous hidden state representations.

In one implementation, the recurrent module 3110 applies three-dimensional (3D) convolutions to the convolved representations and previous hidden state representations and produces the current hidden state representations, mathematically formulated as:

$h_t = W1_{3DCONV} V_t + W2_{3DCONV} h_{t-1}$, where $h_t$ represents a current hidden state representation produced at a current time step t, $V_t$ represents a set or group of convolved representations that form an input volume at a current sliding window at the current time step t, $W1_{3DCONV}$ represents weights of a first 3D convolution filter applied to $V_t$, $h_{t-1}$ represents a previous hidden state representation produced at a previous time step t−1, and $W2_{3DCONV}$ represents weights of a second 3D convolution filter applied to $h_{t-1}$.

In some implementations, $W1_{3DCONV}$ and $W2_{3DCONV}$ are the same because the weights are shared.

An output module 3112 then produces base calls 3114 based on the recurrent output 3110. In some implementations, the output module 3112 comprises one or more fully-connected layers and a classification layer (e.g., softmax). In such implementations, the current hidden state representations are processed through the fully-connected layers and the outputs of the fully-connected layers are processed through the classification layer to produce the base calls 3114.

The base calls 3114 include a base call for at least one of the clusters and for at least one of the sequencing cycles. In some implementations, the base calls 3114 include a base call for each of the clusters and for each of sequencing cycles. So, for example, when the input data 3102 includes image data for twenty-five clusters and for fifteen sequencing cycles, the base calls 3102 include a base call sequence of fifteen base calls for each of the twenty-five clusters.

3D Convolutions

Figure 31B:
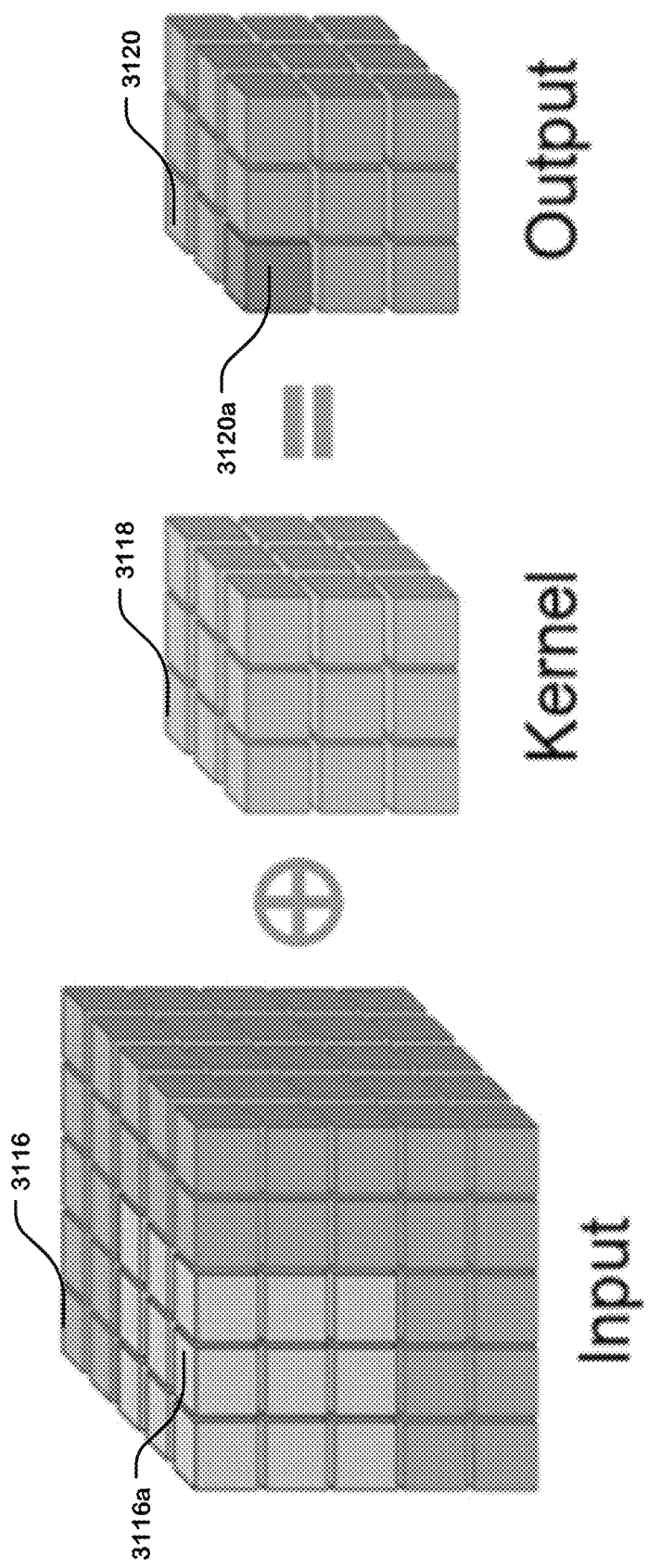
FIG. 31b shows one implementation of 3D convolutions used by the recurrent module of the hybrid neural network to produce the current hidden state representations.

FIG. 31b shows one implementation of 3D convolutions 3100b used by the recurrent module 3110 of the hybrid neural network 3100b to produce the current hidden state representations.

A 3D convolution is a mathematical operation where each voxel present in the input volume is multiplied by a voxel in the equivalent position of the convolution kernel. At the end, the sum of the results is added to the output volume. In FIG. 31b, it is possible to observe the representation of the 3D convolution operation, where the voxels 3116a highlighted in the input 3116 are multiplied with their respective voxels in the kernel 3118. After these calculations, their sum 3120a is added to the output 3120.

Since the coordinates of the input volume are given by (x,y,z) and the convolution kernel has size (P,Q,R), the 3D convolution operation can be mathematically defined as:

$$O_{xyz} = \sum_{p=0}^{P-1} \sum_{q=0}^{Q-1} \sum_{r=0}^{R-1} K_{pqr} I_{(x+p)(y+q)(z+r)},$$

where

O is the result of the convolution,
I is the input volume,
K is the convolution kernel, and
(p,q,r) are the coordinates of K.

The bias term is omitted from the above equation to improve clarity.

3D convolutions, in addition to extracting spatial information from matrices like 2D convolutions, extract information present between consecutive matrices. This allows them to map both spatial information of 3D objects and temporal information of a set of sequential images.

Convolution Module

Figure 32:
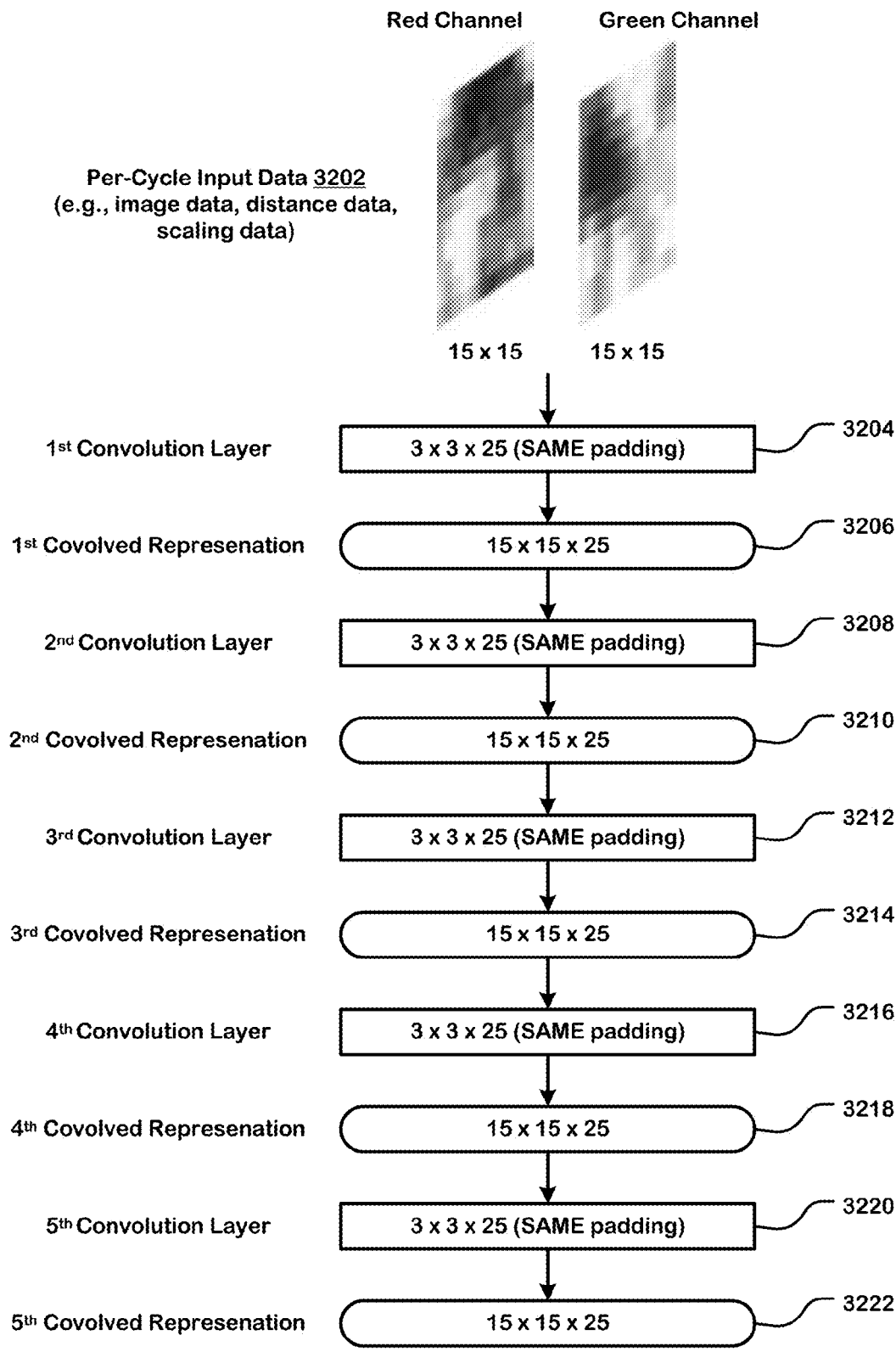
FIG. 32 illustrates one implementation of processing, through a cascade of convolution layers of the convolution module, per-cycle input data for a single sequencing cycle among the series oft sequencing cycles to be base called.

FIG. 32 illustrates one implementation of processing, through a cascade of convolution layers 3200 of the convolution module 3104, per-cycle input data 3202 for a single sequencing cycle among the series oft sequencing cycles to be base called.

The convolution module 3104 separately processes each per-cycle input data in a sequence of per-cycle input data through the cascade of convolution layers 3200. The sequence of per-cycle input data is generated for a series oft sequencing cycles of a sequencing run that are to be base called, where t is any number between 1 and 1000. So, for example, when the series includes fifteen sequencing cycles, the sequence of per-cycle input data comprises fifteen different per-cycle input data.

In one implementation, each per-cycle input data includes only image channels (e.g., a red channel and a green channel) or image data (e.g., the image data 202 described above). The image channels or the image data depict intensity emissions of one or more clusters and their surrounding background captured at a respective sequencing cycle in the series. In another implementation, each per-cycle input data, in addition to the image channels or the image data, also includes supplemental channels such as the distance channels and the scaling channel (e.g., the input data 1800 described above).

In the illustrated implementation, the per-cycle input data 3202 includes two image channels, namely, a red channel and a green channel, for the single sequencing cycle among the series oft sequencing cycles to be base called. Each image channel is encoded in an image patch of size 15×15. The convolution module 3104 comprises five convolution layers. Each convolution layer has a bank of twenty-five convolution filters of size 3×3. Further, the convolution filters use so-called SAME padding that preserves the height and width of the input images or tensors. With the SAME padding, a padding is added to the input features such that the output feature map has the same size as the input features. In contrast, so-called VALID padding means no padding.

The first convolution layer 3204 processes the per-cycle input data 3202 and produces a first convolved representation 3206 of size 15×15×25. The second convolution layer 3208 processes the first convolved representation 3206 and produces a second convolved representation 3210 of size 15×15×25. The third convolution layer 3212 processes the second convolved representation 3210 and produces a third convolved representation 3214 of size 15×15×25. The fourth convolution layer 3216 processes the third convolved representation 3214 and produces a fourth convolved representation 3218 of size 15×15×25. The fifth convolution layer 3220 processes the fourth convolved representation 3218 and produces a fifth convolved representation 3222 of size 15×15×25. Note that the SAME padding preserves the spatial dimensions of the resulting convolved representations (e.g., 15×15). In some implementations, the number of convolution filters in the convolution layers are a power of two, such as 2, 4, 16, 32, 64, 128, 256, 512, and 1024.

As convolutions become deeper, information can be lost. To account for this, in some implementations, we use skip connections (1) to reintroduce the original per-cycle input data and (2) to combine low-level spatial features extracted by earlier convolution layers with high-level spatial features extracted by later convolution layers. We observe that this improves base calling accuracy.

Figure 33:
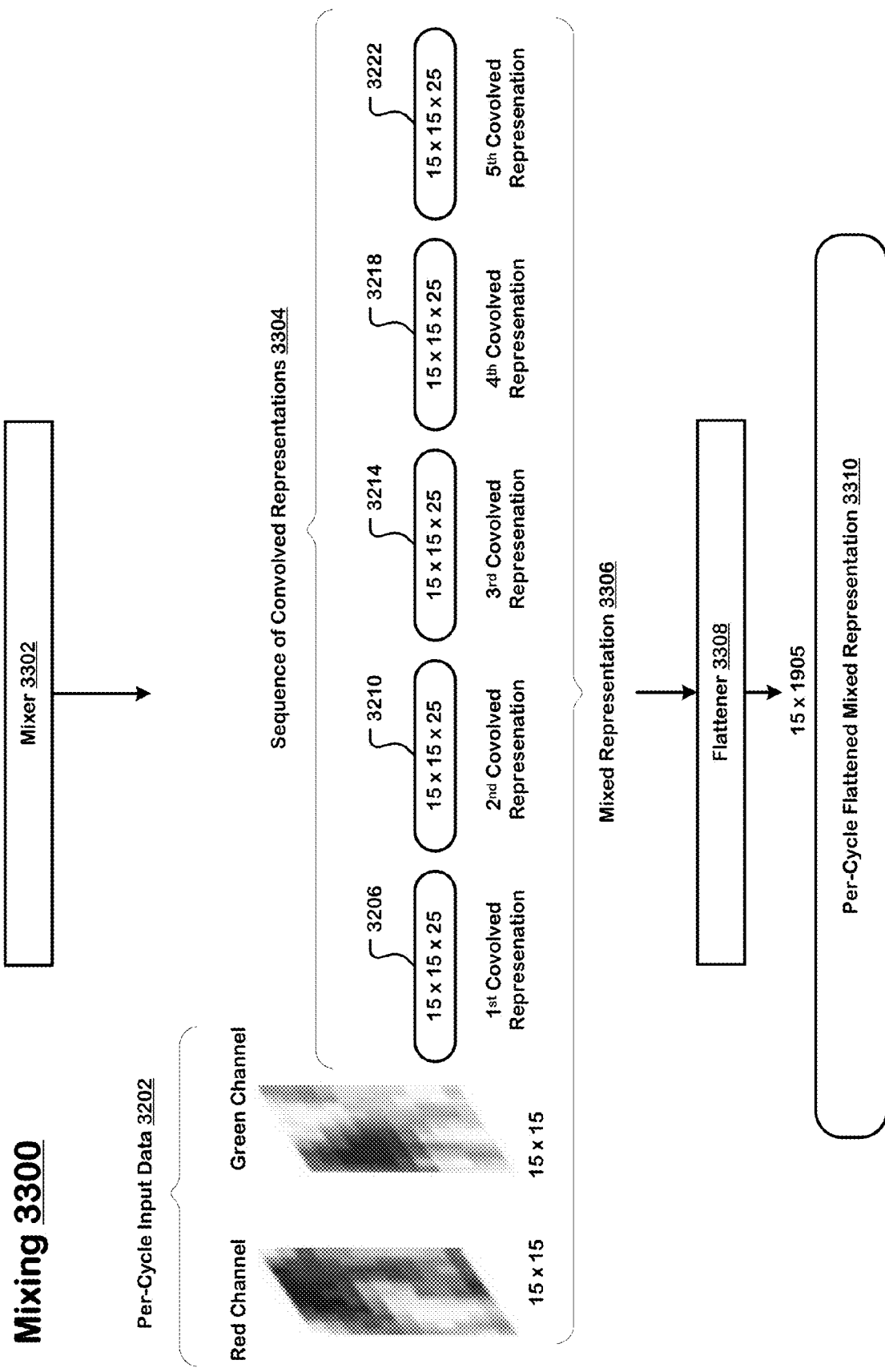
FIG. 33 depicts one implementation of mixing the single sequencing cycle's per-cycle input data with its corresponding convolved representations produced by the cascade of convolution layers of the convolution module.

FIG. 33 depicts one implementation of mixing 3300 the single sequencing cycle's per-cycle input data 3202 with its corresponding convolved representations 3206, 3210, 3214, 3218, and 3222 produced by the cascade of convolution layers 3200 of the convolution module 3104. The convolved representations 3206, 3210, 3214, 3218, and 3222 are concatenated to form a sequence of convolved representations 3304, which in turn is concatenated with the per-cycle input data 3202 to produce a mixed representation 3306. In other implementations, summation is used instead of concatenation. Also, the mixing 3300 is operationalized by the mixer 3302.

A flattener 3308 then flattens the mixed representation 3306 and produces a per-cycle flattened mixed representation 3310. In some implementations, the flattened mixed representation 3310 is a high dimensional vector or two-dimensional (2D) array that shares at least one dimension size with the per-cycle input data 3202 and the convolved representations 3206, 3210, 3214, 3218, and 3222 (e.g., 15×1905, i.e., same row-wise dimension). This induces symmetry in the data that facilitates feature extraction in downstream 3D convolutions.

FIGS. 32 and 33 illustrate processing of the per-cycle image data 3202 for the single sequencing cycle among the series of t sequencing cycles to be base called. The convolution module 3104 separately processes respective per-cycle image data for each of the t sequencing cycles and produces a respective per-cycle flattened mixed presentation for each of the t sequencing cycles.

Stacking

Figure 34:
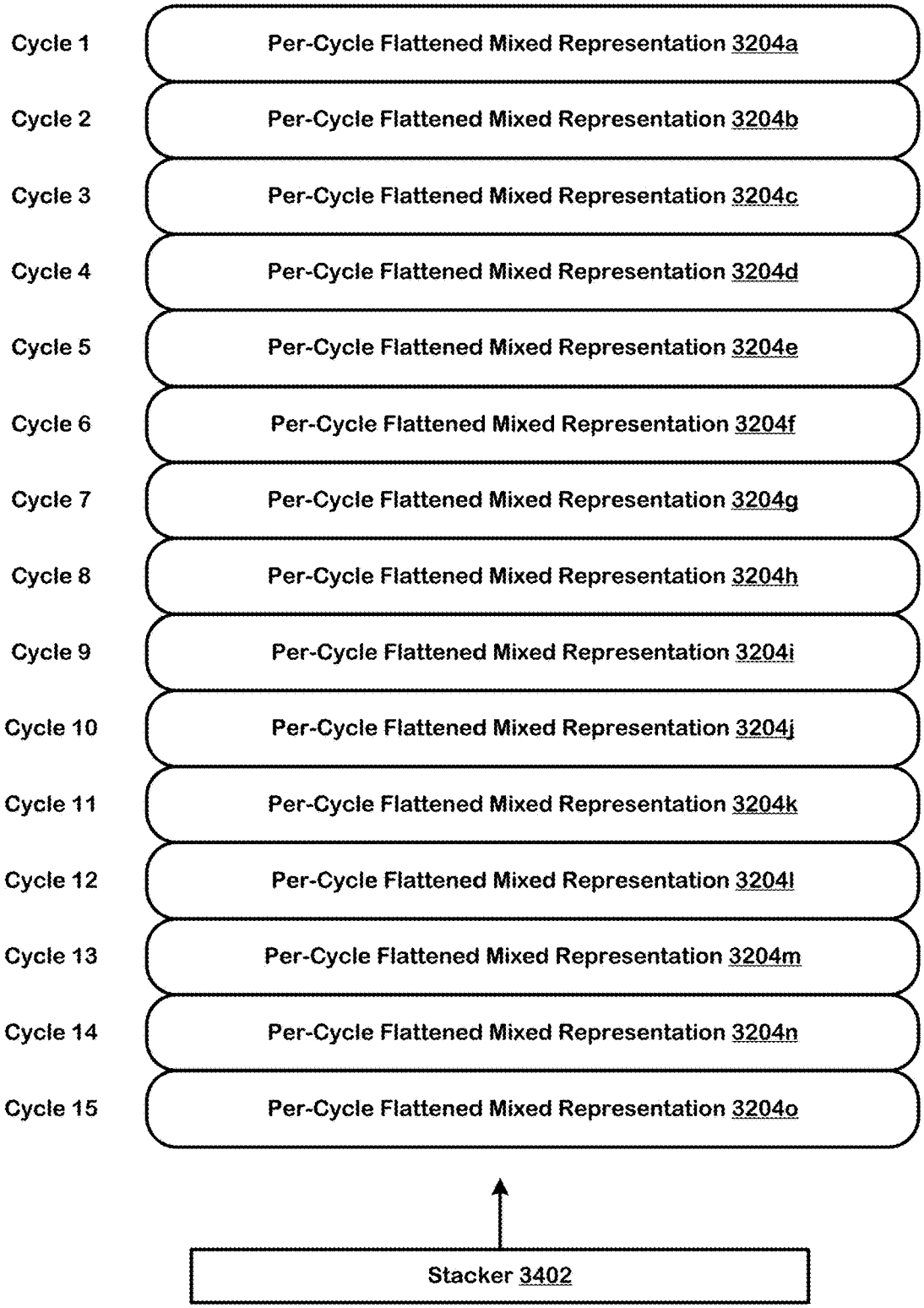
FIG. 34 shows one implementation of arranging flattened mixed representations of successive sequencing cycles as a stack.

FIG. 34 shows one implementation of arranging flattened mixed representations of successive sequencing cycles as a stack 3400. In the illustrated implementation, fifteen flattened mixed representations 3204a to 3204o for fifteen sequencing cycles are stacked in the stack 3400. Stack 3400 is a 3D input volume that makes available features from both spatial and temporal dimensions (i.e., multiple sequencing cycles) in a same receptive field of a 3D convolution filter. The stacking is operationalized by the stacker 3402. In other implementations, stack 3400 can be a tensor of any dimensionality (e.g., 1D, 2D, 4D, 5D, etc.).

Recurrent Module

We use recurrent processing to capture long-term dependencies in the sequencing data and, in particular, to account for second order contributions in cross-cycle sequencing images from pre-phasing and phasing. Recurrent processing is used for analysis of sequential data because of the usage of time steps. A current hidden state representation at a current time step is a function of (i) the previous hidden state representation from a previous time step and (ii) the current input at the current time step.

Figure 35A:
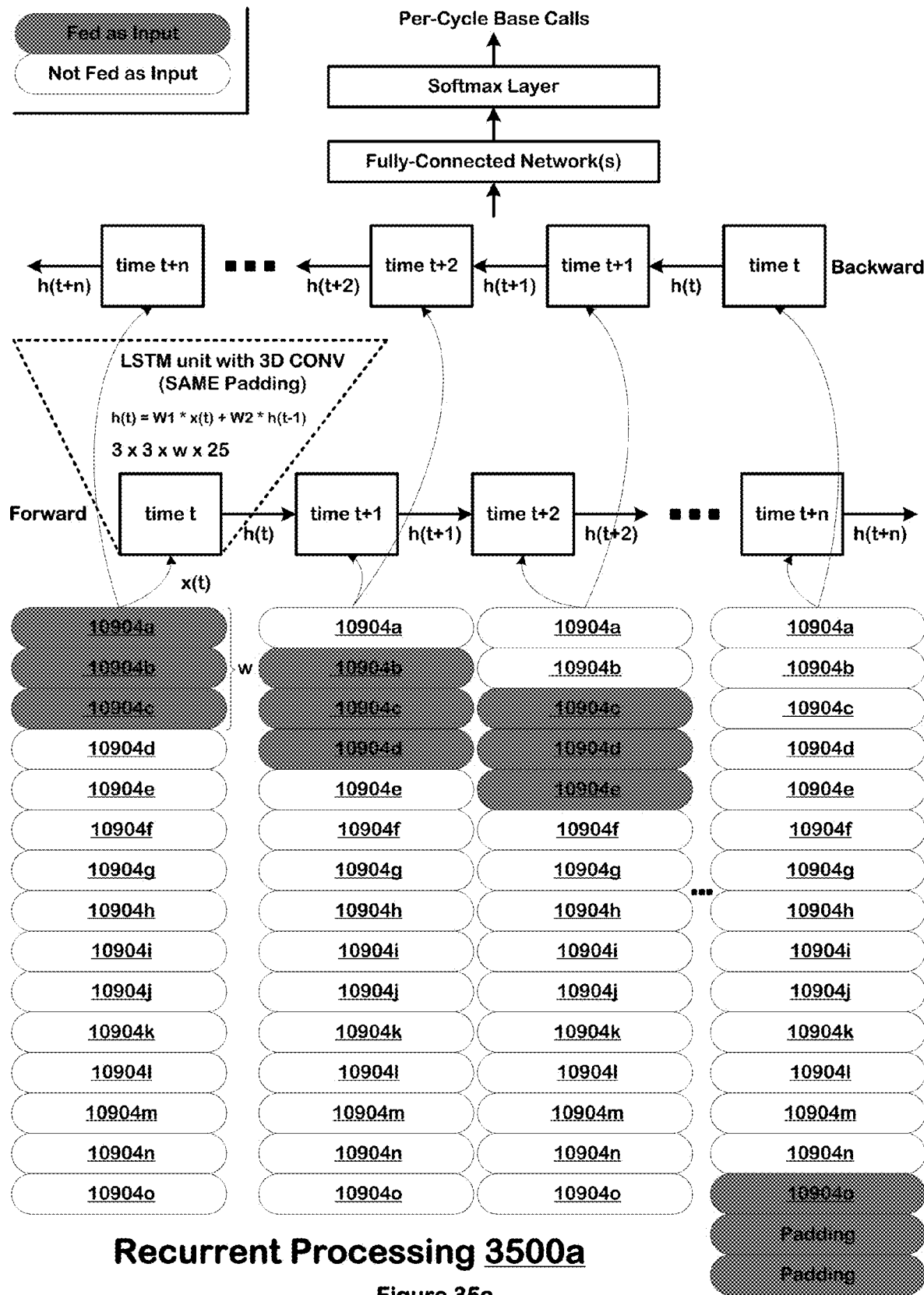
FIG. 35a illustrates one implementation of subjecting the stack of FIG. 34 to recurrent application of 3D convolutions in forward and backward directions and producing base calls for each of the clusters at each of the t sequencing cycles in the series.

The recurrent module 3108 subjects the stack 3400 to recurrent application of 3D convolutions (i.e., recurrent processing 3500) in forward and backward directions and produces base calls for each of the clusters at each of the t sequencing cycles in the series. The 3D convolutions are used to extract spatio-temporal features from a subset of the flattened mixed representations in the stack 3400 on a sliding window basis. Each sliding window (w) corresponds to a respective sequencing cycle and is highlighted in FIG. 35a in orange. In some implementations, w is parameterized to be 1, 2, 3, 5, 7, 9, 15, 21, etc., depending on the total number of sequencing cycles being simultaneously base called. In one implementation, w is a fraction of the total number of sequencing cycles being simultaneously base called.

So, for example, consider that each sliding window contains three successive flattened mixed representations from the stack 3400 that comprises the fifteen flattened mixed representations 3204a to 3204o. Then, the first three flattened mixed representations 3204a to 3204c in the first sliding window correspond to the first sequencing cycle, the next three flattened mixed representations 3204b to 3204d in the second sliding window correspond to the second sequencing cycle, and so on. In some implementations, padding is used to encode adequate number of flattened mixed representations in the final sliding window corresponding to the final sequencing cycle, starting with the final flattened mixed representation 3204o.

At each time step, the recurrent module 3108 accepts (1) the current input x(t) and (2) the previous hidden state representation h(t−1) and computes the current hidden state representation h(t). The current input x(t) includes only a subset of the flattened mixed representations from the stack 3400 that fall within the current sliding window ((w), in orange). Therefore, each current input x(t), at each time step, is a 3D volume of a plurality of flattened mixed representations (e.g., 1, 2, 3, 5, 7, 9, 15, or 21 flattened mixed representations, depending on w). For example, when (i) a single flattened mixed representation is two-dimensional (2D) with dimensions 15×1905 and (ii) w is 7, then each current input x(t), at each time step, is a 3D volume with dimensions 15×1905×7.

The recurrent module 3108 applies a first 3D convolution ($W1_{3DCONV}$) to the current input x(t) and a second 3D convolution ($W2_{3DCONV}$) to the previous hidden state representation h(t−1) to produce the current hidden state representation h(t). In some implementations, $W1_{3DCONV}$ and $W2_{3DCONV}$ are the same because the weights are shared.

Gated Processing

In one implementation, the recurrent module 3108 processes the current input x(t) and the previous hidden state representation h(t−1) through a gated network such as long short-term memory (LSTM) network or gated recurrent unit (GRU) network. For example, in the LSTM implementation, the current input x(t), along with the previous hidden state representation h(t−1), is processed through each of the four gates of an LSTM unit: input gate, activation gate, forget gate, and output gate. This is illustrated in FIG. 35b, which shows one implementation of processing 3500b the current input x(t) and the previous hidden state representation h(t−1) through an LSTM unit that applies 3D convolutions to the current input x(t) and the previous hidden state representation h(t−1) and produces the current hidden state representation h(t) as output. In such an implementation, the weights of the input, activation, forget, and output gates apply 3D convolutions.

In some implementations, the gated units (LSTM or GRU) do not use the non-linearity/squashing functions like hyperbolic tangent and sigmoid.

In one implementation, the current input x(t), the previous hidden state representation h(t−1), and the current hidden state representation h(t) are all 3D volume with same dimensionality and are processed through or produced by the input, activation, forget, and output gates as 3D volume.

In one implementation, the 3D convolutions of the recurrent module 3108 use a bank of twenty-five convolution filters of size 3×3, along with the SAME padding. In some implementations, the size of the convolution filters is 5×5. In some implementations, the number of convolution filters used by the recurrent module 3108 are factorized by a power of two, such as 2, 4, 16, 32, 64, 128, 256, 512, and 1024.

Bi-Directional Processing

The recurrent module 3108 first processes the stack 3400 from the beginning to the end (top-down) on the sliding window basis and produces a sequence of current hidden state representations (vectors) for the forward traversal $\vec{h}_t = 3DCONV(x_t + \vec{h}_{t-1})$.

The recurrent module 3108 then processes the stack 3400 from the end to the beginning (bottom-up) on the sliding window basis and produces a sequence of current hidden state representations (vectors) for the backward/reverse traversal $\overleftarrow{h}_t = 3DCONV(x_t + \overleftarrow{h}_{t-1})$.

In some implementations, for both the directions, at each time step, the processing uses the gates of an LSTM or a GRU. For example, at each time step, a forward current input x(t) is processed through the input, activation, forget, and output gates of an LSTM unit to produce a forward current hidden state representation $\vec{h}_t$ and a backward current input x(t) is processed through the input, activation, forget, and output gates of another LSTM unit to produce a backward current hidden state representation $\overleftarrow{h}_t$.

Then, for each time step/sliding window/sequencing cycle, the recurrent module 3108 combines (concatenates or sums or averages) the corresponding forward and backward current hidden state representations and produces a combined hidden state representation $$\overset{c}{h}_t = [\vec{h}_t; \overleftarrow{h}_t].$$

The combined hidden representation $\overset{c}{h}_t$ is then processed through one or more fully-connected networks to produce a dense representation. The dense representation is then processed through a softmax layer to produce likelihoods of bases incorporated in each of the clusters at a given sequencing cycle being A, C, T, and G. The bases are classified as A, C, T, or G based on the likelihoods. This is done for each of the t sequencing cycles in the series (or each time step/sliding window), either in parallel or sequentially.

One skilled in the art will appreciate that, in other implementations, the hybrid architecture can process input data for fewer or greater number of sequencing cycles and can comprise fewer or greater number of convolution and recurrent layers. Also, the dimensionality of the input data, the current and previous hidden representations, the convolution filters, the resulting feature maps, and the output can be different. Also, the number of convolution filters in a convolution layer can be different. It can use different padding and striding configurations. It can use a different classification function (e.g., sigmoid or regression) and may or may not include a fully-connected layer. It can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolution. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous SGD. It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tan h)), batch normalization layers, regularization layers, dropout, pooling layers (e.g., max or average pooling), global average pooling layers, and attention mechanisms.

Experimental Results and Observations

Figure 36:
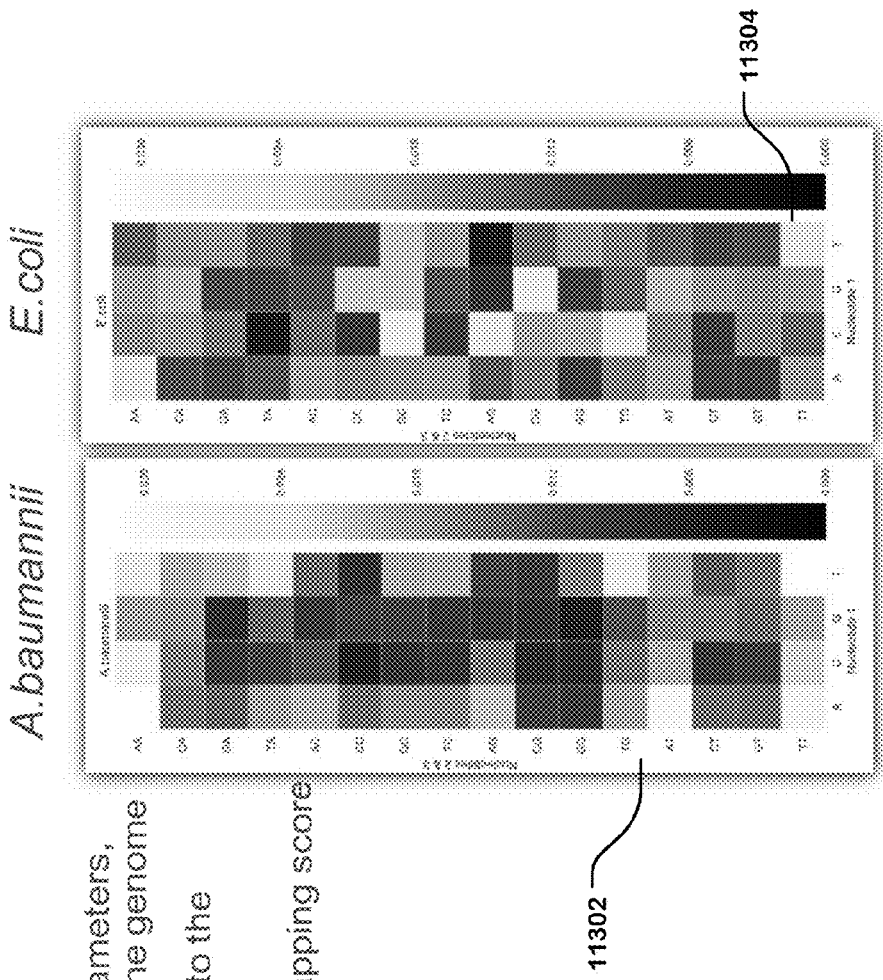
FIG. 36 shows one implementation of balancing trinucleotides (3-mers) in the training data used to train the neural network-based base caller.

FIG. 36 shows one implementation of balancing trinucleotides (3-mers) in the training data used to train the neural network based base caller 218. Balancing results in very little learning of statistics about genome in the training data and in turn improves generalization. Heat map 3602 shows balanced 3-mers in the training data for a first organism called "A. baumanni". Heap map 3604 shows balanced 3-mers in the training data for a second organism called "E. coli".

Figure 37:
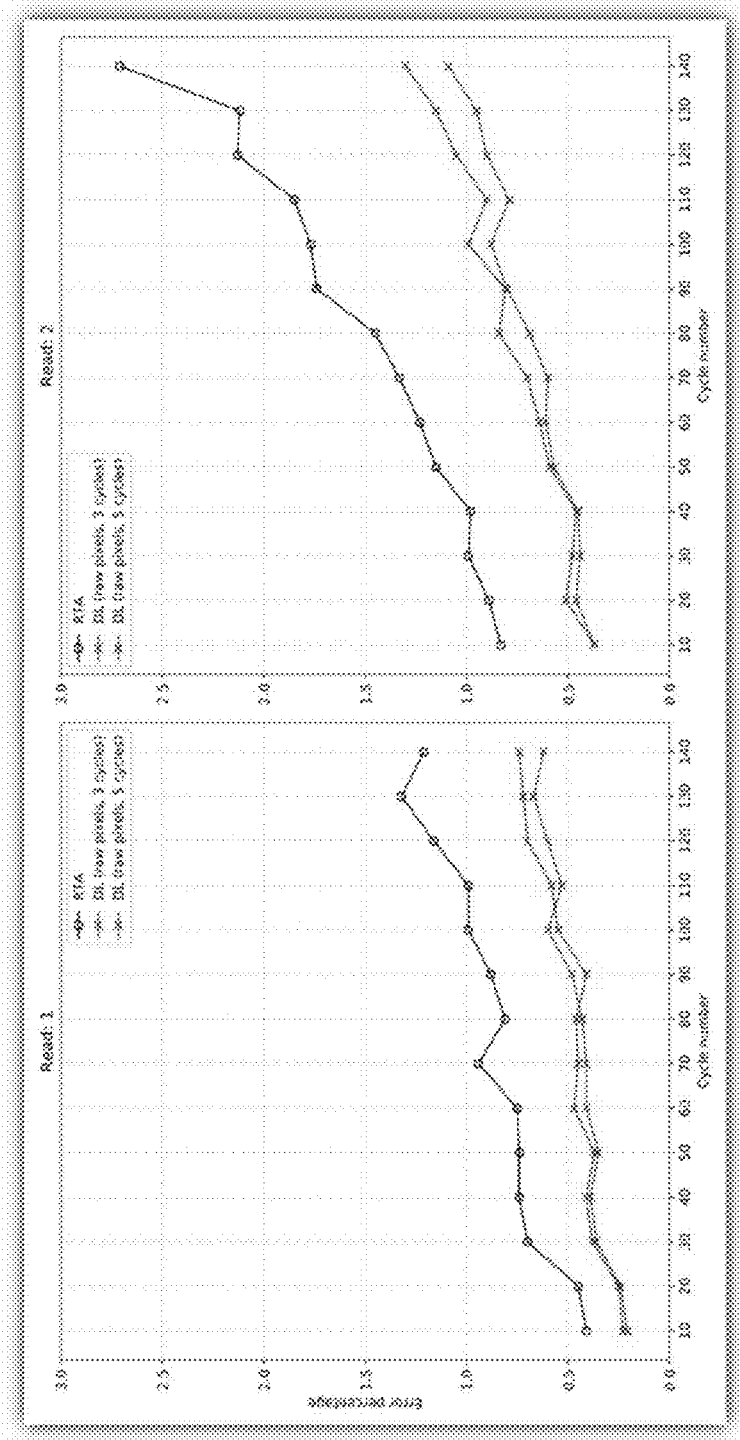
FIG. 37 compares base calling accuracy of the RTA base caller against the neural network-based base caller.

FIG. 37 compares base calling accuracy of the RTA base caller against the neural network-based base caller 218. As illustrated in FIG. 37, the RTA base caller has a higher error percentage in two sequencing runs (Read: 1 and Read: 2). That is, the neural network-based base caller 218 outperforms the RTA base caller in both the sequencing runs.

Figure 38:
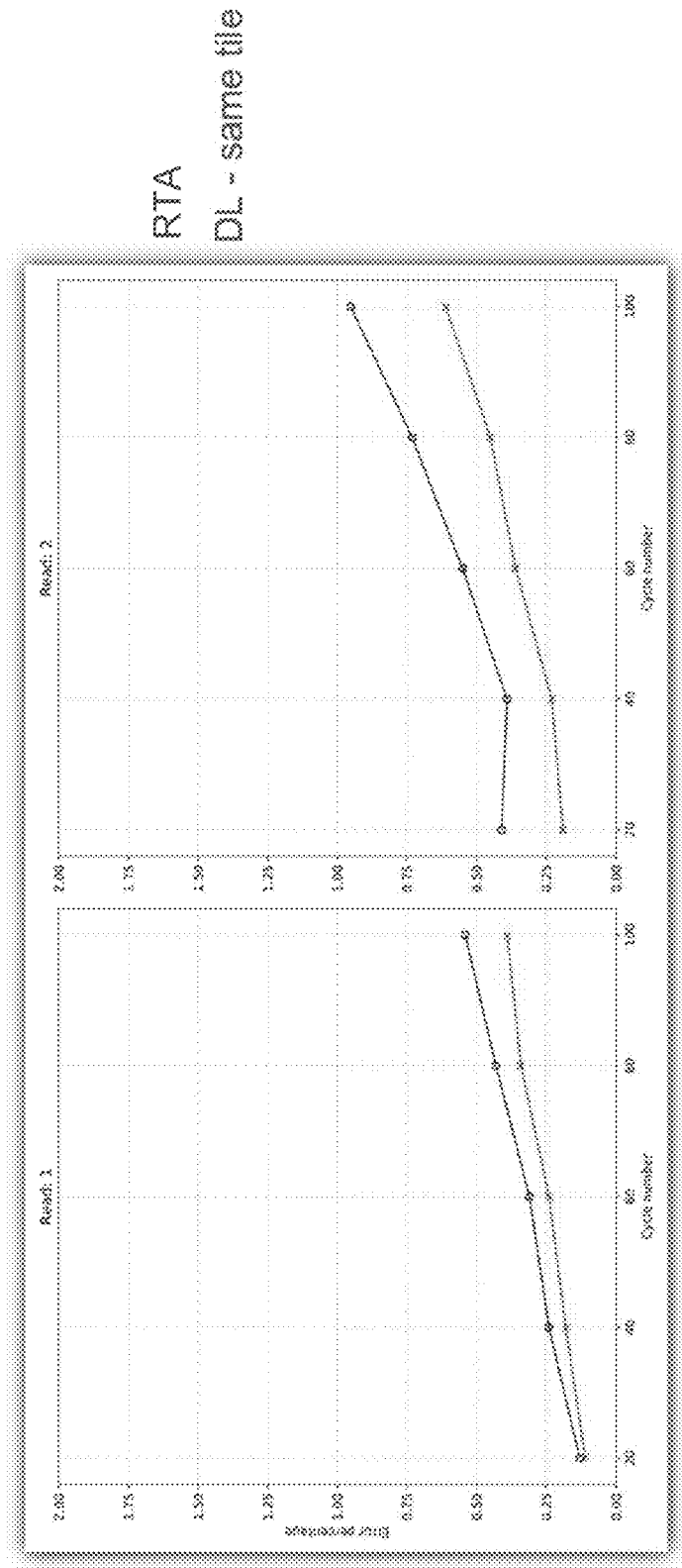
FIG. 38 compares tile-to-tile generalization of the RTA base caller with that of the neural network-based base caller on a same tile.

FIG. 38 compares tile-to-tile generalization of the RTA base caller with that of the neural network-based base caller 218 on a same tile. That is, with the neural network-based base caller 218, the inference (testing) is performed on data for the same tile whose data is used in the training.

Figure 39:
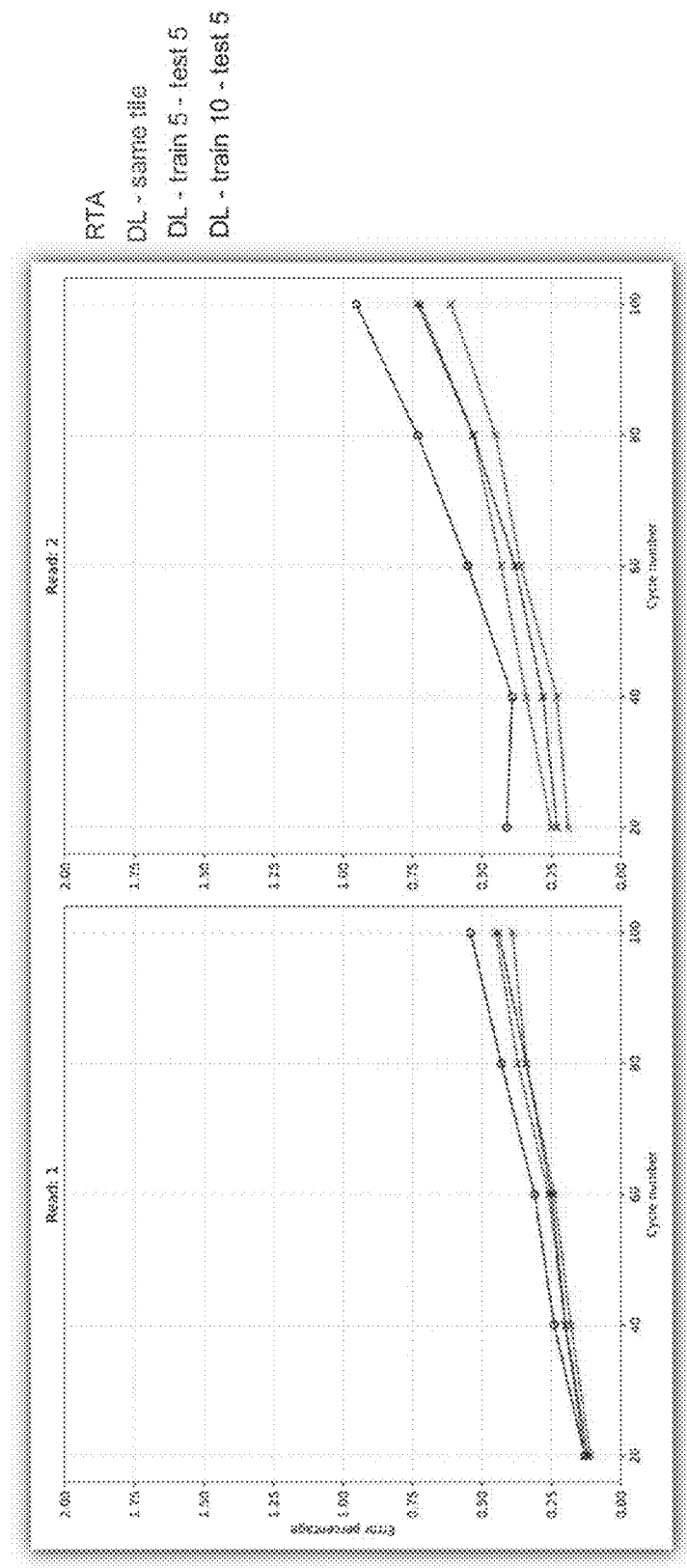
FIG. 39 compares tile-to-tile generalization of the RTA base caller with that of the neural network-based base caller on a same tile and on different tiles.

FIG. 39 compares tile-to-tile generalization of the RTA base caller with that of the neural network-based base caller 218 on a same tile and on different tiles. That is, the neural network-based base caller 218 is trained on data for clusters on a first tile, but performs inference on data from clusters on a second tile. In the same tile implementation, the neural network-based base caller 218 is trained on data from clusters on tile five and tested on data from clusters on tile five. In the different tile implementation, the neural network-based base caller 218 is trained on data from clusters on tile ten and tested on data from clusters on tile five.

Figure 40:
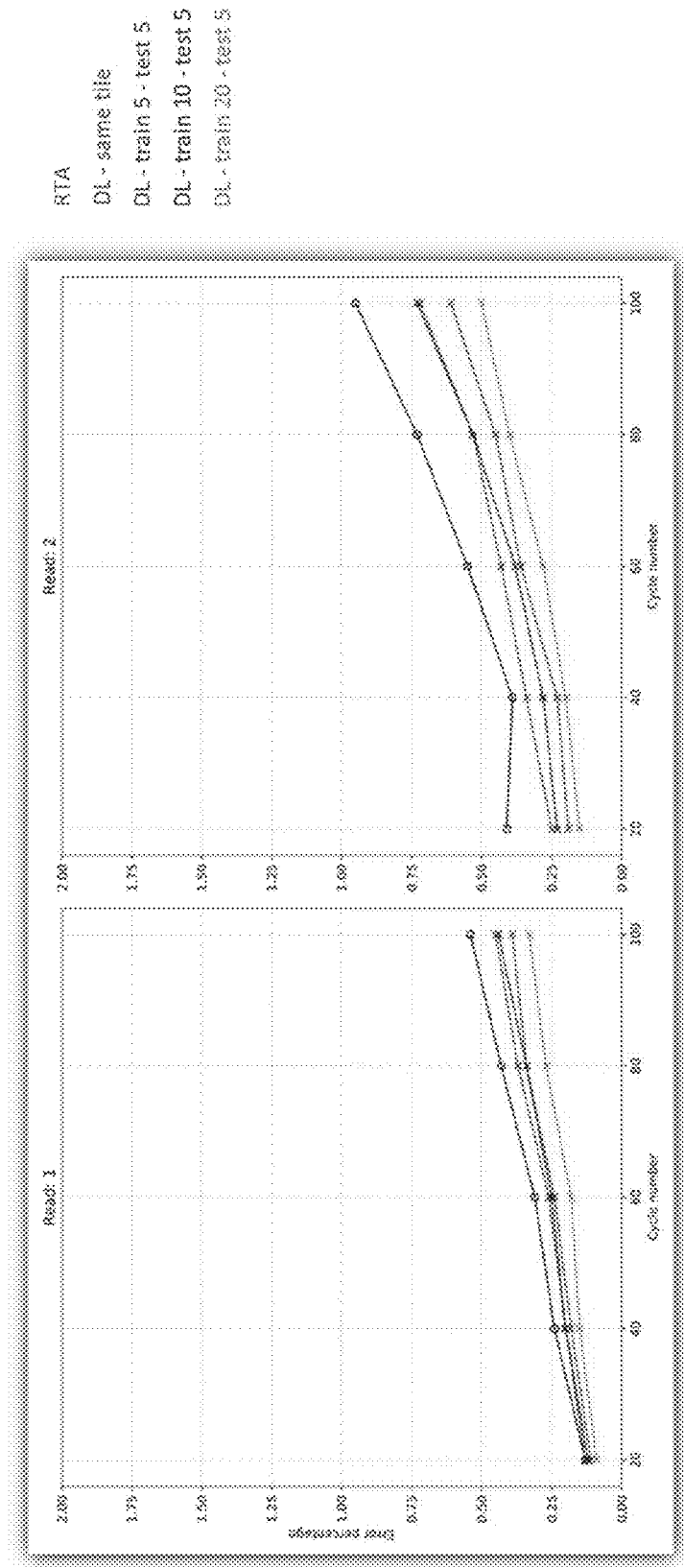
FIG. 40 also compares tile-to-tile generalization of the RTA base caller with that of the neural network-based base caller on different tiles.
Figure 42:
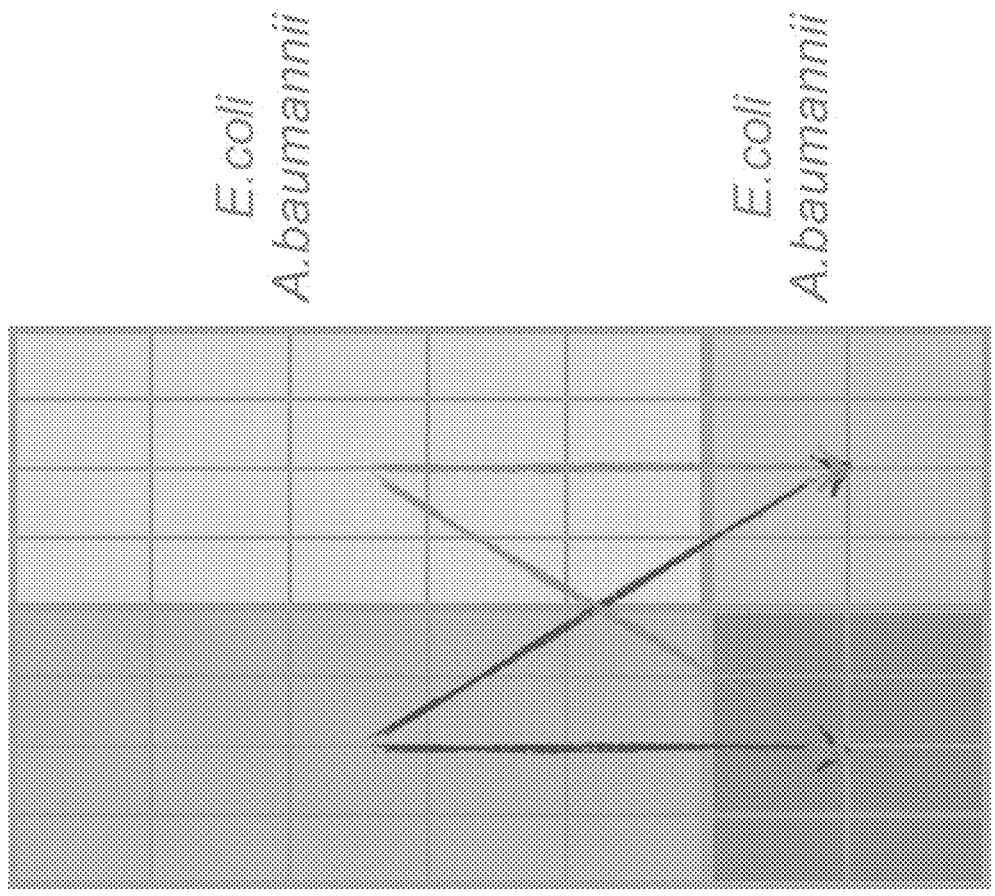
FIGS. 42, 43, 44, and 45 show lane-to-lane generalization of the neural network-based base caller on training data from *A. baumanni* and *E. coli*.

FIG. 40 also compares tile-to-tile generalization of the RTA base caller with that of the neural network-based base caller 218 on different tiles. In the different tile implementations, the neural network-based base caller 218 is once trained on data from clusters on tile ten and tested on data from clusters on tile five, and then trained on data from clusters on tile twenty and tested on data from clusters on tile five.

FIG. 41 shows how different sizes of the image patches fed as input to the neural network-based base caller 218 effect the base calling accuracy. In both sequencing runs (Read: 1 and Read: 2), the error percentage decreases as the patch size increases from 3×3 to 11×11. That is, the neural network-based base caller 218 produces more accurate base calls with larger image patches. In some implementations, base calling accuracy is balanced against compute efficiency by using image patches that are not larger than 100×100 pixels. In other implementations, image patches as large as 3000×3000 pixels (and larger) are used.

FIGS. 42, 43, 44, and 45 show lane-to-lane generalization of the neural network-based base caller 218 on training data from *A. baumanni* and *E. coli*.

Figure 43:
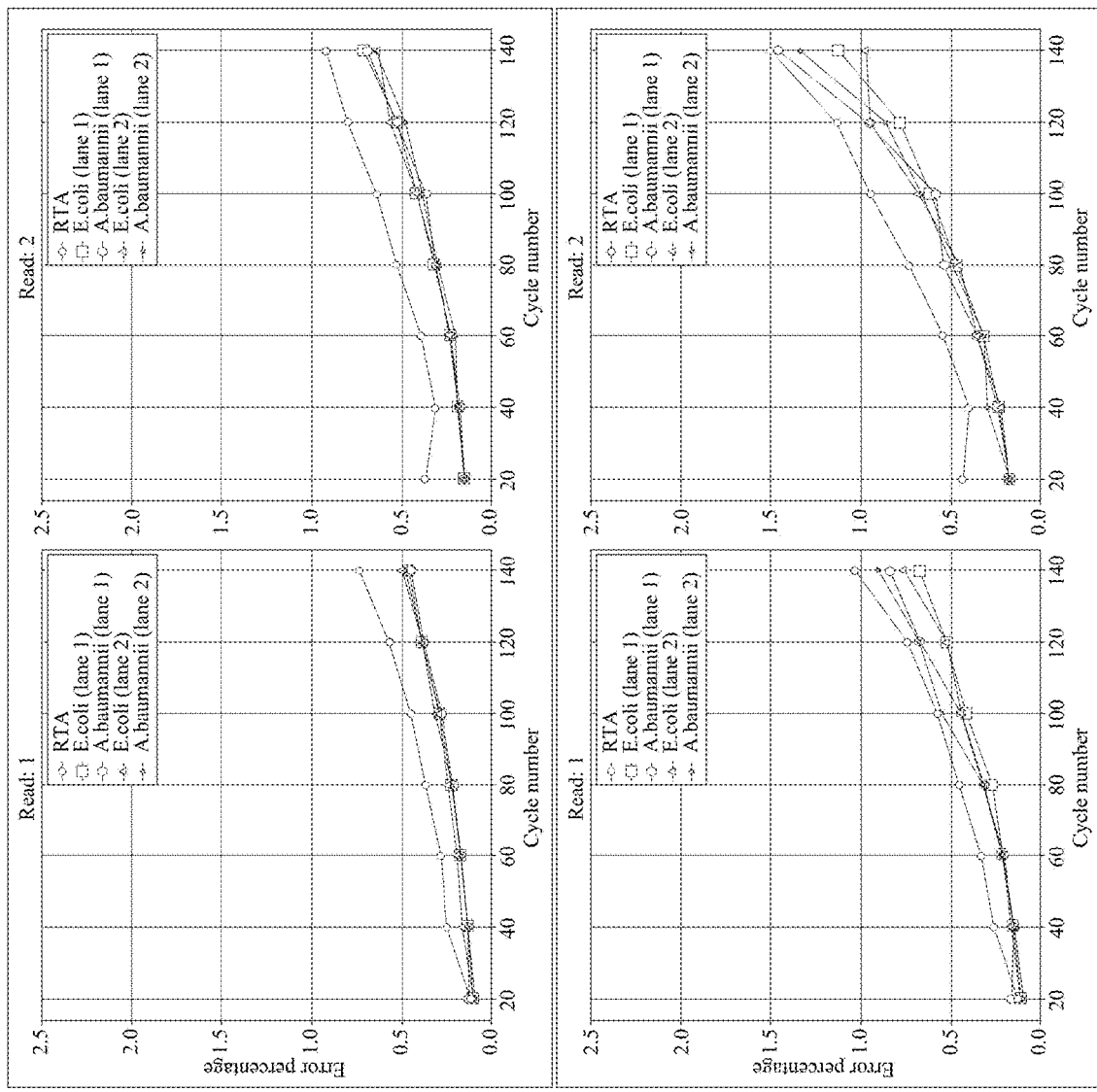

Turning to FIG. 43, in one implementation, the neural network-based base caller 218 is trained on *E. coli* data from clusters on a first lane of a flow cell and tested on *A. baumanni* data from clusters on both the first and second lanes of the flow cell. In another implementation, the neural network-based base caller 218 is trained on *A. baumanni* data from clusters on the first lane and tested on the *A. baumanni* data from clusters on both the first and second lanes. In yet another implementation, the neural network-based base caller 218 is trained on *E. coli* data from clusters on the second lane and tested on the *A. baumanni* data from clusters on both the first and second lanes. In yet further implementation, the neural network-based base caller 218 is trained on *A. baumanni* data from clusters on the second lane and tested on the *A. baumanni* data from clusters on both the first and second lanes.

In one implementation, the neural network-based base caller 218 is trained on *E. coli* data from clusters on a first lane of a flow cell and tested on *E. coli* data from clusters on both the first and second lanes of the flow cell. In another implementation, the neural network-based base caller 218 is trained on *A. baumanni* data from clusters on the first lane and tested on the *E. coli* data from clusters on both the first and second lanes. In yet another implementation, the neural network-based base caller 218 is trained on *E. coli* data from clusters on the second lane and tested on the *E. coli* data from clusters on the first lane. In yet further implementation, the neural network-based base caller 218 is trained on *A. baumanni* data from clusters on the second lane and tested on the *E. coli* data from clusters on both the first and second lanes.

In FIG. 43, the base calling accuracy (measured by the error percentage) is shown for each of these implementations for two sequencing runs (e.g., Read: 1 and Read: 2).

Figure 44:
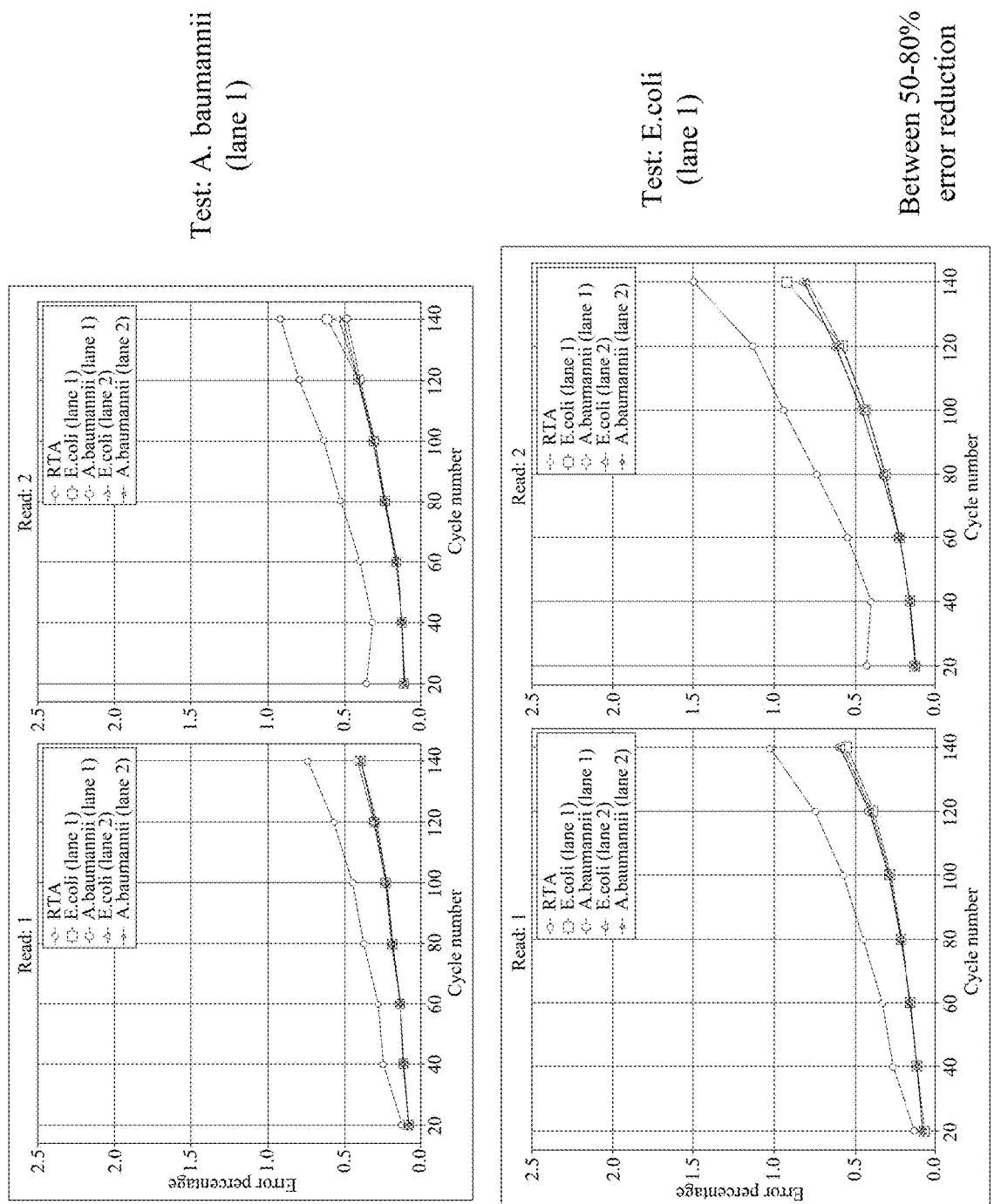

Turning to FIG. 44, in one implementation, the neural network-based base caller 218 is trained on *E. coli* data from clusters on a first lane of a flow cell and tested on *A. baumanni* data from clusters on the first lane. In another implementation, the neural network-based base caller 218 is trained on *A. baumanni* data from clusters on the first lane and tested on the *A. baumanni* data from clusters on the first lane. In yet another implementation, the neural network-based base caller 218 is trained on *E. coli* data from clusters on the second lane and tested on the *A. baumanni* data from clusters on the first lane. In yet further implementation, the neural network-based base caller 218 is trained on *A. baumanni* data from clusters on the second lane and tested on the *A. baumanni* data from clusters on the first lane.

In one implementation, the neural network-based base caller 218 is trained on *E. coli* data from clusters on a first lane of a flow cell and tested on *E. coli* data from clusters on the first lane. In another implementation, the neural network-based base caller 218 is trained on *A. baumanni* data from clusters on the first lane and tested on the *E. coli* data from clusters on the first lane. In yet another implementation, the neural network-based base caller 218 is trained on *E. coli* data from clusters on the second lane and tested on the *E. coli* data from clusters on the first lane. In yet further implementation, the neural network-based base caller 218 is trained on *A. baumanni* data from clusters on the second lane and tested on the *E. coli* data from clusters on the first lane.

In FIG. 44, the base calling accuracy (measured by the error percentage) is shown for each of these implementations for two sequencing runs (e.g., Read: 1 and Read: 2). Comparing FIG. 43 with FIG. 44, it can be seen that the implementations covered by the later result in an error reduction between fifty to eighty percent.

Figure 45:
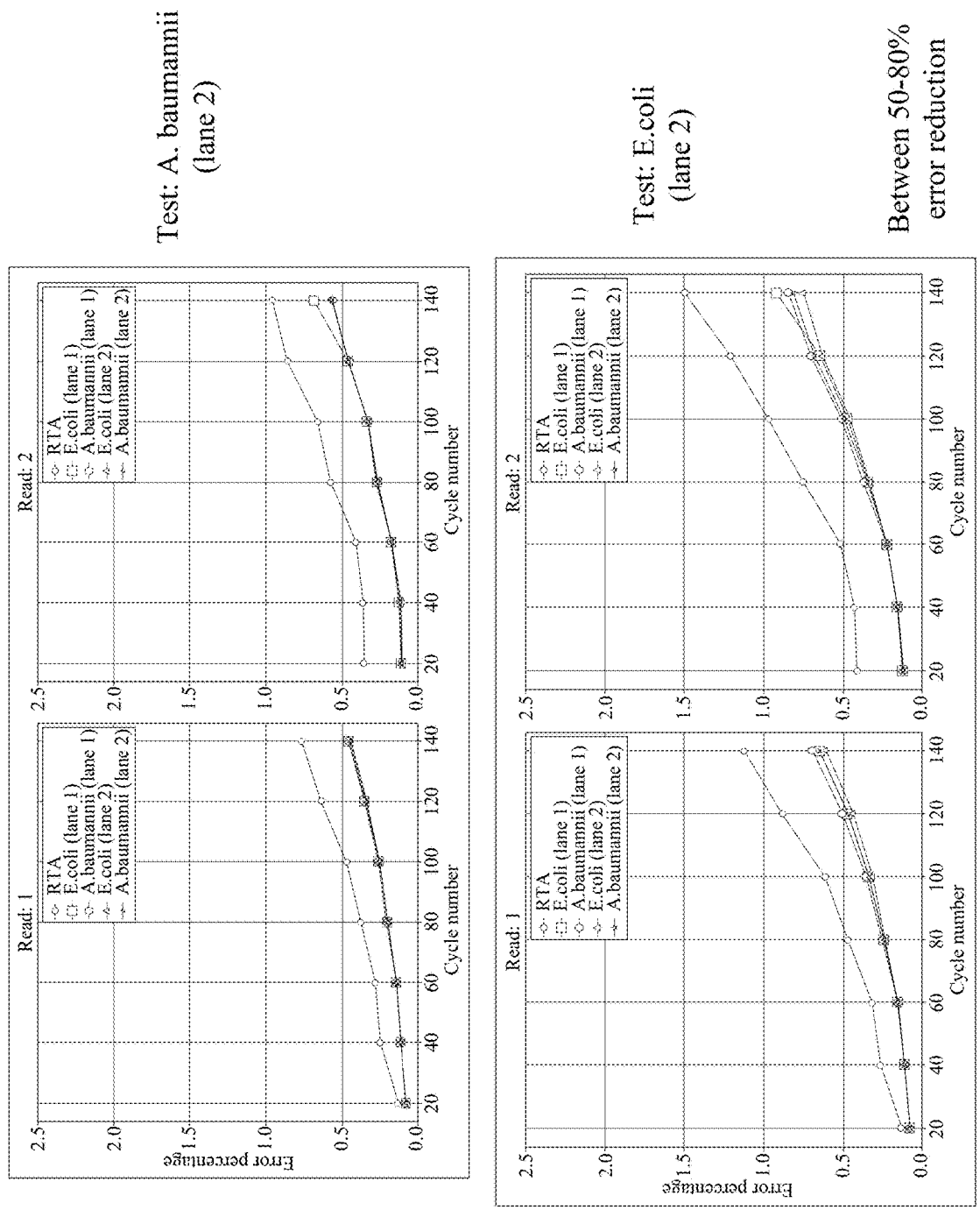

Turning to FIG. 45, in one implementation, the neural network-based base caller 218 is trained on *E. coli* data from clusters on a first lane of a flow cell and tested on *A. baumanni* data from clusters on the second lane. In another implementation, the neural network-based base caller 218 is trained on *A. baumanni* data from clusters on the first lane and tested on the *A. baumanni* data from clusters on the second lane. In yet another implementation, the neural network-based base caller 218 is trained on *E. coli* data from clusters on the second lane and tested on the *A. baumanni* data from clusters on the first lane. In second first lane. In yet further implementation, the neural network-based base caller 218 is trained on *A. baumanni* data from clusters on the second lane and tested on the *A. baumanni* data from clusters on the second lane.

In one implementation, the neural network-based base caller 218 is trained on *E. coli* data from clusters on a first lane of a flow cell and tested on *E. coli* data from clusters on the second lane. In another implementation, the neural network-based base caller 218 is trained on *A. baumanni* data from clusters on the first lane and tested on the *E. coli* data from clusters on the second lane. In yet another implementation, the neural network based base caller 218 is trained on *E. coli* data from clusters on the second lane and tested on the *E. coli* data from clusters on the second lane. In yet further implementation, the neural network-based base caller 218 is trained on *A. baumanni* data from clusters on the second lane and tested on the *E. coli* data from clusters on the second lane.

In FIG. 45, the base calling accuracy (measured by the error percentage) is shown for each of these implementations for two sequencing runs (e.g., Read: 1 and Read: 2). Comparing FIG. 43 with FIG. 45, it can be seen that the implementations covered by the later result in an error reduction between fifty to eighty percent.

Figure 46:
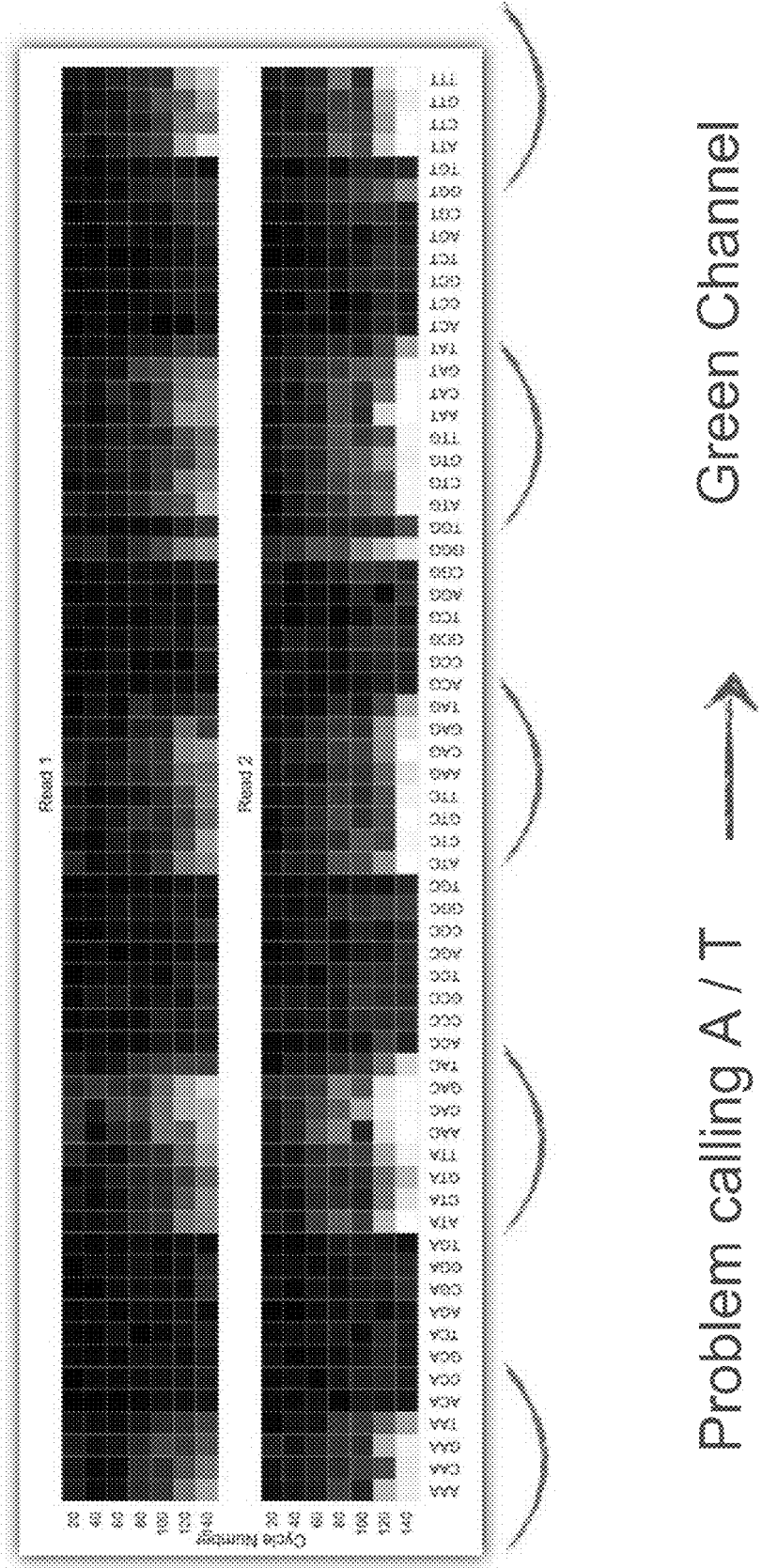
FIG. 46 depicts an error profile for the lane-to-lane generalization discussed above with respect to FIGS. 42, 43, 44, and 45.

FIG. 46 depicts an error profile for the lane-to-lane generalization discussed above with respect to FIGS. 42, 43, 44, and 45. In one implementation, the error profile detects error in base calling A and T bases in the green channel.

Figure 47:
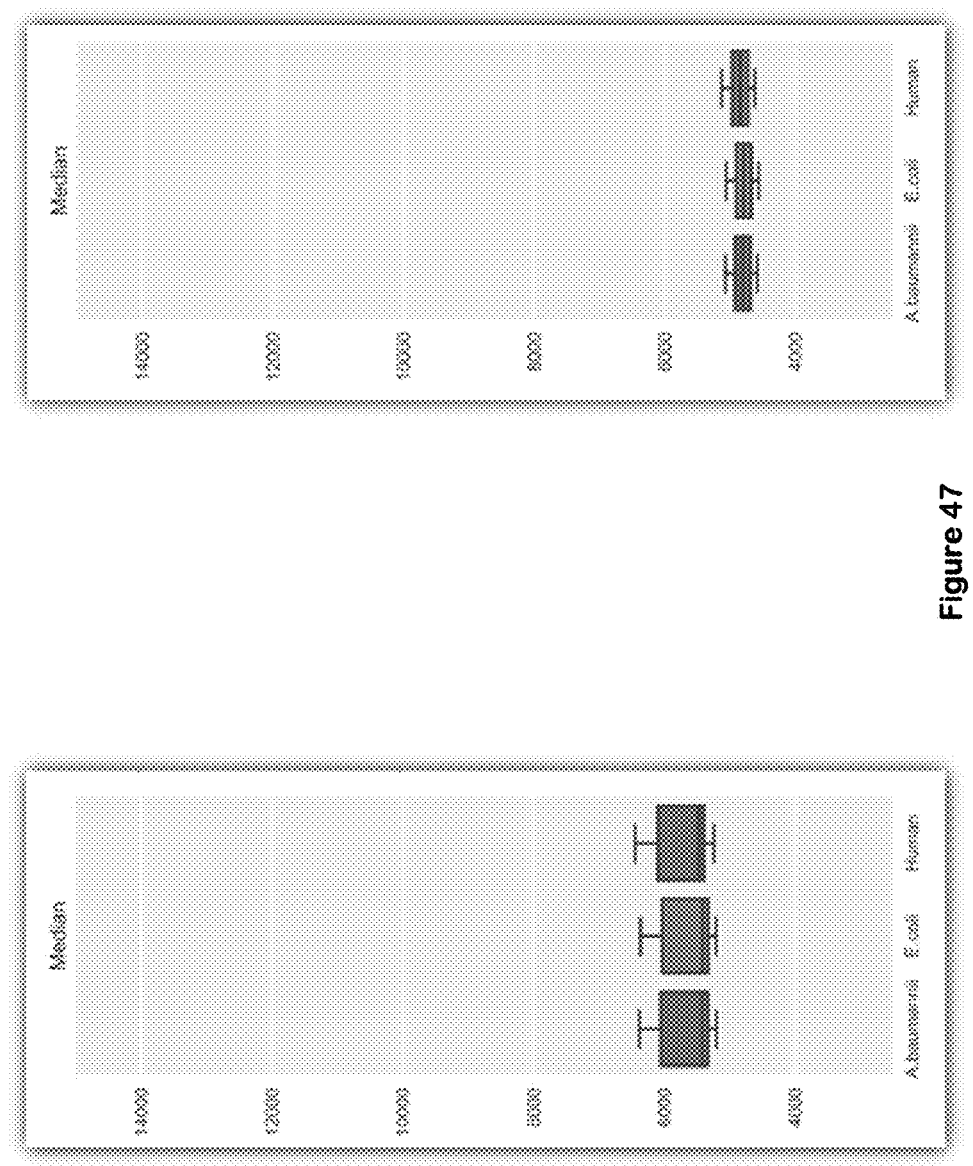
FIG. 47 attributes the source of the error detected by the error profile of FIG. 46 to low cluster intensity in the green channel.

FIG. 47 attributes the source of the error detected by the error profile of FIG. 46 to low cluster intensity in the green channel.

Figure 48:
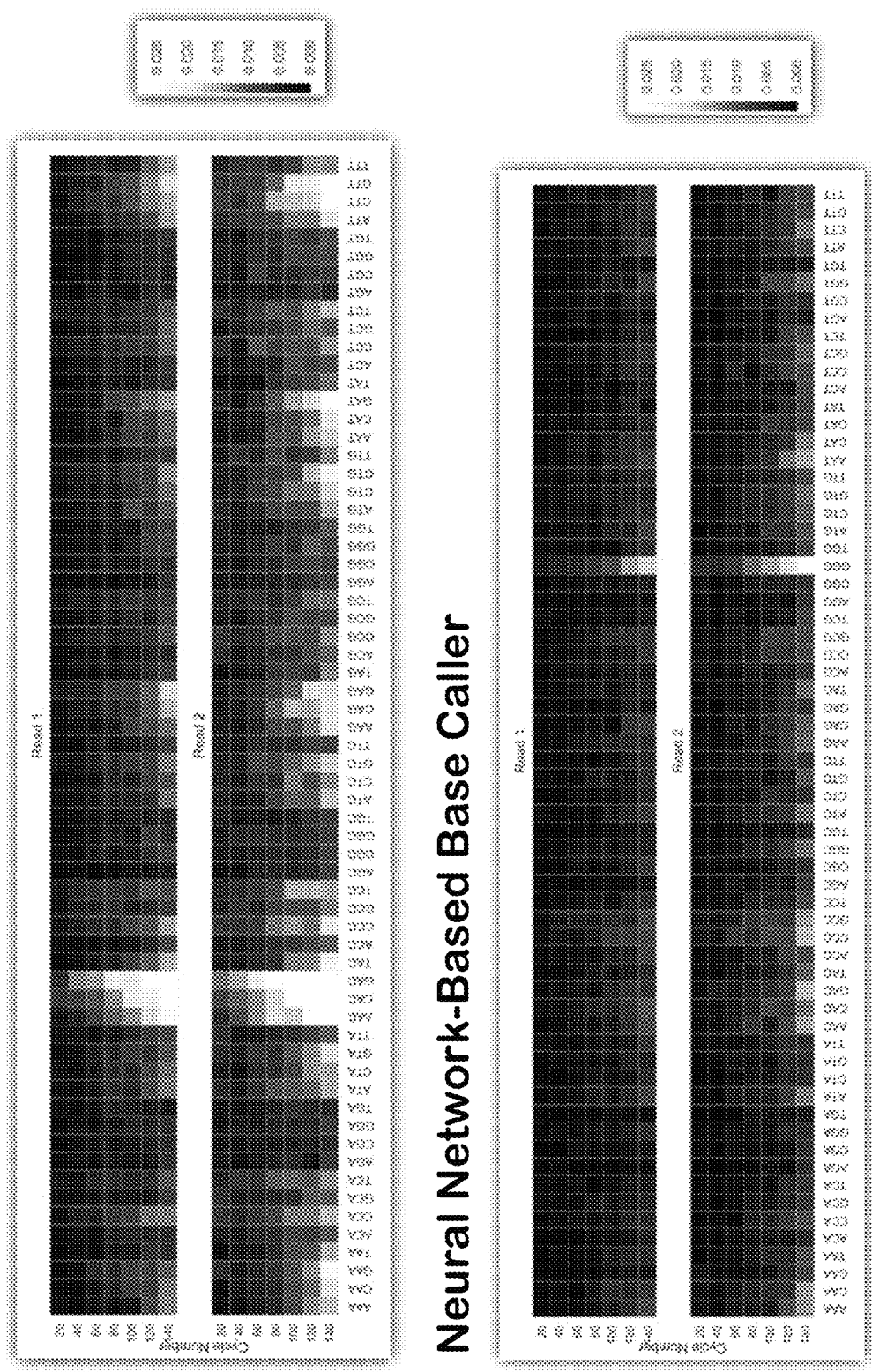
FIG. 48 compares error profiles of the RTA base caller and the neural network-based base caller for two sequencing runs (Read 1 and Read 2).

FIG. 48 compares error profiles of the RTA base caller and the neural network-based base caller 218 for two sequencing runs (Read 1 and Read 2). The comparison confirms superior base calling accuracy of the neural network-based base caller 218.

Figure 49A:
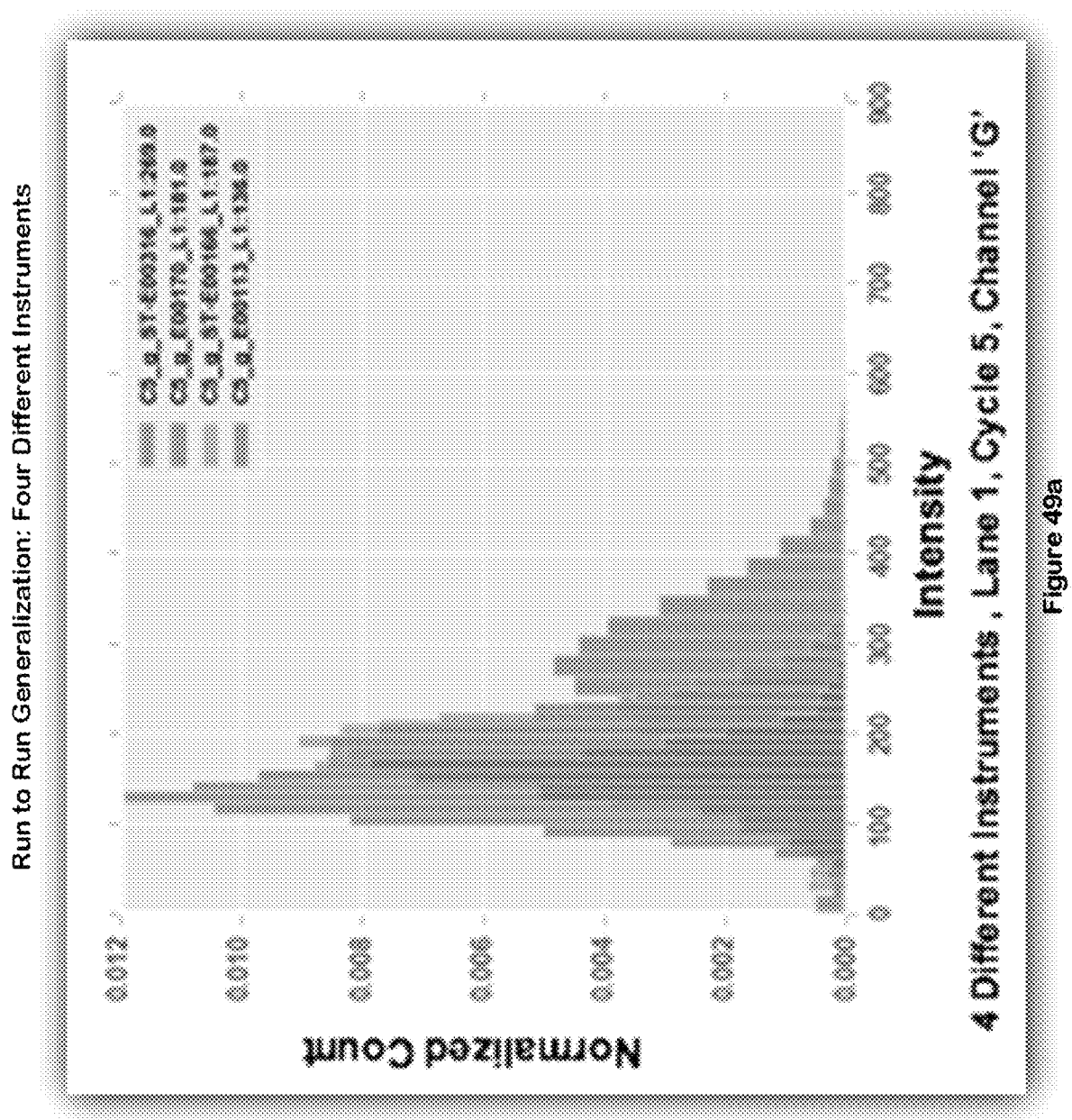
FIG. 49a shows run-to-run generalization of the neural network-based base caller on four different instruments.

FIG. 49*a* shows run-to-run generalization of the neural network-based base caller 218 on four different instruments.

Figure 49B:
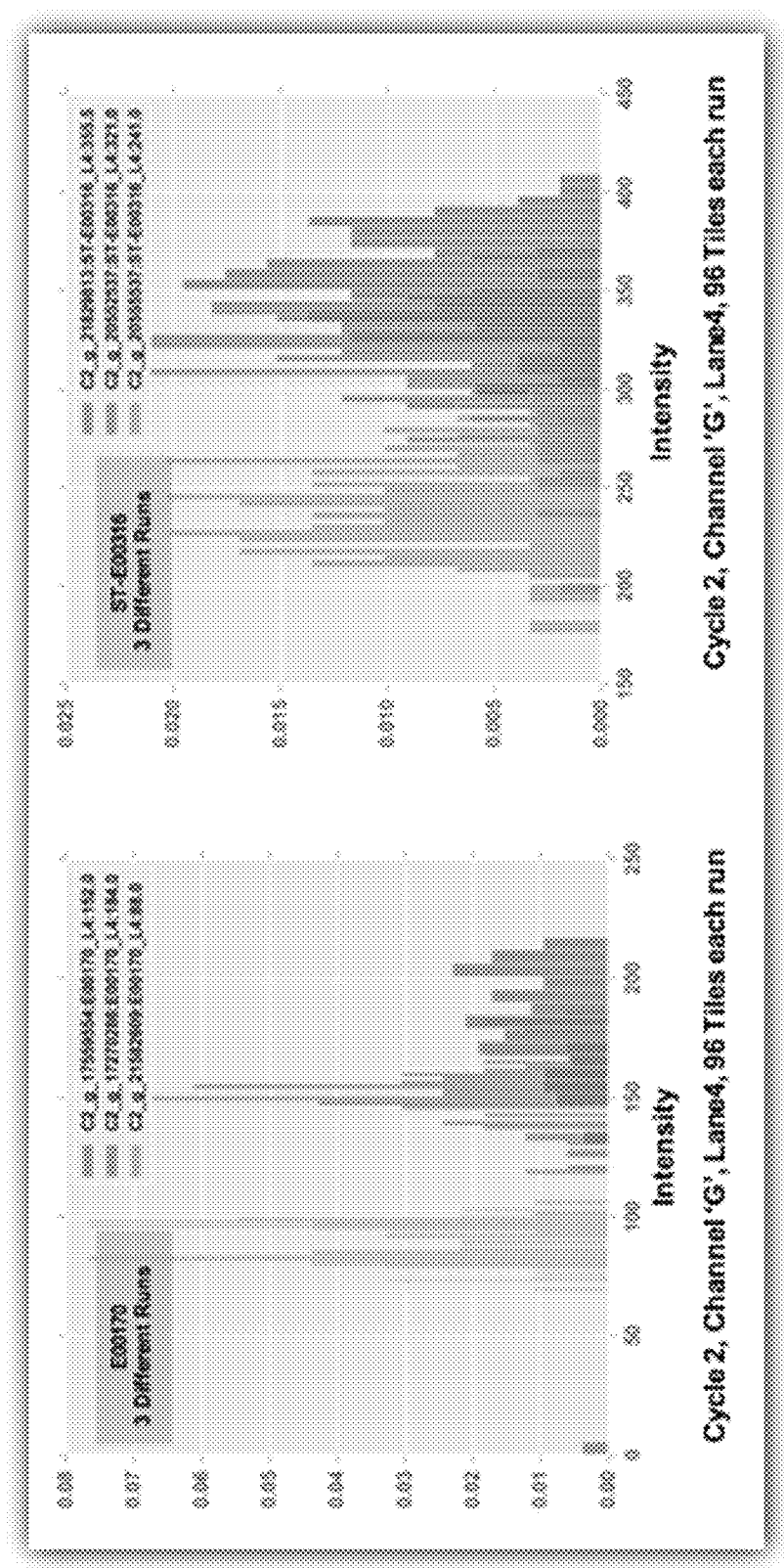
FIG. 49b shows run-to-run generalization of the neural network-based base caller on four different runs executed on a same instrument.

FIG. 49*b* shows run-to-run generalization of the neural network-based base caller 218 on four different runs executed on a same instrument.

Figure 50:
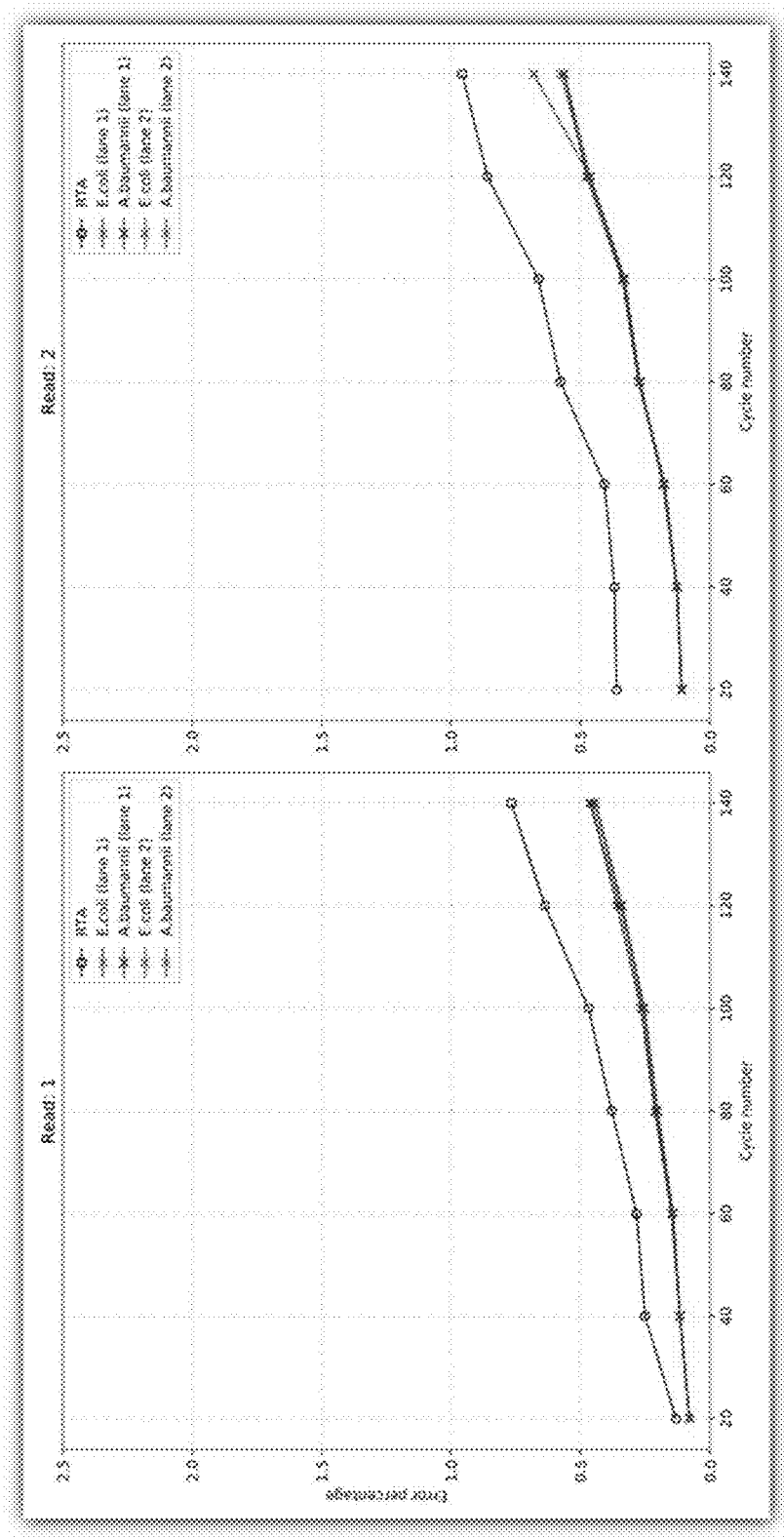
FIG. 50 shows the genome statistics of the training data used to train the neural network-based base caller.

FIG. 50 shows the genome statistics of the training data used to train the neural network-based base caller 218.

Figure 51:
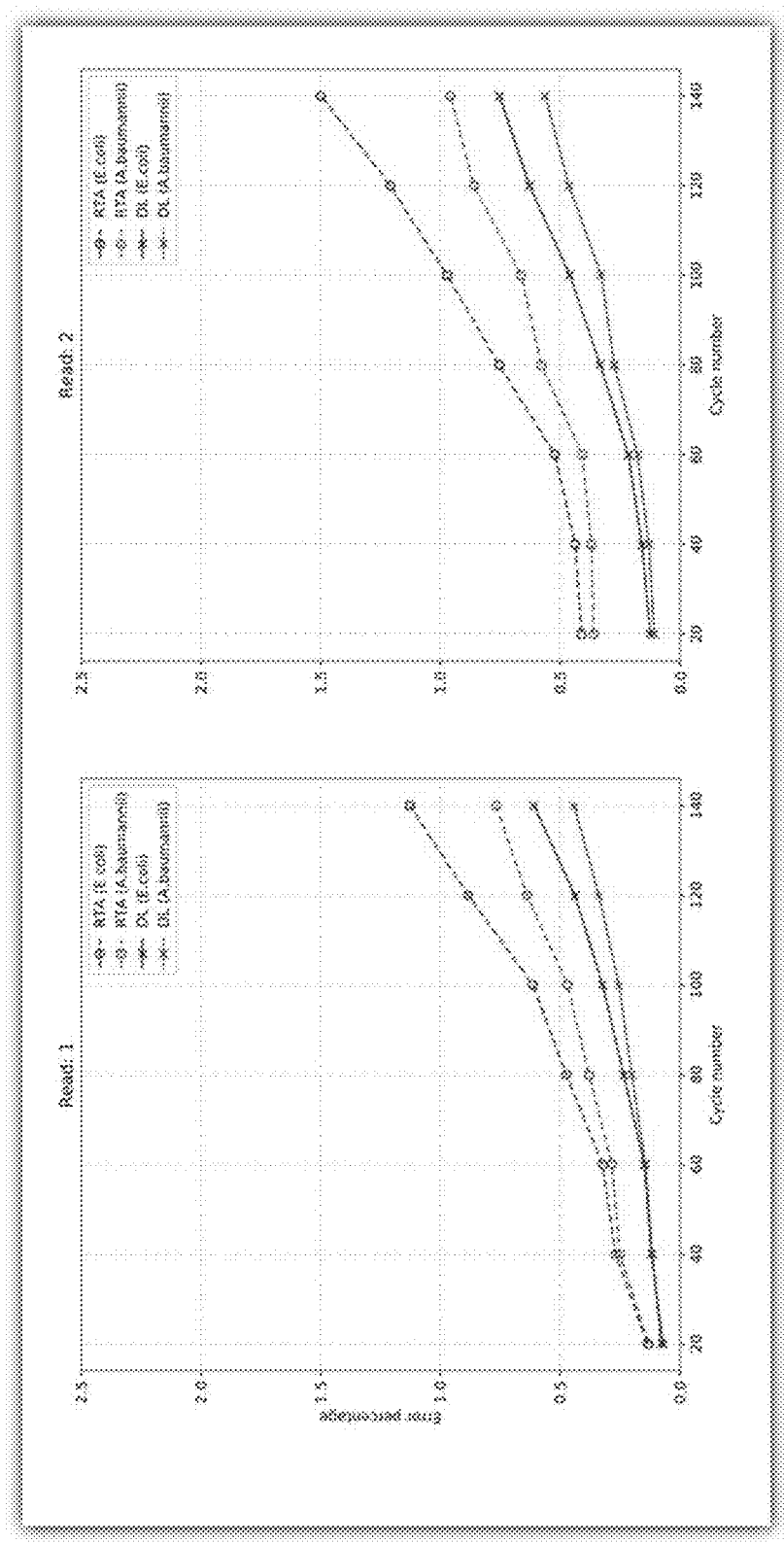
FIG. 51 shows the genome context of the training data used to train the neural network-based base caller.

FIG. 51 shows the genome context of the training data used to train the neural network-based base caller 218.

Figure 52:
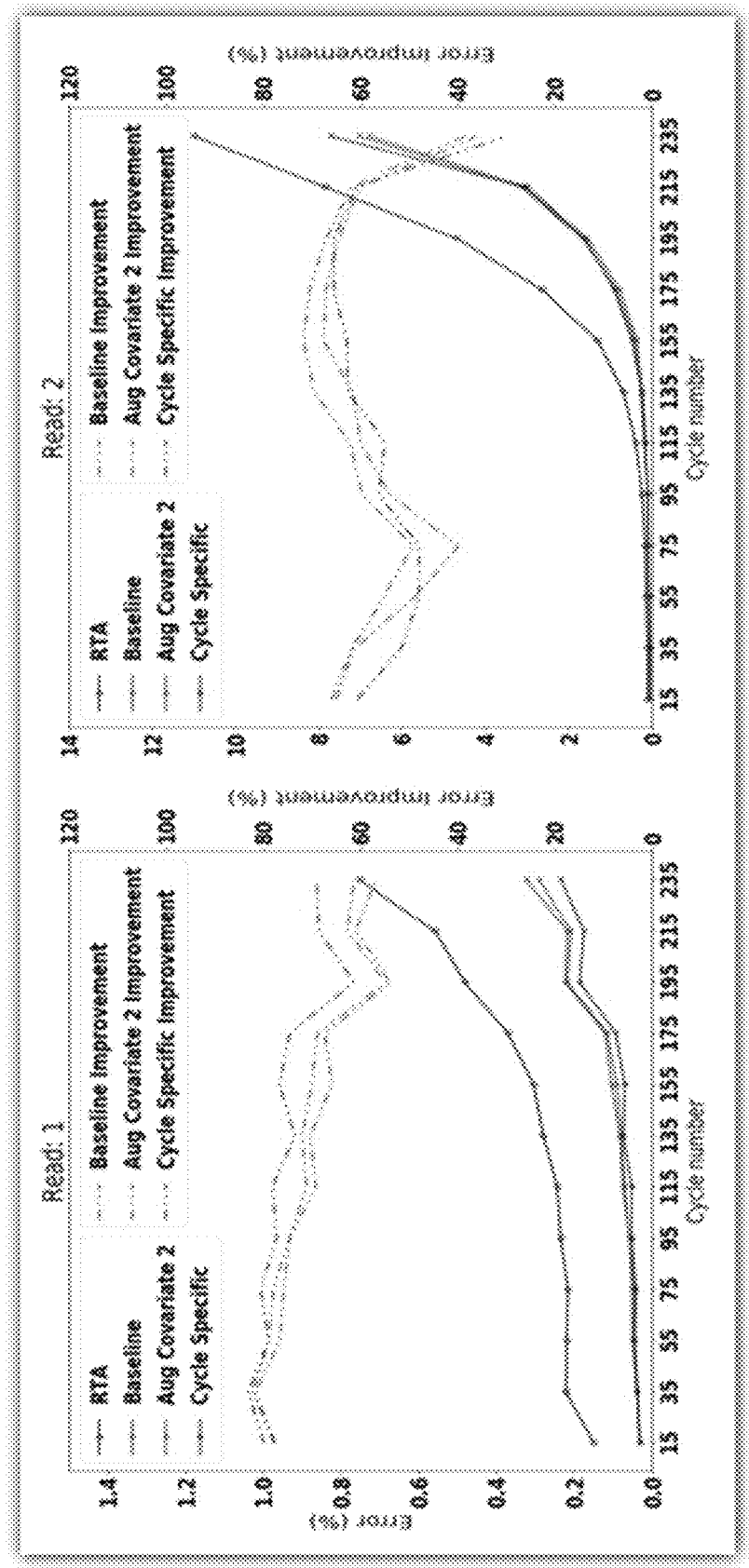
FIG. 52 shows the base calling accuracy of the neural network-based base caller in base calling long reads (e.g., 2×250).

FIG. 52 shows the base calling accuracy of the neural network-based base caller 218 in base calling long reads (e.g., 2×250).

Figure 53:
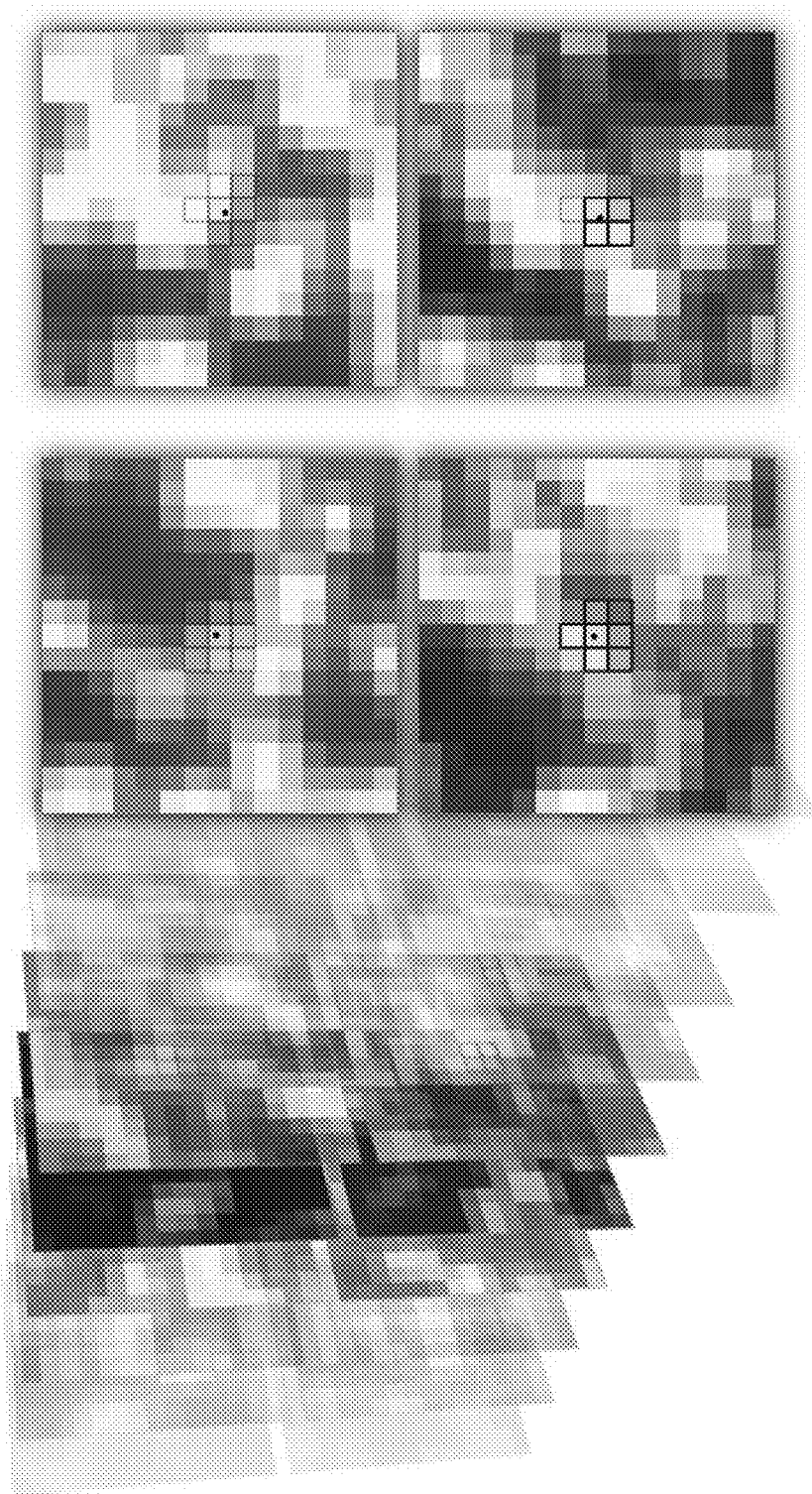
FIG. 53 illustrates one implementation of how the neural network-based base caller attends to the central cluster pixel(s) and its neighboring pixels across image patches.

FIG. 53 illustrates one implementation of how the neural network-based base caller 218 attends to the central cluster pixel(s) and its neighboring pixels across image patches.

Figure 54:
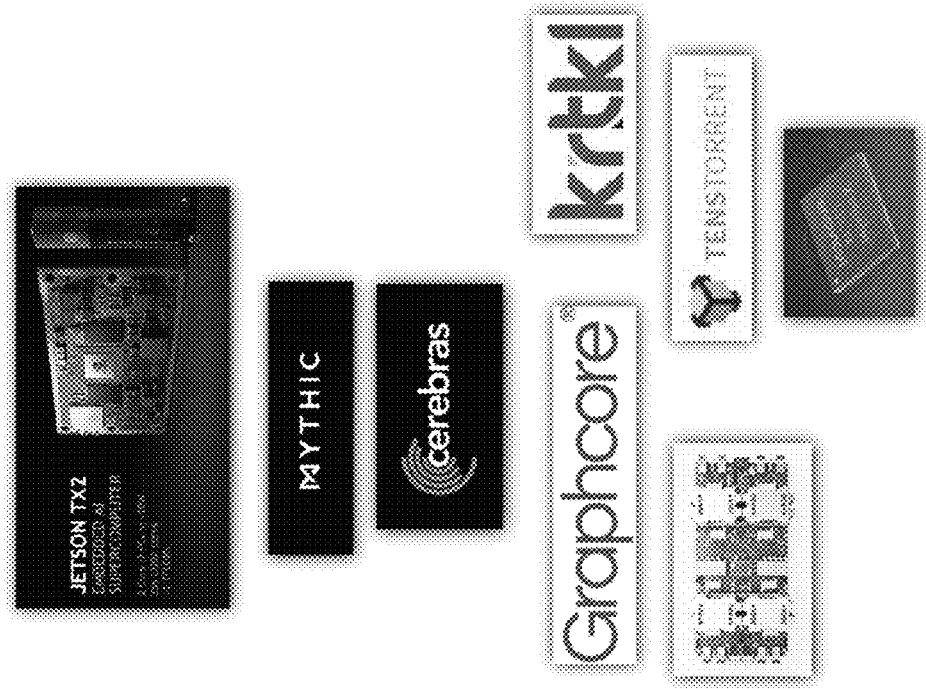
FIG. 54 shows various hardware components and configurations used to train and run the neural network-based base caller, according to one implementation. In other implementations, different hardware components and configurations are used.

FIG. 54 shows various hardware components and configurations used to train and run the neural network-based base caller 218, according to one implementation. In other implementations, different hardware components and configurations are used.

Figure 55:
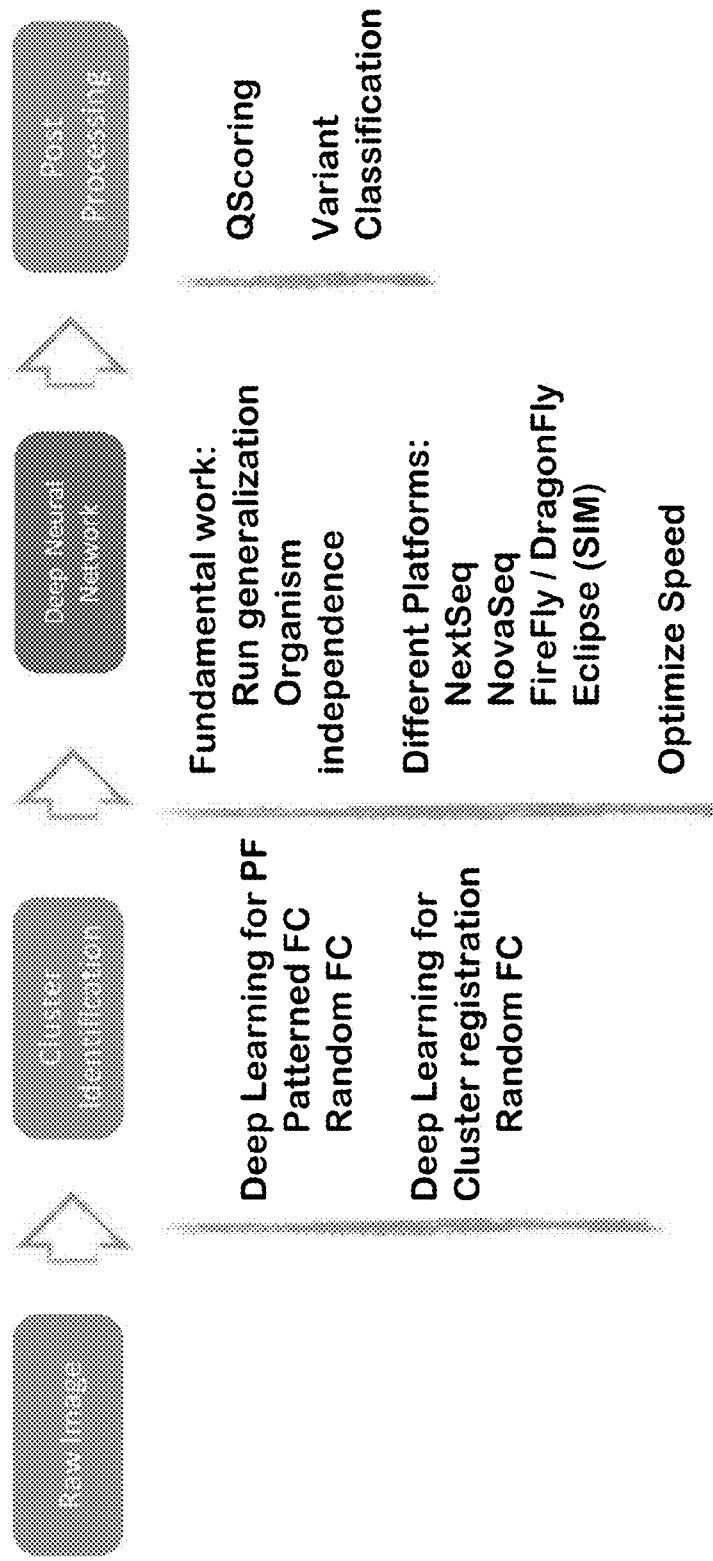
FIG. 55 shows various sequencing tasks that can be performed using the neural network-based base caller.

FIG. 55 shows various sequencing tasks that can be performed using the neural network-based base caller 218. Some examples include quality scoring (QScoring) and variant classification. FIG. 55 also lists some example sequencing instruments for which the neural network-based base caller 218 performs base calling.

Figure 56:
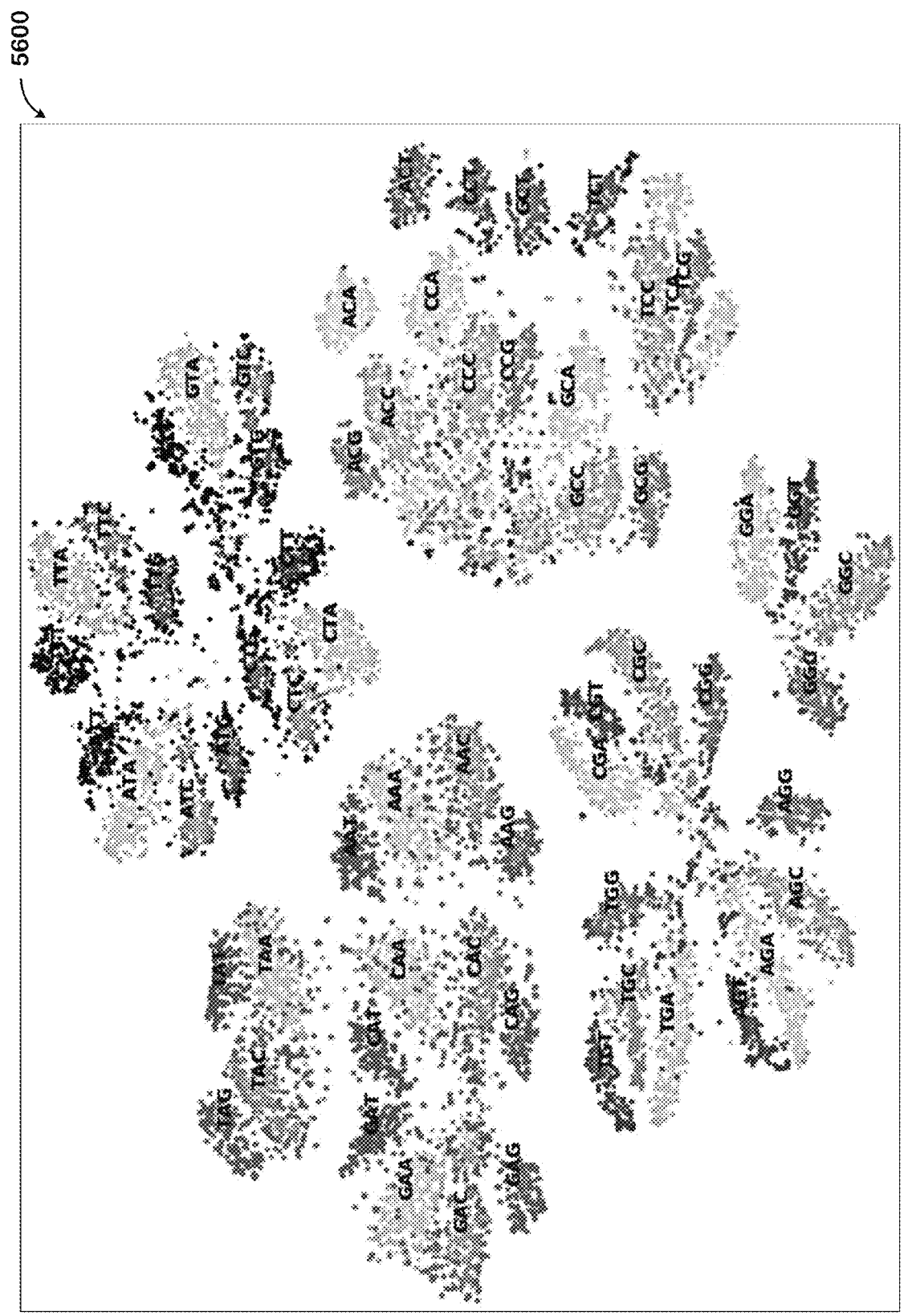
FIG. 56 is a scatter plot visualized by t-Distributed Stochastic Neighbor Embedding (t-SNE) and portrays base calling results of the neural network based base caller.

FIG. 56 is a scatter plot 5600 visualized by t-Distributed Stochastic Neighbor Embedding (t-SNE) and portrays base calling results of the neural network-based base caller 218. Scatter plot 5600 shows that the base calling results are clustered into 64 ($4^3$) groups, with each group mostly corresponding to a particular input 3-mer (trinucleotide repeating pattern). This is the case because the neural network-based base caller 218 processes input data for at least three sequencing cycles and learns sequence-specific motifs to produce a current base call based on the previous and successive base calls.

Quality Scoring

Quality scoring refers to the process of assigning a quality score to each base call. Quality scores are defined according to the Phred framework, which transforms the values of predictive features of sequencing traces to a probability based on a quality table. The quality table is obtained by training on calibration data sets and is updated when characteristics of the sequencing platform change. The probabilistic interpretation of quality scores allows fair integration of different sequencing reads in the downstream analysis such as variant calling and sequence assembly. Thus, a valid model to define quality scores is indispensable for any base caller.

We first describe what quality scores are. A quality score is a measure of the probability of a sequencing error in a base call. A high quality score implies that a base call is more reliable and less likely to be incorrect. For example, if the quality score of a base is Q30, the probability that this base is called incorrectly is 0.001. This also indicates that the base call accuracy is 99.9%.

The following table shows the relationship between the base call quality scores and their corresponding error probability, base call accuracy rate, and base call error rate:

aspects of base call reliability. They have been empirically determined to correlate with the quality of the base call.

A quality model, also known as a quality table or Q-table, lists combinations of quality predictor values and relates them to corresponding quality scores; this relationship is determined by a calibration process using empirical data. To estimate a new quality score, the quality predictor values are computed for a new base call and compared to values in the pre-calibrated quality table.

We now describe how a quality table is calibrated. Calibration is a process in which a statistical quality table is derived from empirical data that includes various well-characterized human and non-human samples sequenced on a number of instruments. Using a modified version of the Phred algorithm, a quality table is developed and refined using characteristics of the raw signals and error rates determined by aligning reads to the appropriate references.

We now describe why quality tables change from time to time. Quality tables provide quality scores for runs generated by specific instrument configurations and versions of chemistry. When significant characteristics of the sequencing platform change, such as new hardware, software, or chemistry versions, the quality model requires recalibration. For example, improvements in sequencing chemistry require quality table recalibration to accurately score the new data, which consumes a substantial amount of processing time and computational resources.

Neural Network-Based Quality Scoring

We disclose neural network-based techniques for quality scoring that do not use the quality predictor values or the quality tables and instead infer quality scores from confidence over predictions of well-calibrated neural networks. In the context of neural networks, "calibration" refers to the consistency or correlation between subjective forecasts and empirical long-run frequencies. This is a frequentist notion of certainty: if a neural network claims that 90% of the time a particular label is the correct label, then, during evaluation, 90% of all labels ascribed probability 90% of being correct, should be the correct label. Note that calibration is an orthogonal concern to accuracy: a neural network's predictions may be accurate and yet miscalibrated.

The disclosed neural networks are well-calibrated because they are trained on large-scale training sets with diverse sequencing characteristics that adequately model the base calling domain of real-world sequencing runs. In particular, sequencing images obtained from a variety of sequencing platforms, sequencing instruments, sequencing protocols, sequencing chemistries, sequencing reagents,

| Quality Score | Error Probability | Base Call Error Rate | Base Call Accuracy Rate |
|---|---|---|---|
| Q10 | 0.1 (1 in 10) | 10% | 90% |
| Q20 | 0.01 (1 in 100) | 1% | 99% |
| Q30 | 0.001 (1 in 1,000) | 0.1% | 99.9% |
| Q40 | 0.0001 (1 in 10,000) | 0.01% | 99.99% |
| Q50 | 0.00001 (1 in 100,000) | 0.001% | 99.999% |
| Q60 | 0.000001 (1 in 1,000,000) | 0.0001% | 99.9999% |

We now describe how quality scores are generated. During a sequencing run, a quality score is assigned to each base call for every cluster, on every tile, for every sequencing cycle. Illumina quality scores are calculated for each base call in a two-step process. For each base call, a number of quality predictor values are computed. Quality predictor values are observable properties of clusters from which base calls are extracted. These include properties such as intensity profiles and signal-to-noise ratios and measure various cluster densities, and flow cells are used as training examples to train the neural networks. In other implementations, different base calling and quality scoring models are respectively used for different sequencing platforms, sequencing instruments, sequencing protocols, sequencing chemistries, sequencing reagents, cluster densities, and/or flow cells.

For each of the four base call classes (A, C, T, and G), large numbers of sequencing images are used as training examples that identify intensity patterns representative of the respective base call class under a wide range of sequencing conditions. This in turn obviates the need of extending classification capabilities of the neural networks to new classes not present in the training. Furthermore, each training example is accurately labelled with a corresponding ground truth based on aligning reads to the appropriate references. What results is well-calibrated neural networks whose confidence over predictions can be interpreted as a certainty measure for quality scoring, expressed mathematically below.

Let $Y=\{A,C,T,G\}$ denote the set of class labels for the base call classes A, C, T, and G and X denote a space of inputs. Let $N_\theta(y|x)$ denote the probability distribution one of the disclosed neural networks predicts on an input $x \in X$ and $\theta$ denote the neural network's parameters. For a training example $x_i$ with correct label $y_i$, the neural network predicts label $\hat{y}_i = \text{argmax}_{y \in Y} N_\theta(y|x_i)$. The prediction gets correctness score $c_i=1$ if $\hat{y}_i = y_i$ and 0 otherwise and a confidence score $r_i = N_\theta(\hat{y}_i|x_i)$.

The neural network $N_\theta(y|x)$ is well-calibrated over a data distribution D because over all $(x_i, y_i) \in D$ and $r_i = \alpha$ the probability that $c_i=1$ is $\alpha$. For example, out of a sample from D, given 100 predictions, each with confidence 0.8, 80 are correctly classified by the neural network $N_\theta(y|x)$. More formally, $P_{\theta,D}(r,c)$ denotes the distribution over r and c values of the predictions of the neural network $N_\theta(y|X)$ on D and is expressed as $P_{\theta,D}(c=1|r=I_\alpha)=\alpha \; \forall \alpha \in [0,1]$, where $I_\alpha$ denotes a small non-zero interval around $\alpha$.

Because the well-calibrated neural networks are trained on diverse training sets, unlike the quality predictor values or the quality tables, they are not specific to instrument configurations and chemistry versions. This has two advantages. First, for different types of sequencing instruments, the well-calibrated neural networks obviate the need of deriving different quality tables from separate calibration processes. Second, for a same sequencing instrument, they obviate the need of recalibration when characteristics of the sequencing instrument change. More details follow.

Inferring Quality Scores from Softmax Confidence Probabilities

The first well-calibrated neural network is the neural network-based base caller 218 that processes input data derived from the sequencing images 108 and produces base call confidence probabilities for the base being A, C, T, and G. Base call confidence probabilities can also be considered likelihoods or classification scores. In one implementation, the neural network based base caller 218 uses a softmax function to generate the base call confidence probabilities as softmax scores.

Quality scores are inferred from the base call confidence probabilities generated by the softmax function of the neural network-based base caller 218 because the softmax scores are calibrated (i.e., they are representative of the ground truth correctness likelihood) and thus naturally correspond to the quality scores.

We demonstrate correspondence between the base call confidence probabilities and the quality scores by selecting a set of the base call confidence probabilities produced by the neural network-based base caller 218 during training and determining their base calling error rate (or base calling accuracy rate).

So, for example, we select the base call confidence probability "0.90" produced by the neural network-based base caller 218. We take numerous (e.g., ranging from 10000 to 1000000) instances when the neural network-based base caller 218 made the base call prediction with 0.90 softmax score. The numerous instances can be obtained either from the validation set or the test set. We then, based on comparison to corresponding ground truth base calls associated with respective ones of the numerous instances, determine in how many of the numerous instances the base call prediction was correct.

We observe that the base call was correctly predicted in ninety percent of the numerous instances, with ten percent miscalls. This means that for the 0.90 softmax score, the base calling error rate is 10% and the base calling accuracy rate is 90%, which in turn corresponds to quality score Q10 (see table above). Similarly, for other softmax scores like 0.99, 0.999, 0.9999, 0.99999, and 0.999999 we observe correspondence with quality scores Q20, Q30, Q40, Q50, and Q60, respectively. This is illustrated in FIG. 59*a*. In other implementations, we observe correspondence between the softmax scores and quality scores such as Q9, Q11, Q12, Q23, Q25, Q29, Q37, and Q39.

We also observe correspondence with binned quality scores. For example, 0.80 softmax score corresponds to binned quality score Q06, 0.95 softmax score corresponds to binned quality score Q15, 0.993 softmax score corresponds to binned quality score Q22, 0.997 softmax score corresponds to binned quality score Q27, 0.9991 softmax score corresponds to binned quality score Q33, 0.9995 softmax score corresponds to binned quality score Q37, and 0.9999 softmax score corresponds to binned quality score Q40. This is illustrated in FIG. 59*b*.

The sample size used herein are large to avoid small sample issues and can, for example, range from 10000 to 1000000. In some implementations, the sample size of instances used to determine the base calling error rates (or the base calling accuracy rates) is selected based on the softmax score being evaluated. For example, for 0.99 softmax score, the sample includes one hundred instances, for 0.999 softmax score, the sample includes one thousand instances, for 0.9999 softmax score, the sample includes ten thousand instances, for 0.99999 softmax score, the sample includes hundred thousand instances, and for 0.999999 softmax score, the sample includes one million instances.

Regarding softmax, softmax is an output activation function for multiclass classification. Formally, training a so-called softmax classifier is regression to a class probability, rather than a true classifier as it does not return the class but rather a confidence prediction of each class's likelihood. The softmax function takes a class of values and converts them to probabilities that sum to one. The softmax function squashes a k-dimensional vector of arbitrary real values to k-dimensional vector of real values within the range zero to one. Thus, using the softmax function ensures that the output is a valid, exponentially normalized probability mass function (nonnegative and summing to one).

Consider that $\tilde{y}_i$ is the i th element of the vector $\tilde{y}=[\tilde{y}_1, \tilde{y}_2, \ldots \tilde{y}_n]$:

$$\tilde{y}_i = (softmax(\tilde{z}))_i = \frac{\exp(\tilde{z}_i)}{\sum_{j=1}^{j=N} \exp(\tilde{z}_j)},$$

where $\tilde{y}$ is a vector of length n, where n is the number of classes in the classification. These elements have values between zero and one, and sum to one so that they represent a valid probability distribution.

Figure 57:
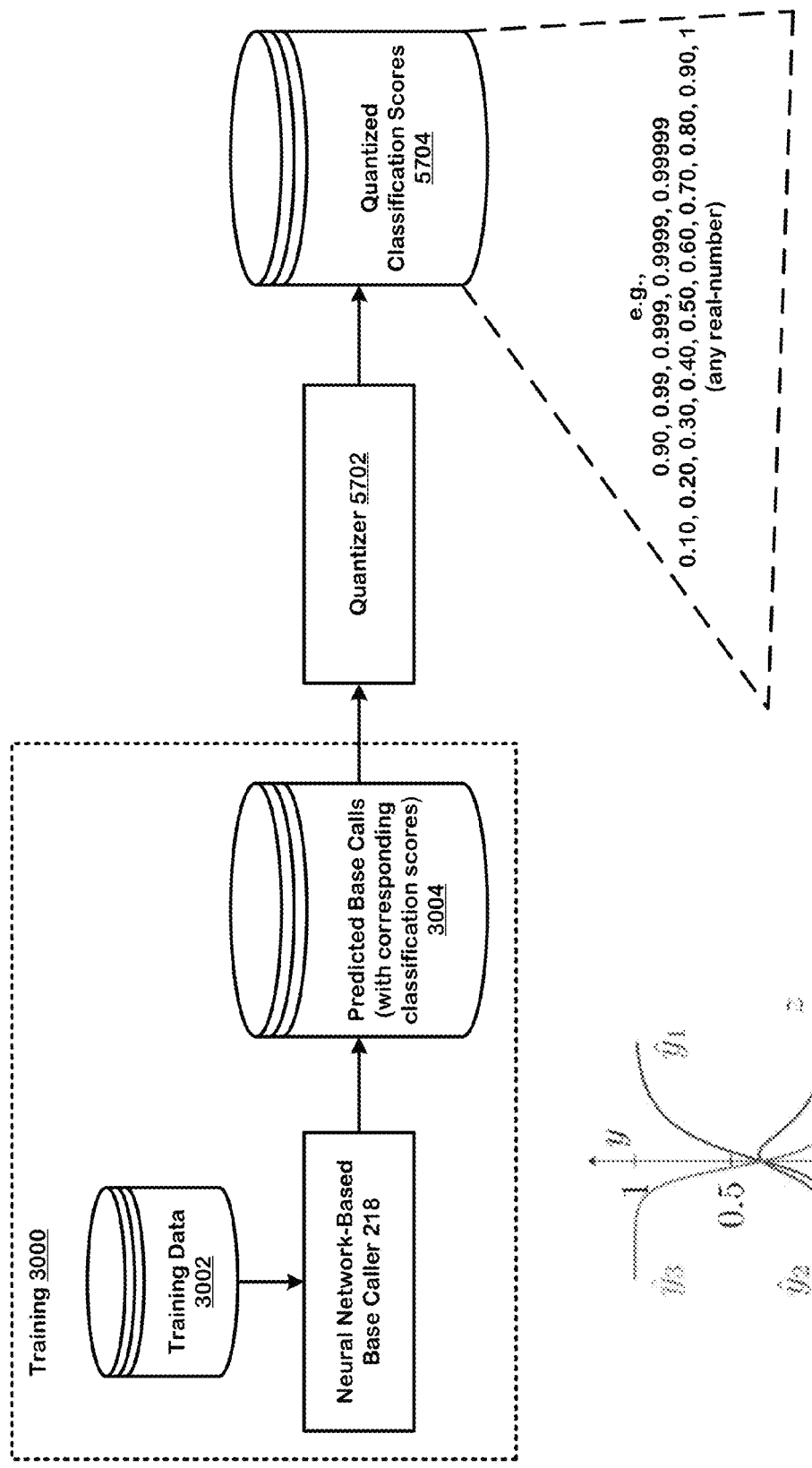
FIG. 57 illustrates one implementation of selecting the base call confidence probabilities made by the neural network-based base caller for quality scoring.

An example softmax activation function 5706 is shown in FIG. 57. Softmax 5706 is applied to three classes as $$z \mapsto \text{softmax}\left(\left[z; \frac{z}{10}; -2z\right]\right).$$

Note that the three outputs always sum to one. They thus define a discrete probability mass function.

When used for classification, $\tilde{y}_i$ gives the probability of being in class i.

$$P(Y=i|\vec{z}) = (\text{softmax}(\vec{z}))_i = \tilde{y}_i$$

The name "softmax" can be somewhat confusing. The function is more closely related to the argmax function than the max function. The term "soft" derives from the fact that the softmax function is continuous and differentiable. The argmax function, with its result represented as a one-hot vector, is not continuous or differentiable. The softmax function thus provides a "softened" version of the argmax. It would perhaps be better to call the softmax function "softargmax," but the current name is an entrenched convention.

FIG. 57 illustrates one implementation of selecting 5700 the base call confidence probabilities 3004 of the neural network-based base caller 218 for quality scoring. The base call confidence probabilities 3004 of the neural network-based base caller 218 can be classification scores (e.g., softmax scores or sigmoid scores) or regression scores. In one implementation, the base call confidence probabilities 3004 are produced during the training 3000.

In some implementations, the selection 5700 is done based on quantization, which is performed by a quantizer 5702 that accesses the base call confidence probabilities 3004 and produces quantized classification scores 5704. The quantized classification scores 5704 can be any real-number. In one implementation, the quantized classification scores 5704 are selected based on a selection formula defined as $$0.9 \sum_{i=1}^{n} 0.1^{(i-1)}.$$

In another implementation, the quantized classification scores 5704 are selected based on a selection formula defined as $$\bigvee_{i=1}^{n=10} 0.1i.$$

Figure 58:
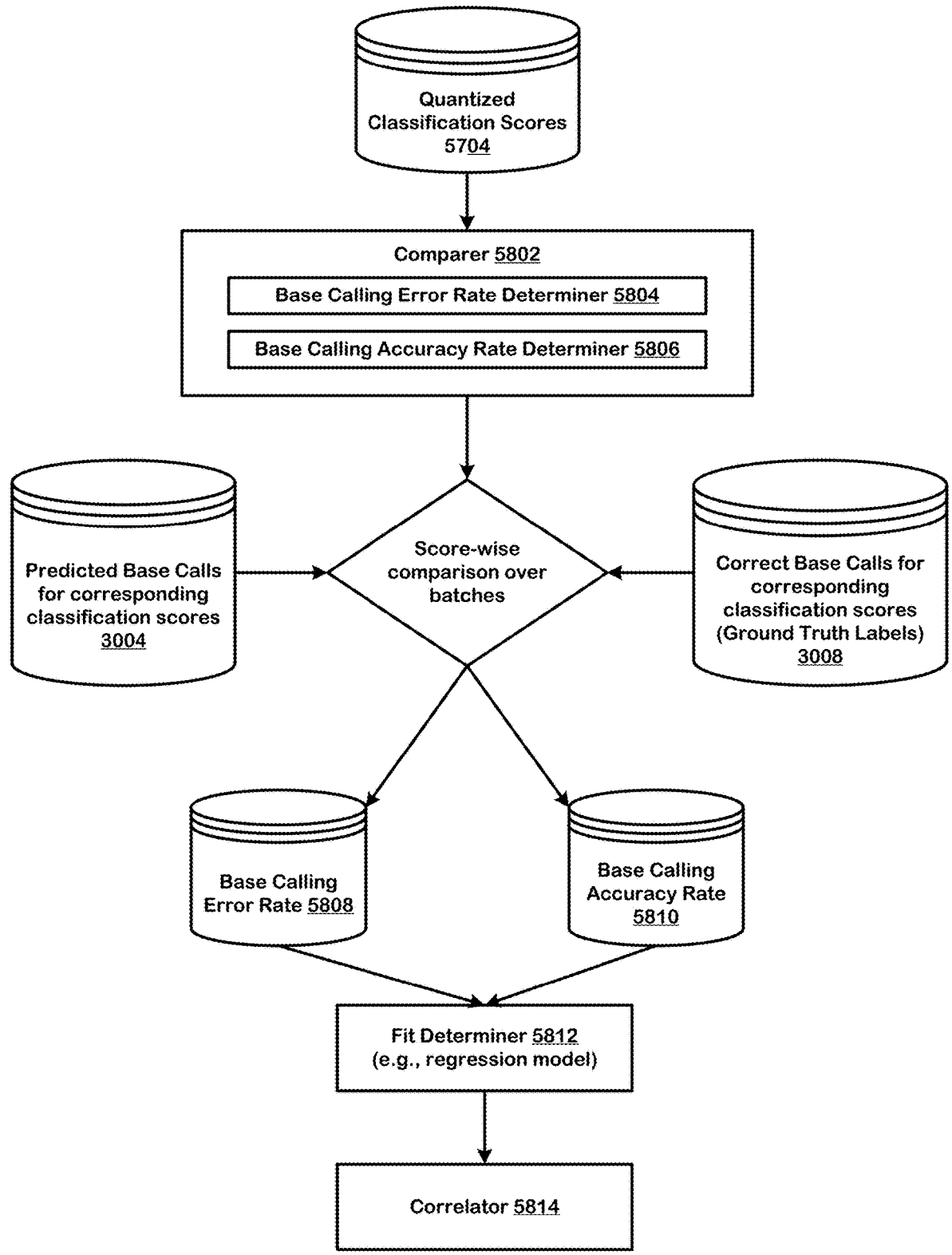
FIG. 58 shows one implementation of the neural network-based quality scoring.

FIG. 58 shows one implementation of the neural network-based quality scoring 5800. For each of the quantized classification scores 5704, a base calling error rate 5808 and/or a base calling accuracy rate 5810 is determined by comparing its base call predictions 3004 against corresponding ground truth base calls 3008 (e.g., over batches with varying sample size). The comparison is performed by a comparer 5802, which in turn includes a base calling error rate determiner 5804 and a base calling accuracy rate determiner 5806.

Then, to establish the correspondence between the quantized classification scores 5704 and the quality scores, a fit is determined between the quantized classification scores 5704 and their base calling error rate 5808 (and/or their base calling accuracy rate 5810) by a fit determiner 5812. In one implementation, the fit determiner 5812 is a regression model.

Based on the fit, the quality scores are correlated with the quantized classification scores 5704 by a correlator 5814.

FIGS. 59a-59b depict one implementation of correspondence 5900 between the quality scores and the base call confidence predictions made by the neural network-based base caller 218. The base call confidence probabilities of the neural network based base caller 218 can be classification scores (e.g., softmax scores or sigmoid scores) or regression scores. FIG. 59a is a quality score correspondence scheme 5900a for quality scores. FIG. 59b is a quality score correspondence scheme 5900a for binned quality scores.

Inference

Figure 60:
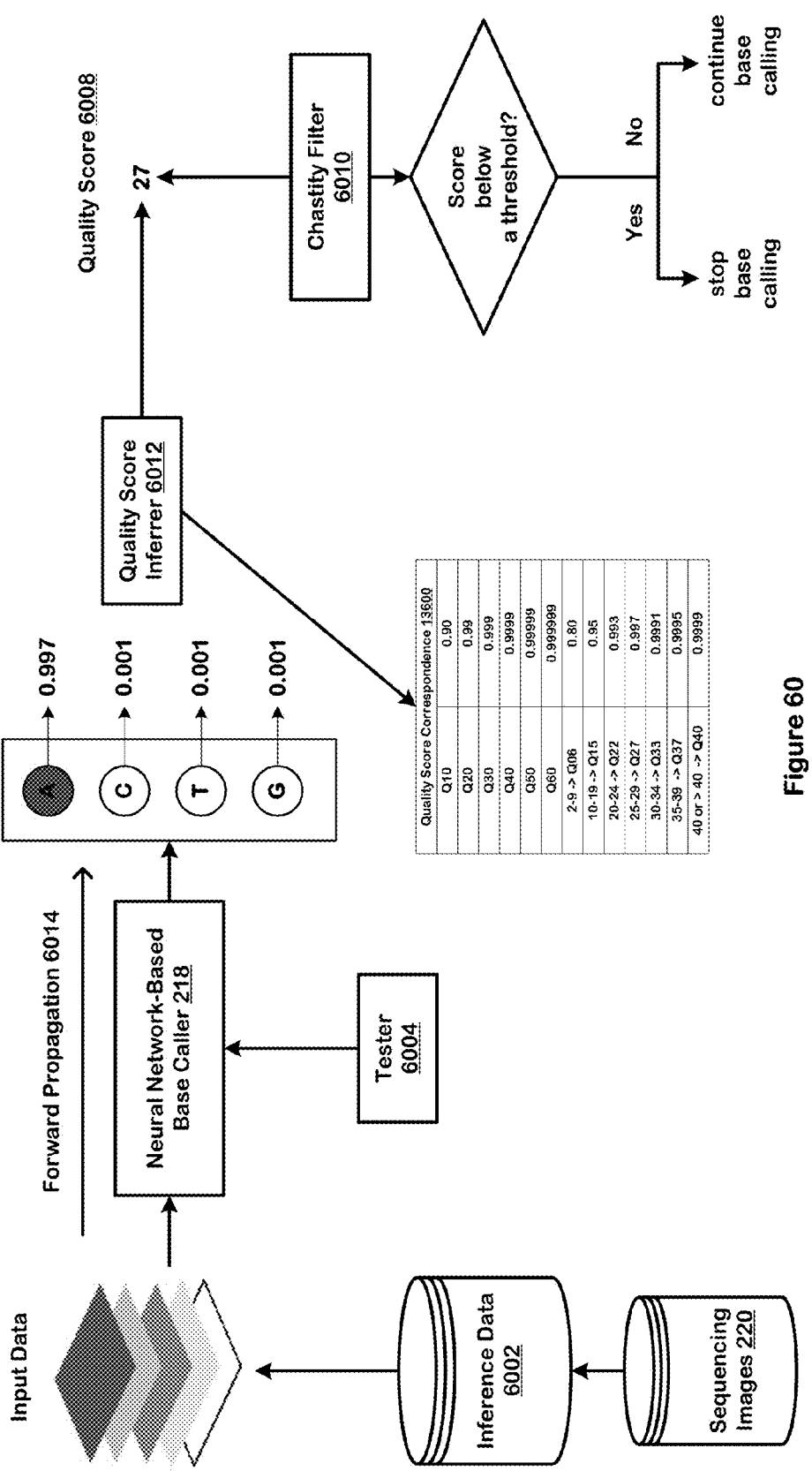
FIG. 60 shows one implementation of inferring quality scores from base call confidence predictions made by the neural network-based base caller during inference.

FIG. 60 shows one implementation of inferring quality scores from base call confidence predictions made by the neural network-based base caller 218 during inference 6000. The base call confidence probabilities of the neural network-based base caller 218 can be classification scores (e.g., softmax scores or sigmoid scores) or regression scores.

During the inference 6000, the predicted base call 6006 is assigned the quality score 6008 to which its base call confidence probability (i.e., the highest softmax score (in red)) most corresponds. In some implementations, the quality score correspondence 5900 is made by looking up the quality score correspondence schemes 5900a-5900b and is operationalized by a quality score inferrer 6012.

In some implementations, a chastity filter 6010 terminates the base calling of a given cluster when the quality score 6008 assigned to its called base, or an average quality score over successive base calling cycles, falls below a preset threshold.

The inference 6000 includes hundreds, thousands, and/or millions of iterations of forward propagation 6014, including parallelization techniques such as batching. The inference 6000 is performed on inference data 6002 that includes the input data (with the image channels derived from the sequencing images 108 and/or the supplemental channels (e.g., the distance channels, the scaling channel)). The inference 6000 is operationalized by a tester 6004.

Directly Predicting Base Call Quality

The second well-calibrated neural network is the neural network-based quality scorer 6102 that processes input data derived from the sequencing images 108 and directly produces a quality indication.

In one implementation, the neural network-based quality scorer 6102 is a multilayer perceptron (MLP). In another implementation, the neural network based quality scorer 6102 is a feedforward neural network. In yet another implementation, the neural network-based quality scorer 6102 is a fully-connected neural network. In a further implementation, the neural network-based quality scorer 6102 is a fully convolutional neural network. In yet further implementation, the neural network-based quality scorer 6102 is a semantic segmentation neural network.

In one implementation, the neural network-based quality scorer 6102 is a convolutional neural network (CNN) with a plurality of convolution layers. In another implementation, it is a recurrent neural network (RNN) such as a long short-term memory network (LSTM), bi-directional LSTM (Bi-LSTM), or a gated recurrent unit (GRU). In yet another implementation, it includes both a CNN and a RNN.

In yet other implementations, the neural network-based quality scorer 6102 can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous SGD. It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tan h)), batch normalization layers, regularization layers, dropout, pooling layers (e.g., max or average pooling), global average pooling layers, and attention mechanisms.

In some implementations, the neural network-based quality scorer 6102 has the same architecture as the neural network-based base caller 218.

The input data can include the image channels derived from the sequencing images 108 and/or the supplemental channels (e.g., the distance channels, the scaling channel). The neural network-based quality scorer 6102 processes the input data and produces an alternative representation of the input data. The alternative representation is a convolved representation in some implementations and a hidden representation in other implementations. The alternative representation is then processed by an output layer to produce an output. The output is used to produce the quality indication.

In one implementation, the same input data is fed to the neural network-based base caller 218 and the neural network-based quality scorer 6102 to produce (i) a base call from the neural network-based base caller 218 and (ii) a corresponding quality indication from the neural network-based quality scorer 6102. In some implementations, the neural network-based base caller 218 and the neural network-based quality scorer 6102 are jointly trained with end-to-end backpropagation.

In one implementation, the neural network-based quality scorer 6102 outputs a quality indication for a single target cluster for a particular sequencing cycle. In another implementation, it outputs a quality indication for each target cluster in a plurality of target clusters for the particular sequencing cycle. In yet another implementation, it outputs a quality indication for each target cluster in a plurality of target clusters for each sequencing cycle in a plurality of sequencing cycles, thereby producing a quality indication sequence for each target cluster.

In one implementation, the neural network-based quality scorer 6102 is a convolutional neural network trained on training examples comprising data from the sequencing images 108 and labeled with base call quality ground truths. The neural network-based quality scorer 6102 is trained using a backpropagation-based gradient update technique that progressively matches base call quality predictions 6104 of the convolutional neural network 6102 with the base call quality ground truths 6108. In some implementations, we label a base as 0 if it was a wrong base call and 1 if otherwise. As a result, the output corresponds to the probability of error. In one implementation, this obviates the need of using the sequence context as input features.

An input module of the convolutional neural network 6102 feeds data from the sequencing images 108 captured at one or more sequencing cycles to the convolutional neural network 6102 for determining quality of one or more bases called for one or more clusters.

An output module of the convolutional neural network 6102 translates analysis by the convolutional neural network 6102 into an output 6202 that identifies the quality of the one or more bases called for the one or more clusters.

In one implementation, the output module further comprises a softmax classification layer that produces likelihoods for the quality status being high-quality, medium-quality (optional, as indicated by dotted lines), and low-quality. In another implementation, the output module further comprises a softmax classification layer that produces likelihoods for the quality status being high-quality and low-quality. A person skilled in the art will appreciate that other classes that bucket quality scores differently and discernibly can be used. The softmax classification layer produces likelihoods for the quality being assigned a plurality of quality scores. Based on the likelihoods, the quality is assigned a quality score from one of the plurality of quality scores. The quality scores are logarithmically based on base calling error probabilities. The plurality of quality scores includes Q6, Q10, Q15, Q20, Q22, Q27, Q30, Q33, Q37, Q40, and Q50. In another implementation, the output module further comprises a regression layer that produces continuous values which identify the quality.

In some implementations, the neural network-based quality scorer 6102 further comprises a supplemental input module that supplements the data from the sequencing images 108 with quality predictor values for the bases called and feeds the quality predictor values to the convolutional neural network 6102 along with the data from the sequencing images.

In some implementations, the quality predictor values include online overlap, purity, phasing, start5, hexamer score, motif accumulation, endiness, approximate homopolymer, intensity decay, penultimate chastity, signal overlap with background (SOWB), and/or shifted purity G adjustment. In other implementations, the quality predictor values include peak height, peak width, peak location, relative peak locations, peak height ration, peak spacing ration, and/or peak correspondence. Additional details about the quality predictor values can be found in US Patent Publication Nos. 2018/0274023 and 2012/0020537, which are incorporated by reference as if fully set forth herein.

Training

Figure 61:
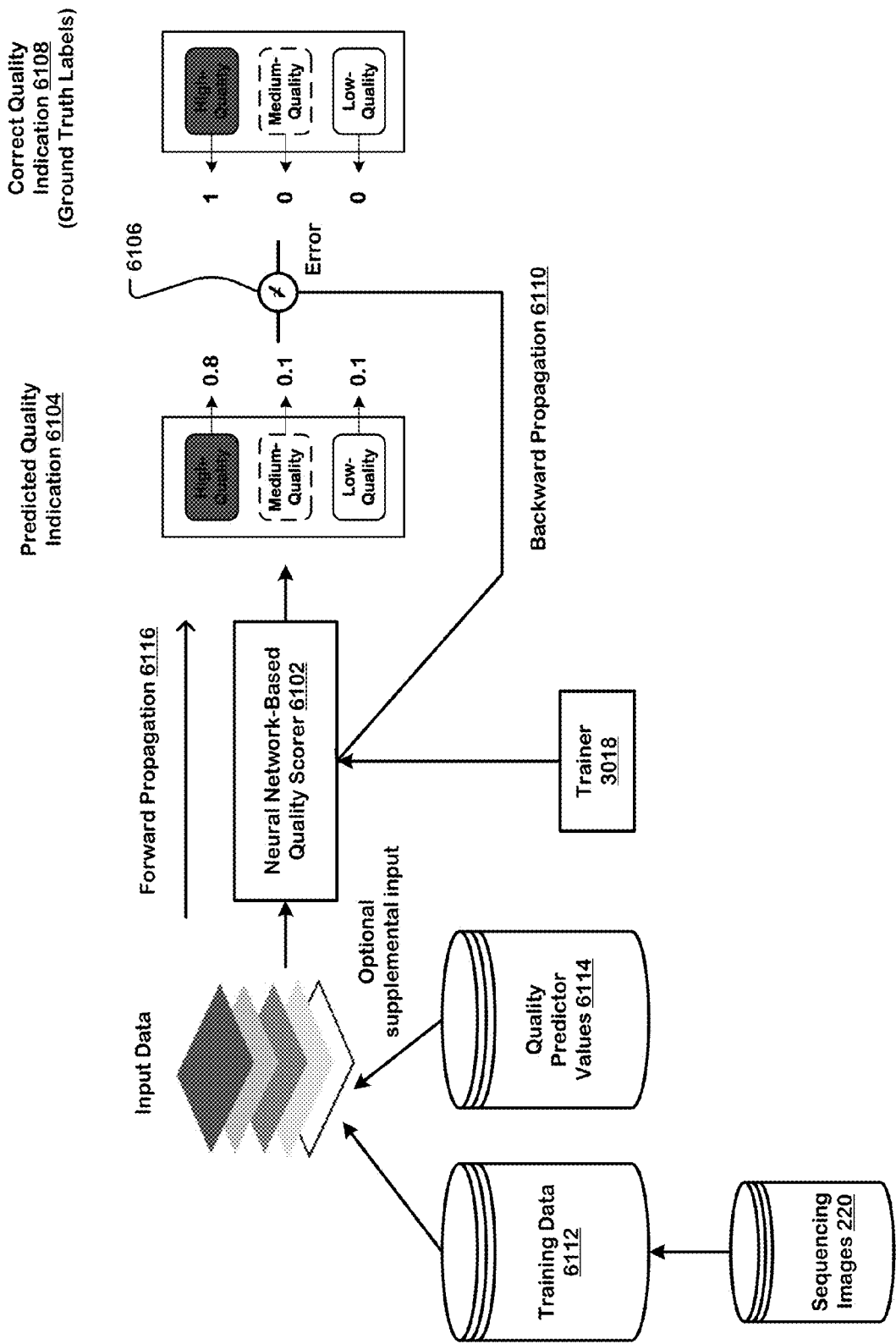
FIG. 61 shows one implementation of training the neural network-based quality scorer to process input data derived from the sequencing images and directly produce quality indications.

FIG. 61 shows one implementation of training 6100 the neural network-based quality scorer 6102 to process input data derived from the sequencing images 108 and directly produce quality indications. The neural network-based quality scorer 6102 is trained using a backpropagation-based gradient update technique that compares the predicted quality indications 6104 against the correct quality indications 6108 and computes an error 6106 based on the comparison. The error 6106 is then used to calculate gradients, which are applied to the weights and parameters of the neural network-based quality scorer 6102 during backward propagation 6110. The training 6100 is operationalized by the trainer 1510 using a stochastic gradient update algorithm such as ADAM.

The trainer 1510 uses training data 6112 (derived from the sequencing images 108) to train the neural network-based quality scorer 6102 over thousands and millions of iterations of the forward propagation 6116 that produces the predicted quality indications and the backward propagation 6110 that updates the weights and parameters based on the error 6106. In some implementations, the training data 6112 is supplemented with the quality predictor values 6114. Additional details about the training 6100 can be found in Appendix entitled "Deep Learning Tools".

Inference

Figure 62:
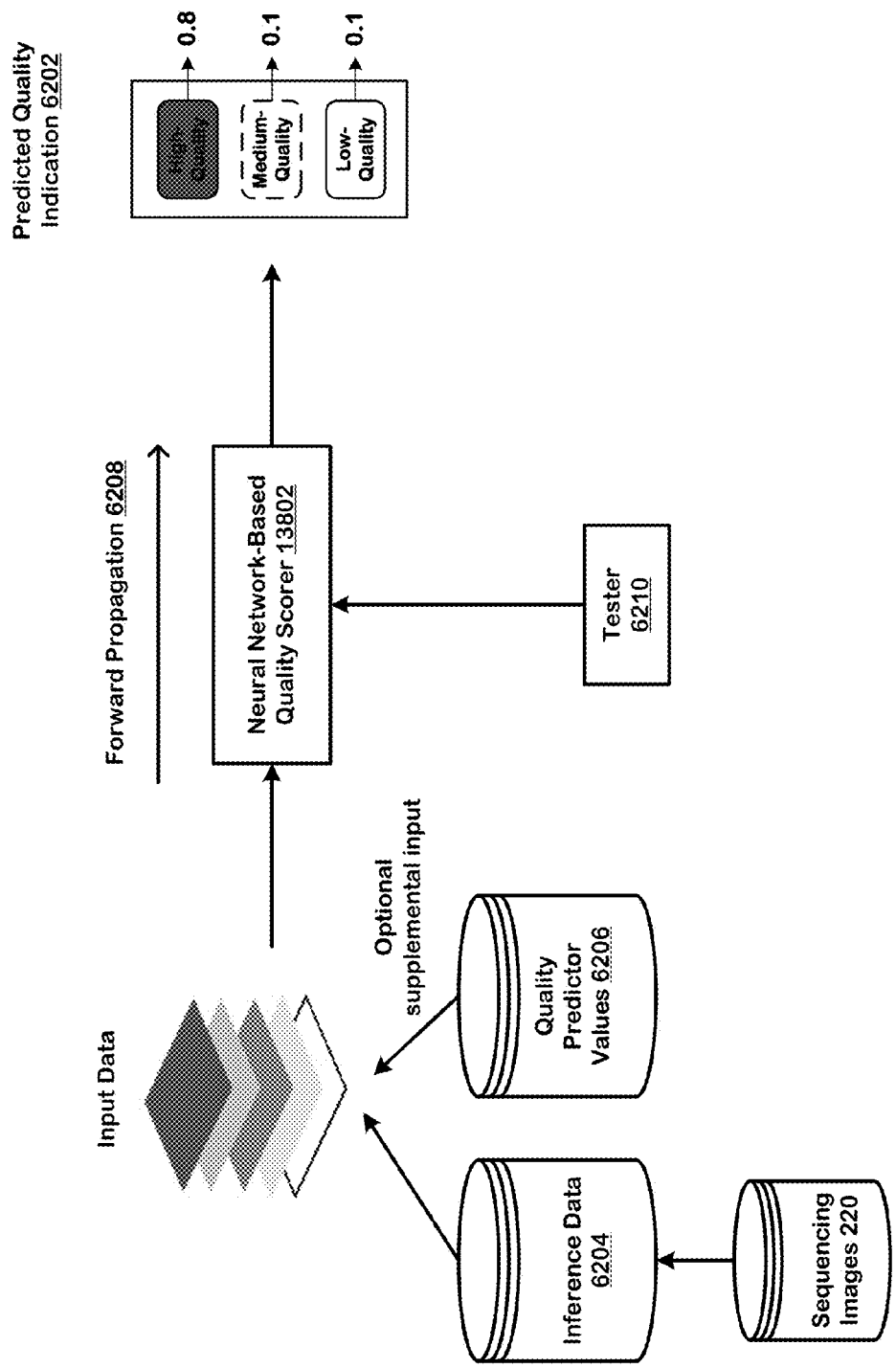
FIG. 62 shows one implementation of directly producing quality indications as outputs of the neural network-based quality scorer during inference.

FIG. 62 shows one implementation of directly producing quality indications as outputs of the neural network-based quality scorer 6102 during inference 6200. The inference 6200 includes hundreds, thousands, and/or millions of iterations of forward propagation 6208, including parallelization techniques such as batching. The inference 6200 is performed on inference data 6204 that includes the input data (with the image channels derived from the sequencing images 108 and/or the supplemental channels (e.g., the distance channels, the scaling channel)). In some implementations, the inference data 6204 is supplemented with the quality predictor values 6206. The inference 6200 is operationalized by a tester 6210.

Data Pre-Processing

In some implementations, the technology disclosed uses pre-processing techniques that apply to pixels in the image data 202 and produce pre-processed image data 202*p*. In such implementations, instead of the image data 202, the pre-processed image data 202*p* is provided as input to the neural network-based base caller 218. The data pre-processing is operationalized by a data pre-processor 6602, which in turn can contain a data normalizer 6632 and a data augmenter 6634.

Figure 66:
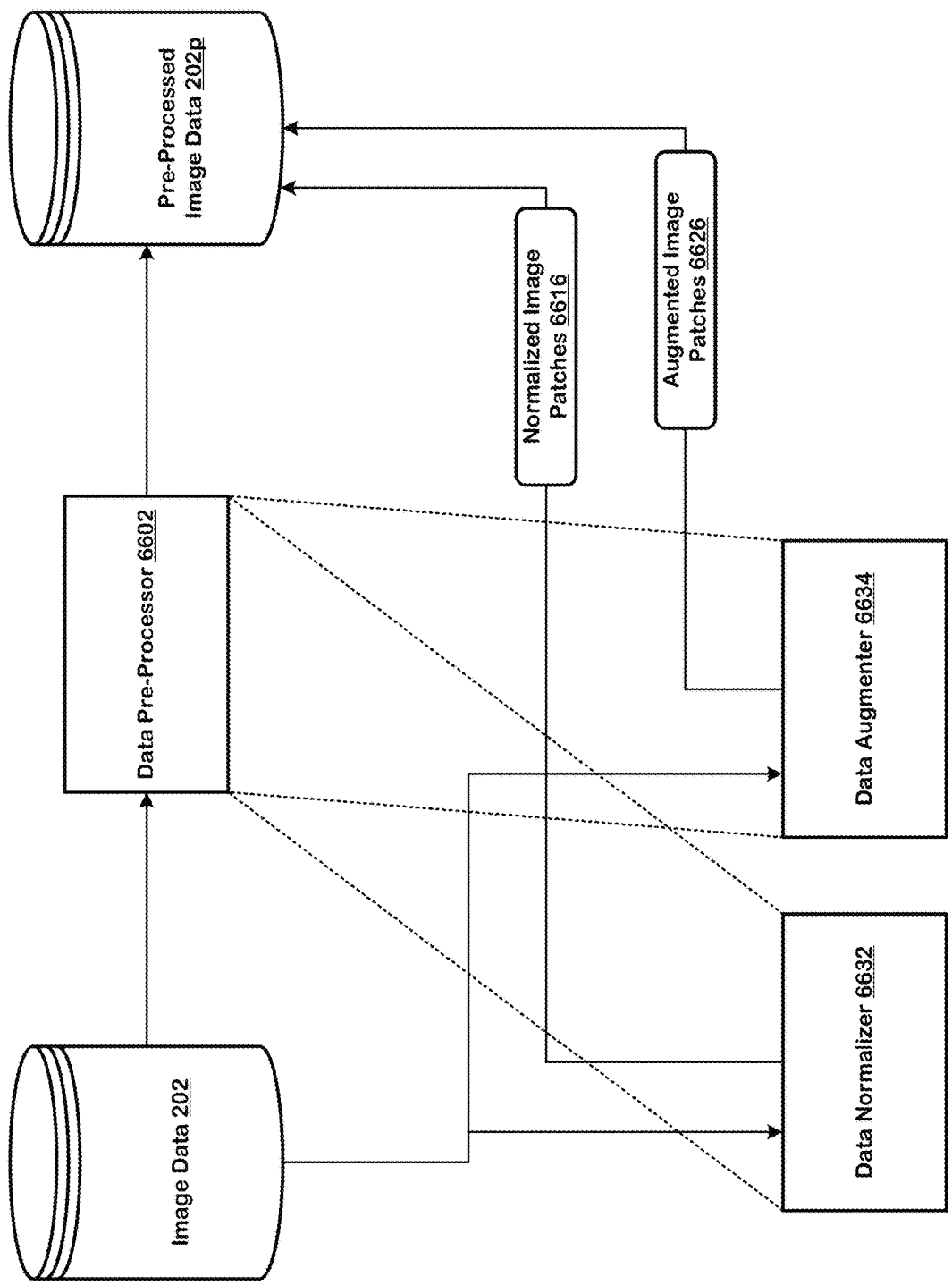
FIG. 66 shows different implementations of data pre-processing, which can include data normalization and data augmentation.

FIG. 66 shows different implementations of data pre-processing, which can include data normalization and data augmentation.

Data Normalization

In one implementation, data normalization is applied on pixels in the image data 202 on an image patch-by-image patch basis. This includes normalizing intensity values of pixels in an image patch such that a pixel intensity histogram of the resulting normalized image patch has a fifth percentile of zero and a ninety-fifth percentile of one. That is, in the normalized image patch, (i) 5% of the pixels have intensity values less than zero and (ii) another 5% of the pixels have intensity values greater than one. Respective image patches of the image data 202 can be normalized separately, or the image data 202 can be normalized all at once. What results is normalized image patches 6616, which are one example of the pre-processed image data 202*p*. The data normalization is operationalized by the data normalizer 6632.

Data Augmentation

In one implementation, data augmentation is applied on the intensity values of the pixels in the image data 202. This includes (i) multiplying the intensity values of all the pixels in the image data 202 with a same scaling factor and (ii) adding a same offset value to the scaled intensity values of all the pixels in the image data 202. For a single pixel, this can be expressed by the following formulation:

$$\text{augmented pixel intensity (API)} = aX + b$$

where a is the scaling factor, X is the original pixel intensity, b is the offset value, aX is the scaled pixel intensity What results is augmented image patches 6626, which are also one example of the pre-processed image data 202*p*. The data augmentation is operationalized by the data augmenter 6634.

Figure 67:
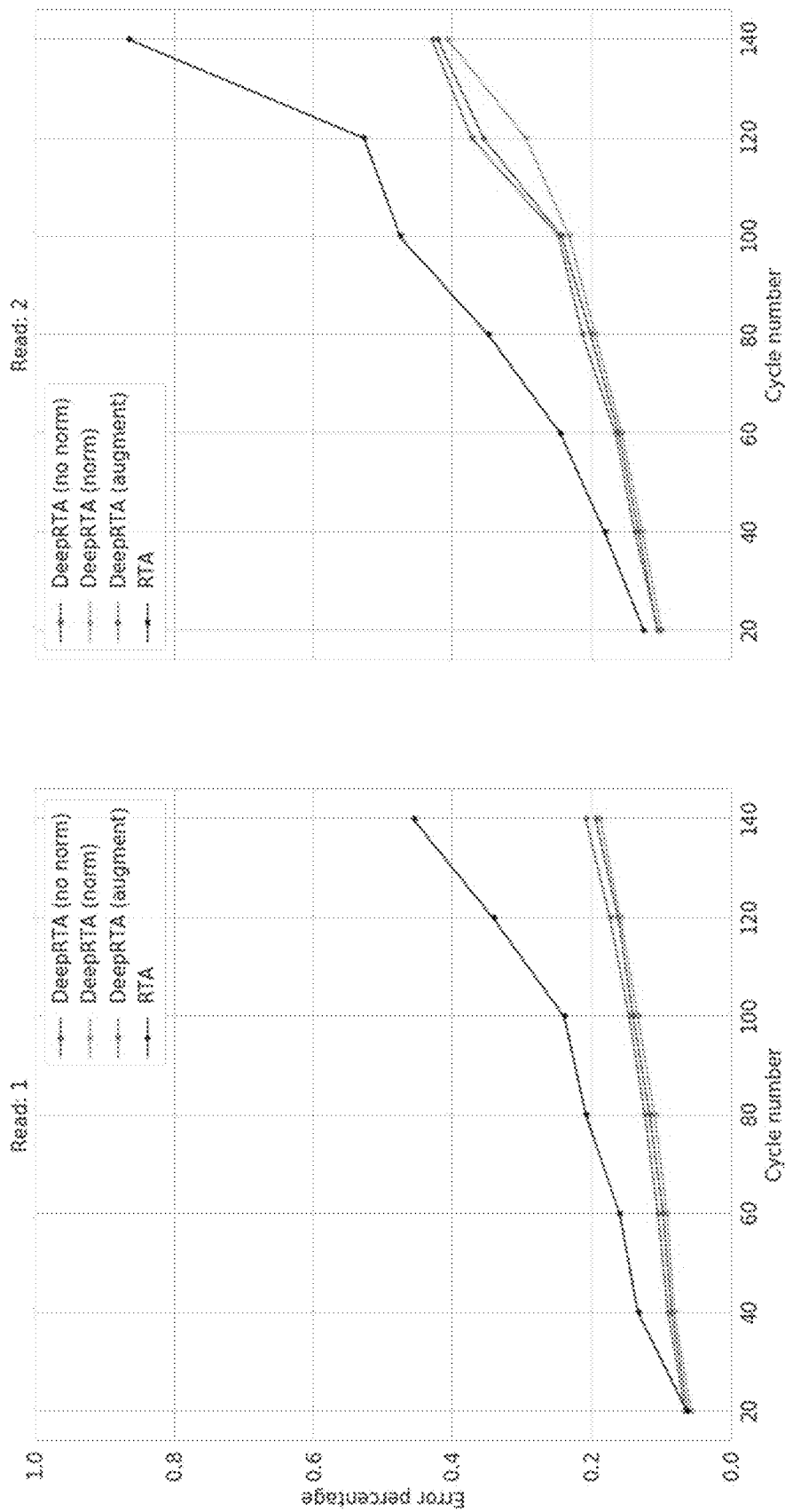
FIG. 67 shows that the data normalization technique (DeepRTA (norm)) and the data augmentation technique (DeepRTA (augment)) of FIG. 66 reduce the base calling error percentage when the neural network-based base caller is trained on bacterial data and tested on human data, where the bacterial data and the human data share the same assay (e.g., both contain intronic data).

FIG. 67 shows that the data normalization technique (DeepRTA (norm)) and the data augmentation technique (DeepRTA (augment)) of FIG. 66 reduce the base calling error percentage when the neural network based base caller 218 is trained on bacterial data and tested on human data, where the bacterial data and the human data share the same assay (e.g., both contain intronic data).

Figure 68:
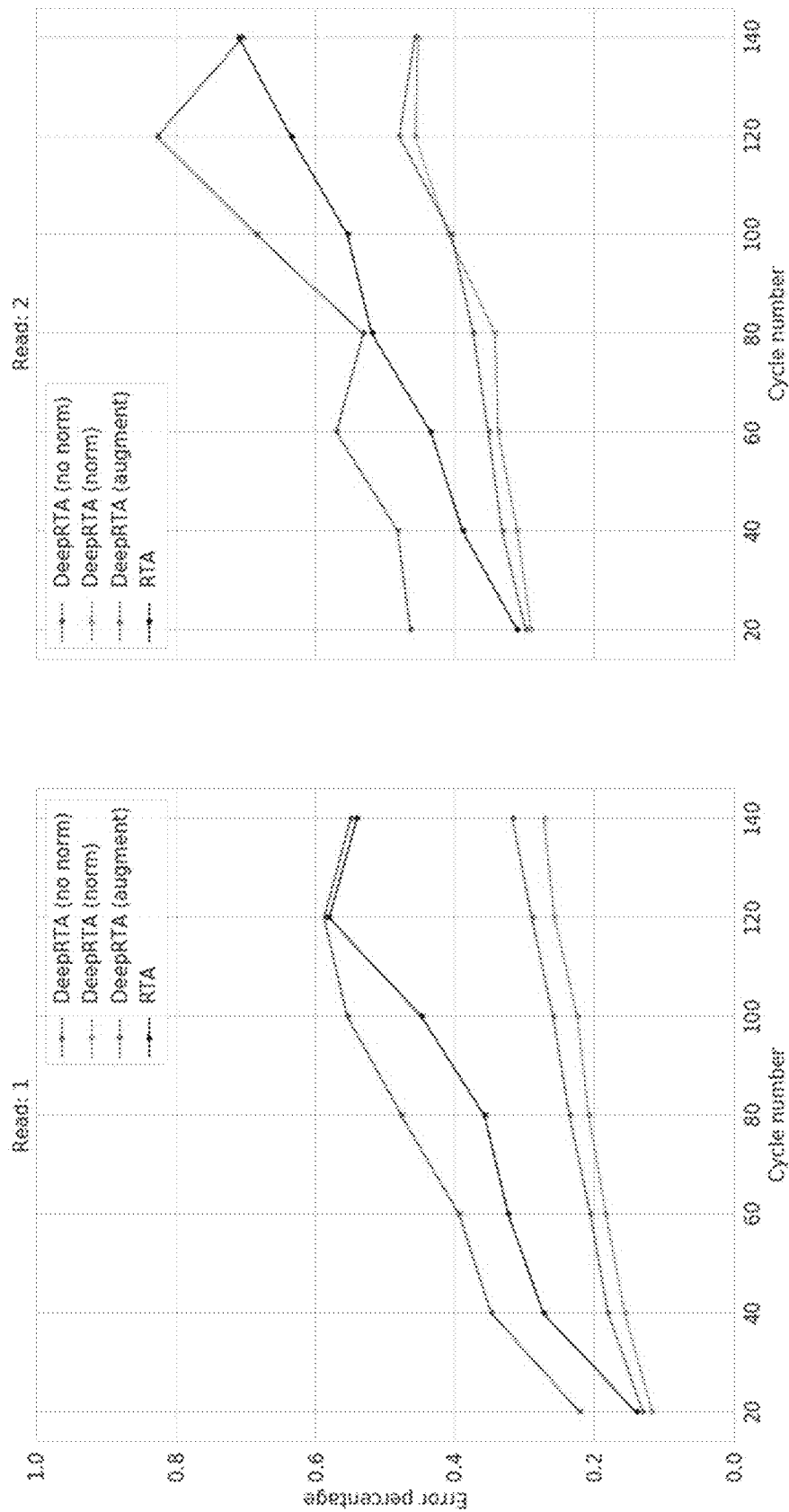
FIG. 68 shows that the data normalization technique (DeepRTA (norm)) and the data augmentation technique (DeepRTA (augment)) of FIG. 66 reduce the base calling error percentage when the neural network-based base caller is trained on non-exonic data (e.g., intronic data) and tested on exonic data.

FIG. 68 shows that the data normalization technique (DeepRTA (norm)) and the data augmentation technique (DeepRTA (augment)) of FIG. 66 reduce the base calling error percentage when the neural network-based base caller 218 is trained on non-exonic data (e.g., intronic data) and tested on exonic data.

In other words, the data normalization and the data augmentation techniques of FIG. 66 allow the neural network-based base caller 218 to generalize better on data not seen in training and thus reduce overfitting.

In one implementation, the data augmentation is applied during both training and inference. In another implementation, the data augmentation is applied only during the training. In yet another implementation, the data augmentation is applied only during the inference.

Sequencing System

Figure 63A:
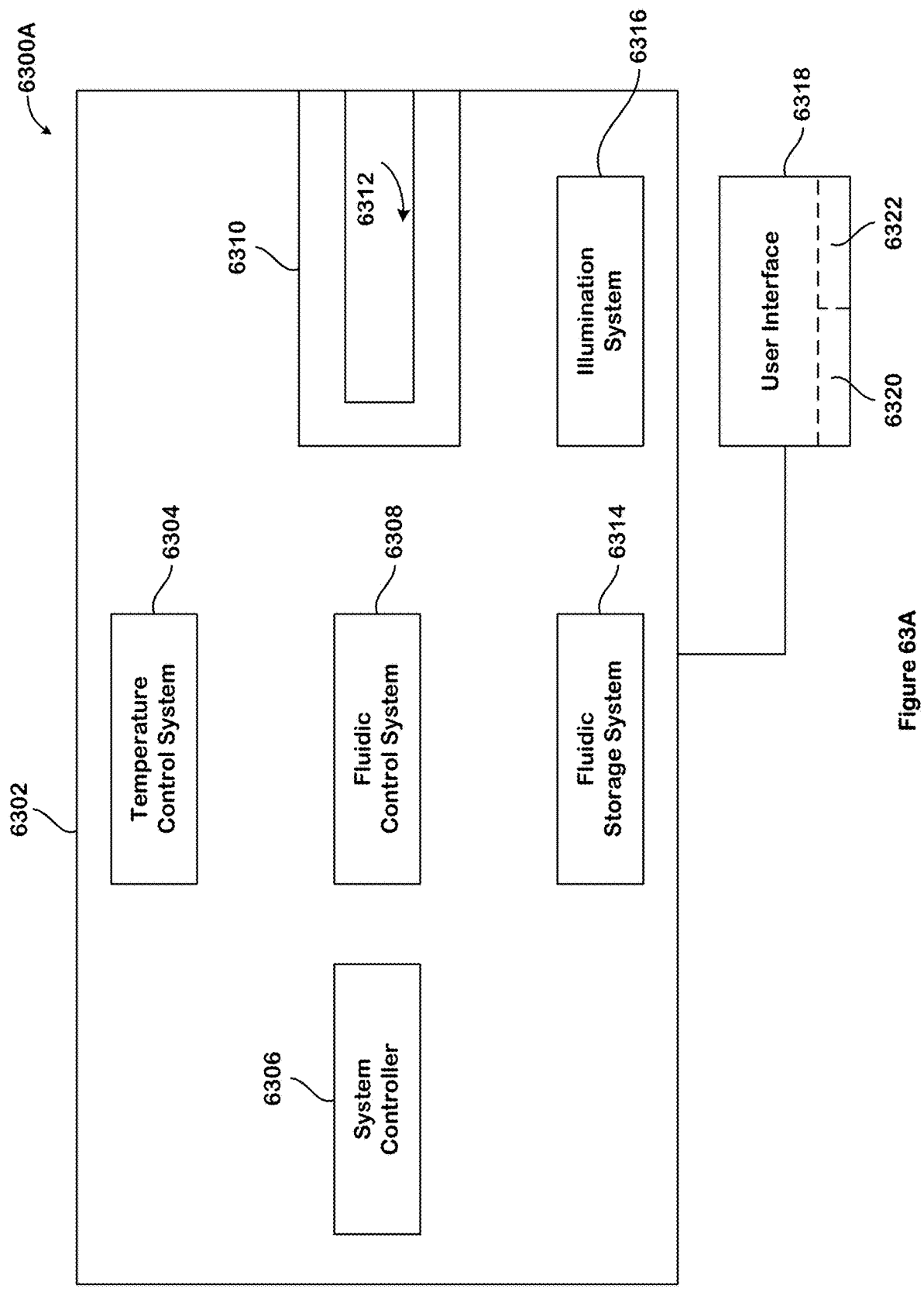
FIGS. 63A and 63B depict one implementation of a sequencing system. The sequencing system comprises a configurable processor.
Figure 63B:
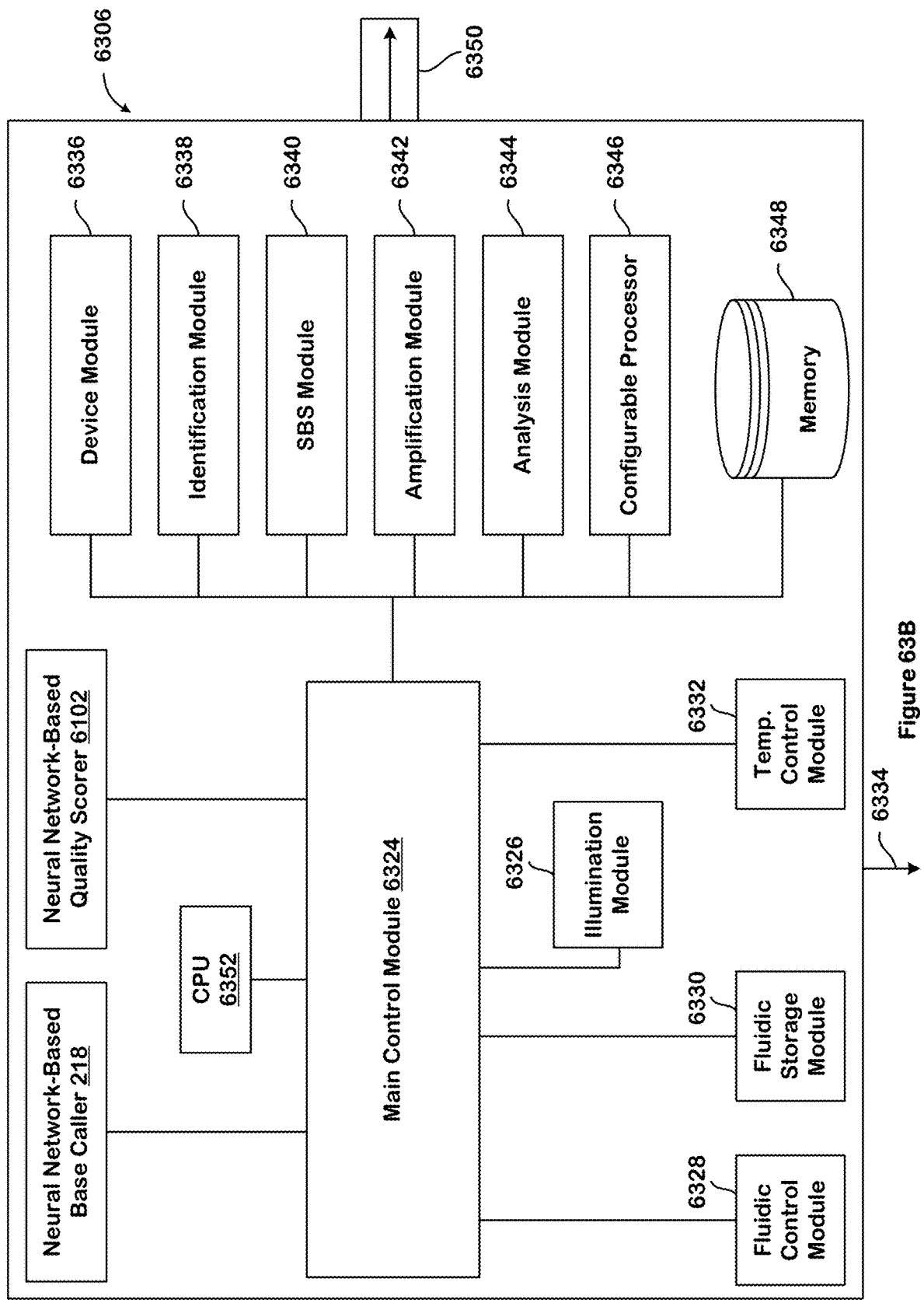

FIGS. 63A and 63B depict one implementation of a sequencing system 6300A. The sequencing system 6300A comprises a configurable processor 6346. The configurable processor 6346 implements the base calling techniques disclosed herein. The sequencing system is also referred to as a "sequencer."

The sequencing system 6300A can operate to obtain any information or data that relates to at least one of a biological or chemical substance. In some implementations, the sequencing system 6300A is a workstation that may be similar to a bench-top device or desktop computer. For example, a majority (or all) of the systems and components for conducting the desired reactions can be within a common housing 6302.

In particular implementations, the sequencing system 6300A is a nucleic acid sequencing system configured for various applications, including but not limited to de novo sequencing, resequencing of whole genomes or target genomic regions, and metagenomics. The sequencer may also be used for DNA or RNA analysis. In some implementations, the sequencing system 6300A may also be configured to generate reaction sites in a biosensor. For example, the sequencing system 6300A may be configured to receive a sample and generate surface attached clusters of clonally amplified nucleic acids derived from the sample. Each cluster may constitute or be part of a reaction site in the biosensor.

The exemplary sequencing system 6300A may include a system receptacle or interface 6310 that is configured to interact with a biosensor 6312 to perform desired reactions within the biosensor 6312. In the following description with respect to FIG. 63A, the biosensor 6312 is loaded into the system receptacle 6310. However, it is understood that a cartridge that includes the biosensor 6312 may be inserted into the system receptacle 6310 and in some states the cartridge can be removed temporarily or permanently. As described above, the cartridge may include, among other things, fluidic control and fluidic storage components.

In particular implementations, the sequencing system 6300A is configured to perform a large number of parallel reactions within the biosensor 6312. The biosensor 6312 includes one or more reaction sites where desired reactions can occur. The reaction sites may be, for example, immobilized to a solid surface of the biosensor or immobilized to beads (or other movable substrates) that are located within corresponding reaction chambers of the biosensor. The reaction sites can include, for example, clusters of clonally amplified nucleic acids. The biosensor 6312 may include a solid-state imaging device (e.g., CCD or CMOS imager) and a flow cell mounted thereto. The flow cell may include one or more flow channels that receive a solution from the sequencing system 6300A and direct the solution toward the reaction sites. Optionally, the biosensor 6312 can be configured to engage a thermal element for transferring thermal energy into or out of the flow channel.

The sequencing system 6300A may include various components, assemblies, and systems (or sub-systems) that interact with each other to perform a predetermined method or assay protocol for biological or chemical analysis. For example, the sequencing system 6300A includes a system controller 6306 that may communicate with the various components, assemblies, and sub-systems of the sequencing system 6300A and also the biosensor 6312. For example, in addition to the system receptacle 6310, the sequencing system 6300A may also include a fluidic control system 6308 to control the flow of fluid throughout a fluid network of the sequencing system 6300A and the biosensor 6312; a fluid storage system 6314 that is configured to hold all fluids (e.g., gas or liquids) that may be used by the bioassay system; a temperature control system 6304 that may regulate the temperature of the fluid in the fluid network, the fluid storage system 6314, and/or the biosensor 6312; and an illumination system 6316 that is configured to illuminate the biosensor 6312. As described above, if a cartridge having the biosensor 6312 is loaded into the system receptacle 6310, the cartridge may also include fluidic control and fluidic storage components.

Also shown, the sequencing system 6300A may include a user interface 6318 that interacts with the user. For example, the user interface 6318 may include a display 6320 to display or request information from a user and a user input device 6322 to receive user inputs. In some implementations, the display 6320 and the user input device 6322 are the same device. For example, the user interface 6318 may include a touch-sensitive display configured to detect the presence of an individual's touch and also identify a location of the touch on the display. However, other user input devices 6322 may be used, such as a mouse, touchpad, keyboard, keypad, handheld scanner, voice-recognition system, motion-recognition system, and the like. As will be discussed in greater detail below, the sequencing system 6300A may communicate with various components, including the biosensor 6312 (e.g., in the form of a cartridge), to perform the desired reactions. The sequencing system 6300A may also be configured to analyze data obtained from the biosensor to provide a user with desired information.

The system controller 6306 may include any processor-based or microprocessor-based system, including systems using microcontrollers, reduced instruction set computers (RISC), application specific integrated circuits (ASICs), field programmable gate array (FPGAs), coarse-grained reconfigurable architectures (CGRAs), logic circuits, and any other circuit or processor capable of executing functions described herein. The above examples are exemplary only, and are thus not intended to limit in any way the definition and/or meaning of the term system controller. In the exemplary implementation, the system controller 6306 executes a set of instructions that are stored in one or more storage elements, memories, or modules in order to at least one of obtain and analyze detection data. Detection data can include a plurality of sequences of pixel signals, such that a sequence of pixel signals from each of the millions of sensors (or pixels) can be detected over many base calling cycles. Storage elements may be in the form of information sources or physical memory elements within the sequencing system 6300A.

The set of instructions may include various commands that instruct the sequencing system 6300A or biosensor 6312 to perform specific operations such as the methods and processes of the various implementations described herein. The set of instructions may be in the form of a software program, which may form part of a tangible, non-transitory computer readable medium or media. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the sequencing system 6300A, processed in response to user inputs, or processed in response to a request made by another processing machine (e.g., a remote request through a communication link). In the illustrated implementation, the system controller 6306 includes an analysis module 6344. In other implementations, system controller 6306 does not include the analysis module 6344 and instead has access to the analysis module 6344 (e.g., the analysis module 6344 may be separately hosted on cloud).

The system controller 6306 may be connected to the biosensor 6312 and the other components of the sequencing system 6300A via communication links. The system controller 6306 may also be communicatively connected to off-site systems or servers. The communication links may be hardwired, corded, or wireless. The system controller 6306 may receive user inputs or commands, from the user interface 6318 and the user input device 6322.

The fluidic control system 6308 includes a fluid network and is configured to direct and regulate the flow of one or more fluids through the fluid network. The fluid network may be in fluid communication with the biosensor 6312 and the fluid storage system 6314. For example, select fluids may be drawn from the fluid storage system 6314 and directed to the biosensor 6312 in a controlled manner, or the fluids may be drawn from the biosensor 6312 and directed toward, for example, a waste reservoir in the fluid storage system 6314. Although not shown, the fluidic control system 6308 may include flow sensors that detect a flow rate or pressure of the fluids within the fluid network. The sensors may communicate with the system controller 6306.

The temperature control system 6304 is configured to regulate the temperature of fluids at different regions of the fluid network, the fluid storage system 6314, and/or the biosensor 6312. For example, the temperature control system 6304 may include a thermocycler that interfaces with the biosensor 6312 and controls the temperature of the fluid that flows along the reaction sites in the biosensor 6312. The temperature control system 6304 may also regulate the temperature of solid elements or components of the sequencing system 6300A or the biosensor 6312. Although not shown, the temperature control system 6304 may include sensors to detect the temperature of the fluid or other components. The sensors may communicate with the system controller 6306.

The fluid storage system 6314 is in fluid communication with the biosensor 6312 and may store various reaction components or reactants that are used to conduct the desired reactions therein. The fluid storage system 6314 may also store fluids for washing or cleaning the fluid network and biosensor 6312 and for diluting the reactants. For example, the fluid storage system 6314 may include various reservoirs to store samples, reagents, enzymes, other biomolecules, buffer solutions, aqueous, and non-polar solutions, and the like. Furthermore, the fluid storage system 6314 may also include waste reservoirs for receiving waste products from the biosensor 6312. In implementations that include a cartridge, the cartridge may include one or more of a fluid storage system, fluidic control system or temperature control system. Accordingly, one or more of the components set forth herein as relating to those systems can be contained within a cartridge housing. For example, a cartridge can have various reservoirs to store samples, reagents, enzymes, other biomolecules, buffer solutions, aqueous, and non-polar solutions, waste, and the like. As such, one or more of a fluid storage system, fluidic control system or temperature control system can be removably engaged with a bioassay system via a cartridge or other biosensor.

The illumination system 6316 may include a light source (e.g., one or more LEDs) and a plurality of optical components to illuminate the biosensor. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In implementations that use an illumination system, the illumination system 6316 may be configured to direct an excitation light to reaction sites. As one example, fluorophores may be excited by green wavelengths of light, as such the wavelength of the excitation light may be approximately 532 nm. In one implementation, the illumination system 6316 is configured to produce illumination that is parallel to a surface normal of a surface of the biosensor 6312. In another implementation, the illumination system 6316 is configured to produce illumination that is off-angle relative to the surface normal of the surface of the biosensor 6312. In yet another implementation, the illumination system 6316 is configured to produce illumination that has plural angles, including some parallel illumination and some off-angle illumination.

The system receptacle or interface 6310 is configured to engage the biosensor 6312 in at least one of a mechanical, electrical, and fluidic manner. The system receptacle 6310 may hold the biosensor 6312 in a desired orientation to facilitate the flow of fluid through the biosensor 6312. The system receptacle 6310 may also include electrical contacts that are configured to engage the biosensor 6312 so that the sequencing system 6300A may communicate with the biosensor 6312 and/or provide power to the biosensor 6312. Furthermore, the system receptacle 6310 may include fluidic ports (e.g., nozzles) that are configured to engage the biosensor 6312. In some implementations, the biosensor 6312 is removably coupled to the system receptacle 6310 in a mechanical manner, in an electrical manner, and also in a fluidic manner.

In addition, the sequencing system 6300A may communicate remotely with other systems or networks or with other bioassay systems 6300A. Detection data obtained by the bioassay system(s) 6300A may be stored in a remote database.

FIG. 63B is a block diagram of a system controller 6306 that can be used in the system of FIG. 63A. In one implementation, the system controller 6306 includes one or more processors or modules that can communicate with one another. Each of the processors or modules may include an algorithm (e.g., instructions stored on a tangible and/or non-transitory computer readable storage medium) or sub-algorithms to perform particular processes. The system controller 6306 is illustrated conceptually as a collection of modules, but may be implemented utilizing any combination of dedicated hardware boards, DSPs, processors, etc. Alternatively, the system controller 6306 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

During operation, a communication port 6350 may transmit information (e.g., commands) to or receive information (e.g., data) from the biosensor 6312 (FIG. 63A) and/or the sub-systems 6308, 6314, 6304 (FIG. 63A). In implementations, the communication port 6350 may output a plurality of sequences of pixel signals. A communication link 6334 may receive user input from the user interface 6318 (FIG. 63A) and transmit data or information to the user interface 6318. Data from the biosensor 6312 or sub-systems 6308, 6314, 6304 may be processed by the system controller 6306 in real-time during a bioassay session. Additionally or alternatively, data may be stored temporarily in a system memory during a bioassay session and processed in slower than real-time or off-line operation.

As shown in FIG. 63B, the system controller 6306 may include a plurality of modules 6326-6348 that communicate with a main control module 6324, along with a central processing unit (CPU) 6352. The main control module 6324 may communicate with the user interface 6318 (FIG. 63A). Although the modules 6326-6348 are shown as communicating directly with the main control module 6324, the modules 6326-6348 may also communicate directly with each other, the user interface 6318, and the biosensor 6312. Also, the modules 6326-6348 may communicate with the main control module 6324 through the other modules.

The plurality of modules 6326-6348 include system modules 6328-6332, 6326 that communicate with the sub-systems 6308, 6314, 6304, and 6316, respectively. The fluidic control module 6328 may communicate with the fluidic control system 6308 to control the valves and flow sensors of the fluid network for controlling the flow of one or more fluids through the fluid network. The fluid storage module 6330 may notify the user when fluids are low or when the waste reservoir is at or near capacity. The fluid storage module 6330 may also communicate with the temperature control module 6332 so that the fluids may be stored at a desired temperature. The illumination module 6326 may communicate with the illumination system 6316 to illuminate the reaction sites at designated times during a protocol, such as after the desired reactions (e.g., binding events) have occurred. In some implementations, the illumination module 6326 may communicate with the illumination system 6316 to illuminate the reaction sites at designated angles.

The plurality of modules 6326-6348 may also include a device module 6336 that communicates with the biosensor 6312 and an identification module 6338 that determines identification information relating to the biosensor 6312. The device module 6336 may, for example, communicate with the system receptacle 6310 to confirm that the biosensor has established an electrical and fluidic connection with the sequencing system 6300A. The identification module 6338 may receive signals that identify the biosensor 6312. The identification module 6338 may use the identity of the biosensor 6312 to provide other information to the user. For example, the identification module 6338 may determine and then display a lot number, a date of manufacture, or a protocol that is recommended to be run with the biosensor 6312.

The plurality of modules 6326-6348 also includes an analysis module 6344 (also called signal processing module or signal processor) that receives and analyzes the signal data (e.g., image data) from the biosensor 6312. Analysis module 6344 includes memory (e.g., RAM or Flash) to store detection/image data. Detection data can include a plurality of sequences of pixel signals, such that a sequence of pixel signals from each of the millions of sensors (or pixels) can be detected over many base calling cycles. The signal data may be stored for subsequent analysis or may be transmitted to the user interface 6318 to display desired information to the user. In some implementations, the signal data may be processed by the solid-state imager (e.g., CMOS image sensor) before the analysis module 6344 receives the signal data.

The analysis module 6344 is configured to obtain image data from the light detectors at each of a plurality of sequencing cycles. The image data is derived from the emission signals detected by the light detectors and process the image data for each of the plurality of sequencing cycles through the neural network-based quality scorer 6102 and/or the neural network-based base caller 218 and produce a base call for at least some of the analytes at each of the plurality of sequencing cycle. The light detectors can be part of one or more over-head cameras (e.g., Illumina's GAIIx's CCD camera taking images of the clusters on the biosensor 6312 from the top), or can be part of the biosensor 6312 itself (e.g., Illumina's iSeq's CMOS image sensors underlying the clusters on the biosensor 6312 and taking images of the clusters from the bottom).

The output of the light detectors is the sequencing images, each depicting intensity emissions of the clusters and their surrounding background. The sequencing images depict intensity emissions generated as a result of nucleotide incorporation in the sequences during the sequencing. The intensity emissions are from associated analytes and their surrounding background. The sequencing images are stored in memory 6348.

Protocol modules 6340 and 6342 communicate with the main control module 6324 to control the operation of the sub-systems 6308, 6314, and 6304 when conducting predetermined assay protocols. The protocol modules 6340 and 6342 may include sets of instructions for instructing the sequencing system 6300A to perform specific operations pursuant to predetermined protocols. As shown, the protocol module may be a sequencing-by-synthesis (SBS) module 6340 that is configured to issue various commands for performing sequencing-by-synthesis processes. In SBS, extension of a nucleic acid primer along a nucleic acid template is monitored to determine the sequence of nucleotides in the template. The underlying chemical process can be polymerization (e.g., as catalyzed by a polymerase enzyme) or ligation (e.g., catalyzed by a ligase enzyme). In a particular polymerase-based SBS implementation, fluorescently labeled nucleotides are added to a primer (thereby extending the primer) in a template dependent fashion such that detection of the order and type of nucleotides added to the primer can be used to determine the sequence of the template. For example, to initiate a first SBS cycle, commands can be given to deliver one or more labeled nucleotides, DNA polymerase, etc., into/through a flow cell that houses an array of nucleic acid templates. The nucleic acid templates may be located at corresponding reaction sites. Those reaction sites where primer extension causes a labeled nucleotide to be incorporated can be detected through an imaging event. During an imaging event, the illumination system 6316 may provide an excitation light to the reaction sites. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for implementations that use reversible termination a command can be given to deliver a deblocking reagent to the flow cell (before or after detection occurs). One or more commands can be given to effect wash(es) between the various delivery steps. The cycle can then be repeated n times to extend the primer by n nucleotides, thereby detecting a sequence of length n. Exemplary sequencing techniques are described, for example, in Bentley et al., Nature 456:53-59 (20063); WO 04/0163497; U.S. Pat. No. 7,057,026; WO 91/066763; WO 07/123744; U.S. Pat. Nos. 7,329,492; 7,211,414; 7,315,019; 7,405,2631, and US 20063/01470630632, each of which is incorporated herein by reference.

For the nucleotide delivery step of an SBS cycle, either a single type of nucleotide can be delivered at a time, or multiple different nucleotide types (e.g., A, C, T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, an excitation source need only provide excitation at a single wavelength or in a single range of wavelengths. For a nucleotide delivery configuration where delivery results in multiple different nucleotides being present in the flow cell at one time, sites that incorporate different nucleotide types can be distinguished based on different fluorescent labels that are attached to respective nucleotide types in the mixture. For example, four different nucleotides can be used, each having one of four different fluorophores. In one implementation, the four different fluorophores can be distinguished using excitation in four different regions of the spectrum. For example, four different excitation radiation sources can be used. Alternatively, fewer than four different excitation sources can be used, but optical filtration of the excitation radiation from a single source can be used to produce different ranges of excitation radiation at the flow cell.

In some implementations, fewer than four different colors can be detected in a mixture having four different nucleotides. For example, pairs of nucleotides can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. Exemplary apparatus and methods for distinguishing four different nucleotides using detection of fewer than four colors are described for example in US Pat. App. Ser. Nos. 61/5363,294 and 61/619,63763, which are incorporated herein by reference in their entireties. U.S. application Ser. No. 13/624,200, which was filed on Sep. 21, 2012, is also incorporated by reference in its entirety.

The plurality of protocol modules may also include a sample-preparation (or generation) module 6342 that is configured to issue commands to the fluidic control system 6308 and the temperature control system 6304 for amplifying a product within the biosensor 6312. For example, the biosensor 6312 may be engaged to the sequencing system 6300A. The amplification module 6342 may issue instructions to the fluidic control system 6308 to deliver necessary amplification components to reaction chambers within the biosensor 6312. In other implementations, the reaction sites may already contain some components for amplification, such as the template DNA and/or primers. After delivering the amplification components to the reaction chambers, the amplification module 6342 may instruct the temperature control system 6304 to cycle through different temperature stages according to known amplification protocols. In some implementations, the amplification and/or nucleotide incorporation is performed isothermally.

The SBS module 6340 may issue commands to perform bridge PCR where clusters of clonal amplicons are formed on localized areas within a channel of a flow cell. After generating the amplicons through bridge PCR, the amplicons may be "linearized" to make single stranded template DNA, or sstDNA, and a sequencing primer may be hybridized to a universal sequence that flanks a region of interest. For example, a reversible terminator-based sequencing by synthesis method can be used as set forth above or as follows.

Each base calling or sequencing cycle can extend an sstDNA by a single base which can be accomplished for example by using a modified DNA polymerase and a mixture of four types of nucleotides. The different types of nucleotides can have unique fluorescent labels, and each nucleotide can further have a reversible terminator that allows only a single base incorporation to occur in each cycle. After a single base is added to the sstDNA, excitation light may be incident upon the reaction sites and fluorescent emissions may be detected. After detection, the fluorescent label and the terminator may be chemically cleaved from the sstDNA. Another similar base calling or sequencing cycle may follow. In such a sequencing protocol, the SBS module 6340 may instruct the fluidic control system 6308 to direct a flow of reagent and enzyme solutions through the biosensor 6312. Exemplary reversible terminator-based SBS methods which can be utilized with the apparatus and methods set forth herein are described in US Patent Application Publication No. 2007/0166705 A1, US Patent Application Publication No. 2006/016363901 A1, U.S. Pat. No. 7,057,026, US Patent Application Publication No. 2006/0240439 A1, US Patent Application Publication No. 2006/026314714709 A1, PCT Publication No. WO 05/0656314, US Patent Application Publication No. 2005/014700900 A1, PCT Publication No. WO 06/063B199 and PCT Publication No. WO 07/01470251, each of which is incorporated herein by reference in its entirety. Exemplary reagents for reversible terminator-based SBS are described in U.S. Pat. Nos. 7,541,444; 7,057,026; 7,414,14716; U.S. Pat. Nos. 7,427,673; 7,566,537; 7,592,435 and WO 07/1463353663, each of which is incorporated herein by reference in its entirety.

In some implementations, the amplification and SBS modules may operate in a single assay protocol where, for example, template nucleic acid is amplified and subsequently sequenced within the same cartridge.

The sequencing system 6300A may also allow the user to reconfigure an assay protocol. For example, the sequencing system 6300A may offer options to the user through the user interface 6318 for modifying the determined protocol. For example, if it is determined that the biosensor 6312 is to be used for amplification, the sequencing system 6300A may request a temperature for the annealing cycle. Furthermore, the sequencing system 6300A may issue warnings to a user if a user has provided user inputs that are generally not acceptable for the selected assay protocol.

In implementations, the biosensor 6312 includes millions of sensors (or pixels), each of which generates a plurality of sequences of pixel signals over successive base calling cycles. The analysis module 6344 detects the plurality of sequences of pixel signals and attributes them to corresponding sensors (or pixels) in accordance to the row-wise and/or column-wise location of the sensors on an array of sensors.

FIG. 63C is a simplified block diagram of a system for analysis of sensor data from the sequencing system 6300A, such as base call sensor outputs. In the example of FIG. 63C, the system includes the configurable processor 6346. The configurable processor 6346 can execute a base caller (e.g., the neural network-based quality scorer 6102 and/or the neural network-based base caller 218) in coordination with a runtime program executed by the central processing unit (CPU) 6352 (i.e., a host processor). The sequencing system 6300A comprises the biosensor 6312 and flow cells. The flow cells can comprise one or more tiles in which clusters of genetic material are exposed to a sequence of analyte flows used to cause reactions in the clusters to identify the bases in the genetic material. The sensors sense the reactions for each cycle of the sequence in each tile of the flow cell to provide tile data. Genetic sequencing is a data intensive operation, which translates base call sensor data into sequences of base calls for each cluster of genetic material sensed in during a base call operation.

The system in this example includes the CPU 6352, which executes a runtime program to coordinate the base call operations, memory 6348B to store sequences of arrays of tile data, base call reads produced by the base calling operation, and other information used in the base call operations. Also, in this illustration the system includes memory 6348A to store a configuration file (or files), such as FPGA bit files, and model parameters for the neural networks used to configure and reconfigure the configurable processor 6346, and execute the neural networks. The sequencing system 6300A can include a program for configuring a configurable processor and in some embodiments a reconfigurable processor to execute the neural networks.

The sequencing system 6300A is coupled by a bus 6389 to the configurable processor 6346. The bus 6389 can be implemented using a high throughput technology, such as in one example bus technology compatible with the PCIe standards (Peripheral Component Interconnect Express) currently maintained and developed by the PCI-SIG (PCI Special Interest Group). Also in this example, a memory 6348A is coupled to the configurable processor 6346 by bus 6393. The memory 6348A can be on-board memory, disposed on a circuit board with the configurable processor 6346. The memory 6348A is used for high speed access by the configurable processor 6346 of working data used in the base call operation. The bus 6393 can also be implemented using a high throughput technology, such as bus technology compatible with the PCIe standards.

Configurable processors, including field programmable gate arrays FPGAs, coarse grained reconfigurable arrays CGRAs, and other configurable and reconfigurable devices, can be configured to implement a variety of functions more efficiently or faster than might be achieved using a general purpose processor executing a computer program. Configuration of configurable processors involves compiling a functional description to produce a configuration file, referred to sometimes as a bitstream or bit file, and distributing the configuration file to the configurable elements on the processor. The configuration file defines the logic functions to be executed by the configurable processor, by configuring the circuit to set data flow patterns, use of distributed memory and other on-chip memory resources, lookup table contents, operations of configurable logic blocks and configurable execution units like multiply-and-accumulate units, configurable interconnects and other elements of the configurable array. A configurable processor is reconfigurable if the configuration file may be changed in the field, by changing the loaded configuration file. For example, the configuration file may be stored in volatile SRAM elements, in non-volatile read-write memory elements, and in combinations of the same, distributed among the array of configurable elements on the configurable or reconfigurable processor. A variety of commercially available configurable processors are suitable for use in a base calling operation as described herein. Examples include Google's Tensor Processing Unit (TPU)™, rackmount solutions like GX4 Rackmount Series™, GX9 Rackmount Series™, NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, Xilinx Alveo™ U200, Xilinx Alveo™ U250, Xilinx Alveo™ U280, Intel/Altera Stratix™ GX2800, Intel/Altera Stratix™ GX2800, and Intel Stratix™ GX10M. In some examples, a host CPU can be implemented on the same integrated circuit as the configurable processor.

Embodiments described herein implement the neural network-based quality scorer 6102 and/or the neural network-based base caller 218 using the configurable processor 6346. The configuration file for the configurable processor 6346 can be implemented by specifying the logic functions to be executed using a high level description language HDL or a register transfer level RTL language specification. The specification can be compiled using the resources designed for the selected configurable processor to generate the configuration file. The same or similar specification can be compiled for the purposes of generating a design for an application-specific integrated circuit which may not be a configurable processor.

Alternatives for the configurable processor configurable processor 6346, in all embodiments described herein, therefore include a configured processor comprising an application specific ASIC or special purpose integrated circuit or set of integrated circuits, or a system-on-a-chip SOC device, or a graphics processing unit (GPU) processor or a coarse-grained reconfigurable architecture (CGRA) processor, configured to execute a neural network based base call operation as described herein.

In general, configurable processors and configured processors described herein, as configured to execute runs of a neural network, are referred to herein as neural network processors.

The configurable processor 6346 is configured in this example by a configuration file loaded using a program executed by the CPU 6352, or by other sources, which configures the array of configurable elements 6391 (e.g., configuration logic blocks (CLB) such as look up tables (LUTs), flip-flops, compute processing units (PMUs), and compute memory units (CMUs), configurable I/O blocks, programmable interconnects), on the configurable processor to execute the base call function. In this example, the configuration includes data flow logic 6397 which is coupled to the buses 6389 and 6393 and executes functions for distributing data and control parameters among the elements used in the base call operation.

Also, the configurable processor 6346 is configured with base call execution logic 6397 to execute the neural network-based quality scorer 6102 and/or the neural network-based base caller 218. The logic 6397 comprises multi-cycle execution clusters (e.g., 6379) which, in this example, includes execution cluster 1 through execution cluster X. The number of multi-cycle execution clusters can be selected according to a trade-off involving the desired throughput of the operation, and the available resources on the configurable processor 6346.

The multi-cycle execution clusters are coupled to the data flow logic 6397 by data flow paths 6399 implemented using configurable interconnect and memory resources on the configurable processor 6346. Also, the multi-cycle execution clusters are coupled to the data flow logic 6397 by control paths 6395 implemented using configurable interconnect and memory resources for example on the configurable processor 6346, which provide control signals indicating available execution clusters, readiness to provide input units for execution of a run of the neural network-based quality scorer 6102 and/or the neural network-based base caller 218 to the available execution clusters, readiness to provide trained parameters for the neural network-based quality scorer 6102 and/or the neural network based base caller 218, readiness to provide output patches of base call classification data, and other control data used for execution of the neural network-based quality scorer 6102 and/or the neural network-based base caller 218.

The configurable processor 6346 is configured to execute runs of the neural network-based quality scorer 6102 and/or the neural network-based base caller 218 using trained parameters to produce classification data for the sensing cycles of the base calling operation. A run of the neural network based quality scorer 6102 and/or the neural network-based base caller 218 is executed to produce classification data for a subject sensing cycle of the base calling operation. A run of the neural network-based quality scorer 6102 and/or the neural network-based base caller 218 operates on a sequence including a number N of arrays of tile data from respective sensing cycles of N sensing cycles, where the N sensing cycles provide sensor data for different base call operations for one base position per operation in time sequence in the examples described herein. Optionally, some of the N sensing cycles can be out of sequence if needed according to a particular neural network model being executed. The number N can be any number greater than one. In some examples described herein, sensing cycles of the N sensing cycles represent a set of sensing cycles for at least one sensing cycle preceding the subject sensing cycle and at least one sensing cycle following the subject cycle in time sequence. Examples are described herein in which the number N is an integer equal to or greater than five.

The data flow logic 6397 is configured to move tile data and at least some trained parameters of the model parameters from the memory 6348A to the configurable processor 6346 for runs of the neural network-based quality scorer 6102 and/or the neural network-based base caller 218, using input units for a given run including tile data for spatially aligned patches of the N arrays. The input units can be moved by direct memory access operations in one DMA operation, or in smaller units moved during available time slots in coordination with the execution of the neural network deployed.

Tile data for a sensing cycle as described herein can comprise an array of sensor data having one or more features. For example, the sensor data can comprise two images which are analyzed to identify one of four bases at a base position in a genetic sequence of DNA, RNA, or other genetic material. The tile data can also include metadata about the images and the sensors. For example, in embodiments of the base calling operation, the tile data can comprise information about alignment of the images with the clusters such as distance from center information indicating the distance of each pixel in the array of sensor data from the center of a cluster of genetic material on the tile.

During execution of the neural network-based quality scorer 6102 and/or the neural network-based base caller 218 as described below, tile data can also include data produced during execution of the neural network-based quality scorer 6102 and/or the neural network-based base caller 218, referred to as intermediate data, which can be reused rather than recomputed during a run of the neural network-based quality scorer 6102 and/or the neural network-based base caller 218. For example, during execution of the neural network-based quality scorer 6102 and/or the neural network-based base caller 218, the data flow logic 6397 can write intermediate data to the memory 6348A in place of the sensor data for a given patch of an array of tile data. Embodiments like this are described in more detail below.

As illustrated, a system is described for analysis of base call sensor output, comprising memory (e.g., 6348A) accessible by the runtime program storing tile data including sensor data for a tile from sensing cycles of a base calling operation. Also, the system includes a neural network processor, such as configurable processor 6346 having access to the memory. The neural network processor is configured to execute runs of a neural network using trained parameters to produce classification data for sensing cycles. As described herein, a run of the neural network is operating on a sequence of N arrays of tile data from respective sensing cycles of N sensing cycles, including a subject cycle, to produce the classification data for the subject cycle. The data flow logic 908 is provided to move tile data and the trained parameters from the memory to the neural network processor for runs of the neural network using input units including data for spatially aligned patches of the N arrays from respective sensing cycles of N sensing cycles.

Also, a system is described in which the neural network processor has access to the memory, and includes a plurality of execution clusters, the execution clusters in the plurality of execution clusters configured to execute a neural network. The data flow logic 6397 has access to the memory and to execution clusters in the plurality of execution clusters, to provide input units of tile data to available execution clusters in the plurality of execution clusters, the input units including a number N of spatially aligned patches of arrays of tile data from respective sensing cycles, including a subject sensing cycle, and to cause the execution clusters to apply the N spatially aligned patches to the neural network to produce output patches of classification data for the spatially aligned patch of the subject sensing cycle, where N is greater than 1.

Figure 64A:
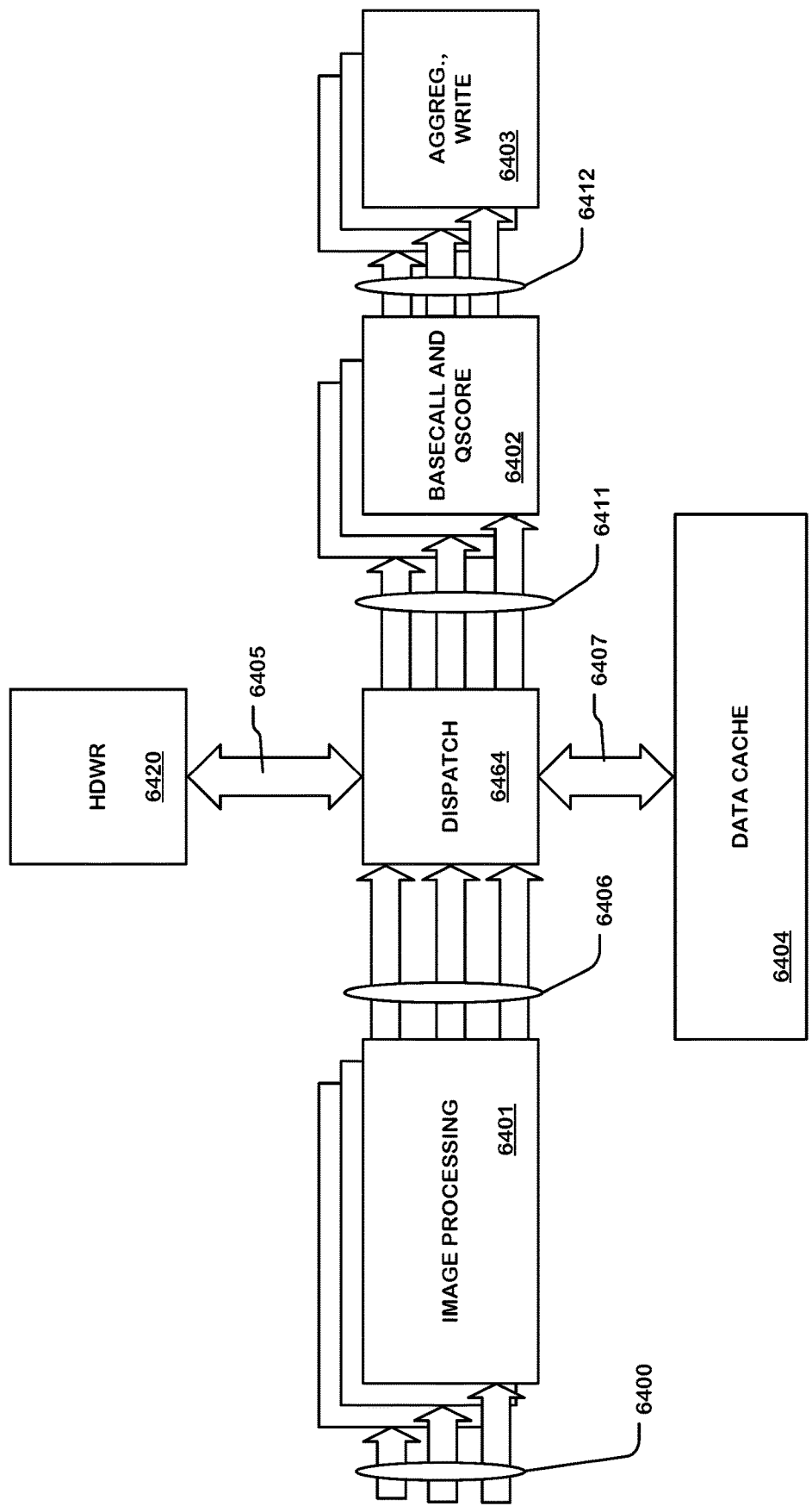
FIG. 64A is a simplified diagram showing aspects of the base calling operation, including functions of a runtime program executed by a host processor.

FIG. 64A is a simplified diagram showing aspects of the base calling operation, including functions of a runtime program executed by a host processor. In this diagram, the output of image sensors from a flow cell are provided on lines 6400 to image processing threads 6401, which can perform processes on images such as alignment and arrangement in an array of sensor data for the individual tiles and resampling of images, and can be used by processes which calculate a tile cluster mask for each tile in the flow cell, which identifies pixels in the array of sensor data that correspond to clusters of genetic material on the corresponding tile of the flow cell. The outputs of the image processing threads 6401 are provided on lines 6406 to a dispatch logic 6410 in the CPU which routes the arrays of tile data to a data cache 6404 (e.g., SSD storage) on a high-speed bus 6407, or on high-speed bus 6405 to the neural network processor hardware 6420, such as the configurable processor 6346 of FIG. 63C, according to the state of the base calling operation. The processed and transformed images can be stored on the data cache 6404 for sensing cycles that were previously used. The hardware 6420 returns classification data output by the neural network to the dispatch logic 6464, which passes the information to the data cache 6404, or on lines 6411 to threads 6402 that perform base call and quality score computations using the classification data, and can arrange the data in standard formats for base call reads. The outputs of the threads 6402 that perform base calling and quality score computations are provided on lines 6412 to threads 6403 that aggregate the base call reads, perform other operations such as data compression, and write the resulting base call outputs to specified destinations for utilization by the customers.

In some embodiments, the host can include threads (not shown) that perform final processing of the output of the hardware 6420 in support of the neural network. For example, the hardware 6420 can provide outputs of classification data from a final layer of the multi-cluster neural network. The host processor can execute an output activation function, such as a softmax function, over the classification data to configure the data for use by the base call and quality score threads 6402. Also, the host processor can execute input operations (not shown), such as batch normalization of the tile data prior to input to the hardware 6420.

Figure 64B:
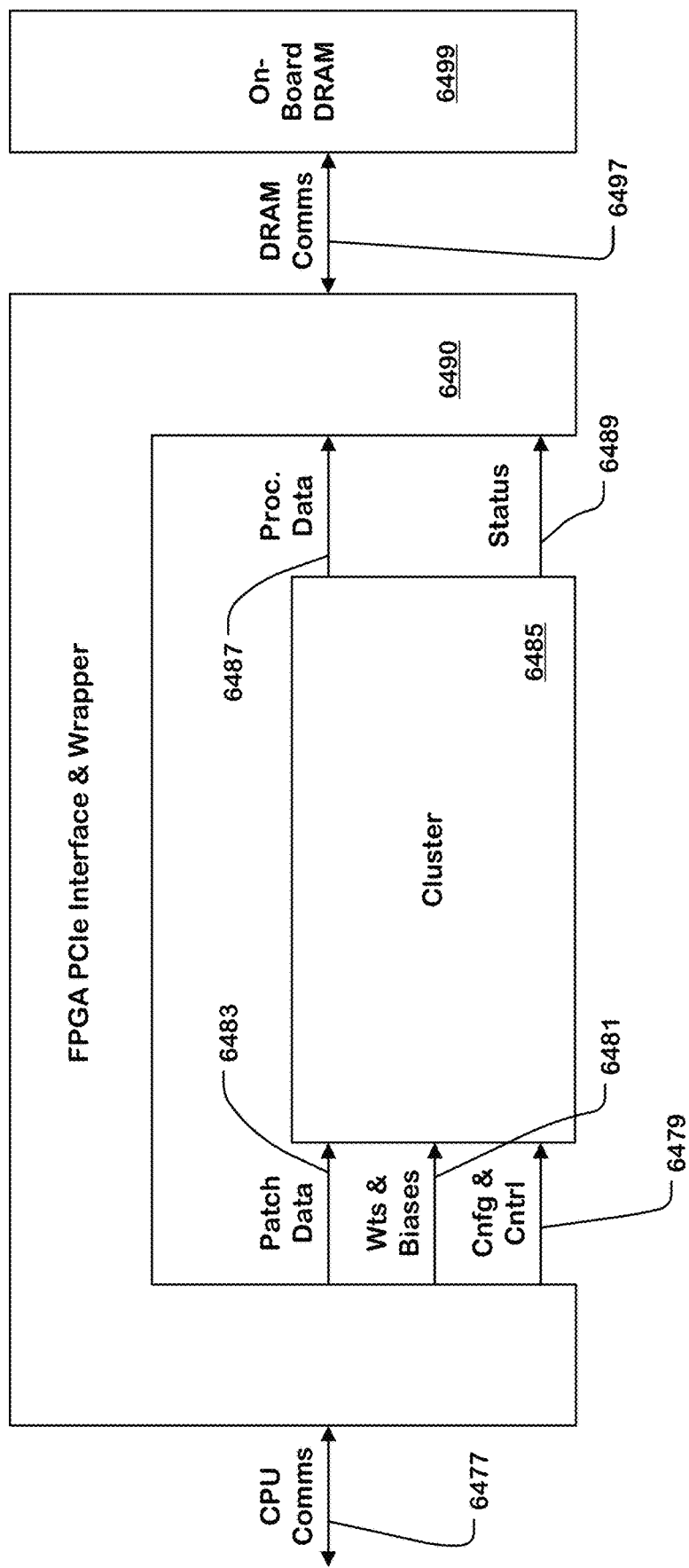
FIG. 64B is a simplified diagram of a configuration of a configurable processor such as the one depicted in FIG. 63C.

FIG. 64B is a simplified diagram of a configuration of a configurable processor 6346 such as that of FIG. 63C. In FIG. 64B, the configurable processor 6346 comprises an FPGA with a plurality of high speed PCIe interfaces. The FPGA is configured with a wrapper 6490 which comprises the data flow logic 6397 described with reference to FIG. 63C. The wrapper 6490 manages the interface and coordination with a runtime program in the CPU across the CPU communication link 6477 and manages communication with the on-board DRAM 6499 (e.g., memory 6348A) via DRAM communication link 6497. The data flow logic 6397 in the wrapper 6490 provides patch data retrieved by traversing the arrays of tile data on the on-board DRAM 6499 for the number N cycles to a cluster 6485, and retrieves process data 6487 from the cluster 6485 for delivery back to the on-board DRAM 6499. The wrapper 6490 also manages transfer of data between the on-board DRAM 6499 and host memory, for both the input arrays of tile data, and for the output patches of classification data. The wrapper transfers patch data on line 6483 to the allocated cluster 6485. The wrapper provides trained parameters, such as weights and biases on line 6481 to the cluster 6485 retrieved from the on-board DRAM 6499. The wrapper provides configuration and control data on line 6479 to the cluster 6485 provided from, or generated in response to, the runtime program on the host via the CPU communication link 6477. The cluster can also provide status signals on line 6489 to the wrapper 6490, which are used in cooperation with control signals from the host to manage traversal of the arrays of tile data to provide spatially aligned patch data, and to execute the multi-cycle neural network over the patch data using the resources of the cluster 6485.

As mentioned above, there can be multiple clusters on a single configurable processor managed by the wrapper 6490 configured for executing on corresponding ones of multiple patches of the tile data. Each cluster can be configured to provide classification data for base calls in a subject sensing cycle using the tile data of multiple sensing cycles described herein.

In examples of the system, model data, including kernel data like filter weights and biases can be sent from the host CPU to the configurable processor, so that the model can be updated as a function of cycle number. A base calling operation can comprise, for a representative example, on the order of hundreds of sensing cycles. Base calling operation can include paired end reads in some embodiments. For example, the model trained parameters may be updated once every 20 cycles (or other number of cycles), or according to update patterns implemented for particular systems and neural network models. In some embodiments including paired end reads in which a sequence for a given string in a genetic cluster on a tile includes a first part extending from a first end down (or up) the string, and a second part extending from a second end up (or down) the string, the trained parameters can be updated on the transition from the first part to the second part.

In some examples, image data for multiple cycles of sensing data for a tile can be sent from the CPU to the wrapper 6490. The wrapper 6490 can optionally do some pre-processing and transformation of the sensing data and write the information to the on-board DRAM 6499. The input tile data for each sensing cycle can include arrays of sensor data including on the order of 4000×3000 pixels per sensing cycle per tile or more, with two features representing colors of two images of the tile, and one or two bytes per feature per pixel. For an embodiment in which the number N is three sensing cycles to be used in each run of the multi-cycle neural network, the array of tile data for each run of the multi-cycle neural network can consume on the order of hundreds of megabytes per tile. In some embodiments of the system, the tile data also includes an array of DFC data, stored once per tile, or other type of metadata about the sensor data and the tiles.

In operation, when a multi-cycle cluster is available, the wrapper allocates a patch to the cluster. The wrapper fetches a next patch of tile data in the traversal of the tile and sends it to the allocated cluster along with appropriate control and configuration information. The cluster can be configured with enough memory on the configurable processor to hold a patch of data including patches from multiple cycles in some systems, that is being worked on in place, and a patch of data that is to be worked on when the current patch of processing is finished using a ping-pong buffer technique or raster scanning technique in various embodiments.

When an allocated cluster completes its run of the neural network for the current patch and produces an output patch, it will signal the wrapper. The wrapper will read the output patch from the allocated cluster, or alternatively the allocated cluster will push the data out to the wrapper. Then the wrapper will assemble output patches for the processed tile in the DRAM 6499. When the processing of the entire tile has been completed, and the output patches of data transferred to the DRAM, the wrapper sends the processed output array for the tile back to the host/CPU in a specified format. In some embodiments, the on-board DRAM 6499 is managed by memory management logic in the wrapper 6490. The runtime program can control the sequencing operations to complete analysis of all the arrays of tile data for all the cycles in the run in a continuous flow to provide real time analysis.

Technical Improvements and Terminology

Base calling includes incorporation or attachment of a fluorescently-labeled tag with an analyte. The analyte can be a nucleotide or an oligonucleotide, and the tag can be for a particular nucleotide type (A, C, T, or G). Excitation light is directed toward the analyte having the tag, and the tag emits a detectable fluorescent signal or intensity emission. The intensity emission is indicative of photons emitted by the excited tag that is chemically attached to the analyte.

Throughout this application, including the claims, when phrases such as or similar to "images, image data, or image regions depicting intensity emissions of analytes and their surrounding background" are used, they refer to the intensity emissions of the tags attached to the analytes. A person skilled in the art will appreciate that the intensity emissions of the attached tags are representative of or equivalent to the intensity emissions of the analytes to which the tags are attached, and are therefore used interchangeably. Similarly, properties of the analytes refer to properties of the tags attached to the analytes or of the intensity emissions from the attached tags. For example, a center of an analyte refers to the center of the intensity emissions emitted by a tag attached to the analyte. In another example, the surrounding background of an analyte refers to the surrounding background of the intensity emissions emitted by a tag attached to the analyte.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The technology disclosed uses neural networks to improve the quality and quantity of nucleic acid sequence information that can be obtained from a nucleic acid sample such as a nucleic acid template or its complement, for instance, a DNA or RNA polynucleotide or other nucleic acid sample. Accordingly, certain implementations of the technology disclosed provide higher throughput polynucleotide sequencing, for instance, higher rates of collection of DNA or RNA sequence data, greater efficiency in sequence data collection, and/or lower costs of obtaining such sequence data, relative to previously available methodologies.

The technology disclosed uses neural networks to identify the center of a solid-phase nucleic acid cluster and to analyze optical signals that are generated during sequencing of such clusters, to discriminate unambiguously between adjacent, abutting or overlapping clusters in order to assign a sequencing signal to a single, discrete source cluster. These and related implementations thus permit retrieval of meaningful information, such as sequence data, from regions of high-density cluster arrays where useful information could not previously be obtained from such regions due to confounding effects of overlapping or very closely spaced adjacent clusters, including the effects of overlapping signals (e.g., as used in nucleic acid sequencing) emanating therefrom.

As described in greater detail below, in certain implementations there is provided a composition that comprises a solid support having immobilized thereto one or a plurality of nucleic acid clusters as provided herein. Each cluster comprises a plurality of immobilized nucleic acids of the same sequence and has an identifiable center having a detectable center label as provided herein, by which the identifiable center is distinguishable from immobilized nucleic acids in a surrounding region in the cluster. Also described herein are methods for making and using such clusters that have identifiable centers.

The presently disclosed implementations will find uses in numerous situations where advantages are obtained from the ability to identify, determine, annotate, record or otherwise assign the position of a substantially central location within a cluster, such as high-throughput nucleic acid sequencing, development of image analysis algorithms for assigning optical or other signals to discrete source clusters, and other applications where recognition of the center of an immobilized nucleic acid cluster is desirable and beneficial.

In certain implementations, the present invention contemplates methods that relate to high-throughput nucleic acid analysis such as nucleic acid sequence determination (e.g., "sequencing"). Exemplary high-throughput nucleic acid analyses include without limitation de novo sequencing, re-sequencing, whole genome sequencing, gene expression analysis, gene expression monitoring, epigenetic analysis, genome methylation analysis, allele specific primer extension (APSE), genetic diversity profiling, whole genome polymorphism discovery and analysis, single nucleotide polymorphism analysis, hybridization based sequence determination methods, and the like. One skilled in the art will appreciate that a variety of different nucleic acids can be analyzed using the methods and compositions of the present invention.

Although the implementations of the present invention are described in relation to nucleic acid sequencing, they are applicable in any field where image data acquired at different time points, spatial locations or other temporal or physical perspectives is analyzed. For example, the methods and systems described herein are useful in the fields of molecular and cell biology where image data from microarrays, biological specimens, cells, organisms and the like is acquired and at different time points or perspectives and analyzed. Images can be obtained using any number of techniques known in the art including, but not limited to, fluorescence microscopy, light microscopy, confocal microscopy, optical imaging, magnetic resonance imaging, tomography scanning or the like. As another example, the methods and systems described herein can be applied where image data obtained by surveillance, aerial or satellite imaging technologies and the like is acquired at different time points or perspectives and analyzed. The methods and systems are particularly useful for analyzing images obtained for a field of view in which the analytes being viewed remain in the same locations relative to each other in the field of view. The analytes may however have characteristics that differ in separate images, for example, the analytes may appear different in separate images of the field of view. For example, the analytes may appear different with regard to the color of a given analyte detected in different images, a change in the intensity of signal detected for a given analyte in different images, or even the appearance of a signal for a given analyte in one image and disappearance of the signal for the analyte in another image.

Examples described herein may be used in various biological or chemical processes and systems for academic or commercial analysis. More specifically, examples described herein may be used in various processes and systems where it is desired to detect an event, property, quality, or characteristic that is indicative of a designated reaction. For example, examples described herein include light detection devices, biosensors, and their components, as well as bioassay systems that operate with biosensors. In some examples, the devices, biosensors and systems may include a flow cell and one or more light sensors that are coupled together (removably or fixedly) in a substantially unitary structure.

The devices, biosensors and bioassay systems may be configured to perform a plurality of designated reactions that may be detected individually or collectively. The devices, biosensors and bioassay systems may be configured to perform numerous cycles in which the plurality of designated reactions occurs in parallel. For example, the devices, biosensors and bioassay systems may be used to sequence a dense array of DNA features through iterative cycles of enzymatic manipulation and light or image detection/acquisition. As such, the devices, biosensors and bioassay systems (e.g., via one or more cartridges) may include one or more microfluidic channel that delivers reagents or other reaction components in a reaction solution to a reaction site of the devices, biosensors and bioassay systems. In some examples, the reaction solution may be substantially acidic, such as comprising a pH of less than or equal to about 5, or less than or equal to about 4, or less than or equal to about 3. In some other examples, the reaction solution may be substantially alkaline/basic, such as comprising a pH of greater than or equal to about 8, or greater than or equal to about 9, or greater than or equal to about 10. As used herein, the term "acidity" and grammatical variants thereof refer to a pH value of less than about 7, and the terms "basicity," "alkalinity" and grammatical variants thereof refer to a pH value of greater than about 7.

In some examples, the reaction sites are provided or spaced apart in a predetermined manner, such as in a uniform or repeating pattern. In some other examples, the reaction sites are randomly distributed. Each of the reaction sites may be associated with one or more light guides and one or more light sensors that detect light from the associated reaction site. In some examples, the reaction sites are located in reaction recesses or chambers, which may at least partially compartmentalize the designated reactions therein.

As used herein, a "designated reaction" includes a change in at least one of a chemical, electrical, physical, or optical property (or quality) of a chemical or biological substance of interest, such as an analyte-of-interest. In particular examples, a designated reaction is a positive binding event, such as incorporation of a fluorescently labeled biomolecule with an analyte-of-interest, for example. More generally, a designated reaction may be a chemical transformation, chemical change, or chemical interaction. A designated reaction may also be a change in electrical properties. In particular examples, a designated reaction includes the incorporation of a fluorescently-labeled molecule with an analyte. The analyte may be an oligonucleotide and the fluorescently-labeled molecule may be a nucleotide. A designated reaction may be detected when an excitation light is directed toward the oligonucleotide having the labeled nucleotide, and the fluorophore emits a detectable fluorescent signal. In alternative examples, the detected fluorescence is a result of chemiluminescence or bioluminescence. A designated reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore, or decrease fluorescence by co-locating a quencher and fluorophore.

As used herein, a "reaction solution," "reaction component" or "reactant" includes any substance that may be used to obtain at least one designated reaction. For example, potential reaction components include reagents, enzymes, samples, other biomolecules, and buffer solutions, for example. The reaction components may be delivered to a reaction site in a solution and/or immobilized at a reaction site. The reaction components may interact directly or indirectly with another substance, such as an analyte-of-interest immobilized at a reaction site. As noted above, the reaction solution may be substantially acidic (i.e., include a relatively high acidity) (e.g., comprising a pH of less than or equal to about 5, a pH less than or equal to about 4, or a pH less than or equal to about 3) or substantially alkaline/basic (i.e., include a relatively high alkalinity/basicity) (e.g., comprising a pH of greater than or equal to about 8, a pH of greater than or equal to about 9, or a pH of greater than or equal to about 10).

As used herein, the term "reaction site" is a localized region where at least one designated reaction may occur. A reaction site may include support surfaces of a reaction structure or substrate where a substance may be immobilized thereon. For example, a reaction site may include a surface of a reaction structure (which may be positioned in a channel of a flow cell) that has a reaction component thereon, such as a colony of nucleic acids thereon. In some such examples, the nucleic acids in the colony have the same sequence, being for example, clonal copies of a single stranded or double stranded template. However, in some examples a reaction site may contain only a single nucleic acid molecule, for example, in a single stranded or double stranded form.

A plurality of reaction sites may be randomly distributed along the reaction structure or arranged in a predetermined manner (e.g., side-by-side in a matrix, such as in microarrays). A reaction site can also include a reaction chamber or recess that at least partially defines a spatial region or volume configured to compartmentalize the designated reaction. As used herein, the term "reaction chamber" or "reaction recess" includes a defined spatial region of the support structure (which is often in fluid communication with a flow channel). A reaction recess may be at least partially separated from the surrounding environment other or spatial regions. For example, a plurality of reaction recesses may be separated from each other by shared walls, such as a detection surface. As a more specific example, the reaction recesses may be nanowells comprising an indent, pit, well, groove, cavity or depression defined by interior surfaces of a detection surface and have an opening or aperture (i.e., be open-sided) so that the nanowells can be in fluid communication with a flow channel.

In some examples, the reaction recesses of the reaction structure are sized and shaped relative to solids (including semi-solids) so that the solids may be inserted, fully or partially, therein. For example, the reaction recesses may be sized and shaped to accommodate a capture bead. The capture bead may have clonally amplified DNA or other substances thereon. Alternatively, the reaction recesses may be sized and shaped to receive an approximate number of beads or solid substrates. As another example, the reaction recesses may be filled with a porous gel or substance that is configured to control diffusion or filter fluids or solutions that may flow into the reaction recesses.

In some examples, light sensors (e.g., photodiodes) are associated with corresponding reaction sites. A light sensor that is associated with a reaction site is configured to detect light emissions from the associated reaction site via at least one light guide when a designated reaction has occurred at the associated reaction site. In some cases, a plurality of light sensors (e.g. several pixels of a light detection or camera device) may be associated with a single reaction site. In other cases, a single light sensor (e.g. a single pixel) may be associated with a single reaction site or with a group of reaction sites. The light sensor, the reaction site, and other features of the biosensor may be configured so that at least some of the light is directly detected by the light sensor without being reflected.

As used herein, a "biological or chemical substance" includes biomolecules, samples-of-interest, analytes-of-interest, and other chemical compound(s). A biological or chemical substance may be used to detect, identify, or analyze other chemical compound(s), or function as intermediaries to study or analyze other chemical compound(s). In particular examples, the biological or chemical substances include a biomolecule. As used herein, a "biomolecule" includes at least one of a biopolymer, nucleoside, nucleic acid, polynucleotide, oligonucleotide, protein, enzyme, polypeptide, antibody, antigen, ligand, receptor, polysaccharide, carbohydrate, polyphosphate, cell, tissue, organism, or fragment thereof or any other biologically active chemical compound(s) such as analogs or mimetics of the aforementioned species. In a further example, a biological or chemical substance or a biomolecule includes an enzyme or reagent used in a coupled reaction to detect the product of another reaction such as an enzyme or reagent, such as an enzyme or reagent used to detect pyrophosphate in a pyrosequencing reaction. Enzymes and reagents useful for pyrophosphate detection are described, for example, in U.S. Patent Publication No. 2005/0244870 A1, which is incorporated by reference in its entirety.

Biomolecules, samples, and biological or chemical substances may be naturally occurring or synthetic and may be suspended in a solution or mixture within a reaction recess or region. Biomolecules, samples, and biological or chemical substances may also be bound to a solid phase or gel material. Biomolecules, samples, and biological or chemical substances may also include a pharmaceutical composition. In some cases, biomolecules, samples, and biological or chemical substances of interest may be referred to as targets, probes, or analytes.

As used herein, a "biosensor" includes a device that includes a reaction structure with a plurality of reaction sites that is configured to detect designated reactions that occur at or proximate to the reaction sites. A biosensor may include a solid-state light detection or "imaging" device (e.g., CCD or CMOS light detection device) and, optionally, a flow cell mounted thereto. The flow cell may include at least one flow channel that is in fluid communication with the reaction sites. As one specific example, the biosensor is configured to fluidically and electrically couple to a bioassay system. The bioassay system may deliver a reaction solution to the reaction sites according to a predetermined protocol (e.g., sequencing-by-synthesis) and perform a plurality of imaging events. For example, the bioassay system may direct reaction solutions to flow along the reaction sites. At least one of the reaction solutions may include four types of nucleotides having the same or different fluorescent labels. The nucleotides may bind to the reaction sites, such as to corresponding oligonucleotides at the reaction sites. The bioassay system may then illuminate the reaction sites using an excitation light source (e.g., solid-state light sources, such as light-emitting diodes (LEDs)). The excitation light may have a predetermined wavelength or wavelengths, including a range of wavelengths. The fluorescent labels excited by the incident excitation light may provide emission signals (e.g., light of a wavelength or wavelengths that differ from the excitation light and, potentially, each other) that may be detected by the light sensors.

As used herein, the term "immobilized," when used with respect to a biomolecule or biological or chemical substance, includes substantially attaching the biomolecule or biological or chemical substance at a molecular level to a surface, such as to a detection surface of a light detection device or reaction structure. For example, a biomolecule or biological or chemical substance may be immobilized to a surface of the reaction structure using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to the surface may be based upon the properties of the surface, the liquid medium carrying the biomolecule or biological or chemical substance, and the properties of the biomolecules or biological or chemical substances themselves. In some cases, the surface may be functionalized (e.g., chemically or physically modified) to facilitate immobilizing the biomolecules (or biological or chemical substances) to the surface.

In some examples, nucleic acids can be immobilized to the reaction structure, such as to surfaces of reaction recesses thereof. In particular examples, the devices, biosensors, bioassay systems and methods described herein may include the use of natural nucleotides and also enzymes that are configured to interact with the natural nucleotides. Natural nucleotides include, for example, ribonucleotides or deoxyribonucleotides. Natural nucleotides can be in the mono-, di-, or tri-phosphate form and can have a base selected from adenine (A), Thymine (T), uracil (U), guanine (G) or cytosine (C). It will be understood, however, that non-natural nucleotides, modified nucleotides or analogs of the aforementioned nucleotides can be used.

As noted above, a biomolecule or biological or chemical substance may be immobilized at a reaction site in a reaction recess of a reaction structure. Such a biomolecule or biological substance may be physically held or immobilized within the reaction recesses through an interference fit, adhesion, covalent bond, or entrapment. Examples of items or solids that may be disposed within the reaction recesses include polymer beads, pellets, agarose gel, powders, quantum dots, or other solids that may be compressed and/or held within the reaction chamber. In certain implementations, the reaction recesses may be coated or filled with a hydrogel layer capable of covalently binding DNA oligonucleotides. In particular examples, a nucleic acid superstructure, such as a DNA ball, can be disposed in or at a reaction recess, for example, by attachment to an interior surface of the reaction recess or by residence in a liquid within the reaction recess. A DNA ball or other nucleic acid superstructure can be performed and then disposed in or at a reaction recess. Alternatively, a DNA ball can be synthesized in situ at a reaction recess. A substance that is immobilized in a reaction recess can be in a solid, liquid, or gaseous state.

As used herein, the term "analyte" is intended to mean a point or area in a pattern that can be distinguished from other points or areas according to relative location. An individual analyte can include one or more molecules of a particular type. For example, an analyte can include a single target nucleic acid molecule having a particular sequence or an analyte can include several nucleic acid molecules having the same sequence (and/or complementary sequence, thereof). Different molecules that are at different analytes of a pattern can be differentiated from each other according to the locations of the analytes in the pattern. Example analytes include without limitation, wells in a substrate, beads (or other particles) in or on a substrate, projections from a substrate, ridges on a substrate, pads of gel material on a substrate, or channels in a substrate.

Any of a variety of target analytes that are to be detected, characterized, or identified can be used in an apparatus, system or method set forth herein. Exemplary analytes include, but are not limited to, nucleic acids (e.g., DNA, RNA or analogs thereof), proteins, polysaccharides, cells, antibodies, epitopes, receptors, ligands, enzymes (e.g. kinases, phosphatases or polymerases), small molecule drug candidates, cells, viruses, organisms, or the like.

The terms "analyte", "nucleic acid", "nucleic acid molecule", and "polynucleotide" are used interchangeably herein. In various implementations, nucleic acids may be used as templates as provided herein (e.g., a nucleic acid template, or a nucleic acid complement that is complementary to a nucleic acid nucleic acid template) for particular types of nucleic acid analysis, including but not limited to nucleic acid amplification, nucleic acid expression analysis, and/or nucleic acid sequence determination or suitable combinations thereof. Nucleic acids in certain implementations include, for instance, linear polymers of deoxyribonucleotides in 3'-5' phosphodiester or other linkages, such as deoxyribonucleic acids (DNA), for example, single- and double-stranded DNA, genomic DNA, copy DNA or complementary DNA (cDNA), recombinant DNA, or any form of synthetic or modified DNA. In other implementations, nucleic acids include for instance, linear polymers of ribonucleotides in 3'-5' phosphodiester or other linkages such as ribonucleic acids (RNA), for example, single- and double-stranded RNA, messenger (mRNA), copy RNA or complementary RNA (cRNA), alternatively spliced mRNA, ribosomal RNA, small nucleolar RNA (snoRNA), microRNAs (miRNA), small interfering RNAs (sRNA), piwi RNAs (piRNA), or any form of synthetic or modified RNA. Nucleic acids used in the compositions and methods of the present invention may vary in length and may be intact or full-length molecules or fragments or smaller parts of larger nucleic acid molecules. In particular implementations, a nucleic acid may have one or more detectable labels, as described elsewhere herein.

The terms "analyte", "cluster", "nucleic acid cluster", "nucleic acid colony", and "DNA cluster" are used interchangeably and refer to a plurality of copies of a nucleic acid template and/or complements thereof attached to a solid support. Typically and in certain preferred implementations, the nucleic acid cluster comprises a plurality of copies of template nucleic acid and/or complements thereof, attached via their 5' termini to the solid support. The copies of nucleic acid strands making up the nucleic acid clusters may be in a single or double stranded form. Copies of a nucleic acid template that are present in a cluster can have nucleotides at corresponding positions that differ from each other, for example, due to presence of a label moiety. The corresponding positions can also contain analog structures having different chemical structure but similar Watson-Crick base-pairing properties, such as is the case for uracil and thymine.

Colonies of nucleic acids can also be referred to as "nucleic acid clusters". Nucleic acid colonies can optionally be created by cluster amplification or bridge amplification techniques as set forth in further detail elsewhere herein. Multiple repeats of a target sequence can be present in a single nucleic acid molecule, such as a concatamer created using a rolling circle amplification procedure.

The nucleic acid clusters of the invention can have different shapes, sizes and densities depending on the conditions used. For example, clusters can have a shape that is substantially round, multi-sided, donut-shaped or ring-shaped. The diameter of a nucleic acid cluster can be designed to be from about 0.2 µm to about 6 µm, about 0.3 µm to about 4 µm, about 0.4 µm to about 3 µm, about 0.5 µm to about 2 µm, about 0.75 µm to about 1.5 µm, or any intervening diameter. In a particular implementation, the diameter of a nucleic acid cluster is about 0.5 µm, about 1 µm, about 1.5 µm, about 2 µm, about 2.5 µm, about 3 µm, about 4 µm, about 5 µm, or about 6 µm. The diameter of a nucleic acid cluster may be influenced by a number of parameters, including, but not limited to the number of amplification cycles performed in producing the cluster, the length of the nucleic acid template or the density of primers attached to the surface upon which clusters are formed. The density of nucleic acid clusters can be designed to typically be in the range of $0.1/mm^2$, $1/mm^2$, $10/mm^2$, $100/mm^2$, $1,000/mm^2$, $10,000/mm^2$ to $100,000/mm^2$. The present invention further contemplates, in part, higher density nucleic acid clusters, for example, $100,000/mm^2$ to $1,000,000/mm^2$ and $1,000,000/mm^2$ to $10,000,000/mm^2$.

As used herein, an "analyte" is an area of interest within a specimen or field of view. When used in connection with microarray devices or other molecular analytical devices, an analyte refers to the area occupied by similar or identical molecules. For example, an analyte can be an amplified oligonucleotide or any other group of a polynucleotide or polypeptide with a same or similar sequence. In other implementations, an analyte can be any element or group of elements that occupy a physical area on a specimen. For example, an analyte could be a parcel of land, a body of water or the like. When an analyte is imaged, each analyte will have some area. Thus, in many implementations, an analyte is not merely one pixel.

The distances between analytes can be described in any number of ways. In some implementations, the distances between analytes can be described from the center of one analyte to the center of another analyte. In other implementations, the distances can be described from the edge of one analyte to the edge of another analyte, or between the outer-most identifiable points of each analyte. The edge of an analyte can be described as the theoretical or actual physical boundary on a chip, or some point inside the boundary of the analyte. In other implementations, the distances can be described in relation to a fixed point on the specimen or in the image of the specimen.

Generally several implementations will be described herein with respect to a method of analysis. It will be understood that systems are also provided for carrying out the methods in an automated or semi-automated way. Accordingly, this disclosure provides neural network based template generation and base calling systems, wherein the systems can include a processor; a storage device; and a program for image analysis, the program including instructions for carrying out one or more of the methods set forth herein. Accordingly, the methods set forth herein can be carried out on a computer, for example, having components set forth herein or otherwise known in the art.

The methods and systems set forth herein are useful for analyzing any of a variety of objects. Particularly useful objects are solid supports or solid-phase surfaces with attached analytes. The methods and systems set forth herein provide advantages when used with objects having a repeating pattern of analytes in an xy plane. An example is a microarray having an attached collection of cells, viruses, nucleic acids, proteins, antibodies, carbohydrates, small molecules (such as drug candidates), biologically active molecules or other analytes of interest.

An increasing number of applications have been developed for arrays with analytes having biological molecules such as nucleic acids and polypeptides. Such microarrays typically include deoxyribonucleic acid (DNA) or ribonucleic acid (RNA) probes. These are specific for nucleotide sequences present in humans and other organisms. In certain applications, for example, individual DNA or RNA probes can be attached at individual analytes of an array. A test sample, such as from a known person or organism, can be exposed to the array, such that target nucleic acids (e.g., gene fragments, mRNA, or amplicons thereof) hybridize to complementary probes at respective analytes in the array. The probes can be labeled in a target specific process (e.g., due to labels present on the target nucleic acids or due to enzymatic labeling of the probes or targets that are present in hybridized form at the analytes). The array can then be examined by scanning specific frequencies of light over the analytes to identify which target nucleic acids are present in the sample.

Biological microarrays may be used for genetic sequencing and similar applications. In general, genetic sequencing comprises determining the order of nucleotides in a length of target nucleic acid, such as a fragment of DNA or RNA. Relatively short sequences are typically sequenced at each analyte, and the resulting sequence information may be used in various bioinformatics methods to logically fit the sequence fragments together so as to reliably determine the sequence of much more extensive lengths of genetic material from which the fragments were derived. Automated, computer-based algorithms for characteristic fragments have been developed, and have been used more recently in genome mapping, identification of genes and their function, and so forth Microarrays are particularly useful for characterizing genomic content because a large number of variants are present and this supplants the alternative of performing many experiments on individual probes and targets. The microarray is an ideal format for performing such investigations in a practical manner.

Any of a variety of analyte arrays (also referred to as "microarrays") known in the art can be used in a method or system set forth herein. A typical array contains analytes, each having an individual probe or a population of probes. In the latter case, the population of probes at each analyte is typically homogenous having a single species of probe. For example, in the case of a nucleic acid array, each analyte can have multiple nucleic acid molecules each having a common sequence. However, in some implementations the populations at each analyte of an array can be heterogeneous. Similarly, protein arrays can have analytes with a single protein or a population of proteins typically, but not always, having the same amino acid sequence. The probes can be attached to the surface of an array for example, via covalent linkage of the probes to the surface or via non-covalent interaction(s) of the probes with the surface. In some implementations, probes, such as nucleic acid molecules, can be attached to a surface via a gel layer as described, for example, in U.S. patent application Ser. No. 13/784,368 and US Pat. App. Pub. No. 2011/0059865 A1, each of which is incorporated herein by reference.

Example arrays include, without limitation, a BeadChip Array available from Illumina, Inc. (San Diego, Calif.) or others such as those where probes are attached to beads that are present on a surface (e.g. beads in wells on a surface) such as those described in U.S. Pat. Nos. 6,266,459; 6,355, 431; 6,770,441; 6,859,570; or 7,622,294; or PCT Publication No. WO 00/63437, each of which is incorporated herein by reference. Further examples of commercially available microarrays that can be used include, for example, an Affymetrix® GeneChip® microarray or other microarray synthesized in accordance with techniques sometimes referred to as VLSIPS™ (Very Large Scale Immobilized Polymer Synthesis) technologies. A spotted microarray can also be used in a method or system according to some implementations of the present disclosure. An example spotted microarray is a CodeLink™ Array available from Amersham Biosciences. Another microarray that is useful is one that is manufactured using inkjet printing methods such as SurePrint™ Technology available from Agilent Technologies.

Other useful arrays include those that are used in nucleic acid sequencing applications. For example, arrays having amplicons of genomic fragments (often referred to as clusters) are particularly useful such as those described in Bentley et al., Nature 456:53-59 (2008), WO 04/018497; WO 91/06678; WO 07/123744; U.S. Pat. Nos. 7,329,492; 7,211,414; 7,315,019; 7,405,281, or 7,057,026; or US Pat. App. Pub. No. 2008/0108082 A1, each of which is incorporated herein by reference. Another type of array that is useful for nucleic acid sequencing is an array of particles produced from an emulsion PCR technique. Examples are described in Dressman et al., Proc. Natl. Acad. Sci. USA 100:8817-8822 (2003), WO 05/010145, US Pat. App. Pub. No. 2005/0130173 or US Pat. App. Pub. No. 2005/0064460, each of which is incorporated herein by reference in its entirety.

Arrays used for nucleic acid sequencing often have random spatial patterns of nucleic acid analytes. For example, HiSeq or MiSeq sequencing platforms available from Illumina Inc. (San Diego, Calif.) utilize flow cells upon which nucleic acid arrays are formed by random seeding followed by bridge amplification. However, patterned arrays can also be used for nucleic acid sequencing or other analytical applications. Example patterned arrays, methods for their manufacture and methods for their use are set forth in U.S. Ser. No. 13/787,396; U.S. Ser. No. 13/783,043; U.S. Ser. No. 13/784,368; US Pat. App. Pub. No. 2013/0116153 A1; and US Pat. App. Pub. No. 2012/0316086 A1, each of which is incorporated herein by reference. The analytes of such patterned arrays can be used to capture a single nucleic acid template molecule to seed subsequent formation of a homogenous colony, for example, via bridge amplification. Such patterned arrays are particularly useful for nucleic acid sequencing applications.

The size of an analyte on an array (or other object used in a method or system herein) can be selected to suit a particular application. For example, in some implementations, an analyte of an array can have a size that accommodates only a single nucleic acid molecule. A surface having a plurality of analytes in this size range is useful for constructing an array of molecules for detection at single molecule resolution. Analytes in this size range are also useful for use in arrays having analytes that each contain a colony of nucleic acid molecules. Thus, the analytes of an array can each have an area that is no larger than about 1 mm$^2$, no larger than about 500 µm$^2$, no larger than about 100 µm$^2$, no larger than about 10 µm$^2$, no larger than about 1 µm$^2$, no larger than about 500 nm$^2$, or no larger than about 100 nm$^2$, no larger than about 10 nm$^2$, no larger than about 5 nm$^2$, or no larger than about 1 nm$^2$. Alternatively or additionally, the analytes of an array will be no smaller than about 1 mm$^2$, no smaller than about 500 µm$^2$, no smaller than about 100 µm$^2$, no smaller than about 10 µm$^2$, no smaller than about 1 µm$^2$, no smaller than about 500 nm$^2$, no smaller than about 100 nm$^2$, no smaller than about 10 nm$^2$, no smaller than about 5 nm$^2$, or no smaller than about 1 nm$^2$. Indeed, an analyte can have a size that is in a range between an upper and lower limit selected from those exemplified above. Although several size ranges for analytes of a surface have been exemplified with respect to nucleic acids and on the scale of nucleic acids, it will be understood that analytes in these size ranges can be used for applications that do not include nucleic acids. It will be further understood that the size of the analytes need not necessarily be confined to a scale used for nucleic acid applications.

For implementations that include an object having a plurality of analytes, such as an array of analytes, the analytes can be discrete, being separated with spaces between each other. An array useful in the invention can have analytes that are separated by edge to edge distance of at most 100 µm, 50 µm, 10 µm, 5 µm, 1 µm, 0.5 µm, or less. Alternatively or additionally, an array can have analytes that are separated by an edge to edge distance of at least 0.5 µm, 1 µm, 5 µm, 10 µm, 50 µm, 100 µm, or more. These ranges can apply to the average edge to edge spacing for analytes as well as to the minimum or maximum spacing.

In some implementations the analytes of an array need not be discrete and instead neighboring analytes can abut each other. Whether or not the analytes are discrete, the size of the analytes and/or pitch of the analytes can vary such that arrays can have a desired density. For example, the average analyte pitch in a regular pattern can be at most 100 µm, 50 µm, 10 µm, 5 µm, 1 µm, 0.5 µm, or less. Alternatively or additionally, the average analyte pitch in a regular pattern can be at least 0.5 µm, 1 µm, 5 µm, 10 µm, 50 µm, 100 µm, or more. These ranges can apply to the maximum or minimum pitch for a regular pattern as well. For example, the maximum analyte pitch for a regular pattern can be at most 100 µm, 50 µm, 10 µm, 5 µm, 1 µm, 0.5 µm, or less; and/or the minimum analyte pitch in a regular pattern can be at least 0.5 µm, 1 µm, 5 µm, 10 µm, 50 µm, 100 µm, or more.

The density of analytes in an array can also be understood in terms of the number of analytes present per unit area. For example, the average density of analytes for an array can be at least about $1 \times 10^3$ analytes/mm$^2$, $1 \times 10^4$ analytes/mm$^2$, $1 \times 10^5$ analytes/mm$^2$, $1 \times 10^6$ analytes/mm$^2$, $1 \times 10^7$ analytes/mm$^2$, $1 \times 10^8$ analytes/mm$^2$, or $1 \times 10^9$ analytes/mm$^2$, or higher. Alternatively or additionally the average density of analytes for an array can be at most about $1 \times 10^9$ analytes/mm$^2$, $1 \times 10^8$ analytes/mm$^2$, $1 \times 10^7$ analytes/mm$^2$, $1 \times 10^6$ analytes/mm$^2$, $1 \times 10^5$ analytes/mm$^2$, $1 \times 10^4$ analytes/mm$^2$, or $1 \times 10^3$ analytes/mm$^2$, or less.

The above ranges can apply to all or part of a regular pattern including, for example, all or part of an array of analytes.

The analytes in a pattern can have any of a variety of shapes. For example, when observed in a two dimensional plane, such as on the surface of an array, the analytes can appear rounded, circular, oval, rectangular, square, symmetric, asymmetric, triangular, polygonal, or the like. The analytes can be arranged in a regular repeating pattern including, for example, a hexagonal or rectilinear pattern. A pattern can be selected to achieve a desired level of packing. For example, round analytes are optimally packed in a hexagonal arrangement. Of course other packing arrangements can also be used for round analytes and vice versa.

A pattern can be characterized in terms of the number of analytes that are present in a subset that forms the smallest geometric unit of the pattern. The subset can include, for example, at least about 2, 3, 4, 5, 6, 10 or more analytes. Depending upon the size and density of the analytes the geometric unit can occupy an area of less than 1 $mm^2$, 500 $\mu m^2$, 100 $\mu m^2$, 50 $\mu m^2$, 10 $\mu m^2$, 1 $\mu m^2$, 500 $nm^2$, 100 $nm^2$, 50 $nm^2$, 10 $nm^2$, or less. Alternatively or additionally, the geometric unit can occupy an area of greater than 10 $nm^2$, 50 $nm^2$, 100 $nm^2$, 500 $nm^2$, 1 $\mu m^2$, 10 $\mu m^2$, 50 $\mu m^2$, 100 $\mu m^2$, 500 $\mu m^2$, 1 $mm^2$, or more. Characteristics of the analytes in a geometric unit, such as shape, size, pitch and the like, can be selected from those set forth herein more generally with regard to analytes in an array or pattern.

An array having a regular pattern of analytes can be ordered with respect to the relative locations of the analytes but random with respect to one or more other characteristic of each analyte. For example, in the case of a nucleic acid array, the nuclei acid analytes can be ordered with respect to their relative locations but random with respect to one's knowledge of the sequence for the nucleic acid species present at any particular analyte. As a more specific example, nucleic acid arrays formed by seeding a repeating pattern of analytes with template nucleic acids and amplifying the template at each analyte to form copies of the template at the analyte (e.g., via cluster amplification or bridge amplification) will have a regular pattern of nucleic acid analytes but will be random with regard to the distribution of sequences of the nucleic acids across the array. Thus, detection of the presence of nucleic acid material generally on the array can yield a repeating pattern of analytes, whereas sequence specific detection can yield non-repeating distribution of signals across the array.

It will be understood that the description herein of patterns, order, randomness and the like pertain not only to analytes on objects, such as analytes on arrays, but also to analytes in images. As such, patterns, order, randomness and the like can be present in any of a variety of formats that are used to store, manipulate or communicate image data including, but not limited to, a computer readable medium or computer component such as a graphical user interface or other output device.

As used herein, the term "image" is intended to mean a representation of all or part of an object. The representation can be an optically detected reproduction. For example, an image can be obtained from fluorescent, luminescent, scatter, or absorption signals. The part of the object that is present in an image can be the surface or other xy plane of the object. Typically, an image is a 2 dimensional representation, but in some cases information in the image can be derived from 3 or more dimensions. An image need not include optically detected signals. Non-optical signals can be present instead. An image can be provided in a computer readable format or medium such as one or more of those set forth elsewhere herein.

As used herein, "image" refers to a reproduction or representation of at least a portion of a specimen or other object. In some implementations, the reproduction is an optical reproduction, for example, produced by a camera or other optical detector. The reproduction can be a non-optical reproduction, for example, a representation of electrical signals obtained from an array of nanopore analytes or a representation of electrical signals obtained from an ion-sensitive CMOS detector. In particular implementations non-optical reproductions can be excluded from a method or apparatus set forth herein. An image can have a resolution capable of distinguishing analytes of a specimen that are present at any of a variety of spacings including, for example, those that are separated by less than 100 μm, 50 μm, 10 μm, 5 μm, 1 μm or 0.5 μm.

As used herein, "acquiring", "acquisition" and like terms refer to any part of the process of obtaining an image file. In some implementations, data acquisition can include generating an image of a specimen, looking for a signal in a specimen, instructing a detection device to look for or generate an image of a signal, giving instructions for further analysis or transformation of an image file, and any number of transformations or manipulations of an image file.

As used herein, the term "template" refers to a representation of the location or relation between signals or analytes. Thus, in some implementations, a template is a physical grid with a representation of signals corresponding to analytes in a specimen. In some implementations, a template can be a chart, table, text file or other computer file indicative of locations corresponding to analytes. In implementations presented herein, a template is generated in order to track the location of analytes of a specimen across a set of images of the specimen captured at different reference points. For example, a template could be a set of x,y coordinates or a set of values that describe the direction and/or distance of one analyte with respect to another analyte.

As used herein, the term "specimen" can refer to an object or area of an object of which an image is captured. For example, in implementations where images are taken of the surface of the earth, a parcel of land can be a specimen. In other implementations where the analysis of biological molecules is performed in a flow cell, the flow cell may be divided into any number of subdivisions, each of which may be a specimen. For example, a flow cell may be divided into various flow channels or lanes, and each lane can be further divided into 2, 3, 4, 5, 6, 7, 8, 9, 10, 20, 30, 40, 50, 60 70, 80, 90, 100, 110, 120, 140, 160, 180, 200, 400, 600, 800, 1000 or more separate regions that are imaged. One example of a flow cell has 8 lanes, with each lane divided into 120 specimens or tiles. In another implementation, a specimen may be made up of a plurality of tiles or even an entire flow cell. Thus, the image of each specimen can represent a region of a larger surface that is imaged.

It will be appreciated that references to ranges and sequential number lists described herein include not only the enumerated number but all real numbers between the enumerated numbers.

As used herein, a "reference point" refers to any temporal or physical distinction between images. In a preferred implementation, a reference point is a time point. In a more preferred implementation, a reference point is a time point or cycle during a sequencing reaction. However, the term "reference point" can include other aspects that distinguish or separate images, such as angle, rotational, temporal, or other aspects that can distinguish or separate images.

As used herein, a "subset of images" refers to a group of images within a set. For example, a subset may contain 1, 2, 3, 4, 6, 8, 10, 12, 14, 16, 18, 20, 30, 40, 50, 60 or any number of images selected from a set of images. In particular implementations, a subset may contain no more than 1, 2, 3, 4, 6, 8, 10, 12, 14, 16, 18, 20, 30, 40, 50, 60 or any number of images selected from a set of images. In a preferred implementation, images are obtained from one or more sequencing cycles with four images correlated to each cycle. Thus, for example, a subset could be a group of 16 images obtained through four cycles.

A base refers to a nucleotide base or nucleotide, A (adenine), C (cytosine), T (thymine), or G (guanine). This application uses "base(s)" and "nucleotide(s)" interchangeably.

The term "chromosome" refers to the heredity-bearing gene carrier of a living cell, which is derived from chromatin strands comprising DNA and protein components (especially histones). The conventional internationally recognized individual human genome chromosome numbering system is employed herein.

The term "site" refers to a unique position (e.g., chromosome ID, chromosome position and orientation) on a reference genome. In some implementations, a site may be a residue, a sequence tag, or a segment's position on a sequence. The term "locus" may be used to refer to the specific location of a nucleic acid sequence or polymorphism on a reference chromosome.

The term "sample" herein refers to a sample, typically derived from a biological fluid, cell, tissue, organ, or organism containing a nucleic acid or a mixture of nucleic acids containing at least one nucleic acid sequence that is to be sequenced and/or phased. Such samples include, but are not limited to sputum/oral fluid, amniotic fluid, blood, a blood fraction, fine needle biopsy samples (e.g., surgical biopsy, fine needle biopsy, etc.), urine, peritoneal fluid, pleural fluid, tissue explant, organ culture and any other tissue or cell preparation, or fraction or derivative thereof or isolated therefrom. Although the sample is often taken from a human subject (e.g., patient), samples can be taken from any organism having chromosomes, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc.

The term "sequence" includes or represents a strand of nucleotides coupled to each other. The nucleotides may be based on DNA or RNA. It should be understood that one sequence may include multiple sub-sequences. For example, a single sequence (e.g., of a PCR amplicon) may have 350 nucleotides. The sample read may include multiple sub-sequences within these 350 nucleotides. For instance, the sample read may include first and second flanking subsequences having, for example, 20-50 nucleotides. The first and second flanking sub-sequences may be located on either side of a repetitive segment having a corresponding sub-sequence (e.g., 40-100 nucleotides). Each of the flanking sub-sequences may include (or include portions of) a primer sub-sequence (e.g., 10-30 nucleotides). For ease of reading, the term "sub-sequence" will be referred to as "sequence," but it is understood that two sequences are not necessarily separate from each other on a common strand. To differentiate the various sequences described herein, the sequences may be given different labels (e.g., target sequence, primer sequence, flanking sequence, reference sequence, and the like). Other terms, such as "allele," may be given different labels to differentiate between like objects. The application uses "read(s)" and "sequence read(s)" interchangeably.

The term "paired-end sequencing" refers to sequencing methods that sequence both ends of a target fragment. Paired-end sequencing may facilitate detection of genomic rearrangements and repetitive segments, as well as gene fusions and novel transcripts. Methodology for paired-end sequencing are described in PCT publication WO07010252, PCT application Serial No. PCTGB2007/003798 and US patent application publication US 2009/0088327, each of which is incorporated by reference herein. In one example, a series of operations may be performed as follows; (a) generate clusters of nucleic acids; (b) linearize the nucleic acids; (c) hybridize a first sequencing primer and catty out repeated cycles of extension, scanning and deblocking, as set forth above; (d) "invert" the target nucleic acids on the flow cell surface by synthesizing a complimentary copy; (e) linearize the resynthesized strand; and (f) hybridize a second sequencing primer and catty out repeated cycles of extension, scanning and deblocking, as set forth above. The inversion operation can be carried out be delivering reagents as set forth above for a single cycle of bridge amplification.

The term "reference genome" or "reference sequence" refers to any particular known genome sequence, whether partial or complete, of any organism which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences. A genome includes both the genes and the noncoding sequences of the DNA. The reference sequence may be larger than the reads that are aligned to it. For example, it may be at least about 100 times larger, or at least about 1000 times larger, or at least about 10,000 times larger, or at least about 105 times larger, or at least about 106 times larger, or at least about 107 times larger. In one example, the reference genome sequence is that of a full length human genome. In another example, the reference genome sequence is limited to a specific human chromosome such as chromosome 13. In some implementations, a reference chromosome is a chromosome sequence from human genome version hg19. Such sequences may be referred to as chromosome reference sequences, although the term reference genome is intended to cover such sequences. Other examples of reference sequences include genomes of other species, as well as chromosomes, sub-chromosomal regions (such as strands), etc., of any species. In various implementations, the reference genome is a consensus sequence or other combination derived from multiple individuals. However, in certain applications, the reference sequence may be taken from a particular individual. In other implementations, the "genome" also covers so-called "graph genomes", which use a particular storage format and representation of the genome sequence. In one implementation, graph genomes store data in a linear file. In another implementation, the graph genomes refer to a representation where alternative sequences (e.g., different copies of a chromosome with small differences) are stored as different paths in a graph. Additional information regarding graph genome implementations can be found in https://www.biorxiv.org/content/biorxiv/early/2018/03/20/194530.full.pdf, the content of which is hereby incorporated herein by reference in its entirety.

The term "read" refer to a collection of sequence data that describes a fragment of a nucleotide sample or reference. The term "read" may refer to a sample read and/or a reference read. Typically, though not necessarily, a read represents a short sequence of contiguous base pairs in the sample or reference. The read may be represented symbolically by the base pair sequence (in ATCG) of the sample or reference fragment. It may be stored in a memory device and processed as appropriate to determine whether the read matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

Next-generation sequencing methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). Depending on the sequencing methods, the length of each read may vary from about 30 bp to more than 10,000 bp. For example, the DNA sequencing method using SOLiD sequencer generates nucleic acid reads of about 50 bp. For another example, Ion Torrent Sequencing generates nucleic acid reads of up to 400 bp and 454 pyrosequencing generates nucleic acid reads of about 700 bp. For yet another example, single-molecule real-time sequencing methods may generate reads of 10,000 bp to 15,000 bp. Therefore, in certain implementations, the nucleic acid sequence reads have a length of 30-100 bp, 50-200 bp, or 50-400 bp.

The terms "sample read", "sample sequence" or "sample fragment" refer to sequence data for a genomic sequence of interest from a sample. For example, the sample read comprises sequence data from a PCR amplicon having a forward and reverse primer sequence. The sequence data can be obtained from any select sequence methodology. The sample read can be, for example, from a sequencing-by-synthesis (SBS) reaction, a sequencing-by-ligation reaction, or any other suitable sequencing methodology for which it is desired to determine the length and/or identity of a repetitive element. The sample read can be a consensus (e.g., averaged or weighted) sequence derived from multiple sample reads. In certain implementations, providing a reference sequence comprises identifying a locus-of-interest based upon the primer sequence of the PCR amplicon.

The term "raw fragment" refers to sequence data for a portion of a genomic sequence of interest that at least partially overlaps a designated position or secondary position of interest within a sample read or sample fragment. Non-limiting examples of raw fragments include a duplex stitched fragment, a simplex stitched fragment, a duplex un-stitched fragment and a simplex un-stitched fragment. The term "raw" is used to indicate that the raw fragment includes sequence data having some relation to the sequence data in a sample read, regardless of whether the raw fragment exhibits a supporting variant that corresponds to and authenticates or confirms a potential variant in a sample read. The term "raw fragment" does not indicate that the fragment necessarily includes a supporting variant that validates a variant call in a sample read. For example, when a sample read is determined by a variant call application to exhibit a first variant, the variant call application may determine that one or more raw fragments lack a corresponding type of "supporting" variant that may otherwise be expected to occur given the variant in the sample read.

The terms "mapping", "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain implementations, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

The term "indel" refers to the insertion and/or the deletion of bases in the DNA of an organism. A micro-indel represents an indel that results in a net change of 1 to 50 nucleotides. In coding regions of the genome, unless the length of an indel is a multiple of 3, it will produce a frameshift mutation. Indels can be contrasted with point mutations. An indel inserts and deletes nucleotides from a sequence, while a point mutation is a form of substitution that replaces one of the nucleotides without changing the overall number in the DNA. Indels can also be contrasted with a Tandem Base Mutation (TBM), which may be defined as substitution at adjacent nucleotides (primarily substitutions at two adjacent nucleotides, but substitutions at three adjacent nucleotides have been observed.

The term "variant" refers to a nucleic acid sequence that is different from a nucleic acid reference. Typical nucleic acid sequence variant includes without limitation single nucleotide polymorphism (SNP), short deletion and insertion polymorphisms (Indel), copy number variation (CNV), microsatellite markers or short tandem repeats and structural variation. Somatic variant calling is the effort to identify variants present at low frequency in the DNA sample. Somatic variant calling is of interest in the context of cancer treatment. Cancer is caused by an accumulation of mutations in DNA. A DNA sample from a tumor is generally heterogeneous, including some normal cells, some cells at an early stage of cancer progression (with fewer mutations), and some late-stage cells (with more mutations). Because of this heterogeneity, when sequencing a tumor (e.g., from an FFPE sample), somatic mutations will often appear at a low frequency. For example, a SNV might be seen in only 10% of the reads covering a given base. A variant that is to be classified as somatic or germline by the variant classifier is also referred to herein as the "variant under test".

The term "noise" refers to a mistaken variant call resulting from one or more errors in the sequencing process and/or in the variant call application.

The term "variant frequency" represents the relative frequency of an allele (variant of a gene) at a particular locus in a population, expressed as a fraction or percentage. For example, the fraction or percentage may be the fraction of all chromosomes in the population that carry that allele. By way of example, sample variant frequency represents the relative frequency of an allele/variant at a particular locus/position along a genomic sequence of interest over a "population" corresponding to the number of reads and/or samples obtained for the genomic sequence of interest from an individual. As another example, a baseline variant frequency represents the relative frequency of an allele/variant at a particular locus/position along one or more baseline genomic sequences where the "population" corresponding to the number of reads and/or samples obtained for the one or more baseline genomic sequences from a population of normal individuals.

The term "variant allele frequency (VAF)" refers to the percentage of sequenced reads observed matching the variant divided by the overall coverage at the target position. VAF is a measure of the proportion of sequenced reads carrying the variant.

The terms "position", "designated position", and "locus" refer to a location or coordinate of one or more nucleotides within a sequence of nucleotides. The terms "position", "designated position", and "locus" also refer to a location or coordinate of one or more base pairs in a sequence of nucleotides.

The term "haplotype" refers to a combination of alleles at adjacent sites on a chromosome that are inherited together. A haplotype may be one locus, several loci, or an entire chromosome depending on the number of recombination events that have occurred between a given set of loci, if any occurred.

The term "threshold" herein refers to a numeric or non-numeric value that is used as a cutoff to characterize a sample, a nucleic acid, or portion thereof (e.g., a read). A threshold may be varied based upon empirical analysis. The threshold may be compared to a measured or calculated value to determine whether the source giving rise to such value suggests should be classified in a particular manner. Threshold values can be identified empirically or analytically. The choice of a threshold is dependent on the level of confidence that the user wishes to have to make the classification. The threshold may be chosen for a particular purpose (e.g., to balance sensitivity and selectivity). As used herein, the term "threshold" indicates a point at which a course of analysis may be changed and/or a point at which an action may be triggered. A threshold is not required to be a predetermined number. Instead, the threshold may be, for instance, a function that is based on a plurality of factors. The threshold may be adaptive to the circumstances. Moreover, a threshold may indicate an upper limit, a lower limit, or a range between limits.

In some implementations, a metric or score that is based on sequencing data may be compared to the threshold. As used herein, the terms "metric" or "score" may include values or results that were determined from the sequencing data or may include functions that are based on the values or results that were determined from the sequencing data. Like a threshold, the metric or score may be adaptive to the circumstances. For instance, the metric or score may be a normalized value. As an example of a score or metric, one or more implementations may use count scores when analyzing the data. A count score may be based on number of sample reads. The sample reads may have undergone one or more filtering stages such that the sample reads have at least one common characteristic or quality. For example, each of the sample reads that are used to determine a count score may have been aligned with a reference sequence or may be assigned as a potential allele. The number of sample reads having a common characteristic may be counted to determine a read count. Count scores may be based on the read count. In some implementations, the count score may be a value that is equal to the read count. In other implementations, the count score may be based on the read count and other information. For example, a count score may be based on the read count for a particular allele of a genetic locus and a total number of reads for the genetic locus. In some implementations, the count score may be based on the read count and previously-obtained data for the genetic locus. In some implementations, the count scores may be normalized scores between predetermined values. The count score may also be a function of read counts from other loci of a sample or a function of read counts from other samples that were concurrently run with the sample-of-interest. For instance, the count score may be a function of the read count of a particular allele and the read counts of other loci in the sample and/or the read counts from other samples. As one example, the read counts from other loci and/or the read counts from other samples may be used to normalize the count score for the particular allele.

The terms "coverage" or "fragment coverage" refer to a count or other measure of a number of sample reads for the same fragment of a sequence. A read count may represent a count of the number of reads that cover a corresponding fragment. Alternatively, the coverage may be determined by multiplying the read count by a designated factor that is based on historical knowledge, knowledge of the sample, knowledge of the locus, etc.

The term "read depth" (conventionally a number followed by "x") refers to the number of sequenced reads with overlapping alignment at the target position. This is often expressed as an average or percentage exceeding a cutoff over a set of intervals (such as exons, genes, or panels). For example, a clinical report might say that a panel average coverage is 1,105× with 98% of targeted bases covered >100×.

The terms "base call quality score" or "Q score" refer to a PHRED-scaled probability ranging from 0-50 inversely proportional to the probability that a single sequenced base is correct. For example, a T base call with Q of 20 is considered likely correct with a probability of 99.99%. Any base call with Q<20 should be considered low quality, and any variant identified where a substantial proportion of sequenced reads supporting the variant are of low quality should be considered potentially false positive.

The terms "variant reads" or "variant read number" refer to the number of sequenced reads supporting the presence of the variant.

Regarding "strandedness" (or DNA strandedness), the genetic message in DNA can be represented as a string of the letters A, G, C, and T. For example, 5'-AGGACA-3'. Often, the sequence is written in the direction shown here, i.e., with the 5' end to the left and the 3' end to the right. DNA may sometimes occur as single-stranded molecule (as in certain viruses), but normally we find DNA as a double-stranded unit. It has a double helical structure with two antiparallel strands. In this case, the word "antiparallel" means that the two strands run in parallel, but have opposite polarity. The double-stranded DNA is held together by pairing between bases and the pairing is always such that adenine (A) pairs with thymine (T) and cytosine (C) pairs with guanine (G). This pairing is referred to as complementarity, and one strand of DNA is said to be the complement of the other. The double-stranded DNA may thus be represented as two strings, like this: 5'-AGGACA-3' and 3'-TCCTGT-5'. Note that the two strands have opposite polarity. Accordingly, the strandedness of the two DNA strands can be referred to as the reference strand and its complement, forward and reverse strands, top and bottom strands, sense and antisense strands, or Watson and Crick strands.

The reads alignment (also called reads mapping) is the process of figuring out where in the genome a sequence is from. Once the alignment is performed, the "mapping quality" or the "mapping quality score (MAPQ)" of a given read quantifies the probability that its position on the genome is correct. The mapping quality is encoded in the phred scale where P is the probability that the alignment is not correct. The probability is calculated as: $P=10^{(-MAQ/10)}$, where MAPQ is the mapping quality. For example, a mapping quality of 40=10 to the power of −4, meaning that there is a 0.01% chance that the read was aligned incorrectly. The mapping quality is therefore associated with several alignment factors, such as the base quality of the read, the complexity of the reference genome, and the paired-end information. Regarding the first, if the base quality of the read is low, it means that the observed sequence might be wrong and thus its alignment is wrong. Regarding the second, the mappability refers to the complexity of the genome. Repeated regions are more difficult to map and reads falling in these regions usually get low mapping quality. In this context, the MAPQ reflects the fact that the reads are not uniquely aligned and that their real origin cannot be determined. Regarding the third, in case of paired-end sequencing data, concordant pairs are more likely to be well aligned. The higher is the mapping quality, the better is the alignment. A read aligned with a good mapping quality usually means that the read sequence was good and was aligned with few mismatches in a high mappability region. The MAPQ value can be used as a quality control of the alignment results. The proportion of reads aligned with an MAPQ higher than 20 is usually for downstream analysis.

As used herein, a "signal" refers to a detectable event such as an emission, preferably light emission, for example, in an image. Thus, in preferred implementations, a signal can represent any detectable light emission that is captured in an image (i.e., a "spot"). Thus, as used herein, "signal" can refer to both an actual emission from an analyte of the specimen, and can refer to a spurious emission that does not correlate to an actual analyte. Thus, a signal could arise from noise and could be later discarded as not representative of an actual analyte of a specimen.

As used herein, the term "clump" refers to a group of signals. In particular implementations, the signals are derived from different analytes. In a preferred implementation, a signal clump is a group of signals that cluster together. In a more preferred implementation, a signal clump represents a physical region covered by one amplified oligonucleotide. Each signal clump should be ideally observed as several signals (one per template cycle, and possibly more due to cross-talk). Accordingly, duplicate signals are detected where two (or more) signals are included in a template from the same clump of signals.

As used herein, terms such as "minimum," "maximum," "minimize," "maximize" and grammatical variants thereof can include values that are not the absolute maxima or minima. In some implementations, the values include near maximum and near minimum values. In other implementations, the values can include local maximum and/or local minimum values. In some implementations, the values include only absolute maximum or minimum values.

As used herein, "cross-talk" refers to the detection of signals in one image that are also detected in a separate image. In a preferred implementation, cross-talk can occur when an emitted signal is detected in two separate detection channels. For example, where an emitted signal occurs in one color, the emission spectrum of that signal may overlap with another emitted signal in another color. In a preferred implementation, fluorescent molecules used to indicate the presence of nucleotide bases A, C, G and T are detected in separate channels. However, because the emission spectra of A and C overlap, some of the C color signal may be detected during detection using the A color channel. Accordingly, cross-talk between the A and C signals allows signals from one color image to appear in the other color image. In some implementations, G and T cross-talk. In some implementations, the amount of cross-talk between channels is asymmetric. It will be appreciated that the amount of cross-talk between channels can be controlled by, among other things, the selection of signal molecules having an appropriate emission spectrum as well as selection of the size and wavelength range of the detection channel.

As used herein, "register", "registering", "registration" and like terms refer to any process to correlate signals in an image or data set from a first time point or perspective with signals in an image or data set from another time point or perspective. For example, registration can be used to align signals from a set of images to form a template. In another example, registration can be used to align signals from other images to a template. One signal may be directly or indirectly registered to another signal. For example, a signal from image "S" may be registered to image "G" directly. As another example, a signal from image "N" may be directly registered to image "G", or alternatively, the signal from image "N" may be registered to image "S", which has previously been registered to image "G". Thus, the signal from image "N" is indirectly registered to image "G".

As used herein, the term "fiducial" is intended to mean a distinguishable point of reference in or on an object. The point of reference can be, for example, a mark, second object, shape, edge, area, irregularity, channel, pit, post or the like. The point of reference can be present in an image of the object or in another data set derived from detecting the object. The point of reference can be specified by an x and/or y coordinate in a plane of the object. Alternatively or additionally, the point of reference can be specified by a z coordinate that is orthogonal to the xy plane, for example, being defined by the relative locations of the object and a detector. One or more coordinates for a point of reference can be specified relative to one or more other analytes of an object or of an image or other data set derived from the object.

As used herein, the term "optical signal" is intended to include, for example, fluorescent, luminescent, scatter, or absorption signals. Optical signals can be detected in the ultraviolet (UV) range (about 200 to 390 nm), visible (VIS) range (about 391 to 770 nm), infrared (IR) range (about 0.771 to 25 microns), or other range of the electromagnetic spectrum. Optical signals can be detected in a way that excludes all or part of one or more of these ranges.

As used herein, the term "signal level" is intended to mean an amount or quantity of detected energy or coded information that has a desired or predefined characteristic. For example, an optical signal can be quantified by one or more of intensity, wavelength, energy, frequency, power, luminance or the like. Other signals can be quantified according to characteristics such as voltage, current, electric field strength, magnetic field strength, frequency, power, temperature, etc. Absence of signal is understood to be a signal level of zero or a signal level that is not meaningfully distinguished from noise.

As used herein, the term "simulate" is intended to mean creating a representation or model of a physical thing or action that predicts characteristics of the thing or action. The representation or model can in many cases be distinguishable from the thing or action. For example, the representation or model can be distinguishable from a thing with respect to one or more characteristic such as color, intensity of signals detected from all or part of the thing, size, or shape. In particular implementations, the representation or model can be idealized, exaggerated, muted, or incomplete when compared to the thing or action. Thus, in some implementations, a representation of model can be distinguishable from the thing or action that it represents, for example, with respect to at least one of the characteristics set forth above. The representation or model can be provided in a computer readable format or medium such as one or more of those set forth elsewhere herein.

As used herein, the term "specific signal" is intended to mean detected energy or coded information that is selectively observed over other energy or information such as background energy or information. For example, a specific signal can be an optical signal detected at a particular intensity, wavelength or color; an electrical signal detected at a particular frequency, power or field strength; or other signals known in the art pertaining to spectroscopy and analytical detection.

As used herein, the term "swath" is intended to mean a rectangular portion of an object. The swath can be an elongated strip that is scanned by relative movement between the object and a detector in a direction that is parallel to the longest dimension of the strip. Generally, the width of the rectangular portion or strip will be constant along its full length. Multiple swaths of an object can be parallel to each other. Multiple swaths of an object can be adjacent to each other, overlapping with each other, abutting each other, or separated from each other by an interstitial area.

As used herein, the term "variance" is intended to mean a difference between that which is expected and that which is observed or a difference between two or more observations. For example, variance can be the discrepancy between an expected value and a measured value. Variance can be represented using statistical functions such as standard deviation, the square of standard deviation, coefficient of variation or the like.

As used herein, the term "xy coordinates" is intended to mean information that specifies location, size, shape, and/or orientation in an xy plane. The information can be, for example, numerical coordinates in a Cartesian system. The coordinates can be provided relative to one or both of the x and y axes or can be provided relative to another location in the xy plane. For example, coordinates of a analyte of an object can specify the location of the analyte relative to location of a fiducial or other analyte of the object.

As used herein, the term "xy plane" is intended to mean a 2 dimensional area defined by straight line axes x and y. When used in reference to a detector and an object observed by the detector, the area can be further specified as being orthogonal to the direction of observation between the detector and object being detected.

As used herein, the term "z coordinate" is intended to mean information that specifies the location of a point, line or area along an axes that is orthogonal to an xy plane. In particular implementations, the z axis is orthogonal to an area of an object that is observed by a detector. For example, the direction of focus for an optical system may be specified along the z axis.

In some implementations, acquired signal data is transformed using an affine transformation. In some such implementations, template generation makes use of the fact that the affine transforms between color channels are consistent between runs. Because of this consistency, a set of default offsets can be used when determining the coordinates of the analytes in a specimen. For example, a default offsets file can contain the relative transformation (shift, scale, skew) for the different channels relative to one channel, such as the A channel. In other implementations, however, the offsets between color channels drift during a run and/or between runs, making offset-driven template generation difficult. In such implementations, the methods and systems provided herein can utilize offset-less template generation, which is described further below.

In some aspects of the above implementations, the system can comprise a flow cell. In some aspects, the flow cell comprises lanes, or other configurations, of tiles, wherein at least some of the tiles comprise one or more arrays of analytes. In some aspects, the analytes comprise a plurality of molecules such as nucleic acids. In certain aspects, the flow cell is configured to deliver a labeled nucleotide base to an array of nucleic acids, thereby extending a primer hybridized to a nucleic acid within a analyte so as to produce a signal corresponding to a analyte comprising the nucleic acid. In preferred implementations, the nucleic acids within a analyte are identical or substantially identical to each other.

In some of the systems for image analysis described herein, each image in the set of images includes color signals, wherein a different color corresponds to a different nucleotide base. In some aspects, each image of the set of images comprises signals having a single color selected from at least four different colors. In some aspects, each image in the set of images comprises signals having a single color selected from four different colors. In some of the systems described herein, nucleic acids can be sequenced by providing four different labeled nucleotide bases to the array of molecules so as to produce four different images, each image comprising signals having a single color, wherein the signal color is different for each of the four different images, thereby producing a cycle of four color images that corresponds to the four possible nucleotides present at a particular position in the nucleic acid. In certain aspects, the system comprises a flow cell that is configured to deliver additional labeled nucleotide bases to the array of molecules, thereby producing a plurality of cycles of color images.

In preferred implementations, the methods provided herein can include determining whether a processor is actively acquiring data or whether the processor is in a low activity state. Acquiring and storing large numbers of high-quality images typically requires massive amounts of storage capacity. Additionally, once acquired and stored, the analysis of image data can become resource intensive and can interfere with processing capacity of other functions, such as ongoing acquisition and storage of additional image data. Accordingly, as used herein, the term low activity state refers to the processing capacity of a processor at a given time. In some implementations, a low activity state occurs when a processor is not acquiring and/or storing data. In some implementations, a low activity state occurs when some data acquisition and/or storage is taking place, but additional processing capacity remains such that image analysis can occur at the same time without interfering with other functions.

As used herein, "identifying a conflict" refers to identifying a situation where multiple processes compete for resources. In some such implementations, one process is given priority over another process. In some implementations, a conflict may relate to the need to give priority for allocation of time, processing capacity, storage capacity or any other resource for which priority is given. Thus, in some implementations, where processing time or capacity is to be distributed between two processes such as either analyzing a data set and acquiring and/or storing the data set, a conflict between the two processes exists and can be resolved by giving priority to one of the processes.

Also provided herein are systems for performing image analysis. The systems can include a processor; a storage capacity; and a program for image analysis, the program comprising instructions for processing a first data set for storage and the second data set for analysis, wherein the processing comprises acquiring and/or storing the first data set on the storage device and analyzing the second data set when the processor is not acquiring the first data set. In certain aspects, the program includes instructions for identifying at least one instance of a conflict between acquiring and/or storing the first data set and analyzing the second data set; and resolving the conflict in favor of acquiring and/or storing image data such that acquiring and/or storing the first data set is given priority. In certain aspects, the first data set comprises image files obtained from an optical imaging device. In certain aspects, the system further comprises an optical imaging device. In some aspects, the optical imaging device comprises a light source and a detection device.

As used herein, the term "program" refers to instructions or commands to perform a task or process. The term "program" can be used interchangeably with the term module. In certain implementations, a program can be a compilation of various instructions executed under the same set of commands. In other implementations, a program can refer to a discrete batch or file.

Set forth below are some of the surprising effects of utilizing the methods and systems for performing image analysis set forth herein. In some sequencing implementations, an important measure of a sequencing system's utility is its overall efficiency. For example, the amount of mappable data produced per day and the total cost of installing and running the instrument are important aspects of an economical sequencing solution. To reduce the time to generate mappable data and to increase the efficiency of the system, real-time base calling can be enabled on an instrument computer and can run in parallel with sequencing chemistry and imaging. This allows much of the data processing and analysis to be completed before the sequencing chemistry finishes. Additionally, it can reduce the storage required for intermediate data and limit the amount of data that needs to travel across the network.

While sequence output has increased, the data per run transferred from the systems provided herein to the network and to secondary analysis processing hardware has substantially decreased. By transforming data on the instrument computer (acquiring computer), network loads are dramatically reduced. Without these on-instrument, off-network data reduction techniques, the image output of a fleet of DNA sequencing instruments would cripple most networks.

The widespread adoption of the high-throughput DNA sequencing instruments has been driven in part by ease of use, support for a range of applications, and suitability for virtually any lab environment. The highly efficient algorithms presented herein allow significant analysis functionality to be added to a simple workstation that can control sequencing instruments. This reduction in the requirements for computational hardware has several practical benefits that will become even more important as sequencing output levels continue to increase. For example, by performing image analysis and base calling on a simple tower, heat production, laboratory footprint, and power consumption are kept to a minimum In contrast, other commercial sequencing technologies have recently ramped up their computing infrastructure for primly analysis, with up to five times more processing power, leading to commensurate increases in heat output and power consumption. Thus, in some implementations, the computational efficiency of the methods and systems provided herein enables customers to increase their sequencing throughput while keeping server hardware expenses to a minimum.

Accordingly, in some implementations, the methods and/or systems presented herein act as a state machine, keeping track of the individual state of each specimen, and when it detects that a specimen is ready to advance to the next state, it does the appropriate processing and advances the specimen to that state. A more detailed example of how the state machine monitors a file system to determine when a specimen is ready to advance to the next state according to a preferred implementation is set forth in Example 1 below.

In preferred implementations, the methods and systems provided herein are multi-threaded and can work with a configurable number of threads. Thus, for example in the context of nucleic acid sequencing, the methods and systems provided herein are capable of working in the background during a live sequencing run for real-time analysis, or it can be run using a pre-existing set of image data for off-line analysis. In certain preferred implementations, the methods and systems handle multi-threading by giving each thread its own subset of specimen for which it is responsible. This minimizes the possibility of thread contention.

A method of the present disclosure can include a step of obtaining a target image of an object using a detection apparatus, wherein the image includes a repeating pattern of analytes on the object. Detection apparatus that are capable of high resolution imaging of surfaces are particularly useful. In particular implementations, the detection apparatus will have sufficient resolution to distinguish analytes at the densities, pitches, and/or analyte sizes set forth herein. Particularly useful are detection apparatus capable of obtaining images or image data from surfaces. Example detectors are those that are configured to maintain an object and detector in a static relationship while obtaining an area image. Scanning apparatus can also be used. For example, an apparatus that obtains sequential area images (e.g., so called 'step and shoot' detectors) can be used. Also useful are devices that continually scan a point or line over the surface of an object to accumulate data to construct an image of the surface. Point scanning detectors can be configured to scan a point (i.e., a small detection area) over the surface of an object via a raster motion in the x-y plane of the surface. Line scanning detectors can be configured to scan a line along they dimension of the surface of an object, the longest dimension of the line occurring along the x dimension. It will be understood that the detection device, object or both can be moved to achieve scanning detection. Detection apparatus that are particularly useful, for example in nucleic acid sequencing applications, are described in US Pat App. Pub. Nos. 2012/0270305 A1; 2013/0023422 A1; and 2013/0260372 A1; and U.S. Pat. Nos. 5,528,050; 5,719,391; 8,158,926 and 8,241,573, each of which is incorporated herein by reference.

The implementations disclosed herein may be implemented as a method, apparatus, system or article of manufacture using programming or engineering techniques to produce software, firmware, hardware, or any combination thereof. The term "article of manufacture" as used herein refers to code or logic implemented in hardware or computer readable media such as optical storage devices, and volatile or non-volatile memory devices. Such hardware may include, but is not limited to, field programmable gate arrays (FPGAs), coarse grained reconfigurable architectures (CGRAs), application-specific integrated circuits (ASICs), complex programmable logic devices (CPLDs), programmable logic arrays (PLAs), microprocessors, or other similar processing devices. In particular implementations, information or algorithms set forth herein are present in non-transient storage media.

In particular implementations, a computer implemented method set forth herein can occur in real time while multiple images of an object are being obtained. Such real time analysis is particularly useful for nucleic acid sequencing applications wherein an array of nucleic acids is subjected to repeated cycles of fluidic and detection steps. Analysis of the sequencing data can often be computationally intensive such that it can be beneficial to perform the methods set forth herein in real time or in the background while other data acquisition or analysis algorithms are in process. Example real time analysis methods that can be used with the present methods are those used for the MiSeq and HiSeq sequencing devices commercially available from Illumina, Inc. (San Diego, Calif.) and/or described in US Pat. App. Pub. No. 2012/0020537 A1, which is incorporated herein by reference.

An example data analysis system, formed by one or more programmed computers, with programming being stored on one or more machine readable media with code executed to carry out one or more steps of methods described herein. In one implementation, for example, the system includes an interface designed to permit networking of the system to one or more detection systems (e.g., optical imaging systems) that are configured to acquire data from target objects. The interface may receive and condition data, where appropriate. In particular implementations the detection system will output digital image data, for example, image data that is representative of individual picture elements or pixels that, together, form an image of an array or other object. A processor processes the received detection data in accordance with a one or more routines defined by processing code. The processing code may be stored in various types of memory circuitry.

In accordance with the presently contemplated implementations, the processing code executed on the detection data includes a data analysis routine designed to analyze the detection data to determine the locations and metadata of individual analytes visible or encoded in the data, as well as locations at which no analyte is detected (i.e., where there is no analyte, or where no meaningful signal was detected from an existing analyte). In particular implementations, analyte locations in an array will typically appear brighter than non-analyte locations due to the presence of fluorescing dyes attached to the imaged analytes. It will be understood that the analytes need not appear brighter than their surrounding area, for example, when a target for the probe at the analyte is not present in an array being detected. The color at which individual analytes appear may be a function of the dye employed as well as of the wavelength of the light used by the imaging system for imaging purposes. Analytes to which targets are not bound or that are otherwise devoid of a particular label can be identified according to other characteristics, such as their expected location in the microarray.

Once the data analysis routine has located individual analytes in the data, a value assignment may be carried out. In general, the value assignment will assign a digital value to each analyte based upon characteristics of the data represented by detector components (e.g., pixels) at the corresponding location. That is, for example when imaging data is processed, the value assignment routine may be designed to recognize that a specific color or wavelength of light was detected at a specific location, as indicated by a group or cluster of pixels at the location. In a typical DNA imaging application, for example, the four common nucleotides will be represented by four separate and distinguishable colors. Each color, then, may be assigned a value corresponding to that nucleotide.

As used herein, the terms "module", "system," or "system controller" may include a hardware and/or software system and circuitry that operates to perform one or more functions. For example, a module, system, or system controller may include a computer processor, controller, or other logic-based device that performs operations based on instructions stored on a tangible and non-transitory computer readable storage medium, such as a computer memory. Alternatively, a module, system, or system controller may include a hard-wired device that performs operations based on hard-wired logic and circuitry. The module, system, or system controller shown in the attached figures may represent the hardware and circuitry that operates based on software or hardwired instructions, the software that directs hardware to perform the operations, or a combination thereof. The module, system, or system controller can include or represent hardware circuits or circuitry that include and/or are connected with one or more processors, such as one or computer microprocessors.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are examples only, and are thus not limiting as to the types of memory usable for storage of a computer program.

In the molecular biology field, one of the processes for nucleic acid sequencing in use is sequencing-by-synthesis. The technique can be applied to massively parallel sequencing projects. For example, by using an automated platform, it is possible to carry out hundreds of thousands of sequencing reactions simultaneously. Thus, one of the implementations of the present invention relates to instruments and methods for acquiring, storing, and analyzing image data generated during nucleic acid sequencing.

Enormous gains in the amount of data that can be acquired and stored make streamlined image analysis methods even more beneficial. For example, the image analysis methods described herein permit both designers and end users to make efficient use of existing computer hardware. Accordingly, presented herein are methods and systems which reduce the computational burden of processing data in the face of rapidly increasing data output. For example, in the field of DNA sequencing, yields have scaled 15-fold over the course of a recent year, and can now reach hundreds of gigabases in a single run of a DNA sequencing device. If computational infrastructure requirements grew proportionately, large genome-scale experiments would remain out of reach to most researchers. Thus, the generation of more mw sequence data will increase the need for secondary analysis and data storage, making optimization of data transport and storage extremely valuable. Some implementations of the methods and systems presented herein can reduce the time, hardware, networking, and laboratory infrastructure requirements needed to produce usable sequence data.

The present disclosure describes various methods and systems for carrying out the methods. Examples of some of the methods are described as a series of steps. However, it should be understood that implementations are not limited to the particular steps and/or order of steps described herein. Steps may be omitted, steps may be modified, and/or other steps may be added. Moreover, steps described herein may be combined, steps may be performed simultaneously, steps may be performed concurrently, steps may be split into multiple sub-steps, steps may be performed in a different order, or steps (or a series of steps) may be re-performed in an iterative fashion. In addition, although different methods are set forth herein, it should be understood that the different methods (or steps of the different methods) may be combined in other implementations.

In some implementations, a processing unit, processor, module, or computing system that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

Moreover, the operations of the methods described herein can be sufficiently complex such that the operations cannot be mentally performed by an average human being or a person of ordinary skill in the art within a commercially reasonable time period. For example, the methods may rely on relatively complex computations such that such a person cannot complete the methods within a commercially reasonable time.

Throughout this application various publications, patents or patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

As used herein, the term "each", when used in reference to a collection of items, is intended to identify an individual item in the collection but does not necessarily refer to every item in the collection. Exceptions can occur if explicit disclosure or context clearly dictates otherwise.

Although the invention has been described with reference to the examples provided above, it should be understood that various modifications can be made without departing from the invention.

The modules in this application can be implemented in hardware or software, and need not be divided up in precisely the same blocks as shown in the figures. Some can also be implemented on different processors or computers, or spread among a number of different processors or computers. In addition, it will be appreciated that some of the modules can be combined, operated in parallel or in a different sequence than that shown in the figures without affecting the functions achieved. Also as used herein, the term "module" can include "sub-modules", which themselves can be considered herein to constitute modules. The blocks in the figures designated as modules can also be thought of as flowchart steps in a method.

As used herein, the "identification" of an item of information does not necessarily require the direct specification of that item of information. Information can be "identified" in a field by simply referring to the actual information through one or more layers of indirection, or by identifying one or more items of different information which are together sufficient to determine the actual item of information. In addition, the term "specify" is used herein to mean the same as "identify".

As used herein, a given signal, event or value is "in dependence upon" a predecessor signal, event or value of the predecessor signal, event or value influenced by the given signal, event or value. If there is an intervening processing element, step or time period, the given signal, event or value can still be "in dependence upon" the predecessor signal, event or value. If the intervening processing element or step combines more than one signal, event or value, the signal output of the processing element or step is considered "in dependence upon" each of the signal, event or value inputs. If the given signal, event or value is the same as the predecessor signal, event or value, this is merely a degenerate case in which the given signal, event or value is still considered to be "in dependence upon" or "dependent on" or "based on" the predecessor signal, event or value. "Responsiveness" of a given signal, event or value upon another signal, event or value is defined similarly.

As used herein, "concurrently" or "in parallel" does not require exact simultaneity. It is sufficient if the evaluation of one of the individuals begins before the evaluation of another of the individuals completes.

Computer System

Figure 65:
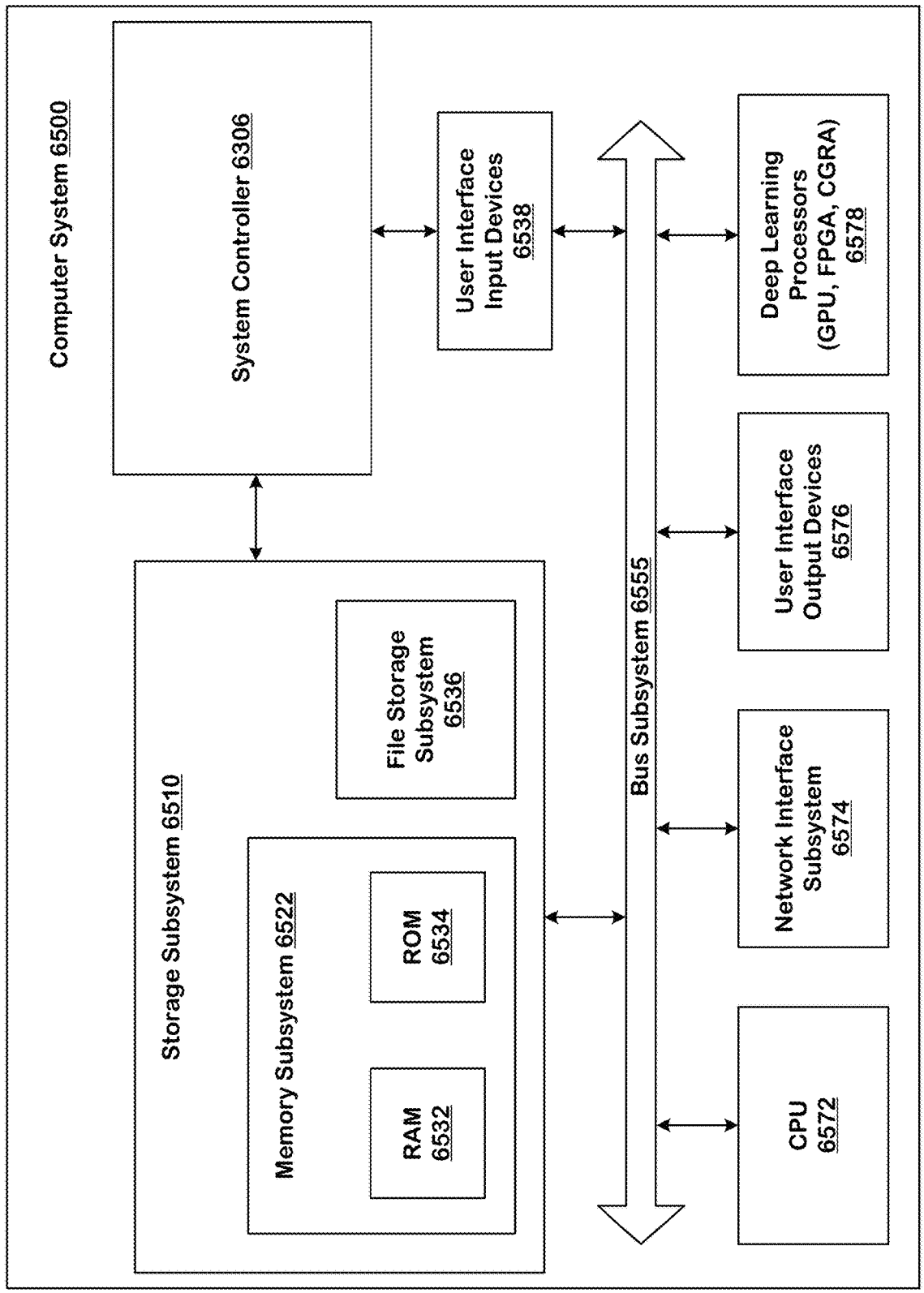
FIG. 65 is a computer system that can be used by the sequencing system of FIG. 63A to implement the technology disclosed herein.

FIG. 65 is a computer system 6500 that can be used by the sequencing system 800A to implement the technology disclosed herein. Computer system 6500 includes at least one central processing unit (CPU) 6572 that communicates with a number of peripheral devices via bus subsystem 6555. These peripheral devices can include a storage subsystem 6510 including, for example, memory devices and a file storage subsystem 6536, user interface input devices 6538, user interface output devices 6576, and a network interface subsystem 6574. The input and output devices allow user interaction with computer system 6500. Network interface subsystem 6574 provides an interface to outside networks, including an interface to corresponding interface devices in other computer systems.

In one implementation, the system controller 7806 is communicably linked to the storage subsystem 6510 and the user interface input devices 6538.

User interface input devices 6538 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 6500.

User interface output devices 6576 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 6500 to the user or to another machine or computer system.

Storage subsystem 6510 stores programming and data constructs that provide the functionality of some or all of the modules and methods described herein. These software modules are generally executed by deep learning processors 6578.

Deep learning processors 6578 can be graphics processing units (GPUs), field-programmable gate arrays (FPGAs), application-specific integrated circuits (ASICs), and/or coarse-grained reconfigurable architectures (CGRAs). Deep learning processors 6578 can be hosted by a deep learning cloud platform such as Google Cloud Platform™ Xilinx™ and Cirrascale™. Examples of deep learning processors 6578 include Google's Tensor Processing Unit (TPU)™, rackmount solutions like GX4 Rackmount Series™, GX65 Rackmount Series™, NVIDIA DGX-1™ Microsoft' Stratix V FPGA™, Graphcore's Intelligent Processor Unit (IPU)™, Qualcomm's Zeroth Platform™ with Snapdragon Processors™ NVIDIA's Volta™, NVIDIA's DRIVE PX™, NVIDIA's JETSON TX1/TX2 MODULE™, Intel's Nirvana™, Movidius VPU™, Fujitsu DPI™ ARM's DynamicIQ™, IBM TrueNorth™, Lambda GPU Server with Testa V100s™, and others.

Memory subsystem 6522 used in the storage subsystem 6510 can include a number of memories including a main random access memory (RAM) 6532 for storage of instructions and data during program execution and a read only memory (ROM) 6534 in which fixed instructions are stored. A file storage subsystem 6536 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 6536 in the storage subsystem 6510, or in other machines accessible by the processor.

Bus subsystem 6555 provides a mechanism for letting the various components and subsystems of computer system 6500 communicate with each other as intended. Although bus subsystem 6555 is shown schematically as a single bus, alternative implementations of the bus subsystem can use multiple busses.

Computer system 6500 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 6500 depicted in FIG. 65 is intended only as a specific example for purposes of illustrating the preferred implementations of the present invention. Many other configurations of computer system 6500 are possible having more or less components than the computer system depicted in FIG. 65.

Particular Implementations

We describe various implementations of neural network based template generation and neural network-based base calling. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

Base Calling—Single Analyte Distance Channel

We disclose a neural network-implemented method of base calling analytes synthesized on a tile of a flow cell during a sequencing run, the sequencing run having a plurality of sequencing cycles, each of the plurality of sequencing cycles generating an image set with one or more images, and each of the images depicting intensity emissions of the analytes and their surrounding background in a respective one of one or more image channels. The method includes processing initial image sets respectively generated at initial ones of the plurality of sequencing cycles through a template generator to identify reference centers of the analytes in a template image. The method includes accessing one or more images in each of a current image set generated at a current one of the plurality of sequencing cycles, of a one or more preceding image sets respectively generated at one or more of the plurality of sequencing cycles preceding the current one of the plurality of sequencing cycles, and of a one or more succeeding image sets respectively generated at one or more of the plurality of sequencing cycles succeeding the current one of the plurality of sequencing cycles. The method includes registering each of the images in the current, preceding, and succeeding image sets with the template image to determine cycle-specific and image channel-specific transformations. The method includes applying the transformations to the reference centers of the analytes to identify transformed centers of the analytes in each of the images. The method includes for a particular one of the analytes being base called, extracting an image patch from each of the images in the current, preceding, succeeding image sets such that each image patch contains in its center pixel a transformed center of the particular one of the analytes identified in a respective one of the images, and depicts intensity emissions of the particular one of the analytes, of some adjacent ones of the analytes, and of their surrounding background in a corresponding one of the image channels. The method includes, for each image patch, generating distance information that identifies distances of its pixels' centers from the transformed center of the particular one of the analytes contained its center pixel. The method includes constructing input data by pixel-wise encoding the distance information into each image patch. The method includes convolving the input data through a convolutional neural network to generate a convolved representation of the input data. The method includes processing the convolved representation through an output layer to produce likelihoods of a base incorporated in the particular one of the analytes at the current one of the plurality of sequencing cycles being A, C, T, and G. The method includes classifying the base as A, C, T, or G based on the likelihoods.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes, for each image patch, generating analyte-attribution information that identifies which of its pixels cover the particular one of the analytes and which of its pixels do not, and constructing the input data by pixel-wise encoding the analyte-attribution information into each image patch In one implementation, the pixels that cover the particular one of the analytes are assigned a non-zero value in the analyte-attribution information. In one implementation, the pixels that do not cover the particular one of the analytes are assigned a zero value in the analyte-attribution information. In one implementation, the method includes providing as input to the convolutional neural network position coordinates of the transformed centers of the analytes. In one such implementation, the input is fed to a first layer of the convolutional neural network. In another such implementation, the input is fed to one or more intermediate layers of the convolutional neural network. In yet another such implementation, the input is fed to a final layer of the convolutional neural network. In one implementation, the method includes providing as input to the convolutional neural network an intensity scaling channel that has scaling values corresponding to pixels of the image patch. In such an implementation, the scaling values are based on a mean intensity of the center pixel of the image patch containing the center of the particular one of the analytes. In one implementation, the intensity scaling channel pixel-wise includes a same scaling value for all the pixels of the image patch. In one implementation, the mean intensity of the center pixel is determined for each of the corresponding one of the image channels.

In one implementation, the mean intensity of the center pixel is determined for a first image channel by averaging intensity values of the center pixel observed during two or more preceding sequencing cycles that produced an A and a T base call for the particular one of the analytes. In one implementation, the mean intensity of the center pixel is determined for a second image channel by averaging intensity values of the center pixel observed during the two or more preceding sequencing cycles that produced an A and a C base call for the particular one of the analytes. In one implementation, the mean intensity of the center pixel is determined for a first image channel by averaging intensity values of the center pixel observed during the two or more preceding sequencing cycles that produced an A base call for the particular one of the analytes. In one implementation, the mean intensity of the center pixel is determined for a second image channel by averaging intensity values of the center pixel observed during the two or more preceding sequencing cycles that produced a G base call for the particular one of the analytes. In one implementation, the mean intensity of the center pixel is determined for a third image channel by averaging intensity values of the center pixel observed during the two or more preceding sequencing cycles that produced a T base call for the particular one of the analytes. In one implementation, the mean intensity of the center pixel is determined for a third image channel by averaging intensity values of the center pixel observed during the two or more preceding sequencing cycles that produced a C base call for the particular one of the analytes.

In one implementation, the sequencing run implements paired-end sequencing that sequences both ends of fragments in the analytes in a forward direction and a reverse direction using a first read primer and a second read primer, thereby producing a read pair for each fragment, the read pair having a forward read and a reverse read. In one implementation, the both ends of the fragments are sequenced serially to produce the forward and reverse reads one after the other. In one implementation, the both ends of the fragments are sequenced simultaneously to produce the forward and reverse reads concurrently. In one implementation, the forward and reverse reads each contain one or more of the fragments. In one implementation, the one or more of the fragments are sequenced serially. In one implementation, the one or more of the fragments are sequenced simultaneously. In one implementation, the sequencing run implements single-read sequencing that sequences the fragments in one direction using a single read primer. In one implementation, the sequencing run implements circular sequencing that sequences double stranded copies of the fragments in a loop, and the loop iterates over a double stranded copy of a given fragment multiple times. In one implementation, the sequencing run implements stacked sequencing that sequences stacked copies of the fragments, and the stacked copies of a given fragment are stacked vertically or horizontally. In one implementation, the size of the image patch ranges from 3×3 pixels to 10000×10000 pixels.

In one implementation, the transformed center is a floating point coordinate value. In such an implementation, the method includes rounding the floating point coordinate value using a rounding operation to produce an integer coordinate value for the transformed center, and identifying the center pixel based on an overlap between its integer coordinates and the integer coordinate value produced for the transformed center. In one implementation, the rounding operation is at least one of floor function, cell function, and/or round function. In one implementation, the rounding operation is at least one of integer function and/or integer plus sign function. In one implementation, the template generator is a neural network based template generator. In one implementation, the output layer is a softmax layer, and the likelihoods are exponentially normalized score distribution of the base incorporated in the particular one of the analytes at the current one of the plurality of sequencing cycles being A, C, T, and G.

In one implementation, each one of the image channels is one of a plurality of filter wavelength bands. In another implementation, each one of the image channels is one of a plurality of image events. In one implementation, the flow cell has at least one patterned surface with an array of wells that occupy the analytes. In another implementation, the flow cell has at least one nonpatterned surface and the analytes are unevenly scattered over the nonpatterned surface. In one implementation, the image set has four images. In another implementation, the image set has two images. In yet another implementation, the image set has one image. In one implementation, the sequencing run utilizes four-channel chemistry. In another implementation, the sequencing run utilizes two-channel chemistry. In yet another implementation, the sequencing run utilizes one-channel chemistry.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a neural network-implemented method of base calling analytes synthesized during a sequencing run. The method includes convolving input data through a convolutional neural network to generate a convolved representation of the input data. The input data includes image patches extracted from one or more images in each of a current image set generated at a current sequencing cycle of the sequencing run, of one or more preceding image sets respectively generated at one or more sequencing cycles of the sequencing run preceding the current sequencing cycle, and of one or more succeeding image sets respectively generated at one or more sequencing cycles of the sequencing run succeeding the current sequencing cycle. Each of the image patches depicts intensity emissions of a target analyte being base called, of some adjacent analytes, and of their surrounding background in a corresponding image channel. The input data further includes distance information which is pixel-wise encoded in each of the image patches to identify distances of an image patch's pixels' centers from a center of the target analyte located in a center pixel of the image patch. The method includes processing the convolved representation through an output layer to produce an output. The method includes base calling the target analyte at the current sequencing cycle based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes processing the convolved representation through the output layer to produce likelihoods of a base incorporated in the target analyte at the current sequencing cycle being A, C, T, and G, and classifying the base as A, C, T, or G based on the likelihoods. In one implementation, the likelihoods are exponentially normalized scores produced by a softmax layer.

In one implementation, the method includes deriving, from the output, an output pair for the target analyte that identifies a class label of a base incorporated in the target analyte at the current sequencing cycle being A, C, T, or G, and base calling the target analyte based on the class label. In one implementation, a class label of 1, 0 identifies an A base, a class label of 0, 1 identifies a C base, a class label of 1, 1 identifies a T base, and a class label of 0, 0 identifies a G base. In another implementation, a class label of 1, 1 identifies an A base, a class label of 0, 1 identifies a C base, a class label of 0.5, 0.5 identifies a T base, and a class label of 0, 0 identifies a G base. In yet another implementation, a class label of 1, 0 identifies an A base, a class label of 0, 1 identifies a C base, a class label of 0.5, 0.5 identifies a T base, and a class label of 0, 0 identifies a G base. In yet further implementation, a class label of 1, 2 identifies an A base, a class label of 0, 1 identifies a C base, a class label of 1, 1 identifies a T base, and a class label of 0, 0 identifies a G base. In one implementation, the method includes deriving, from the output, a class label for the target analyte that identifies a base incorporated in the target analyte at the current sequencing cycle being A, C, T, or G, and base calling the target analyte based on the class label. In one implementation, a class label of 0.33 identifies an A base, a class label of 0.66 identifies a C base, a class label of 1 identifies a T base, and a class label of 0 identifies a G base. In another implementation, a class label of 0.50 identifies an A base, a class label of 0.75 identifies a C base, a class label of 1 identifies a T base, and a class label of 0.25 identifies a G base. In one implementation, the method includes deriving, from the output, a single output value, comparing the single output value against class value ranges corresponding to bases A, C, T, and G, based on the comparing, assigning the single output value to a particular class value range, and base calling the target analyte based on the assigning. In one implementation, the single output value is derived using a sigmoid function, and the single output value ranges from 0 to 1. In another implementation, a class value range of 0-0.25 represents an A base, a class value range of 0.25-0.50 represents a C base, a class value range of 0.50-0.75 represents a T base, and a class value range of 0.75-1 represents a G base.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a neural network-implemented method of base calling analytes synthesized on a tile of a flow cell during a sequencing run, the sequencing run having a plurality of sequencing cycles, each of the plurality of sequencing cycles generating an image set with one or more images, and each of the images depicting intensity emissions of the analytes and their surrounding background in a respective one of one or more image channels. The method includes processing initial image sets respectively generated at initial ones of the plurality of sequencing cycles through a template generator to identify reference centers of the analytes in a template image. The method includes accessing one or more images in each of a current image set generated at a current one of the plurality of sequencing cycles, of a one or more preceding image sets respectively generated at one or more of the plurality of sequencing cycles preceding the current one of the plurality of sequencing cycles, and of a one or more succeeding image sets respectively generated at one or more of the plurality of sequencing cycles succeeding the current one of the plurality of sequencing cycles. The method includes registering each of the images in the current, preceding, and succeeding image sets with the template image to determine cycle-specific and image channel-specific transformations. The method includes applying the transformations to the reference centers of the analytes to identify transformed centers of the analytes in each of the images. The method includes, for a particular one of the analytes being base called, extracting an image patch from each of the images in the current, preceding, succeeding image sets such that each image patch contains in its center pixel a transformed center of the particular one of the analytes identified in a respective one of the images, and depicts intensity emissions of the particular one of the analytes, of some adjacent ones of the analytes, and of their surrounding background in a corresponding one of the image channels. The method includes, for each image patch, generating distance information that identifies distances of its pixels' centers from the transformed center of the particular one of the analytes contained its center pixel. The method includes constructing input data by pixel-wise encoding the distance information into each image patch. The method includes convolving the input data through a convolutional neural network to generate a convolved representation of the input data. The method includes processing the convolved representation through an output layer to produce an output. The method includes base calling the particular one of the analytes at the current one of the plurality of sequencing cycles based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes processing the convolved representation through the output layer to produce likelihoods of a base incorporated in the particular one of the analytes at the current one of the plurality of sequencing cycles being A, C, T, and G, and classifying the base as A, C, T, or G based on the likelihoods.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

In one implementation, computer-implemented method includes processing input data through a neural network and producing an alternative representation of the input data. The input data includes per-cycle image data for each of one or more sequencing cycles of a sequencing run. The per-cycle image data depicts intensity emissions of one or more analytes and their surrounding background captured at a respective sequencing cycle. The method includes processing the alternative representation through an output layer and producing an output. The method includes base calling one or more of the analytes at one or more of the sequencing cycles based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes accompanying the per-cycle image data with supplemental distance information that identifies distances between pixels of the per-cycle image data and one or more of the analytes. In such an implementation, the distances incorporate context about centers, shapes, and/or boundaries of one or more of the analytes in the processing by the neural network and the output layer. In one implementation, the method includes accompanying the per-cycle image data with supplemental scaling information that assigns scaling values to the pixels of the per-cycle image data. In such an implementation, the scaling values account for variance in intensities of one or more of the analytes.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Base Calling—Multi-Analyte Distance Channel

We disclose a neural network-implemented method of base calling analytes synthesized during a sequencing run. The method includes accessing input data that includes a sequence of per-cycle image patch sets generated for a series of sequencing cycles of a sequencing run. Each per-cycle image patch set in the sequence has an image patch for a respective one of one or more image channels. Each image patch has pixel intensity data for pixels that cover a plurality of analytes and their surrounding background, and pixel distance data that identifies each pixel's center-to-center distance from a nearest one of the analytes selected based on center-to-center distances between the pixel and each of the analytes. The method includes convolving the input data through a convolutional neural network to generate a convolved representation of the input data. The method includes processing the convolved representation through an output layer to produce a score distribution for each of the analytes that identifies likelihoods of a base incorporated in a respective one of the analytes at a current sequencing cycle being A, C, T, and G. The method includes base calling each of the analytes based on the likelihoods.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the pixel distance data is pixel-wise encoded into each image patch. In one implementation, the center-to-center distance is derived from a distance formula that uses position coordinates of transformed centers of the analytes and position coordinates of pixel centers. In one implementation, the method includes providing as input to the convolutional neural network intensity scaling channels that have scaling values corresponding to pixels of each image patch, and the scaling values are based on a combination of mean intensities of center pixels in each image patch that contain the transformed centers of the analytes. In one implementation, the intensity scaling channels pixel-wise apply same scaling values to the pixel intensity data of all the pixels of an image patch. In one implementation, the intensity scaling channels pixel-wise apply different scaling values to the pixel intensity data of the pixels of the image patch on a pixel neighborhood basis such that a first scaling value derived from a mean intensity of a first center pixel is applied to a first pixel neighborhood of adjoining pixels that are successively contiguous to the first center pixel, and another scaling value derived from a mean intensity of another center pixel is applied to another pixel neighborhood of adjoining pixels that are successively contiguous to the another center pixel. In one implementation, the pixel neighborhood is a m×n pixel patch centered at the center pixels, and the pixel patch is 3×3 pixels. In one implementation, the pixel neighborhood is a n-connected pixel neighborhood centered at the center pixels. In one implementation, the mean intensities of the center pixels are determined for each of the corresponding one of the image channels. In one implementation, the mean intensities of the center pixels are determined for a first image channel by averaging intensity values of the center pixels observed during two or more preceding sequencing cycles that produced an A and a T base call for respective ones of the analytes. In one implementation, the mean intensities of the center pixels are determined for a second image channel by averaging intensity values of the center pixel observed during the two or more preceding sequencing cycles that produced an A and a C base call for respective ones of the analytes. In one implementation, the mean intensities of the center pixels are determined for a first image channel by averaging intensity values of the center pixel observed during the two or more preceding sequencing cycles that produced an A base call for respective ones of the analytes. In one implementation, the mean intensities of the center pixels are determined for a second image channel by averaging intensity values of the center pixel observed during the two or more preceding sequencing cycles that produced a G base call for respective ones of the analytes. In one implementation, the mean intensities of the center pixels are determined for a third image channel by averaging intensity values of the center pixel observed during the two or more preceding sequencing cycles that produced a T base call for respective ones of the analytes. In one implementation, the mean intensities of the center pixels are determined for a third image channel by averaging intensity values of the center pixel observed during the two or more preceding sequencing cycles that produced a C base call for respective ones of the analytes. In one implementation, the method includes, for each image patch, generating analyte-attribution information that identifies which of its pixels cover the analytes and which of its pixels do not, and constructing the input data by pixel-wise encoding the analyte-attribution information into each image patch. In one implementation, the pixels that cover the analytes are assigned a non-zero value in the analyte-attribution information. In one implementation, the pixels that do not cover the analytes are assigned a zero value in the analyte-attribution information. In one implementation, the size of each image patch ranges from 3×3 pixels to 10000×10000 pixels. In one implementation, the output layer is a softmax layer, and the score distribution is an exponentially normalized score distribution.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a neural network-implemented method of base calling analytes synthesized during a sequencing run. The method includes accessing input data that includes a sequence of per-cycle image patch sets generated for a series of sequencing cycles of a sequencing run. Each per-cycle image patch set in the sequence has an image patch for a respective one of one or more image channels. Each image patch has pixel intensity data for pixels that cover a plurality of analytes and their surrounding background, and pixel distance data that identifies each pixel's center-to-center distance from a nearest one of the analytes selected based on center-to-center distances between the pixel and each of the analytes. The method includes convolving the input data through a convolutional neural network to generate a convolved representation of the input data. The method includes processing the convolved representation through an output layer to produce an output. The method includes base calling each of the analytes at a current sequencing cycle based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes deriving, from the output, a score distribution for each of the analytes that identifies likelihoods of a base incorporated in a respective one of the analytes at the current sequencing cycle being A, C, T, and G, and base calling each of the analytes based on the likelihoods. In one implementation, the output layer is a softmax layer, and the score distribution is an exponentially normalized score distribution. In one implementation, the method includes deriving, from the output, an output pair for each of the analytes that identifies a class label of a base incorporated in a respective one of the analytes at the current sequencing cycle being A, C, T, and G, and base calling each of the analytes based on the class label. In one implementation, the method includes deriving, from the output, a single output value, comparing the single output value against class value ranges corresponding to bases A, C, T, and G, based on the comparing, assigning the single output value to a particular class value range, and base calling each of the analytes based on the assigning. In one implementation, the single output value is derived using a sigmoid function, and the single output value ranges from 0 to 1.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Base Calling—Multi-Analyte Shape-Based Distance Channel

We disclose a neural network-implemented method of base calling analytes synthesized during a sequencing run. The method includes accessing input data that includes a sequence of per-cycle image patch sets generated for a series of sequencing cycles of a sequencing run. Each per-cycle image patch set in the sequence has an image patch for a respective one of one or more image channels. Each image patch depicts intensity emissions of a plurality of analytes and their surrounding background using analyte pixels that depict analyte intensities and background pixels that depict background intensities. Each image patch is encoded with analyte distance data that identifies each analyte pixel's center-to-center distance from an assigned one of the analytes selected based on classifying each analyte pixel to only one of the analytes. The method includes convolving the input data through a convolutional neural network to generate a convolved representation of the input data. The method includes processing the convolved representation through an output layer to produce a score distribution for each of the analytes that identifies likelihoods of a base incorporated in a respective one of the analytes at a current sequencing cycle being A, C, T, and G. The method includes base calling each of the analytes based on the likelihoods.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the analytes have irregular shapes that span multiple analyte pixels and pixel-to-analyte classification is based on the irregular shapes. In one implementation, all background pixels are assigned a same minimum center-to-center distance in the analyte distance data. In one implementation, all background pixels are assigned a same minimum intensity. In one implementation, each analyte pixel is classified to only one of the analytes based on a decay map produced by a neural network based template generator. In such an implementation, the decay map identifies the analytes as disjointed regions of adjoining pixels, centers of the analytes as center pixels at centers of mass of the respective ones of the disjointed regions, and their surrounding background as background pixels not belonging to any of the disjointed regions. In one implementation, the adjoining pixels in the respective ones of the disjointed regions have intensity values weighted according to distance of an adjoining pixel from a center pixel in a disjointed region to which the adjoining pixel belongs. In one implementation, the adjoining pixels in the respective ones of the disjointed regions are categorized as analyte interior pixels belonging to and co-depicting a same analyte and stored in memory on an analyte-by-analyte basis. In one implementation, the center pixels have highest intensity values within the respective ones of the disjointed regions. In one implementation, the background pixels all have a same lowest intensity value in the decay map. In one implementation, the analyte distance data is pixel-wise encoding into each image patch. In one implementation, the center-to-center distance is derived from a distance formula that uses position coordinates of transformed centers of the analytes and position coordinates of pixel centers. In one implementation, the transformed centers of the analytes are derived by applying cycle-specific and image channel-specific transformations to the centers of the analytes identified by the decay map.

In one implementation, the method includes providing as input to the convolutional neural network intensity scaling channels that have scaling values corresponding to pixels of each image patch. In such an implementation, the scaling values are based on a combination of mean intensities of center pixels in each image patch that contain the transformed centers of the analytes. In one implementation, the intensity scaling channels pixel-wise apply different scaling values to the pixel intensity data of the pixels of an image patch on a pixel group basis such that a first scaling value derived from a mean intensity of a first center pixel containing a center of a first analyte is applied to a first pixel group of adjoining pixels that belong to and co-depict the first analyte, and another scaling value derived from a mean intensity of another center pixel containing a center of another analyte is applied to another pixel group of adjoining pixels that belong to and co-depict the another analyte. In one implementation, the mean intensities of the center pixels are determined for each of the corresponding one of the image channels. In one implementation, the method includes, for each image patch, generating analyte-attribution information that identifies which of its pixels cover the analytes and which of its pixels do not, and constructing the input data by pixel-wise encoding the analyte-attribution information into each image patch. In one implementation, the pixels that cover the analytes are assigned a non-zero value in the analyte-attribution information. In another implementation, the pixels that do not cover the analytes are assigned a zero value in the analyte-attribution information.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a neural network-implemented method of base calling analytes synthesized during a sequencing run. The method includes accessing input data that includes a sequence of per-cycle image patch sets generated for a series of sequencing cycles of a sequencing run. Each per-cycle image patch set in the sequence has an image patch for a respective one of one or more image channels. Each image patch depicts intensity emissions of a plurality of analytes and their surrounding background using analyte pixels that depict analyte intensities and background pixels that depict background intensities. Each image patch is encoded with analyte distance data that identifies each analyte pixel's center-to-center distance from an assigned one of the analytes selected based on classifying each analyte pixel to only one of the analytes. The method includes convolving the input data through a convolutional neural network to generate a convolved representation of the input data. The method includes processing the convolved representation through an output layer to produce an output. The method includes base calling each of the analytes at a current sequencing cycle based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Specialized Architecture

We disclose a network-implemented method of base calling analytes using sequencing images that have registration error with respect to each other. The method includes accessing a sequence of per-cycle image patch sets generated for a series of sequencing cycles of a sequencing run. The sequence has registration error between image patches across the per-cycle image patch sets and within the per-cycle image patch sets. Each image patch in the sequence depicts intensity information of a target analyte being base called, of some adjacent analytes, and of their surrounding background in a corresponding image channel at a corresponding sequencing cycle in the series. Each image patch in the sequence is pixel-wise encoded with distance information that identifies distances of its pixels' centers from a center of the target analyte located in its center pixel. The method includes separately processing each per-cycle image patch set through a first convolutional subnetwork to produce an intermediate convolved representation for each sequencing cycle, including applying convolutions that combine the intensity and distance information and combine resulting convolved representations only within a sequencing cycle and not between sequencing cycles. The method includes groupwise processing intermediate convolved representations for successive sequencing cycles in the series through a second convolutional subnetwork to produce a final convolved representation for the series, including applying convolutions that combine the intermediate convolved representations and combine resulting convolved representations between the sequencing cycles. The method includes processing the final convolved representation through an output layer to produce an output. The method includes base calling the target analyte at a current sequencing cycle based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, each image patch in the sequence has pixel intensity data for pixels that cover a plurality of analytes and their surrounding background, and pixel distance data that identifies each pixel's center-to-center distance from a nearest one of the analytes selected based on center-to-center distances between the pixel and each of the analytes. In such an implementation, the method includes base calling each of the analytes at the current sequencing cycle based on the output. In one implementation, each image patch in the sequence depicts intensity emissions of a plurality of analytes and their surrounding background using analyte pixels that depict analyte intensities and background pixels that depict background intensities, and is encoded with analyte distance data that identifies each analyte pixel's center-to-center distance from an assigned one of the analytes selected based on classifying each analyte pixel to only one of the analytes. In such an implementation, the method includes base calling each of the analytes at the current sequencing cycle based on the output. In one implementation, the method includes providing as input to the first convolutional subnetwork position coordinates of the target analyte and/or the adjacent analytes. In one implementation, the method includes providing as input to the second convolutional subnetwork position coordinates of the target analyte and/or the adjacent analytes. In one implementation, the method includes providing as input to the output layer position coordinates of the target analyte and/or the adjacent analytes.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a network-implemented method of base calling analytes using image data with registration error. The method includes accessing input data for a series of sequencing cycles of a sequencing run. The input data has an image tensor for each sequencing cycle. Each image tensor has data for one or more image channels, including, for each image channel, pixel intensity data for pixels covering a target analyte being base called, some adjacent analytes, and surrounding background, and pixel distance data for distances from a center of the target analyte to centers of the pixels. The input data has cross-cycle registration error between pixels across the image tensors and cross-image channel registration error between pixels within the image tensors. The method includes separately processing each input tensor through a spatial convolutional network with a sequence of spatial convolution layers to produce a spatially convolved representation for each sequencing cycle, including beginning with a first spatial convolution layer that combines the pixel intensities and distances only within a sequencing cycle and not between sequencing cycles, and continuing with successive spatial convolution layers that combine outputs of preceding spatial convolution layers only within each sequencing cycle in the series of sequencing cycles and not between the sequencing cycles. The method includes groupwise processing spatially convolved representations for successive sequencing cycles through a temporal convolutional network with a sequence of temporal convolution layers to produce a temporally convolved representation for the series, including beginning with a first temporal convolution layer that combines the spatially convolved representations between the sequencing cycles in the series of sequencing cycles, and continuing with successive temporal convolution layers that combine successive outputs of preceding temporal convolution layers. The method includes processing the temporally convolved representation through an output layer to produce an output. The method includes base calling the target analyte at a current sequencing cycle based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the groupwise processing further includes convolving over successive intermediate convolved representations within overlapping sliding windows. In one implementation, the successive temporal convolution layers combine the successive outputs within overlapping sliding windows. In one implementation, the pixel distance data is pixel-wise encoding into each image tensor. In one implementation, each image tensor in the sequence has pixel intensity data for pixels that cover a plurality of analytes and their surrounding background, and pixel distance data that identifies each pixel's center-to-center distance from a nearest one of the analytes selected based on center-to-center distances between the pixel and each of the analytes. In one implementation, the method includes base calling each of the analytes at the current sequencing cycle based on the output. In one implementation, each image tensor in the sequence depicts intensity emissions of a plurality of analytes and their surrounding background using analyte pixels that depict analyte intensities and background pixels that depict background intensities, and is encoded with analyte distance data that identifies each analyte pixel's center-to-center distance from an assigned one of the analytes selected based on classifying each analyte pixel to only one of the analytes. In one implementation, the method includes base calling each of the analytes at the current sequencing cycle based on the output. In one implementation, the method includes providing as input to the first convolutional subnetwork position coordinates of the target analyte and/or the adjacent analytes. In one implementation, the method includes providing as input to the second convolutional subnetwork position coordinates of the target analyte and/or the adjacent analytes. In one implementation, the method includes providing as input to the output layer position coordinates of the target analyte and/or the adjacent analytes.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Reframing

We disclose a neural network-implemented method of base calling analytes synthesized during a sequencing run. The method includes accessing a sequence of per-cycle image patch sets generated for a series of sequencing cycles of a sequencing run. Each per-cycle image patch set in the sequence has an image patch for a respective one of one or more image channels. Each image patch has pixel intensity data for pixels covering a target analyte being base called, some adjacent analytes, and surrounding background. The method includes reframing the pixels of each image patch to center a center of the target analyte in a center pixel. The method includes convolving reframed image patches through a convolutional neural network to generate a convolved representation of the reframed image patches. The method includes processing the convolved representation through an output layer to produce an output. The method includes base calling the target analyte at a current sequencing cycle based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the reframing further includes intensity interpolation of the pixels of each image patch to compensate for the reframing. In one implementation, the intensity interpolation further includes at least one of nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage. In one implementation, prior to the reframing, the center of the target analyte is located in the center pixel of each image patch at an offset from a center of the center pixel. In one implementation, the reframing further includes requiring that non-center pixels of each image patch are equidistant from respective centers of the target analyte. In one implementation, each image patch in the sequence has pixel intensity data for pixels that depict a plurality of analytes and their surrounding background, and pixel distance data that identifies each pixel's center-to-center distance from a nearest one of the analytes selected based on center-to-center distances between the pixel and each of the analytes. In one implementation, the method includes base calling each of the analytes at the current sequencing cycle based on the output. In one implementation, each image patch in the sequence depicts intensity emissions of a plurality of analytes and their surrounding background using analyte pixels that depict analyte intensities and background pixels that depict background intensities, and is encoded with analyte distance data that identifies each analyte pixel's center-to-center distance from an assigned one of the analytes selected based on classifying each analyte pixel to only one of the analytes. In one implementation, the method includes base calling each of the analytes at the current sequencing cycle based on the output. In one implementation, the method includes providing as input to the first convolutional subnetwork position coordinates of the target analyte and/or the adjacent analytes. In one implementation, the method includes providing as input to the second convolutional subnetwork position coordinates of the target analyte and/or the adjacent analytes. In one implementation, the method includes providing as input to the output layer position coordinates of the target analyte and/or the adjacent analytes.

We disclose a neural network-implemented method of base calling analytes on a flow cell. The method includes accessing a sequence of image sets generated over a plurality of sequencing cycles of a sequencing run that synthesizes the analytes on the flow cell. Each image in the sequence of image sets covers a non-overlapping region of the flow cell and depicts intensity emissions of a subset of the analytes on the non-overlapping region and their surrounding background captured in a corresponding image channel at a respective one of the plurality of sequencing cycles. The method includes determining a nucleotide base (A, C, T, or G) incorporated at a particular one of the plurality of sequencing cycles in a particular one of the subset of the analytes by selecting, from the sequence of image sets, a current image set generated at the particular one of the plurality of sequencing cycles, one or more preceding image sets respectively generated at one or more of the plurality of sequence cycles preceding the particular one of the plurality of sequencing cycles, and one or more succeeding image sets respectively generated at one or more of the plurality of sequencing cycles succeeding the particular one of the plurality of sequencing cycles. The method includes extracting images patches from images in each of the selected image sets. The images patches are centered at the particular one of the subset of the analytes and include additional adjacent analytes from the subset of the analytes. The method includes convolving the image patches through one or more layers of a convolutional neural network to generate a convolved representation of the image patches. The method includes processing the convolved representation through an output layer to produce likelihoods for the nucleotide base being A, C, T, and G. The method includes classifying the nucleotide base as A, C, T, or G based on the likelihoods.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes producing a sequence of base calls for the particular one of the subset of the analytes over the plurality of sequencing cycles by iterating the selecting, the extracting, the convolving, the processing, and the classifying for each of the plurality of sequencing cycles. In one implementation, the method includes producing a sequence of base calls for a plurality of analytes in the subset over the plurality of sequencing cycles by iterating the selecting, the extracting, the convolving, the processing, and the classifying for each of the plurality of sequencing cycles for each of the plurality of analytes in the subset. In one implementation, the non-overlapping region of the flow cell is a tile. In one implementation, the corresponding image channel is one of a plurality of filter wavelength bands. In one implementation, the corresponding image channel is one of a plurality of image events.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Simultaneously Base Calling Multiple Clusters at Multiple Cycles

We disclose a neural network-implemented method of base calling analytes on a flow cell. The method includes obtaining input image data from a sequence of image sets. The sequence of image sets is generated over a plurality of sequencing cycles of a sequencing run that synthesizes the analytes on the flow cell. Each image in the sequence of image sets covers a non-overlapping region of the flow cell and depicts intensity emissions of a subset of the analytes on the non-overlapping region and their surrounding background captured in a corresponding image channel at a respective one of the plurality of sequencing cycles. The method includes processing the input image data through one or more layers of a neural network to generate an alternative representation of the input image data. The method includes processing the alternative representation through an output layer to generate an output that identifies a nucleotide base (A, C, T, or G) incorporated in at least some of the analytes in the subset at each of the each of the plurality of sequencing cycles, thereby producing a sequence of base calls for each of the at least some of the analytes in the subset over the plurality of sequencing cycles.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the output layer is a softmax layer, and the output is an exponentially normalized score distribution of the nucleotide base incorporated at each of the plurality of sequencing cycles in each of the at least some of the analytes in subset being A, C, T, and G. In one implementation, the input image data includes images in the sequence of image sets. In one implementation, the input image data includes at least one image patch from each of the images in the sequence of image sets. In one implementation, the neural network is a convolutional neural network. In another implementation, the neural network is a residual neural network. In yet another implementation, the neural network is a recurrent neural network.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Recurrent Convolution-Based Base Calling

We disclose a neural network based system for base calling. The system comprises a hybrid neural network with a recurrent module and a convolution module. The recurrent module uses inputs from the convolution module. The convolution module processes image data for a series of sequencing cycles of a sequencing run through one or more convolution layers and produces one or more convolved representations of the image data. The image data depicts intensity emissions of one or more analytes and their surrounding background. The recurrent module produces current hidden state representations based on convolving the convolved representations and previous hidden state representations. The output module produces a base call for at least one of the analytes and for at least one of the sequencing cycles based on the current hidden state representations.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

We disclose a neural network-implemented method of base calling. The method includes separately processing each per-cycle input data in a sequence of per-cycle input data through a cascade of convolution layers of a convolutional neural network. The sequence of per-cycle input data is generated for a series of sequencing cycles of a sequencing run, and each per-cycle input data includes image channels that depict intensity emissions of one or more analytes and their surrounding background captured at a respective sequencing cycle. The method includes, for each sequencing cycle, based on the separate processing, producing a convolved representation at each of the convolution layers, thereby producing a sequence of convolved representations, mixing its per-cycle input data with its corresponding sequence of convolved representations and producing a mixed representation, and flattening its mixed representation and producing a flattened mixed representation. The method includes arranging flattened mixed representations of successive sequencing cycles as a stack. The method includes processing the stack in forward and backward directions through a recurrent neural network that convolves over a subset of the flattened mixed representations in the stack on a sliding window basis, with each sliding window corresponding to a respective sequencing cycle, and successively produces a current hidden state representation at each time step for each sequencing cycle based on (i) the subset of the flattened mixed representations in a current sliding window over the stack and (ii) a previous hidden state representation. The method includes base calling each of the analytes at each of the sequencing cycles based on results of processing the stack in forward and backward directions. The recurrent neural network can be a gated recurrent neural network, such as an LSTM and a GRU.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

The method includes base calling each of the analytes at a given sequencing cycle by combining forward and backward current hidden state representations of the given sequencing cycle on a time step-basis and producing a combined hidden state representation, processing the combined hidden state representation through one or more fully-connected networks and producing a dense representation, processing the dense representation through a softmax layer to produce likelihoods of bases incorporated in each of the analytes at the given sequencing cycle being A, C, T, and G, and classifying the bases as A, C, T, or G based on the likelihoods. In one implementation, the combining includes concatenation. In another implementation, the combining includes summation. In yet another implementation, the combining includes averaging.

In one implementation, each per-cycle input data includes distance channels that supplement the image channels and contain center-to-center distances between pixels in the corresponding image channels and one or more analyte centers. In one implementation, each per-cycle input data includes a scaling channel that supplements the image channels and contains scaling values based on mean intensities of one or more pixels in the image channels. In one implementation, the mixing further includes concatenating the convolved representations and the per-cycle input data. In one implementation, the mixing further includes summing the convolved representations and the per-cycle input data. In one implementation, the flattened mixed representation is a two-dimensional array. In one implementation, the subset of the flattened mixed representations is a three-dimensional volume. In one implementation, the recurrent neural network applies three-dimensional convolutions to the three-dimensional volume. In one implementation, the three-dimensional convolutions use SAME padding. In one implementation, the convolution layers use SAME padding. In one implementation, the recurrent neural network is a long short-term memory (LSTM) network that comprises an input gate, an activation gate, a forget gate, and an output gate. In such an implementation, the method includes processing (i) the subset of the flattened mixed representations in the current sliding window over the stack and (ii) the previous hidden state representation through the input gate, the activation gate, the forget gate, and the output gate and producing the current hidden state representation at each time step for each sequencing cycle. The input gate, the activation gate, the forget gate, and the output gate apply convolutions on (i) the subset of the flattened mixed representations in the current sliding window over the stack and (ii) the previous hidden state representation.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

In one implementation, a neural network-implemented method of base calling includes convolving image data for a series of sequencing cycles of a sequencing run through one or more convolution layers of a convolution module and producing one or more convolved representations of the image data. The image data depicts intensity emissions of one or more analytes and their surrounding background. The method includes convolving the convolved representations and previous hidden state representations through a recurrent module and producing current hidden state representations. The method includes processing the current hidden state representations through an output module and producing a base call for at least one of the analytes and for at least one of the sequencing cycles.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Inferring Quality Scores

We disclose a computer-implemented method of assigning quality scores to bases called by a neural network based base caller. The method includes quantizing classification scores of predicted base calls produced by the neural network-based base caller in response to processing training data during training. The method includes selecting a set of quantized classification scores. The method includes for each quantized classification score in the set, determining a base calling error rate by comparing its predicted base calls to corresponding ground truth base calls. The method includes determining a fit between the quantized classification scores and their base calling error rates. That is, for each quantized classification score, a set of training examples in the training data that are assigned the quantized classification score is determined. For each training example in the determined set of training examples, the predicted base call for the training example is compared to the ground truth base call for the training example and an error rate is determined from the comparison across the determined set of training examples to provide the error rate for the particular quantized classification score. The method includes correlating the quality scores to the quantized classification scores based on the fit.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the set of quantized classification scores includes a subset of the classification scores of predicted base calls produced by the neural network-based base caller in response to processing the training data during the training, and the classification scores are real numbers. In one implementation, the set of quantized classification scores includes all the classification scores of predicted base calls produced by the neural network-based base caller in response to processing the training data during the training, and the classification scores are real numbers. In one implementation, the classification scores are exponentially normalized softmax scores that sum to unity and are produced by a softmax output layer of the neural network-based base caller. In one implementation, the set of quantized classification scores is selected based on a selection formula defined as $$0.9 \sum_{i=1}^{n} 0.1^{(i-1)}$$

and applied to the softmax scores. In one implementation, the set of quantized classification scores is selected based on a selection formula defined as $$\bigvee_{i=1}^{n=10} 0.1i$$

and applied to the softmax scores. In one implementation, the method includes, based on the correlation, assigning the quality scores to bases called by the neural network-based base caller during inference. In one implementation, the method includes assigning the quality scores based on applying a quality score correspondence scheme to the bases called by the neural network-based base caller during the inference. In such an implementation, the scheme maps ranges of classification scores, produced by the neural network-based base caller in response to processing inference data, during the inference, to corresponding quantized classification scores in the set. In one implementation, the method includes, during the inference, stopping base calling an analyte whose quality score is below a set threshold for a current base calling cycle. In one implementation, the method includes, during the inference, stopping base calling an analyte whose average quality score is below a set threshold after successive base calling cycles. In one implementation, a sample size used for comparing the predicted base calls to the corresponding ground truth base calls is specific to each quantized classification score. In one implementation, a sample size used for comparing the predicted base calls to the corresponding ground truth base calls is specific to each quantized classification score. In one implementation, the fit is determined using a regression model. In one implementation, the method includes for each quantized classification score, determining a base calling accuracy rate by comparing its predicted base calls to corresponding ground truth base calls, and determining the fit between the quantized classification scores and their base calling accuracy rates. In one implementation, the corresponding ground truth base calls are derived from well-characterized human and non-human samples sequenced on a number of sequencing instruments, sequencing chemistries, and sequencing protocols.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Predicting Quality Scores

We disclose a neural network based quality scorer that runs on numerous processors operating in parallel and is coupled to memory. The system comprises a convolutional neural network running on the numerous processors. The convolutional neural network is trained on training examples comprising data from sequencing images and labeled with base call quality ground truths using a backpropagation-based gradient update technique that progressively matches base call quality predictions of the convolutional neural network with the base call quality ground truths. The system comprises an input module of the convolutional neural network which runs on at least one of the numerous processors and feeds data from sequencing images captured at one or more sequencing cycles to the convolutional neural network for determining quality status of one or more bases called for one or more analytes. The system comprises an output module of the convolutional neural network which runs on at least one of the numerous processors and translates analysis by the convolutional neural network into an output that identifies the quality status of the one or more bases called for the one or more analytes.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the output module further comprises a softmax classification layer that produces likelihoods for the quality status being high-quality, medium-quality, and low-quality. In such an implementation, based on the likelihoods, the quality status is classified as high-quality, medium-quality, or low-quality. In one implementation, the softmax classification layer produces likelihoods for the quality status being assigned a plurality of quality scores. In such an implementation, based on the likelihoods, the quality status is assigned a quality score from one of the plurality of quality scores. In one implementation, the quality scores are logarithmically based on base calling error probabilities, and the plurality of quality scores includes Q6, Q10, Q43, Q20, Q22, Q27, Q30, Q33, Q37, Q40, and Q50. In one implementation, the output module further comprises a regression layer that produces continuous values which identify the quality status. In one implementation, the system comprises a supplemental input module that supplements the data from the sequencing images with quality predictor values for the bases called, and feeds the quality predictor values to the convolutional neural network along with the data from the sequencing images. In one implementation, the quality predictor values include online overlap, purity, phasing, start5, hexamer score, motif accumulation, endiness, approximate homopolymer, intensity decay, penultimate chastity, signal overlap with background (SOWB), and/or shifted purity G adjustment. In one implementation, the quality predictor values include peak height, peak width, peak location, relative peak locations, peak height ratio, peak spacing ratio, and/or peak correspondence.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We also disclose a neural network-implemented method of quality scoring. The method includes feeding data from sequencing images captured at one or more sequencing cycles to a convolutional neural network for determining quality status of one or more bases called for one or more analytes. The convolutional neural network is trained on training examples comprising data from sequencing images and labeled with base call quality ground truths. The training comprises using a backpropagation-based gradient update technique that progressively matches base call quality predictions of the convolutional neural network with the base call quality ground truths. The method includes translating analysis by the convolutional neural network into an output that identifies the quality status of the one or more bases called for the one or more analytes.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, a computer-implemented method includes processing input data for one or more analytes through a neural network and producing an alternative representation of the input data, processing the alternative representation through an output layer to produce an output, the output identifies likelihoods of a base incorporated in a particular one of the analytes being A, C, T, and G, calling bases for one or more of the analytes based on the output, and determining quality of the called bases based on the likelihoods identified by the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a neural network-based quality scorer, which runs on numerous processors operating in parallel and is coupled to memory. The system comprises a neural network running on the numerous processors, trained on training examples comprising data from sequencing images and labeled with base call quality ground truths using a back-propagation-based gradient update technique that progressively matches base call quality predictions of the neural network with the base call quality ground truths. The system comprises an input module of the neural network which runs on at least one of the numerous processors and feeds data from sequencing images captured at one or more sequencing cycles to the neural network for determining quality status of one or more bases called for one or more analytes. The system comprises an output module of the neural network which runs on at least one of the numerous processors and translates analysis by the neural network into an output that identifies the quality status of the one or more bases called for the one or more analytes.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

CLAUSES

The disclosure also includes the following clauses:
Clauses Set 1
1. A computer-implemented method, including:
processing input data through a neural network and producing an alternative representation of the input data, wherein the input data includes per-cycle data for each of one or more sequencing cycles of a sequencing run, and wherein the per-cycle data is indicative of one or more analytes at a respective sequencing cycle;
processing the alternative representation through an output layer and producing an output; and
base calling one or more of the analytes at one or more of the sequencing cycles based on the output.

2. The neural network-implemented method of clause 1, wherein the per-cycle data is indicative of a surrounding background at the respective sequencing cycle.
3. The neural network-implemented method of any of clauses 1-2, wherein the input data is image data and the per-cycle data comprises intensity emissions indicative of the one or more analytes and of the surrounding background captured at the respective sequencing cycle.
4. The computer-implemented method of clause 3, further including accompanying the per-cycle data with supplemental distance information that identifies distances between pixels of the per-cycle data and those pixels that depict the intensity emissions indicative of the one or more of the analytes.
5. The computer-implemented method of clause 3, further including accompanying the per-cycle data with supplemental scaling information that assigns scaling values to the pixels of the per-cycle data.
6. The neural network-implemented method of clause 1, wherein the per-cycle data is indicative of a voltage change detected at the respective sequencing cycle.
7. The neural network-implemented method of clause 1, wherein the per-cycle data is indicative of an electric current signal measured at the respective sequencing cycle.
8. A neural network-implemented method of base calling analytes synthesized during a sequencing run comprising a plurality of sequencing cycles, the method including:
convolving input data through a convolutional neural network to generate a convolved representation of the input data,
wherein the input data includes image patches extracted from one or more images in each of a current image set generated at a current sequencing cycle of the sequencing am, of one or more preceding image sets respectively generated at one or more sequencing cycles of the sequencing run preceding the current sequencing cycle, and of one or more succeeding image sets respectively generated at one or more sequencing cycles of the sequencing run succeeding the current sequencing cycle,
wherein each of the image patches depicts intensity emissions of a target analyte being base called, and
wherein the input data further includes distance information indicating respective distances of pixels of the image patch from a center pixel of the image patch;
processing the convolved representation through an output layer to produce an output; and
base calling the target analyte at the current sequencing cycle based on the output.
9. The neural network-implemented method of clause 8, further including:
providing as input to the convolutional neural network position coordinates of centers of image regions representing respective analytes,
wherein the input is provided to a first layer of the convolutional neural network,
wherein the input is provided to one or more intermediate layers of the convolutional neural network, and
wherein the input is provided to a final layer of the convolutional neural network.
10. The neural network-implemented method of any of clauses 8-9, further including:
providing as input to the convolutional neural network an intensity scaling channel that has scaling values corresponding to pixels of the image patches, and wherein the scaling values are based on a mean intensity of center pixels of the image patches that each contain a particular target analyte.

11. The neural network-implemented method of any of clauses 8-10, wherein the intensity scaling channel pixel-wise includes a same scaling value for all the pixels of the image patches.

12. The neural network-implemented method of clause 8, wherein each image patch further comprises pixel distance data indicating a distance between respective pixels and a nearest one of the plurality of analytes, the nearest one of the plurality of analytes selected based on center-to-center distances between the pixel and each of the analytes.

13. The neural network-implemented method of clause 8, wherein each image patch further comprises analyte distance data that identifies a distance of each analyte pixel from an assigned one of the plurality of analytes selected based on classifying each analyte pixel to only one of the analytes.

14. The neural network-implemented method of any of clauses 8-13, wherein convolving the input data through the convolutional neural network to generate the convolved representation of the input data comprises:
  separately processing each per-cycle image patch set through a first convolutional subnetwork of the convolutional neural network to produce an intermediate convolved representation for each sequencing cycle, including applying convolutions that combine the intensity and distance information and combine resulting convolved representations only within a sequencing cycle and not between sequencing cycles;
  groupwise processing intermediate convolved representations for successive sequencing cycles in the series through a second convolutional subnetwork of the convolutional neural network to produce a final convolved representation for the series, including applying convolutions that combine the intermediate convolved representations and combine resulting convolved representations between the sequencing cycles;
  and wherein processing the convolved representation through the output layer to produce the output comprises processing the final convolved representation through the output layer.

15. The neural network-implemented method of any of clauses 8-14, further including: reframing the pixels of each image patch to center a center of the target analyte in a center pixel to generate reframed image patches; and
  wherein convolving the input data through the convolutional neural network to generate the convolved representation of the input data comprises convolving the reframed image patches through the convolutional neural network to generate the convolved representation.

16. The neural network-implemented method of clause 15, wherein the reframing further includes intensity interpolation of the pixels of each image patch to compensate for the reframing.

17. A neural network-implemented method of base calling, the method including:
  separately processing each per-cycle input data in a sequence of per-cycle input data through a cascade of convolution layers of the convolutional neural network, wherein
    the sequence of per-cycle input data is generated for a series of sequencing cycles of a sequencing arn, and
    each per-cycle input data includes image channels that depict intensity emissions of one or more analytes and their surrounding background captured at a respective sequencing cycle;
  for each sequencing cycle,
    based on the separate processing, producing a convolved representation at each of the convolution layers, thereby producing a sequence of convolved representations,
    mixing its per-cycle input data with its corresponding sequence of convolved representations and producing a mixed representation, and
    flattening its mixed representation and producing a flattened mixed representation;
  arranging flattened mixed representations of successive sequencing cycles as a stack;
  processing the stack in forward and backward directions through a recurrent neural network that
    convolves over a subset of the flattened mixed representations in the stack on a sliding window basis, with each sliding window corresponding to a respective sequencing cycle, and
    successively produces a current hidden state representation at each time step for each sequencing cycle based on (i) the subset of the flattened mixed representations in a current sliding window over the stack and (ii) a previous hidden state representation; and
  base calling each of the analytes at each of the sequencing cycles based on results of processing the stack in forward and backward directions.

18. The neural network-implemented method of clause 17, further including:
  base calling each of the analytes at a given sequencing cycle by:
    combining forward and backward current hidden state representations of the given sequencing cycle on a time step basis and producing a combined hidden state representation, wherein the combining includes concatenation or summation or averaging;
    processing the combined hidden state representation through one or more fully-connected networks and producing a dense representation;
    processing the dense representation through a softmax layer to produce likelihoods of bases incorporated in each of the analytes at the given sequencing cycle being A, C, T, and G; and
    classifying the bases as A, C, T, or G based on the likelihoods.

19. A neural network-based system for base calling, the system comprising:
  a hybrid neural network with a recurrent module and a convolution module, wherein the recurrent module uses inputs from the convolution module;
  the convolution module processing image data for a series of sequencing cycles of a sequencing run through one or more convolution layers and producing one or more convolved representations of the image data, wherein the image data depicts intensity emissions of one or more analytes and their surrounding background;
  the recurrent module producing current hidden state representations based on convolving the convolved representations and previous hidden state representations; and
  an output module producing a base call for at least one of the analytes and for at least one of the sequencing cycles based on the current hidden state representations.

20. A computer-implemented method of base calling clusters, including:
  processing input data through a neural network and producing an alternative representation of the input data,
    wherein the input data includes (i) per-cycle data for each of one or more sequencing cycles of a sequencing run and (ii) supplemental distance information, wherein the per-cycle data comprises pixels that depict intensity emissions indicative of the one or more clusters and of the surrounding background captured at a respective one of the sequencing cycles, wherein the per-cycle data is accompanied with the supplemental distance information that identifies distances between the pixels of the per-cycle data;

wherein, during the processing of the pixels of the per-cycle data by the neural network, the supplemental distance information supplies additive bias that conveys to the neural network which of the pixels of the per-cycle data contain centers of the clusters and which of the pixels of the per-cycle data are farther away from the centers of the clusters;

processing the alternative representation through an output layer and producing an output; and base calling one or more of the clusters at one or more of the sequencing cycles based on the output.

21. The computer-implemented method of clause 20, wherein the additive bias improves accuracy of the base calling.

22. The computer-implemented method of clause 21, wherein the neural network uses the supplemental distance information to assign a sequencing signal to its proper source cluster by attending to central cluster pixels, their neighboring pixels, and alternative representations derived from them more than perimeter cluster pixels, background pixels, and alternative representations derived from them.

Clauses Set 2

1. A computer-implemented method, including:

processing input data for one or more analytes through a neural network-based base caller and producing an alternative representation of the input data;

processing the alternative representation through an output layer to produce an output, wherein the output identifies likelihoods of a base incorporated in a particular one of the analytes being A, C, T, and G;

calling bases for one or more of the analytes based on the output; and determining quality scores of the called bases based on the likelihoods identified by the output.

2. The computer-implemented method of clause 1, wherein determining the quality scores of the called bases based on the likelihoods comprises:

quantizing classification scores of base calls produced by the neural network-based base caller in response to processing training data during training;

selecting a set of quantized classification scores;

for each quantized classification score in the set, determining a base calling error rate by comparing its predicted base calls to corresponding ground truth base calls;

determining a fit between the quantized classification scores and their base calling error rates; and correlating the quality scores to the quantized classification scores based on the fit.

3. The computer-implemented method of any of clauses 1-2, wherein the set of quantized classification scores includes a subset of the classification scores of predicted base calls produced by the neural network-based base caller in response to processing the training data during the training, and wherein the classification scores are real numbers.

4. The computer-implemented method of any of clauses 1-3, wherein the set of quantized classification scores includes all the classification scores of predicted base calls produced by the neural network-based base caller in response to processing the training data during the training, and wherein the classification scores are real numbers.

5. The computer-implemented method of any of clauses 1-4, wherein the classification scores are exponentially normalized softmax scores that sum to unity and are produced by a softmax output layer of the neural network-based base caller.

6. The computer-implemented method of any of clauses 1-5, wherein the set of quantized classification scores is selected based on a selection formula defined as $$0.9 \sum_{i=1}^{n} 0.1^{(i-1)}$$

and applied to the softmax scores.

7. The computer-implemented method of any of clauses 1-6, wherein the set of quantized classification scores is selected based on a selection formula defined as $$\bigvee_{i=1}^{n=10} 0.1i$$

and applied to the softmax scores.

8. The computer-implemented method of any of clauses 1-7, further including:

based on the correlation, assigning the quality scores to bases called by the neural network-based base caller during inference.

9. The computer-implemented method of clause 8, further including:

assigning the quality scores based on applying a quality score correspondence scheme to the bases called by the neural network-based base caller during the inference; and wherein the scheme maps ranges of classification scores, produced by the neural network-based base caller in response to processing inference data during the inference, to corresponding quantized classification scores in the set.

10. The computer-implemented method of any of clauses 8-9, further including:

during the inference, stopping base calling an analyte whose quality score is below a set threshold for a current base calling cycle.

11. The computer-implemented method of any of clauses 8-10, further including:

during the inference, stopping base calling an analyte whose average quality score is below a set threshold after successive base calling cycles.

12. The computer-implemented method of any of clauses 8-11, wherein a sample size used for comparing the predicted base calls to the corresponding ground truth base calls is specific to each quantized classification score.

13. The computer-implemented method of any of clauses 8-12, wherein the fit is determined using a regression model.

14. The computer-implemented method of any of clauses 8-13, further including:

for each quantized classification score, determining a base calling accuracy rate by comparing its predicted base calls to corresponding ground truth base calls; and determining the fit between the quantized classification scores and their base calling accuracy rates.

15. The computer-implemented method of any of clauses 8-14, wherein the corresponding ground truth base calls are derived from well-characterized human and non-human samples sequenced on a number of sequencing instruments, sequencing chemistries, and sequencing protocols.

16. A neural network-based quality scorer, comprising:
numerous processors operating in parallel and coupled to memory;
a neural network running on the numerous processors, trained on training examples comprising data from sequencing images and labeled with base call quality ground truths using a backpropagation-based gradient update technique that progressively matches base call quality predictions of the neural network with the base call quality ground truths that identify known correct base calls;
an input module of the neural network which runs on at least one of the numerous processors and feeds data from sequencing images captured at one or more sequencing cycles to the neural network for determining quality of one or more bases called for one or more analytes; and
an output module of the neural network which runs on at least one of the numerous processors and translates analysis by the neural network into an output that identifies the quality of the one or more bases called for the one or more analytes.

17. The neural network-based quality scorer of clause 16, wherein the neural network is a convolutional neural network.

18. The neural network-based quality scorer of clause 16, wherein the output module further comprises a softmax classification layer that produces likelihoods for the quality being high-quality, medium-quality, and low-quality, further comprising:
based on the likelihoods, classifying the quality as high-quality, medium-quality, or low-quality.

19. The neural network-based quality scorer of clause 16, wherein the softmax classification layer produces likelihoods for the quality being assigned a plurality of quality scores, further comprising:
based on the likelihoods, assigning the quality a quality score from one of the plurality of quality scores.

20. The neural network-based quality scorer of any of clauses 16-19, wherein the quality scores are logarithmically based on base calling error probabilities, and
wherein the plurality of quality scores includes Q6, Q10, Q15, Q20, Q22, Q27, Q30, Q33, Q37, Q40, and Q50.

21. The neural network-based quality scorer of any of clauses 16-20, wherein the output module further comprises a regression layer that produces continuous values which identify the quality.

22. The neural network-based quality scorer of any of clauses 16-21, further comprising:
a supplemental input module that
supplements the data from the sequencing images with quality predictor values for the bases called, and
feeds the quality predictor values to the convolutional neural network along with the data from the sequencing images.

23. The neural network-based quality scorer of clause 22, wherein the quality predictor values include online overlap, purity, phasing, start5, hexamer score, motif accumulation, endiness, approximate homopolymer, intensity decay, penultimate chastity, signal overlap with background (SOWB), and/or shifted purity G adjustment.

24. The neural network-based quality scorer of clause 22, wherein the quality predictor values include peak height, peak width, peak location, relative peak locations, peak height ration, peak spacing ration, and/or peak correspondence.

What is claimed is:

1. A computer-implemented method of quality scoring for a set of base calls, including:
processing input data for one or more analytes through a neural network-based base caller and producing an alternative representation of the input data;
processing the alternative representation through an output layer to produce an output, wherein the output identifies likelihoods of a base incorporated in a particular one of the analytes being A, C, T, and G;
calling bases for one or more of the analytes based on the output; and
determining quality scores of the called bases based on the likelihoods identified by the output by:
quantizing classification scores of base calls produced by the neural network-based base caller in response to processing training data during training;
selecting a set of quantized classification scores;
for each quantized classification score in the set of quantized classification scores, determining a base calling error rate by comparing predicted base calls for the set of quantized classification scores to corresponding ground truth base calls;
determining a fit between the set of quantized classification scores and corresponding base calling error rates; and
correlating the quality scores to the set of quantized classification scores based on the fit.

2. The computer-implemented method of claim 1, wherein the fit demonstrates correspondence between the set of quantized classification scores and the quality scores.

3. The computer-implemented method of claim 1, wherein the set of quantized classification scores includes a subset of the classification scores of predicted base calls produced by the neural network-based base caller in response to processing the training data during the training, and wherein the classification scores of the base calls produced by the neural network-based base caller are real numbers.

4. The computer-implemented method of claim 3, wherein the set of quantized classification scores includes all the classification scores of predicted base calls produced by the neural network-based base caller in response to processing the training data during the training, and wherein the classification scores of the base calls produced by the neural network-based base caller are real numbers.

5. The computer-implemented method of claim 4, wherein the classification scores of the base calls produced by the neural network-based base caller are exponentially normalized softmax scores that sum to unity and are produced by a softmax output layer of the neural network-based base caller.

6. The computer-implemented method of claim 5, wherein the set of quantized classification scores is selected based on a selection formula defined as $$0.9 \sum_{i=1}^{n} 0.1^{(i-1)}$$

and applied to the exponentially normalized softmax scores.

7. The computer-implemented method of claim 6, wherein the set of quantized classification scores is selected based on a selection formula defined as $$\bigvee_{i=1}^{n=10} 0.1i$$

and applied to the exponentially normalized softmax scores.

8. The computer-implemented method of claim 7, further including:
based on the correlation of the quality scores to the set of quantized classification scores, assigning the quality scores to bases called by the neural network-based base caller during inference.

9. The computer-implemented method of claim 8, further including:
assigning the quality scores based on applying a quality score correspondence scheme to the bases called by the neural network-based base caller during the inference; and
wherein the quality score correspondence scheme maps ranges of classification scores, produced by the neural network-based base caller in response to processing inference data during the inference, to corresponding quantized classification scores in the set of quantized classification scores.

10. The computer-implemented method of claim 9, further including:
during the inference, stopping base calling an analyte whose quality score is below a set threshold for a current base calling cycle.

11. The computer-implemented method of claim 10, further including:
during the inference, stopping base calling an analyte whose average quality score is below a set threshold after successive base calling cycles.

12. The computer-implemented method of claim 11, wherein a sample size used for comparing the predicted base calls to the corresponding ground truth base calls is specific to each quantized classification score.

13. The computer-implemented method of claim 12, wherein the fit is determined using a regression model.

14. The computer-implemented method of claim 13, further including:
for each quantized classification score, determining a base calling accuracy rate by comparing its predicted base calls to corresponding ground truth base calls; and
determining the fit between the set of quantized classification scores and corresponding base calling accuracy rates.

15. The computer-implemented method of claim 14, wherein the corresponding ground truth base calls are derived from well-characterized human and non-human samples sequenced on a number of sequencing instruments, sequencing chemistries, and sequencing protocols.

16. A system of quality scoring for a set of base calls, including:
one or more processors coupled to memory,
the memory loaded with computer instructions that, when executed by the one or more processors, cause the system to:
process input data for one or more analytes through a neural network-based base caller and producing an alternative representation of the input data;
process the alternative representation through an output layer to produce an output, wherein the output identifies likelihoods of a base incorporated in a particular one of the analytes being A, C, T, and G;
call bases for one or more of the analytes based on the output; and
determine quality scores of the called bases based on the likelihoods identified by the output by:
quantizing classification scores of base calls produced by the neural network-based base caller in response to processing training data during training;
selecting a set of quantized classification scores;
for each quantized classification score in the set of quantized classification scores, determining a base calling error rate by comparing predicted base calls for the set of quantized classification scores to corresponding ground truth base calls;
determining a fit between the set of quantized classification scores and corresponding base calling error rates; and
correlating the quality scores to the set of quantized classification scores based on the fit.

17. The system of claim 16, wherein the fit demonstrates correspondence between the set of quantized classification scores and the quality scores.

18. The system of claim 16, wherein the set of quantized classification scores includes a subset of the classification scores of predicted base calls produced by the neural network-based base caller in response to processing the training data during the training, and wherein the classification scores of the base calls produced by the neural network-based base caller are real numbers.

19. The system of claim 18, wherein the set of quantized classification scores includes all the classification scores of predicted base calls produced by the neural network-based base caller in response to processing the training data during the training, and wherein the classification scores of the base calls produced by the neural network-based base caller are real numbers.

20. The system of claim 19, wherein the classification scores of the base calls produced by the neural network-based base caller are exponentially normalized softmax scores that sum to unity and are produced by a softmax output layer of the neural network-based base caller.

* * * * *